United States Patent
Mueller et al.

(10) Patent No.: US 9,512,144 B2
(45) Date of Patent: Dec. 6, 2016

(54) IMIDAZOTHIAZOLE SUFONAMIDES AS NEMATICIDES

(71) Applicant: BAYER CROPSCIENCE AKTIENGESELLSCHAFT, Monheim am Rhein (DE)

(72) Inventors: Klaus-Helmut Mueller, Duesseldorf (DE); Hans-Georg Schwarz, Dorsten (DE); Kerstin Ilg, Cologne (DE); Arnd Voerste, Cologne (DE); Olga Malsam, Roesrath (DE); Daniela Portz, Vettweiss (DE); Peter Jeschke, Bergisch Gladbach (DE)

(73) Assignee: BAYER CROPSCIENCE AKTIENGESELLSCHAFT, Monheim am Rhein (DE)

(*) Notice: Subject to any disclaimer, the term of this patent is extended or adjusted under 35 U.S.C. 154(b) by 0 days.

(21) Appl. No.: 14/906,797

(22) PCT Filed: Jul. 21, 2014

(86) PCT No.: PCT/EP2014/065602
§ 371 (c)(1),
(2) Date: Jan. 21, 2016

(87) PCT Pub. No.: WO2015/011082
PCT Pub. Date: Jan. 29, 2015

(65) Prior Publication Data
US 2016/0176898 A1    Jun. 23, 2016

(30) Foreign Application Priority Data

Jul. 23, 2013  (EP) .................................... 13177572

(51) Int. Cl.
| | | |
|---|---|---|
| *C07D 513/04* | (2006.01) |
| *A01N 25/02* | (2006.01) |
| *A01N 43/90* | (2006.01) |
| *A61K 31/429* | (2006.01) |
| *A61K 31/433* | (2006.01) |
| *A61K 45/06* | (2006.01) |

(52) U.S. Cl.
CPC .............. *C07D 513/04* (2013.01); *A01N 25/02* (2013.01); *A01N 43/90* (2013.01); *A61K 31/429* (2013.01); *A61K 31/433* (2013.01); *A61K 45/06* (2013.01)

(58) Field of Classification Search
CPC ...... C07D 513/04; A01N 25/02; A01N 43/90; A61K 31/429; A61K 31/433
See application file for complete search history.

(56) References Cited

U.S. PATENT DOCUMENTS

2012/0114624 A1* 5/2012 Lahm ..................... A01N 55/00
424/93.461

FOREIGN PATENT DOCUMENTS

| EP | 0244166 A2 | 11/1987 | |
| EP | 2540163 A1 | 1/2013 | |
| JP | EP 0778267 A1 * | 6/1997 | ............. A01N 41/06 |
| WO | 2010129500 A2 | 11/2010 | |
| WO | 2012054233 A1 | 4/2012 | |

OTHER PUBLICATIONS

International Search Report from corresponding PCT/EP2014/065602, mailed Oct. 9, 2014.
Rassukana et al., "Synthesis of 3-fluoroimidazo[1,2-a]pyrimidines and 5-fluoroimidazo[2,1-b][1,3]thiazoles via heterocyclization of (N-heteroarylimino)trifluoropyruvates", Journal of Fluorine Chemistry Vo. 131, No. 10: 1044-1048. XP027416246.
Andreani et al., "Potential anti-tumor agents XVI. Imidazo[2,1-b]thiazoles", European Journal of Medicinal Chemistry vol. 23, No. 4:385-389. XP025563397.

* cited by examiner

*Primary Examiner* — John Pak
*Assistant Examiner* — Nathan W Schlientz
(74) *Attorney, Agent, or Firm* — McBee Moore Woodward Vanik IP LLC

(57) ABSTRACT

Disclosed are compounds of formula (I) which possess nematicidal properties

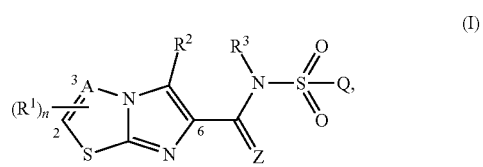

wherein the structural elements have the meaning as indicated in the description.

16 Claims, No Drawings

IMIDAZOTHIAZOLE SUFONAMIDES AS NEMATICIDES

CROSS REFERENCE TO RELATED APPLICATIONS

This application is a §371 National Stage Application of PCT/EP2014/065602, filed 21 Jul. 2014 which claims priority to EP 13177572.8, filed 23 Jul. 2013.

BACKGROUND

Field of the Invention

The present invention relates to imidazothiazole sulfonamides, their use for the control of nematodes in agricultures, compositions containing such compounds and methods for the control of nematodes. This invention relates to certain sulfonamides, their N-oxides, salts and compositions suitable for agronomic and nonagronomic uses, and methods of their use for controlling parasitic nematodes in both agronomic and nonagronomic environments.

The present invention further relates to novel imidazothiazoles, processes and intermediate compounds for their preparation, their use as nematicides, compositions containing such compounds and methods for the control of nematodes using these compounds or their compositions.

DESCRIPTION OF RELATED ART

Nematodes cause a substantial loss in agricultural product including food and industrial crops and are combated with chemical compounds having nematicidal activity. To be useful in agriculture these compounds should have a high activity, a broad spectrum activity against different strains of nematodes and should not be toxic to non-target organisms. Due to widespread development of resistance to anthelmintic agents in nematode parasites, nematodes continue to cause problems in livestock despite the available chemical therapeutic agents. The need continues for new compounds which are more effective, less costly, less toxic, environmentally safer or have different modes of action.

European Patent Application Publication No. 0 244 166 A2 (referred to as P1) discloses compounds of formula (i) as herbicides

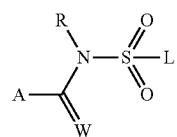

(i)

wherein, inter alia, R is H or an organic substituent, W is O or S, L is an aryl or heteroaryl moiety, and A is selected from a list of bi-, tri- and quadricyclic heterocyclic groups.

PCT patent application publication WO 2010/129500 (P2) discloses compounds of formula (ii) (including all stereoisomers), N-oxides, and salts thereof, and compositions containing them and their use for controlling a parasitic nematode:

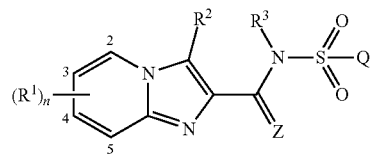

(ii)

wherein, interalia, Z is O or S and Q is phenyl, naphthalenyl, a 5- or 6-membered hetero-aromatic ring or an 8- to 10-membered heteroaromatic bicyclic ring system, each optionally substituted with 1 to 5 substituents.

Anonymously disclosed publication IP com Journal 10, 26 (2010) (P3) describes 10 explicitly listed compounds of general formula (ii) in mixtures with various insecticides in several mixture ratios.

PCT Patent Application Publication WO 2012/054233 (P4) discloses compounds of formula (iii) (including all stereoisomers), N-oxides, and salts thereof, and compositions containing them and their use for controlling a parasitic nematode:

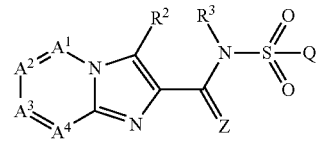

(iii)

wherein, interalia, Z is O or S, Q is phenyl, naphthalenyl, a 5- or 6-membered heteroaromatic ring or an 8- to 10-membered heteroaromatic bicyclic ring system, each optionally substituted with 1 to 5 substituents and $A^1$, $A^2$, $A^3$ and $A^4$ are independently N or $CR^1$, provided that only one of $A^1$, $A^2$, $A^3$ and $A^4$ is N.

PCT Patent Application Publication WO 2013/055584 (P5) discloses solid forms of a certain nematocidal imidazopyridine sulfonamide of formula (ii).

The compounds of the present invention are not disclosed in these publications.

SUMMARY

It is an object of the present invention to provide compounds which can be used as nematicides with a satisfactory or improved nematicidal activity, particularly at relatively low application rates, with a high selectivity and high compatibility in crop-plant cultures.

This invention is directed to compounds of formula (I) (including all stereoisomers), N-oxides, and salts thereof, and compositions containing them and their use for controlling parasitic nematodes:

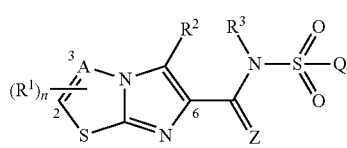

(I)

wherein
A is N or C—$R^1$;
Z is O or S;

each $R^1$ is independently H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$;

$R^2$ is H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$, $C_2$-$C_6$-alkoxyalkyl, $OC(O)R^{7a}$ and $N(R^{10})C(O)R^{7a}$;

$R^3$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $OR^{4a}$, and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or $C_1$-$C_6$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

or phenyl optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

Q is phenyl, naphthalenyl, a 5- or 6-membered heteroaromatic ring or an 8- to 10-membered heteroaromatic bicyclic ring system, each optionally substituted with 1 to 5 substituents independently selected from the group consisting of halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)2NR11R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

particularly Q is selected from the group consisting of (U-1) to (U-61), (U-81) to (U-87), (U-89) to (U-103) and (U-105) to (U-123):

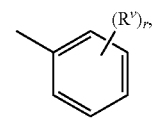

U-1

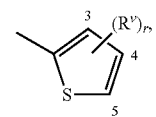

U-2

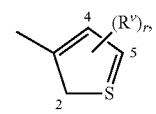

U-3

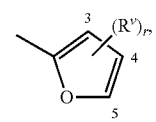

U-4

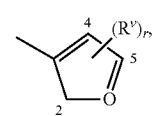

U-5

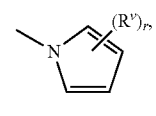

U-6

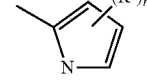

U-7

-continued
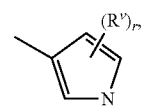 U-8
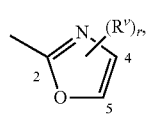 U-9
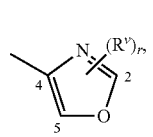 U-10
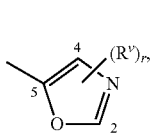 U-11
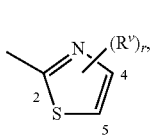 U-12
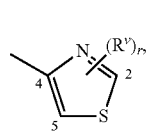 U-13
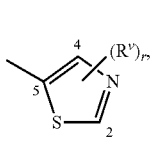 U-14
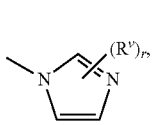 U-15
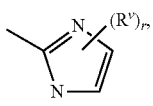 U-16
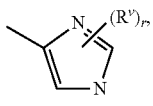 U-17
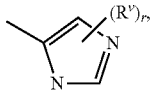 U-18
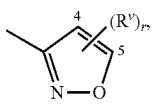 U-19
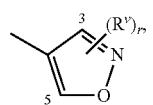 U-20
-continued
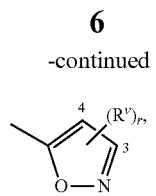 U-21
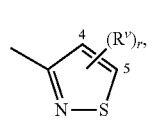 U-22
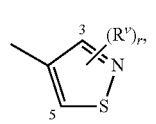 U-23
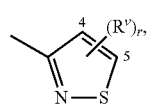 U-22
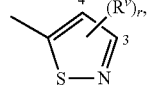 U-24
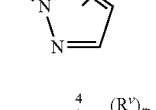 U-25
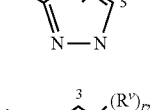 U-26
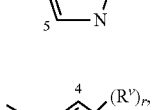 U-27
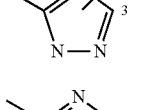 U-28
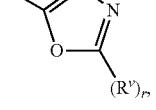 U-29
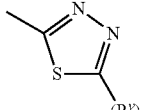 U-30
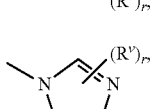 U-31
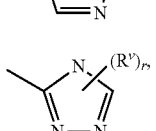 U-32

| | | |
|---|---|---|
| 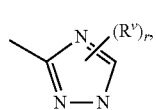 | U-33 | |
| 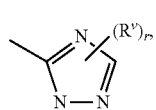 | U-34 | |
| 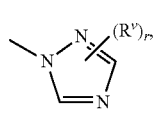 | U-35 | |
| 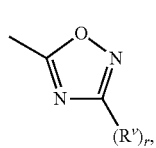 | U-36 | |
| 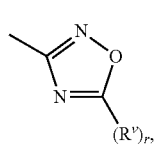 | U-37 | |
| 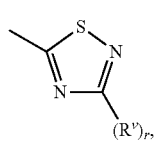 | U-38 | |
| 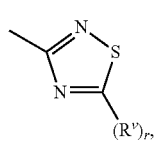 | U-39 | |
| 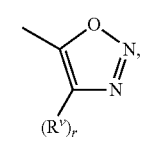 | U-40 | |
| 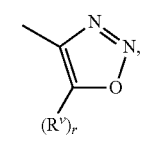 | U-41 | |
| 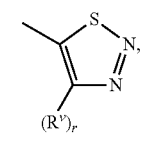 | U-42 | |
| 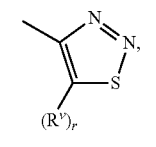 | U-43 | |
| 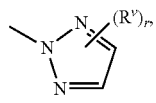 | U-44 | |
| | | |
|---|---|---|
| 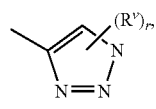 | U-45 | |
| 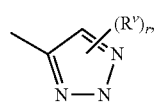 | U-46 | |
| 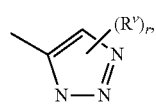 | U-47 | |
| 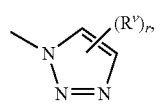 | U-48 | |
| 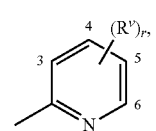 | U-49 | |
| 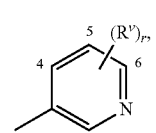 | U-50 | |
| 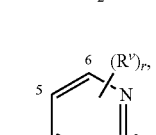 | U-51 | |
| 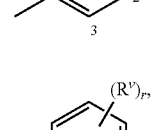 | U-52 | |
| 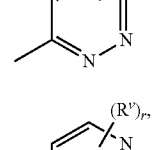 | U-53 | |
| 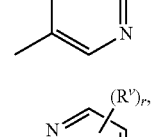 | U-54 | |
| 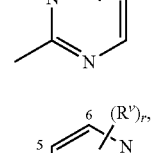 | U-55 | |
| 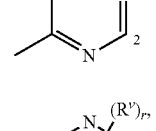 | U-56 | |

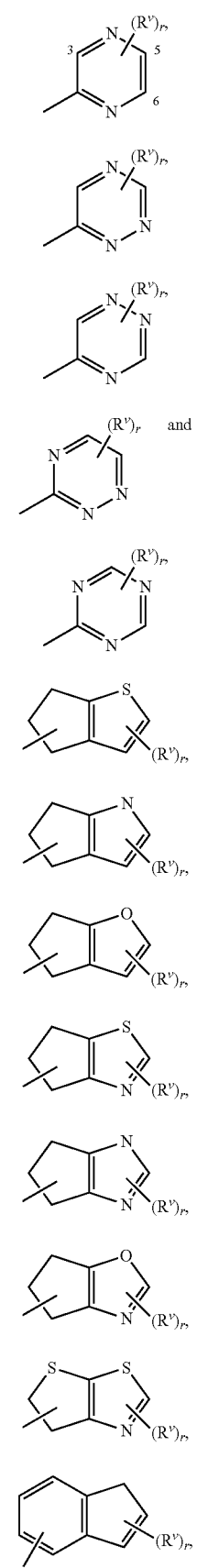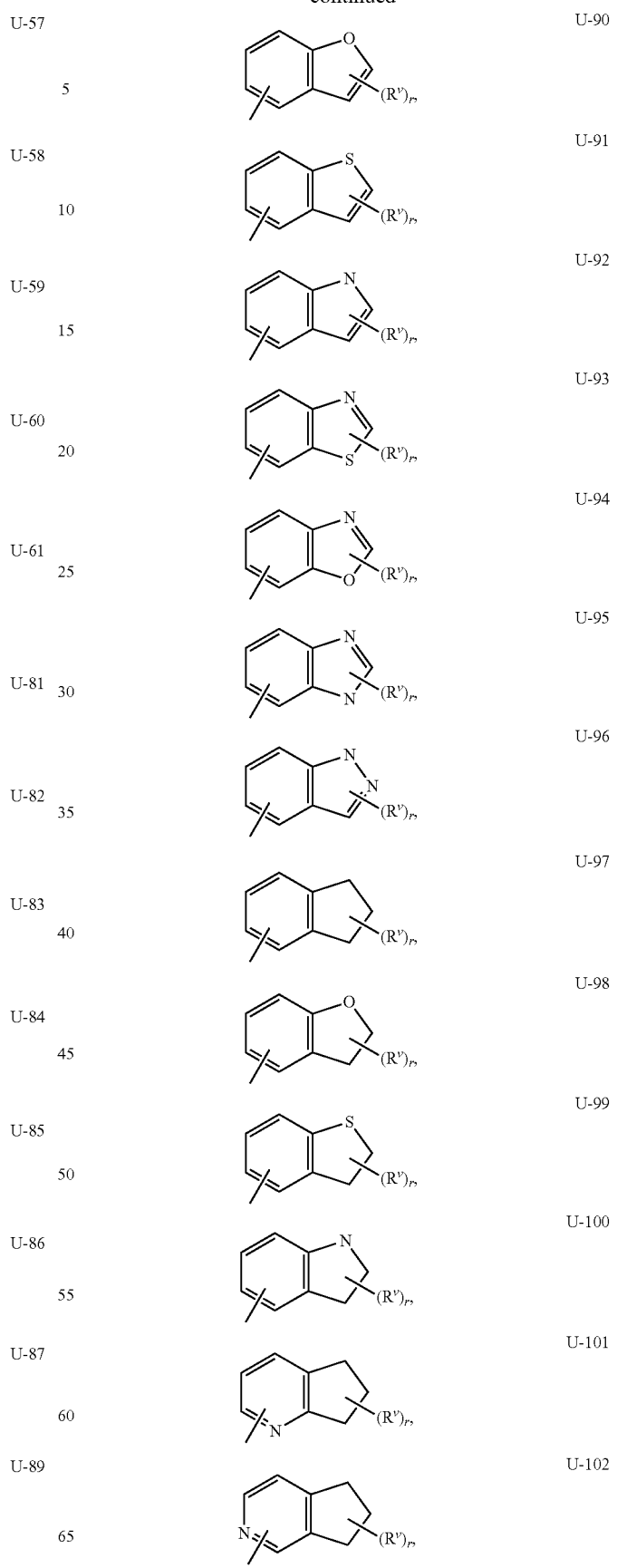

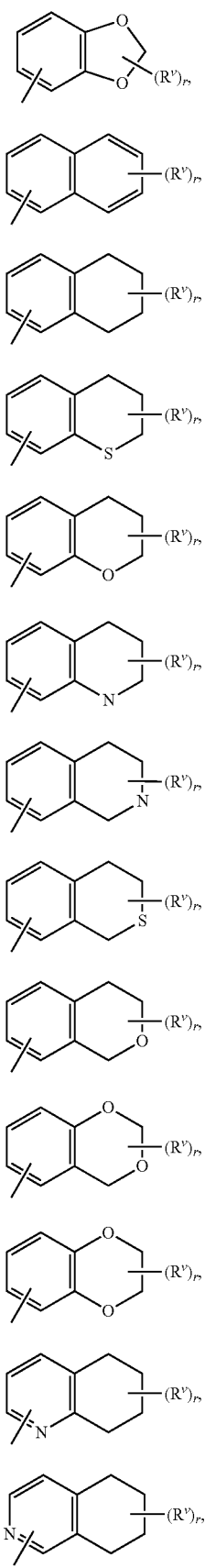

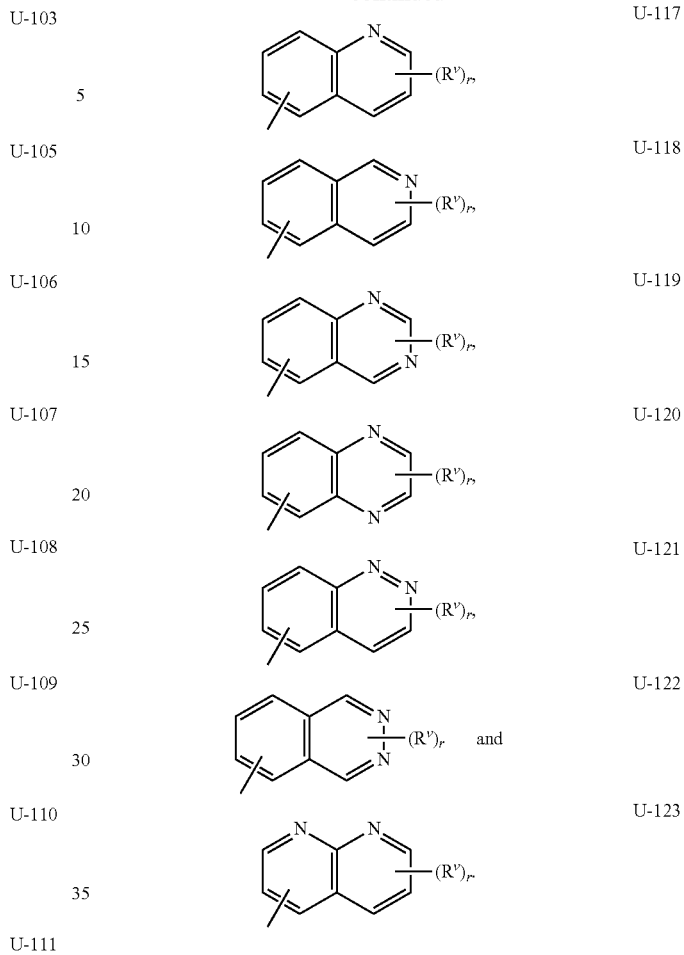

wherein $R^v$ is any substituent as defined in the Summary of the Invention for $R^1$, $R^2$ or $R^3$ and r is 0, 1, 2, 3, 4 or 5, limited by the number of available positions on each U group.

each $R^4$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl, or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or $C_3$-$C_7$-cycloalkyl, $C_4$-$C_8$-cyclolkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{4a}$ is independently H, $C_1$-$C_6$-alkyl or $C_1$-$C_6$-haloalkyl;

each $R^5$ is independently H, $NR^{5a}R^{6a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{5a}$ is independently H or $C_1$-$C_6$-alkyl;

each $R^6$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

each $R^{6a}$ is independently H, $C_1$-$C_6$-alkyl, $C(O)R^{13}$ or $C(O)OR^{13}$;

each $R^7$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{7a}$ is independently $C_1$-$C_6$-alkyl or $C_1$-$C_6$-haloalkyl;

each $R^8$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{8a}$ is independently $C_1$-$C_6$-alkyl or $C_1$-$C_6$-haloalkyl;

each $R^9$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{9a}$ is independently $C_1$-$C_6$-alkyl or $C_1$-$C_6$-haloalkyl;

each $R^{10}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^{7a}$, $C(O)OR^{8a}$, $C(O)NR^{11}R^{12}$, $S(O)_mR^{9a}$ or $S(O)_2NR^{11}R^{12}$;

each $R^{11}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of, cyano, nitro, $OR^{4a}$, $NR^{5a}R^{6a}$, $C(X)R^{7a}$, $C(O)OR^{8a}$, $C(O)NR^{11a}R^{12}$, $S(O)_mR^{9a}$ and $S(O)_2NR^{11a}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11a}R^{12}$, $OR^{4a}$, $C_2$-$C_6$-alkoxyalkyl, $S(O)_mR^{9a}$, $S(O)_2NR^{11a}R^{12}$, $NR^{5a}R^{6a}$, $OC(O)R^{7a}$ and $N(R^{10})C(O)R^{7a}$;

each $R^{11a}$ is independently H, $C_1$-$C_6$-alkyl, $C_2$-$C_6$-alkenyl or $C_2$-$C_6$-alkynyl;

each $R^{12}$ is independently H, $NR^{5a}R^{6a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$- alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

- each $R^{13}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;
- or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;
- each $R^{14}$ is independently $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;
- or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;
- or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;
- or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;
- each $R^{15}$ is independently $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;
- or phenyl optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

X is O or S;

each m is independently 0, 1 or 2;

and n is 0, 1 or 2.

Compounds of the present invention can exist in one or more optical or chiral isomer forms depending on the number of asymmetric centres in the compound. The invention thus relates equally to all the optical isomers and to their racemic or scalemic mixtures (the term "scalemic" denotes a mixture of enantiomers in different proportions) and to the mixtures of all the possible stereoisomers, in all proportions. The diastereoisomers and/or the optical isomers can be separated according to the methods which are known per se by the man ordinary skilled in the art.

Compounds of the present invention can also exist in one or more geometric isomer forms depending on the number of double bonds in the compound, especially all syn/anti (or cis/trans) isomers and to all possible syn/anti (or cis/trans) mixtures. The invention thus relates equally to all geometric isomers and to all possible mixtures, in all proportions. The geometric isomers can be separated according to general methods, which are known per se by the man ordinary skilled in the art.

Compounds of formula (I) may be found in its tautomeric form resulting from the shift of the proton of a hydroxy, sulfanyl or amino group. Such tautomeric forms of such compounds are also part of the present invention. More generally speaking, all tautomeric forms of compounds of formula (I), as well as the tautomeric forms of the compounds which can optionally be used as intermediates in the preparation processes and which will be defined in the description of these processes, are also part of the present invention.

Further, this invention is also directed to N-oxides of the compounds of formula (I) (including all stereoisomers), and salts of the compounds of formula (I) (including all stereoisomers).

Further, this invention is directed to compositions comprising compounds of the invention and their use for controlling a parasitic nematode as described above. This invention also provides a composition comprising a compound of formula (I), an N-oxide, or a salt thereof, and at least one additional component selected from the group consisting of surfactants, solid diluents and liquid diluents. In one embodiment, this invention also provides a composition for controlling a parasitic nematode comprising a compound of formula (I), an N-oxide, or a salt thereof, and at least one additional component selected from the group consisting of surfactants, solid diluents and liquid diluents, said composition optionally further comprising at least one additional active ingredient, preferably a mixing partner as described below.

This invention provides a method for controlling a parasitic nematode comprising contacting the parasitic nematode or its environment with a biologically effective amount of a compound of formula (I), an N-oxide, or a salt thereof, (e.g., as a composition described herein). This invention also relates to such method wherein the parasitic nematode or its environment is contacted with a composition comprising a biologically effective amount of a compound of Formula (I), an N-oxide or a salt thereof, and at least one additional component selected from the group consisting of surfactants, solid diluents and liquid diluents, said composition optionally further comprising a biologically effective amount of at least one additional at least one additional active ingredient, preferably a mixing partner as described below.

This invention also provides a method for protecting a seed from a parasitic nematode comprising contacting the seed with a biologically effective amount of a compound of formula (I), an N-oxide, or a salt thereof, (e.g., as a composition described herein). This invention also relates to a seed which was obtained by such a method.

DETAILED DESCRIPTION OF A PREFERRED EMBODIMENT

As used herein, the terms "comprises", "comprising", "includes", "including", "has", "having", "contains", "containing", "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" excludes any element, step or ingredient not specified. If in the claim, such would close the claim to the inclusion of materials other than those recited except for impurities ordinarily associated therewith. When the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition or method that includes materials, steps, features, components or elements, in addition to those literally disclosed, provided that these additional materials, steps, features, components or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising", it should be readily understood that (unless otherwise stated) the description should be interpreted to also describe such an invention using the terms "consisting essentially of" or "consisting of".

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As used to in the present disclosure and claims, the term "nematode" refers to a living organism of the phylum Nematoda. As generally defined, a "parasite" lives or grows inside or feeds on another living organism (such as a plant, animal or human) described as the "host". As referred to in the present disclosure and claims a "parasitic nematode" is particularly a nematode that injures or damages tissue or causes other forms of disease in plants, animals (particularly vertebrates) or humans.

A parasite "infestation" refers to the presence of parasites in numbers that pose a risk to plants, humans or animals. The presence can be in the environment, e.g., in a human or animal house, or surrounding property or structures, on an agricultural crop or other type of plant, in animal bedding, on the skin or fur of an animal, etc. When the infestation that is referred to is within an animal, e.g., in the blood or other internal tissues, the term infestation is also intended to be synonymous with the term, "infection," as that term is generally understood in the art, unless otherwise stated.

As referred to in the present disclosure and claims, the terms "parasiticidal" and "parasiticidally" refers to observable effects on a parasitic nematode to provide protection of a plant, animal or human from the nematode. Parasiticidal effects typically relate to diminishing the occurrence or activity of the target parasitic nematode. Such effects on the nematode include necrosis, death, retarded growth, diminished mobility or lessened ability to remain on or in the host plant, animal or human, reduced feeding and inhibition of reproduction. These effects on parasitic nematodes provide control (including prevention, reduction or elimination) of parasitic infestation or infection of the plant, animal or human. Therefore "control" of a parasitic nematode means achieving a parasiticidal effect on the nematode. The expressions "parasiticidally effective amount" and "biologically effective amount" in the context of applying a chemical compound to control a parasitic nematode refer an amount of the compound that is sufficient to control the parasitic nematode.

The term "agronomic" refers to the production of field crops such as for food and fiber and includes the growth of soybeans and other legumes, cereal (e.g., wheat, oats, barley, rye, rice, maize/corn), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), residential, agricultural, commercial and industrial structures, turf (e.g., sod farm, pasture, golf course, lawn, sports field, etc.), wood products, stored product, agro-forestry and vegetation management, public health (i.e. human) and animal health (e.g., domesticated animals such as pets, livestock and poultry, undomesticated animals such as wildlife) applications.

Nonagronomic applications include protecting an animal from a parasitic nematode by administering a parasiticidally effective (i.e. biologically effective) amount of a compound of the invention, typically in the form of a composition formulated for veterinary use, to the animal to be protected.

In the above recitations, the term "alkyl", used either alone or in compound words such as "haloalkyl" includes straight-chain or branched alkyl, such as, methyl, ethyl, n-propyl, i-propyl, or the different butyl, pentyl or hexyl isomers. "Alkenyl" includes straight-chain or branched alkenes such as ethenyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl.

"Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$.

"Cycloalkyl" includes, for example, cyclopropyl, cyclobutyl, cyclopentyl and cyclohexyl. The term "cycloalkylalkyl" denotes cycloalkyl substitution on an alkyl moiety. Examples of "cycloalkylalkyl" include cyclopropylmethyl, cyclopentylethyl, and other cycloalkyl moieties bonded to straight-chain or branched alkyl groups. "Cycloalkenyl" includes groups such as cyclopentenyl and cyclohexenyl as well as groups with more than 10 one double bond such as 1,3- and 1,4-cyclohexadienyl. The term "cycloalkylcycloalkyl" denotes cycloalkyl substitution on another cycloalkyl ring, wherein each cycloalkyl ring independently has from 3 to 7 carbon atom ring members. Examples of cycloalkylcycloalkyl include cyclopropylcyclopropyl (such as 1,1'-bicyclopropyl-1-yl, 1,1'-bicyclopropyl-2-yl), cyclohexylcyclopentyl (such as 4-cyclopentylcyclohexyl) and cyclohexylcyclohexyl (such as 1,1'-bicyclohexyl-1-yl), and the different cis- and trans-cycloalkylcycloalkyl isomers, (such as (1R,2S)-1,1'-bicyclopropyl-2-yl and (1R,2R)-1,1'-bicyclopropyl-2-yl).

The term "halogen", either alone or in compound words such as "haloalkyl", or when used in descriptions such as "alkyl substituted with halogen" includes fluorine, chlorine, bromine or iodine. Further, when used in compound words such as "haloalkyl", or when 20 used in descriptions such as "alkyl substituted with halogen" said alkyl may be partially or fully substituted with halogen atoms which may be the same or different. Examples of "haloalkyl" or "alkyl substituted with halogen" include $F_3C$, $ClCH_2$, $CF_3CH_2$ and $CF_3CCl_2$. The terms "haloalkoxy", "haloalkenyl", "haloalkynyl", and the like, are defined analogously to the term "haloalkyl". Examples of "haloalkoxy" include $CF_3O$, $CCl_3CH_2O$, $HCF_2CH_2CH_2O$ and $CF_3CH_2O$. Examples of "haloalkenyl" include $(Cl)_2C=CHCH_2$ and $CF_3CH_2CH=CHCH_2$. Examples of "haloalkynyl" include $HC\equiv CCHCl$, $CF_3C\equiv C$, $CCl_3C\equiv C$ and $FCH_2C\equiv CCH_2$.

The chemical abbreviation C(O) as used herein represents a carbonyl moiety. For example, $C(O)CH_3$ represents an acetyl group. The chemical abbreviations $CO_2$ and C(O)O as used herein represent an ester moiety. For example, $CO_2Me$ and C(O)OMe represent a methyl ester.

"OCN" means $-O-C\equiv N$, and "SCN" means $-S-C\equiv N$.

The total number of carbon atoms in a substituent group is indicated by the "Cj-Cj" prefix where i and j are numbers from 1 to 14. $C_2$-alkoxyalkyl designates $CH_3OCH_2$; $C_3$-alkoxyalkyl designates, for example, $CH_3CH(OCH_3)$, $CH_3OCH_2CH_2$ or $CH_3CH_2OCH_2$; and $C_4$-alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$.

When a compound is substituted with a substituent bearing a subscript that indicates the number of said substituents can exceed 1, said substituents (when they exceed 1) are independently selected from the group of defined substituents, e.g., $R^1$, n is 0, 1, or 2. However, it is to be understood that said subscript which indicates the number of said substituents, e.g. n or r, is limited by the maximum number of available positions to which the residue in question, e.g. $R^1$ or $R^v$, can be bonded to. When a group contains a substituent which can be hydrogen, for example $R^2$, $R^3$ or $R^v$, then when this substituent is taken as hydrogen, it is recognized that this is equivalent to said group being unsubstituted. Therefore, hydrogen substituents are not covered by said subscript(s) which indicate(s) the number of substituents unless otherwise indicated. Such subscripts therefore refer to substituents other than hydrogen unless otherwise indicated. Further, when a variable group is shown to be optionally attached to a position, for example $(R^v)_r$ in U-29 wherein r may be 0, then hydrogen may be at the position even if not recited in the variable group definition. When one or more positions on a group are said to be "not substituted" or "unsubstituted", then hydrogen atoms are attached to take up any free valency.

Unless otherwise indicated, a "ring" or "ring system" as a component of formula (I) (e.g., substituent Q) is carbocyclic or heterocyclic. The term "ring system" denotes two or more fused rings. The term "heterocyclic ring" denotes a ring in which at least one atom forming the ring backbone is not carbon, e.g., nitrogen, oxygen or sulfur. Typically a heterocyclic ring contains no more than 4 nitrogens, no more than 2 oxygens and no more than 2 sulfurs. Unless otherwise indicated, a heterocyclic ring can be a saturated, partially unsaturated, or fully unsaturated ring. The term "heterocyclic ring system" denotes a ring system in which at least one ring of the ring system is a heterocyclic ring. Unless otherwise indicated, heterocyclic rings and ring systems can be attached through any available carbon or nitrogen by replacement of a hydrogen on said carbon or nitrogen.

"Aromatic" indicates that each of the ring atoms is essentially in the same plane and has a π-orbital perpendicular to the ring plane, and in which (4n+2) π electrons, where π is a positive integer, are associated with the ring to comply with Hückel's rule. When a fully unsaturated heterocyclic ring satisfies Hückel's rule, then said ring is also called a "heteroaromatic ring". The term "heteroaromatic ring system" denotes a heterocyclic ring system in which at least one ring of the ring system is aromatic.

As used herein, the following definitions shall apply unless otherwise indicated. The term "optionally substituted" is used interchangeably with the phrase "substituted or unsubstituted" or with the term "(un)substituted". The expression "optionally substituted with 1 to 4 substituents" means that no substituent is present (i.e. unsubstituted) or that 1, 2, 3 or 4 substituents are present (limited by the number of available bonding positions). Unless otherwise indicated, an optionally substituted group may have a substituent at each substitutable position of the group, and each substitution is independent of the other.

When a substituent is a 5- or 6-membered nitrogen-containing heteroaromatic ring, it may be attached to the remainder of formula (I) though any available carbon or nitrogen ring atom, unless otherwise described.

An example of phenyl optionally substituted with one to five substituents is the ring illustrated as U-1. Examples of further optionally substituted 5- or 6-membered heteroaromatic ring include the rings U-2 through U-61 wherein $R^v$ is any substituent as defined in the Summary of the Invention for $R^1$, $R^2$, $R^3$ and r is an integer from 0 to 4, limited by the number of available positions on each U group. As U-29, U-30, U-36, U-37, U-38, U-39, U-40, U-41, U-42 and U-43 have only one available position, for these U groups r is limited to the integers 0 or 1, and r being 0 means that the U group is unsubstituted and a hydrogen is present at the position indicated by $(R^v)_r$.

Further and as noted above, Q can also be (among others) an 8- to 10-membered heteroaromatic bicyclic ring system optionally substituted with substituents selected from a group of substituents as defined in the Summary of Invention. Examples of optionally substituted 8-, 9- or 10-membered heteroaromatic bicyclic ring systems include the rings U-81 through U-123 wherein $R^v$ is any substituent as defined in the Summary of the Invention for Q, and r is typically an integer from 0 to 4.

Although $R^v$ groups are shown in the structures U-1 through U-123, it is noted that they do not need to be present since they are optional substituents. The nitrogen atoms that require substitution to fill their valence are substituted with H or $R^v$. Note that when the attachment point between $(R^v)_r$ and the U group is illustrated as floating, $(R^v)_r$ can be attached to any available carbon atom or nitrogen atom of the U group. Note that when the attachment point on the U group is illustrated as floating, the U group can be attached to the remainder of formula (I) through any available carbon or nitrogen of the U group by replacement of a hydrogen atom. Note that some U groups can only be substituted with less than 4 $R^v$ groups (e.g., U-2 through U-5, U-7 through U-48, and U-52 through U-61).

The compounds of the invention are defined in general terms by the formula (I). In the compounds of the invention, each $R^1$ preferably is independently H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, each $R^1$ is independently halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $S(O)_mR^9$ and $S(O)_2NR^{11}R^{12}$.

Especially preferably, each $R^1$ is independently hydrogen, chlorine, bromine, $C_1$-$C_4$-alkyl (particularly methyl, isopropyl or t-butyl), trifluoromethyl, pentafluoroethyl or $SCH_3$.

$R^2$ preferably is

H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is

H, halogen, cyano, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_4$-alkyl substituted with 1 to 2 substituents independently selected from the group consisting of cyano, $OR^4$ and $S(O)_mR^9$.

Especially preferably, $R^2$ is hydrogen, methyl, chlorine, bromine or iodine.

$R^3$ preferably is

H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is

H, $C_1$-$C_4$-alkyl, $C_2$-$C_3$-alkenyl, $C(X)R^7$ or $C(O)OR^8$;

or $C_1$-$C_2$-alkyl substituted with $OR^4$;

or $C_1$-$C_2$-alkyl substituted with phenyl.

Especially preferably, $R^3$ is hydrogen.

Q preferably is phenyl or a 5- or 6-membered heteroaromatic ring system, each optionally substituted with 1 to 5 substituents independently selected from the group consisting of halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

More preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OS(O)_2R^9$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

Even more preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$, $OS(O)_2R^9$ and $R^{14}$;

Especially preferably, Q is selected from the group consisting of (U-1) to (U-61), (U-81) to (U-87), (U-89) to (U-103) and (U-105) to (U-123).

Each $R^4$ preferably is independently

H, $C_1$-$C_4$-alkyl or $C_1$-$C_4$-haloalkyl;

or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_mR^{9a}$.

More preferably, each $R^5$ is independently
H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$.
Especially preferably, each $R^5$ is independently
H, methyl or ethyl.
Each $R^{5a}$ preferably is independently
H or $C_1$-$C_4$-alkyl.
More preferably, each $R^{5a}$ is independently
H or $C_1$-$C_2$-alkyl.
Especially preferably, each $R^{5a}$ is independently
methyl or ethyl.
Each $R^6$ preferably is independently
H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.
More preferably, each $R^6$ is independently
H, $C_1$-$C_4$-alkyl, $C_1$-$C_4$-haloalkyl, $C_2$-$C_4$-alkenyl or $C_2$-$C_4$-haloalkenyl;
or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.
Especially preferably, each $R^6$ is independently
H, methyl or ethyl.
Each $R^{6a}$ preferably is independently
H, $C_1$-$C_4$-alkyl, $C(O)R^{13}$ or $C(O)OR^{13}$.
More preferably, each $R^{6a}$ is independently
H or $C_1$-$C_4$-alkyl.
Especially preferably, each $R^{6a}$ is independently
H, methyl or ethyl.
Each $R^7$ preferably is independently
H, $C_1$-$C_6$-alkyl, $C_1$-$C_6$-haloalkyl, $C_2$-$C_6$-alkenyl or $C_2$-$C_6$-haloalkenyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.
More preferably, each $R^7$ is independently
H, $C_1$-$C_4$-alkyl or $C_1$-$C_4$-haloalkyl;
or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.
Especially preferably, each $R^7$ is independently
H, methyl, ethyl or trifluoromethyl.
Each $R^{7a}$ preferably is independently
$C_1$-$C_4$-alkyl or $C_1$-$C_4$-haloalkyl.
More preferably, each $R^{7a}$ is independently
$C_1$-$C_4$-alkyl or $C_1$-$C_2$-haloalkyl.
Especially preferably, each $R^{7a}$ is independently
methyl or ethyl.
Each $R^8$ preferably is independently
H, $C_1$-$C_4$-alkyl or $C_1$-$C_4$-haloalkyl.
More preferably, each $R^8$ is independently
$C_1$-$C_2$-alkyl or $C_1$-$C_2$-haloalkyl.
Especially preferably, each $R^8$ is independently
methyl or ethyl.
Each $R^{8a}$ preferably is independently
$C_1$-$C_4$-alkyl or $C_1$-$C_4$-haloalkyl.
More preferably, each $R^{8a}$ is independently
$C_1$-$C_4$-alkyl.

Especially preferably, each $R^{8a}$ is independently
methyl or ethyl.
Each $R^9$ preferably is independently
$C_1$-$C_4$-alkyl or $C_1$-$C_4$-haloalkyl.
More preferably, each $R^9$ is independently
$C_1$-$C_3$-alkyl, $C_1$-$C_2$-haloalkyl.
Especially preferably, each $R^9$ is independently
methyl, ethyl or isopropyl.
Each $R^{9a}$ preferably is independently
$C_1$-$C_4$-alkyl or $C_1$-$C_4$-haloalkyl.
More preferably, each $R^{9a}$ is independently
$C_1$-$C_4$-alkyl or $C_1$-$C_2$-haloalkyl.
Especially preferably, each $R^{9a}$ is independently
methyl, ethyl or trifluoromethyl.
Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.
More preferably, each $R^{10}$ is independently
H, $C_1$-$C_4$-alkyl, $C_2$-$C_3$-alkenyl or $C_3$-$C_7$-cycloalkyl.
Especially preferably, each $R^{10}$ is independently
H or methyl.
Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.
More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.
Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently
methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_m R^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_m R^9$ or $S(O)_2 NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;

or C$_1$-C$_6$-alkyl substituted with a substituent selected from the group consisting of a 5- or 6-membered heteroaromatic ring, each optionally substituted with 1 to 5 substituents independently selected from the group consisting of halogen, cyano, nitro, OR$^4$, NR$^5$R$^6$, C$_1$-C$_4$-alkyl, C$_2$-C$_4$-alkenyl, C$_2$-C$_4$-alkynyl, C$_1$-C$_4$-haloalkyl, C$_2$-C$_4$-haloalkenyl, C$_2$-C$_6$-alkoxyalkyl, C(X)R$^7$, C(O)OR$^8$, C(O)NR$^{11}$R$^{12}$, S(O)$_m$R$^9$, S(O)$_2$NR$^{11}$R$^{12}$, OC(O)R$^{7a}$ or N(R$^{10}$)C(O)R$^{7a}$;

More preferably, each R$^{14}$ is independently

C$_3$-C$_6$-cycloalkyl, each optionally substituted with 1 to 4 substituents independently selected from the group consisting of halogen or C$_1$-C$_4$-alkyl;

or phenyl optionally substituted with 1 to 2 substituents independently selected from the group consisting of halogen, cyano, nitro, OR$^4$, NR$^5$R$^6$, C$_1$-C$_4$-alkyl, C$_2$-C$_4$-alkenyl, C$_2$-C$_4$-alkynyl, C$_1$-C$_4$-haloalkyl, C$_2$-C$_4$-haloalkenyl, C$_2$-C$_6$-alkoxyalkyl, C(X)R$^7$, C(O)OR$^8$, C(O)NR$^{11}$R$^{12}$, S(O)$_m$R$^9$, S(O)$_2$NR$^{11}$R$^{12}$, OC(O)R$^{7a}$ or N(R$^{10}$)C(O)R$^{7a}$;

or C$_1$-C$_6$-alkyl, each substituted with 1 to 2 substituents independently selected from the group consisting of OR$^4$;

or C$_1$-C$_6$-alkyl substituted with a substituent selected from the group consisting of a 5- or 6-membered heteroaromatic ring, each optionally substituted with 1 to 5 substituents independently selected from the group consisting of halogen, cyano, nitro, OR$^4$, NR$^5$R$^6$, C$_1$-C$_4$-alkyl, C$_1$-C$_4$-haloalkyl, C(X)R$^7$, C(O)OR$^8$, C(O)NR$^{11}$R$^{12}$, S(O)$_m$R$^9$ or S(O)$_2$NR$^{11}$R$^{12}$;

Especially preferably, each R$^{14}$ is independently phenyl;

or C$_1$-C$_6$-alkyl substituted with a substituent selected from the group consisting of a 5- or 6-membered heteroaromatic ring, each optionally substituted with 1 to 5 substituents independently selected from the group consisting of halogen, cyano, nitro, OR$^4$, NR$^5$R$^6$, C$_1$-C$_4$-alkyl, C$_1$-C$_4$-haloalkyl, C(X)R$^7$, C(O)OR$^8$, C(O)NR$^{11}$R$^{12}$, S(O)$_m$R$^9$ or S(O)$_2$NR$^{11}$R$^{12}$;

Each R$^{15}$ preferably is independently

C$_1$-C$_4$-alkyl or C$_1$-C$_4$-haloalkyl;

or phenyl optionally substituted with 1 to 5 substituents independently selected from the group consisting of halogen, cyano, OR$^4$, NR$^5$R$^6$, C$_1$-C$_4$-alkyl, C(X)R$^7$, C(O)OR$^8$, C(O)NR$^{11}$R$^{12}$, S(O)$_m$R$^9$ and S(O)$_2$NR$^{11}$R$^{12}$.

More preferably, each R$^{15}$ is independently

C$_1$-C$_4$-alkyl or C$_1$-C$_4$-haloalkyl.

Especially preferably, each R$^{15}$ is independently methyl.

X preferably is O or S. More preferably X is O. Especially preferably X is O.

Z preferably is O or S. More preferably Z is O. Especially preferably Z is O.

Preferably, each m is independently 0, 1 or 2. More preferably, each m is independently 0 or 2.

Especially preferably, each m is independently 0 or 2.

Preferably, n is independently 0, 1 or 2. More preferably, n is 1 or 2. Especially preferably, n is 1 or 2.

In an individual embodiment, Q is U-1. In another individual embodiment, Q is U-2. In another individual embodiment, Q is U-3. In another individual embodiment, Q is U-4. In another individual embodiment, Q is U-5. In another individual embodiment, Q is U-6. In another individual embodiment, Q is U-7. In another individual embodiment, Q is U-8. In another individual embodiment, Q is U-9. In another individual embodiment, Q is U-10. In another individual embodiment, Q is U-11. In another individual embodiment, Q is U-12. In another individual embodiment, Q is U-13. In another individual embodiment, Q is U-14. In another individual embodiment, Q is U-15. In another individual embodiment, Q is U-16. In another individual embodiment, Q is U-17. In another individual embodiment, Q is U-18. In another individual embodiment, Q is U-19. In another individual embodiment, Q is U-20. In another individual embodiment, Q is U-21. In another individual embodiment, Q is U-22. In another individual embodiment, Q is U-23. In another individual embodiment, Q is U-24. In another individual embodiment, Q is U-25. In another individual embodiment, Q is U-26. In another individual embodiment, Q is U-27. In another individual embodiment, Q is U-28. In another individual embodiment, Q is U-29. In another individual embodiment, Q is U-30. In another individual embodiment, Q is U-31. In another individual embodiment, Q is U-32. In another individual embodiment, Q is U-33. In another individual embodiment, Q is U-34. In another individual embodiment, Q is U-35. In another individual embodiment, Q is U-36. In another individual embodiment, Q is U-37. In another individual embodiment, Q is U-38. In another individual embodiment, Q is U-39. In another individual embodiment, Q is U-40. In another individual embodiment, Q is U-41. In another individual embodiment, Q is U-42. In another individual embodiment, Q is U-43. In another individual embodiment, Q is U-44. In another individual embodiment, Q is U-45. In another individual embodiment, Q is U-46. In another individual embodiment, Q is U-47. In another individual embodiment, Q is U-48. In another individual embodiment, Q is U-49. In another individual embodiment, Q is U-50. In another individual embodiment, Q is U-51. In another individual embodiment, Q is U-52. In another individual embodiment, Q is U-53. In another individual embodiment, Q is U-54. In another individual embodiment, Q is U-55. In another individual embodiment, Q is U-56. In another individual embodiment, Q is U-57. In another individual embodiment, Q is U-58. In another individual embodiment, Q is U-59. In another individual embodiment, Q is U-60. In another individual embodiment, Q is U-61. In another individual embodiment, Q is U-81. In another individual embodiment, Q is U-82. In another individual embodiment, Q is U-83. In another individual embodiment, Q is U-84. In another individual embodiment, Q is U-85. In another individual embodiment, Q is U-86. In another individual embodiment, Q is U-87. In another individual embodiment, Q is U-89. In another individual embodiment, Q is U-90. In another individual embodiment, Q is U-91. In another individual embodiment, Q is U-92. In another individual embodiment, Q is U-93. In another individual embodiment, Q is U-94. In another individual embodiment, Q is U-95. In another individual embodiment, Q is U-96. In another individual embodiment, Q is U-97. In another individual embodiment, Q is U-98. In another individual embodiment, Q is U-99. In another individual embodiment, Q is U-100. In another individual embodiment, Q is U-101. In another individual embodiment, Q is U-102. In another individual embodiment, Q is U-103. In another individual embodiment, Q is U-105. In another individual embodiment, Q is U-106. In another individual embodiment, Q is U-107. In another individual embodiment, Q is U-108. In another individual embodiment, Q is U-109. In another individual embodiment, Q is U-110. In another individual embodiment, Q is U-111. In another individual embodiment, Q is U-112. In another individual embodiment, Q is U-113. In another individual embodiment, Q is U-114. In another individual embodiment, Q is U-115. In another individual embodiment, Q is U-116. In another individual embodiment, Q is U-117. In another individual embodiment, Q is U-118. In another individual embodiment, Q is U-119. In another individual embodiment, Q is U-120. In another individual embodiment, Q is U-121. In another individual embodiment, Q is U-122. In another individual embodiment, Q is U-123.

In all cases with Q is defined to be one of (U-1) to (U-61), (U-81) to (U-87), (U-89) to (U-103) or (U-105) to (U-123), each $R^v$ preferably is independently hydrogen, halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$, or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;

or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^v$ is independently hydrogen, halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OS(O)_2R^9$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

or $C_3$-$C_6$-cycloalkyl, each optionally substituted with 1 to 4 substituents independently selected from the group consisting of halogen or $C_1$-$C_4$-alkyl;

or phenyl optionally substituted with 1 to 2 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Even more preferably, each $R^v$ is independently hydrogen, halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$, $OS(O)_2R^9$;

or phenyl;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

Especially preferably, each $R^v$ is independently hydrogen, fluorine, chlorine, bromine, iodine, cyano, methyl, ethyl, isopropyl, t-butyl, trifluoromethyl, $OR^4$, $C(O)CH_3$, $OSO_2CH_3$, $SCH_3$, S-ethyl, S-isopropyl, $SO_2CH_3$, phenyl or $CH_2$-pyrazol-1-yl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 1, 2, 3 or 4. Especially preferably, r is 1, 2 or 3.

A wide variety of synthetic methods are known in the art to enable preparation of aromatic and nonaromatic heterocyclic rings and ring systems; for extensive reviews see the eight volume set of Comprehensive Heterocyclic Chemistry, A. R. Katritzky and C. W. Rees editors-in-chief, Pergamon Press, Oxford, 1984 and the twelve volume set of Comprehensive Heterocyclic Chemistry II, A. R. Katritzky, C. W. Rees and E. F. V. Scriven editors-in-chief, Pergamon Press, Oxford, 1996.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. The compounds of the invention may be present as a mixture of stereoisomers, individual stereoisomers or as an optically active form.

Compounds selected from formula (I), (including all stereoisomers, N-oxides, and salts thereof), typically exist in more than one form, and formula (I) thus includes all crystalline and non-crystalline forms of the compounds that formula (I) represents. Non-crystalline forms include embodiments which are solids such as waxes and gums as well as embodiments which are liquids such as solutions and melts. Crystalline forms include embodiments which represent essentially a single crystal type and embodiments which represent a mixture of polymorphs (i.e. different crystalline types). The term "polymorph" refers to a particular crystalline form of a chemical compound that can crystallize in different crystalline forms, these forms having different arrangements and/or conformations of the molecules in the crystal lattice. Although polymorphs can have the same chemical composition, they can also differ in composition due the presence or absence of co-crystallized water or other molecules, which can be weakly or strongly bound in the lattice. Polymorphs can differ in such chemical, physical and biological properties as crystal shape, density, hardness, color, chemical stability, melting point, hygroscopicity, suspensibility, dissolution rate and biological availability. One skilled in the art will appreciate that a polymorph of a compound represented by formula (I) can exhibit beneficial effects (e.g., suitability for preparation of useful formulations, improved biological performance) relative to another polymorph or a mixture of polymorphs of the same compound represented by formula (I). Preparation and isolation of a particular polymorph of a compound represented by formula (I) can be achieved by methods known to those skilled in the art including, for example, crystallization using selected solvents and temperatures.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and 3-chloroperbenzoic acid (MCPBA), hydrogen peroxide, alkyl hydroperoxides such as t-butyl hydroperoxide, sodium perborate, and dioxiranes such as dimethyldioxirane. These methods for the preparation of N-oxides have been extensively described and reviewed in the literature, see for example: T. L. Gilchrist in Comprehensive Organic Synthesis, vol. 7, pp 748-750, S. V. Ley, Ed., Pergamon Press; M. Tisler and B. Stanovnik in Comprehensive Heterocyclic Chemistry, vol. 3, pp 18-20, A. J. Boulton and A. McKillop, Eds., Pergamon Press; M. R. Grimmett and B. R. T. Keene in Advances in Heterocyclic Chemistry, vol. 43, pp 149-161, A. R. Katritzky, Ed., Academic Press; M. Tisler and B. Stanovnik in Advances in Heterocyclic Chemistry, vol. 9, pp 285-291, A. R. Katritzky and A. J. Boulton, Eds., Academic Press; and G. W. H. Cheeseman and E. S. G. Werstiuk in Advances in Heterocyclic Chemistry, vol. 22, pp 390-392, A. R. Katritzky and A. J. Boulton, Eds., Academic Press.

One skilled in the art recognizes that because in the environment and under physiological conditions salts of chemical compounds are in equilibrium with their corresponding nonsalt forms, salts share the biological utility of the nonsalt forms. Thus a wide variety of salts of the compounds of formula (I) are useful for control of parasitic nematodes. The salts of the compounds of formula (I) include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. When a compound of formula (I) contains an acidic moiety such as a carboxylic acid, phenol or sulfonylamide (i.e. when $R^3$ is H), salts also include those formed with organic or inorganic bases such as pyridine, triethylamine or ammonia, or amides, hydrides, hydroxides or carbonates of sodium, potassium, lithium, calcium, magnesium or barium. Accordingly, the present invention comprises compounds selected from formula (I), N-oxides and salts thereof.

Embodiments of the present invention as described in the Summary of the Invention include those described below. In the following Embodiments, formula (I) includes stereoisomers, N-oxides, and salts thereof, and reference to "a compound of formula (I)" includes the definitions of substituents specified in the Summary of the Invention unless further defined in the embodiments.

EMBODIMENTS

Embodiment 1

The compounds of the invention are defined in general terms by the formula (I). In a preferred embodiment, the compounds of the invention are defined by formula (Ia):

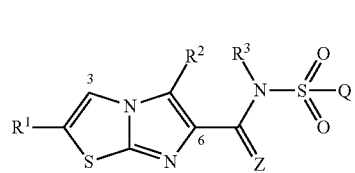

(Ia)

wherein
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, Z, Q, X and m are as defined above in the Summary of the Invention.

$R^1$ preferably is
H, halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, $R^1$ is
halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $S(O)_mR^9$ and $S(O)_2NR^{11}R^{12}$.

Especially preferably, $R^1$ is
hydrogen, chlorine, bromine, $C_1$-$C_4$-alkyl (particularly methyl, isopropyl or t-butyl), trifluoromethyl, pentafluoroethyl or $SCH_3$.

$R^2$ preferably is
H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is
H, halogen, cyano, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_4$-alkyl substituted with 1 to 2 substituents independently selected from the group consisting of cyano, $OR^4$ and $S(O)_mR^9$.

Especially preferably, $R^2$ is hydrogen, methyl, chlorine, bromine or iodine.

$R^3$ preferably is

H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is

H, $C_1$-$C_4$-alkyl, $C_2$-$C_3$-alkenyl, $C(X)R^7$ or $C(O)OR^8$;
or $C_1$-$C_2$-alkyl substituted with $OR^4$;
or $C_1$-$C_2$-alkyl substituted with phenyl.

Especially preferably, $R^3$ is hydrogen.

Q preferably is phenyl or a 5- or 6-membered heteroaromatic ring system, each optionally substituted with 1 to 5 substituents independently selected from the group consisting of halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R)C(O)NR^{11}R^{12}$, $N(R^{10})S(O)_2R^9$, $N(R^{10})S(O)_2NR^{11}R^{12}$ and $R^{14}$;

More preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11a}R^{12}$, $S(O)_mR^9$, $S(O)_2NR^{11a}R^{12}$, $OS(O)_2R^9$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

Even more preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11a}R^{12}$, $S(O)_mR^9$, $S(O)_2NR^{11}R^{12}$, $OS(O)_2R^9$ and $R^{14}$;

Especially preferably, Q is selected from the group consisting of (U-1) to (U-61), (U-81) to (U-87), (U-89) to (U-103) and (U-105) to (U-123).

Each $R^4$ preferably is independently

H, $C_1$-$C_4$-alkyl or $C_1$-$C_4$-haloalkyl;
or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_mR^{9a}$.

More preferably, each $R^5$ is independently

H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$.

Especially preferably, each $R^5$ is independently

H, methyl or ethyl.

Each $R^{5a}$ preferably is independently

H or $C_1$-$C_4$-alkyl.

More preferably, each $R^{5a}$ is independently

H or $C_1$-$C_2$-alkyl.

Especially preferably, each $R^{5a}$ is independently methyl or ethyl.

Each $R^6$ preferably is independently

H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_mR^{9a}$.

More preferably, each $R^6$ is independently

H, $C_1$-$C_4$-alkyl, $C_1$-$C_4$-haloalkyl, $C_2$-$C_4$-alkenyl or $C_2$-$C_4$-haloalkenyl;

or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently

H, methyl or ethyl.

Each $R^{6a}$ preferably is independently

H, $C_1$-$C_4$-alkyl, $C(O)R^{13}$ or $C(O)OR^{13}$.

More preferably, each $R^{6a}$ is independently

H or $C_1$-$C_4$-alkyl.

Especially preferably, each $R^{6a}$ is independently

H, methyl or ethyl.

Each $R^7$ preferably is independently

H, $C_1$-$C_6$-alkyl, $C_1$-$C_6$-haloalkyl, $C_2$-$C_6$-alkenyl or $C_2$-$C_6$-haloalkenyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_mR^{9a}$.

More preferably, each $R^7$ is independently

H, $C_1$-$C_4$-alkyl or $C_1$-$C_4$-haloalkyl;

or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.

Especially preferably, each $R^7$ is independently

H, methyl, ethyl or trifluoromethyl.

Each $R^{7a}$ preferably is independently $C_1$-$C_4$-alkyl or $C_1$-$C_4$-haloalkyl.

More preferably, each $R^{7a}$ is independently $C_1$-$C_4$-alkyl or $C_1$-$C_2$-haloalkyl.

Especially preferably, each $R^{7a}$ is independently methyl or ethyl.

Each $R^8$ preferably is independently
H, $C_1$-$C_4$-alkyl or $C_1$-$C_4$-haloalkyl.

More preferably, each $R^8$ is independently
$C_1$-$C_2$-alkyl or $C_1$-$C_2$-haloalkyl.

Especially preferably, each $R^8$ is independently methyl or ethyl.

Each $R^{8a}$ preferably is independently
$C_1$-$C_4$-alkyl or $C_1$-$C_4$-haloalkyl.

More preferably, each $R^{8a}$ is independently
$C_1$-$C_4$-alkyl.

Especially preferably, each $R^{8a}$ is independently methyl or ethyl.

Each $R^9$ preferably is independently
$C_1$-$C_4$-alkyl or $C_1$-$C_4$-haloalkyl.

More preferably, each $R^9$ is independently
$C_1$-$C_3$-alkyl, $C_1$-$C_2$-haloalkyl.

Especially preferably, each $R^9$ is independently methyl, ethyl or isopropyl.

Each $R^{9a}$ preferably is independently
$C_1$-$C_4$-alkyl or $C_1$-$C_4$-haloalkyl.

More preferably, each $R^{9a}$ is independently
$C_1$-$C_4$-alkyl or $C_1$-$C_2$-haloalkyl.

Especially preferably, each $R^{9a}$ is independently methyl, ethyl or trifluoromethyl.

Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.

More preferably, each $R^{10}$ is independently
H, $C_1$-$C_4$-alkyl, $C_2$-$C_3$-alkenyl or $C_3$-$C_7$-cycloalkyl.

Especially preferably, each $R^{10}$ is independently H or methyl.

Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.

More preferably, each $R^{11}$ is independently
H, $C_1$-$C_4$-alkyl, $C_1$-$C_4$-haloalkyl.

Especially preferably, each $R^{11}$ is independently H, methyl or ethyl.

Each $R^{11a}$ preferably is independently
H, $C_1$-$C_4$-alkyl, $C_2$-$C_3$-alkenyl or $C_2$-$C_3$-alkynyl.

More preferably, each $R^{11a}$ is independently
H, $C_1$-$C_4$-alkyl, allyl or propargyl.

Especially preferably, each $R^{11a}$ is independently H, methyl or ethyl.

Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.

More preferably, each $R^{12}$ is independently
H, $C_1$-$C_4$-alkyl or $C_1$-$C_4$-haloalkyl.

Especially preferably, each $R^{12}$ is independently H, methyl or ethyl.

Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.

More preferably, each $R^{13}$ is independently
H, $C_1$-$C_4$-alkyl or $C_1$-$C_4$-haloalkyl.

Especially preferably, each $R^{13}$ is independently methyl.

Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$;

or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;

or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^{14}$ is independently
$C_3$-$C_6$-cycloalkyl, each optionally substituted with 1 to 4 substituents independently selected from the group consisting of halogen or $C_1$-$C_4$-alkyl;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Each $R^{15}$ preferably is independently
$C_1$-$C_4$-alkyl or $C_1$-$C_4$-haloalkyl;

or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_mR^9$ and $S(O)_2NR^{11}R^{12}$.

More preferably, each $R^{15}$ is independently
$C_1$-$C_4$-alkyl or $C_1$-$C_4$-haloalkyl.

Especially preferably, each $R^{15}$ is independently methyl.

X preferably is O or S. More preferably X is O. Especially preferably X is O.

Z preferably is O or S. More preferably Z is O. Especially preferably Z is O.

Preferably, each m is independently 0, 1 or 2. More preferably, each m is independently 0 or 2.

Especially preferably, each m is independently 0 or 2.

In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently hydrogen, halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R$, $N(R^{10})C(O)NR^{11}R^{12}$, $N(R^{10})S(O)_2R^9$, $N(R^{10})S(O)_2NR^{11}R^{12}$;

$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$, or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;

or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^v$ is independently hydrogen, halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, C(X)NR$^{11}$R$^{12}$, S(O)$_m$R$^9$, S(O)$_2$NR$^{11}$R$^{12}$, OS(O)$_2$R$^9$, N(R$^{10}$)C(O)R$^7$, N(R$^{10}$)C(O)NR$^{11}$R$^{12}$, N(R$^{10}$)S(O)$_2$R$^9$, N(R$^{10}$)S(O)$_2$NR$^{11}$R$^{12}$;

or C$_3$-C$_6$-cycloalkyl, each optionally substituted with 1 to 4 substituents independently selected from the group consisting of halogen or C$_1$-C$_4$-alkyl;

or phenyl optionally substituted with 1 to 2 substituents independently selected from the group consisting of halogen, cyano, nitro, OR$^4$, NR$^5$R$^6$, C$_1$-C$_4$-alkyl, C$_2$-C$_4$-alkenyl, C$_2$-C$_4$-alkynyl, C$_1$-C$_4$-haloalkyl, C$_2$-C$_4$-haloalkenyl, C$_2$-C$_6$-alkoxyalkyl, C(X)R$^7$, C(O)OR$^8$, C(O)NR$^{11}$R$^{12}$, S(O)$_m$R$^9$, S(O)$_2$NR$^{11}$R$^{12}$, OC(O)R$^{7a}$ or N(R$^{10}$)C(O)R$^{7a}$;

or C$_1$-C$_6$-alkyl, each substituted with 1 to 2 substituents independently selected from the group consisting of OR$^4$;

or C$_1$-C$_6$-alkyl substituted with a substituent selected from the group consisting of a 5- or 6-membered heteroaromatic ring, each optionally substituted with 1 to 5 substituents independently selected from the group consisting of halogen, cyano, nitro, OR$^4$, NR$^5$R$^6$, C$_1$-C$_4$-alkyl, C$_1$-C$_4$-haloalkyl, C(X)R$^7$, C(O)OR$^8$, C(O)NR$^{11}$R$^{12}$, S(O)$_m$R$^9$ or S(O)$_2$NR$^{11}$R$^{12}$;

Even more preferably, each R$^v$ is independently hydrogen, halogen, cyano, nitro, OR$^4$, C$_1$-C$_6$-alkyl, C$_1$-C$_6$-haloalkyl, C(X)R$^7$, C(O)OR$^8$, C(X)NR$^{11}$R$^{12}$, S(O)$_m$R$^9$, S(O)$_2$NR$^{11}$R$^{12}$, OS(O)$_2$R$^9$;

or phenyl;

or C$_1$-C$_6$-alkyl substituted with a substituent selected from the group consisting of a 5- or 6-membered heteroaromatic ring, each optionally substituted with 1 to 5 substituents independently selected from the group consisting of halogen, cyano, nitro, OR$^4$, NR$^5$R$^6$, C$_1$-C$_4$-alkyl, C$_1$-C$_4$-haloalkyl, C(X)R$^7$, C(O)OR$^8$, C(O)NR$^{11}$R$^{12}$, S(O)$_m$R$^9$ or S(O)$_2$NR$^{11}$R$^{12}$.

Especially preferably, each R$^v$ is independently hydrogen, fluorine, chlorine, bromine, iodine, cyano, methyl, ethyl, isopropyl, t-butyl, trifluoromethyl, OR$^4$, C(O)CH$_3$, OSO$_2$CH$_3$, SCH$_3$, S-ethyl, S-isopropyl, SO$_2$CH$_3$, phenyl or CH$_2$-pyrazol-1-yl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 1, 2, 3 or 4. Especially preferably, r is 1, 2 or 3.

Embodiment 2

The compounds of the invention are defined in general terms by the formula (I). In another preferred embodiment, the compounds of the invention are defined by formula (Ib):

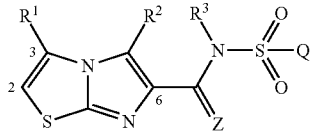

(Ib)

wherein

R$^1$, R$^2$, R$^3$, R$^4$, R$^{4a}$, R$^5$, R$^{5a}$, R$^6$, R$^{6a}$, R$^7$, R$^{7a}$, R$^8$, R$^{8a}$, R$^9$, R$^{9a}$, R$^{10}$, R$^{11}$, R$^{11a}$, R$^{12}$, R$^{13}$, R$^{14}$, R$^{15}$, Z, Q, X and m are as defined above in the Summary of the Invention.

R$^1$ preferably is

H, halogen, cyano, nitro, OR$^4$, NR$^5$R$^6$, C$_1$-C$_6$-alkyl, C$_1$-C$_6$-haloalkyl, C$_2$-C$_6$-alkenyl, C$_2$-C$_6$-haloalkenyl, C(X)R$^7$, C(O)OR$^8$, C(O)NR$^{11}$R$^{12}$, S(O)$_m$R$^9$, S(O)$_2$NR$^{11}$R$^{12}$, N(R$^{10}$)C(O)R$^7$, N(R$^{10}$)C(O)NR$^{11}$R$^{12}$, N(R$^{10}$)S(O)$_2$R$^9$ or N(R$^{10}$)S(O)$_2$NR$^{11}$R$^{12}$;

or C$_3$-C$_7$-cycloalkyl, C$_4$-C$_8$-cycloalkylalkyl, C$_6$-C$_{14}$-cycloalkylcycloalkyl or C$_5$-C$_7$-cycloalkenyl, each optionally substituted with 1 to 4 substituents independently selected from the group consisting of halogen, cyano, nitro, C$_1$-C$_4$-alkyl, C$_1$-C$_4$-haloalkyl, OR$^{4a}$ and S(O)$_m$R$^{9a}$;

or C$_1$-C$_6$-alkyl substituted with 1 to 4 substituents independently selected from the group consisting of cyano, OR$^4$, NR$^5$R$^6$, C(X)R$^7$, S(O)$_m$R$^9$ and S(O)$_2$NR$^{11}$R$^{12}$.

More preferably, R$^1$ is halogen, cyano, nitro, OR$^4$, NR$^5$R$^6$, C$_1$-C$_4$-alkyl, C$_1$-C$_4$-haloalkyl, C(X)R$^7$, C(O)OR$^8$, C(O)NR$^{11}$R$^{12}$, S(O)$_m$R$^9$ or S(O)$_2$NR$^{11}$R$^{12}$;

or C$_3$-C$_7$-cycloalkyl, optionally substituted with 1 to 4 substituents independently selected from the group consisting of halogen, cyano, C$_1$-C$_4$-alkyl and C$_1$-C$_4$-haloalkyl;

or C$_1$-C$_6$-alkyl substituted with 1 to 4 substituents independently selected from the group consisting of cyano, OR$^4$, S(O)$_m$R$^9$ and S(O)$_2$NR$^{11}$R$^{12}$.

Especially preferably, R$^1$ is hydrogen, chlorine, bromine, C$_1$-C$_4$-alkyl (particularly methyl, isopropyl or t-butyl), trifluoromethyl, pentafluoroethyl or SCH$_3$.

R$^2$ preferably is

H, halogen, cyano, nitro, OR$^4$, NR$^5$R$^6$, C$_1$-C$_6$-alkyl, C$_1$-C$_4$-haloalkyl, C$_2$-C$_4$-alkenyl, C$_2$-C$_4$-haloalkenyl, C$_3$-C$_7$-cycloalkyl, S(O)$_m$R$^9$ or S(O)$_2$NR$^{11}$R$^{12}$;

or C$_3$-C$_6$-cycloalkyl, optionally substituted with 1 to 4 substituents independently selected from the group consisting of halogen, cyano, C$_1$-C$_4$-alkyl and C$_1$-C$_4$-haloalkyl;

or C$_1$-C$_6$-alkyl substituted with 1 to 4 substituents independently selected from the group consisting of cyano, OR$^4$, NR$^5$R$^6$, S(O)$_m$R$^9$ and S(O)$_2$NR$^{11}$R$^{12}$.

More preferably, R$^2$ is

H, halogen, cyano, S(O)$_m$R$^9$ or S(O)$_2$NR$^{11}$R$^{12}$;

or C$_3$-C$_6$-cycloalkyl, optionally substituted with 1 to 4 substituents independently selected from the group consisting of halogen, cyano, C$_1$-C$_4$-alkyl and C$_1$-C$_4$-haloalkyl;

or C$_1$-C$_4$-alkyl substituted with 1 to 2 substituents independently selected from the group consisting of cyano, OR$^4$ and S(O)$_m$R$^9$.

Especially preferably, R$^2$ is hydrogen, methyl, chlorine, bromine or iodine.

R$^3$ preferably is

H, C$_1$-C$_6$-alkyl, C$_1$-C$_6$-haloalkyl, C$_2$-C$_4$-alkenyl, C$_2$-C$_4$-haloalkenyl, C$_2$-C$_4$-alkynyl, C$_2$-C$_4$-haloalkynyl, C(X)R$^7$, C(O)OR$^8$ or C(O)NR$^{11}$R$^{12}$;

or C$_3$-C$_7$-cycloalkyl or C$_4$-C$_8$-cycloalkylalkyl, each optionally substituted with 1 to 4 substituents independently selected from the group consisting of halogen, cyano, OR$^{4a}$ and S(O)$_m$R$^{9a}$;

or C$_1$-C$_4$-alkyl substituted with 1 to 4 substituents independently selected from the group consisting of cyano, OR$^4$, C(X)R$^7$ and C(O)OR$^8$;

or C$_1$-C$_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, OR$^4$, C$_1$-C$_4$-haloalkyl, C$_2$-C$_6$-alkoxyalkyl, C(X)R$^7$, C(O)OR$^8$, S(O)$_m$R$^9$ and S(O)$_2$NR$^1$R$^2$.

More preferably, $R^3$ is

H, $C_1$-$C_4$-alkyl, $C_2$-$C_3$-alkenyl, $C(X)R^7$ or $C(O)OR^8$;

or $C_1$-$C_2$-alkyl substituted with $OR^4$;

or $C_1$-$C_2$-alkyl substituted with phenyl.

Especially preferably, $R^3$ is hydrogen.

Q preferably is phenyl or a 5- or 6-membered heteroaromatic ring system, each optionally substituted with 1 to 5 substituents independently selected from the group consisting of halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_m R^9$, $S(O)_2 NR^{11}R^{12}$, $OC(O)R^7$, $OC(O)OR^8$, $OC(O)NR^{11}R^{12}$, $OS(O)_2 R^9$, $OS(O)_2 NR^{11}R^{12}$, $N(R^{10})C(O)R^7$, $N(R^{10})C(O)NR^{11}R^{12}$, $N(R^{10})S(O)_2 R^9$, $N(R^{10})S(O)_2 NR^{11}R^{12}$ and $R^{14}$;

More preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_m R^9$, $S(O)_2 NR^{11}R^{12}$, $OS(O)_2 R^9$, $N(R^{10})C(O)R^7$, $N(R^{10})C(O)NR^{11}R^{12}$, $N(R^{10})S(O)_2 R^9$, $N(R^{10})S(O)_2 NR^{11}R^{12a}$ and $R^{14}$;

Even more preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_m R^9$, $S(O)_2 NR^{11}R^{12}$, $OS(O)_2 R^9$ and $R^{14}$;

Especially preferably, Q is selected from the group consisting of (U-1) to (U-61), (U-81) to (U-87), (U-89) to (U-103) and (U-105) to (U-123).

Each $R^4$ preferably is independently

H, $C_1$-$C_4$-alkyl or $C_1$-$C_4$-haloalkyl;

or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_m R^{9a}$.

More preferably, each $R^5$ is independently

H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$.

Especially preferably, each $R^5$ is independently

H, methyl or ethyl.

Each $R^{5a}$ preferably is independently

H or $C_1$-$C_4$-alkyl.

More preferably, each $R^{5a}$ is independently

H or $C_1$-$C_2$-alkyl.

Especially preferably, each $R^{5a}$ is independently methyl or ethyl.

Each $R^6$ preferably is independently

H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.

More preferably, each $R^6$ is independently

H, $C_1$-$C_4$-alkyl, $C_1$-$C_4$-haloalkyl, $C_2$-$C_4$-alkenyl or $C_2$-$C_4$-haloalkenyl;

or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently

H, methyl or ethyl.

Each $R^{6a}$ preferably is independently

H, $C_1$-$C_4$-alkyl, $C(O)R^{13}$ or $C(O)OR^{13}$.

More preferably, each $R^{6a}$ is independently

H or $C_1$-$C_4$-alkyl.

Especially preferably, each $R^{6a}$ is independently

H, methyl or ethyl.

Each $R^7$ preferably is independently

H, $C_1$-$C_6$-alkyl, $C_1$-$C_6$-haloalkyl, $C_2$-$C_6$-alkenyl or $C_2$-$C_6$-haloalkenyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.

More preferably, each $R^7$ is independently

H, $C_1$-$C_4$-alkyl or $C_1$-$C_4$-haloalkyl;

or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.

Especially preferably, each $R^7$ is independently

H, methyl, ethyl or trifluoromethyl.

Each $R^{7a}$ preferably is independently $C_1$-$C_4$-alkyl or $C_1$-$C_4$-haloalkyl.

More preferably, each $R^{7a}$ is independently $C_1$-$C_4$-alkyl or $C_1$-$C_2$-haloalkyl.

Especially preferably, each $R^{7a}$ is independently methyl or ethyl.

Each $R^8$ preferably is independently

H, $C_1$-$C_4$-alkyl or $C_1$-$C_4$-haloalkyl.

More preferably, each $R^8$ is independently $C_1$-$C_2$-alkyl or $C_1$-$C_2$-haloalkyl.

Especially preferably, each $R^8$ is independently methyl or ethyl.

Each $R^{8a}$ preferably is independently $C_1$-$C_4$-alkyl or $C_1$-$C_4$-haloalkyl.

More preferably, each $R^{8a}$ is independently $C_1$-$C_4$-alkyl.

Especially preferably, each $R^{8a}$ is independently methyl or ethyl.

Each $R^9$ preferably is independently $C_1$-$C_4$-alkyl or $C_1$-$C_4$-haloalkyl.

More preferably, each $R^9$ is independently $C_1$-$C_3$-alkyl, $C_1$-$C_2$-haloalkyl.

Especially preferably, each $R^9$ is independently
methyl, ethyl or isopropyl.
Each $R^{9a}$ preferably is independently
$C_1$-$C_4$-alkyl or $C_1$-$C_4$-haloalkyl.
More preferably, each $R^{9a}$ is independently
$C_1$-$C_4$-alkyl or $C_1$-$C_2$-haloalkyl.
Especially preferably, each $R^{9a}$ is independently
methyl, ethyl or trifluoromethyl.
Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.
More preferably, each $R^{10}$ is independently
H, $C_1$-$C_4$-alkyl, $C_2$-$C_3$-alkenyl or $C_3$-$C_7$-cycloalkyl.
Especially preferably, each $R^{10}$ is independently
H or methyl.
Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.
More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.
Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently
methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;
More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;
Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;
Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_mR^9$ and $S(O)_2NR^{11}R^{12}$.
More preferably, each $R^{15}$ is independently
$C_1$-$C_4$-alkyl or $C_1$-$C_4$-haloalkyl.
Especially preferably, each $R^{15}$ is independently
methyl.
X preferably is O or S. More preferably X is O. Especially preferably X is O.
Z preferably is O or S. More preferably Z is O. Especially preferably Z is O.
Preferably, each m is independently 0, 1 or 2. More preferably, each m is independently 0 or 2.
Especially preferably, each m is independently 0 or 2.
In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently hydrogen, halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$, or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;

or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^v$ is independently hydrogen, halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OS(O)_2R^9$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

or $C_3$-$C_6$-cycloalkyl, each optionally substituted with 1 to 4 substituents independently selected from the group consisting of halogen or $C_1$-$C_4$-alkyl;

or phenyl optionally substituted with 1 to 2 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Even more preferably, each $R^v$ is independently hydrogen, halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$, $OS(O)_2R^9$;

or phenyl;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

Especially preferably, each $R^v$ is independently hydrogen, fluorine, chlorine, bromine, iodine, cyano, methyl, ethyl, isopropyl, t-butyl, trifluoromethyl, $OR^4$, $C(O)CH_3$, $OSO_2CH_3$, $SCH_3$, S-ethyl, S-isopropyl, $SO_2CH_3$, phenyl or $CH_2$-pyrazol-1-yl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 1, 2, 3 or 4. Especially preferably, r is 1, 2 or 3.

Embodiment 3

The compounds of the invention are defined in general terms by the formula (I). In another preferred embodiment, the compounds of the invention are defined by formula (Ic):

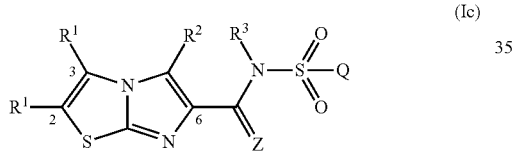

(Ic)

wherein $R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, Z, Q, X and m are as defined above in the Summary of the Invention.

Each $R^1$ preferably is independently halogen, cyano, nitro, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C(X)R^7$, $C(O)OR^8$, $C(O)NR^{11}R^{12}$, $S(O)_mR^9$, $S(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, $OR^4$, $NR^5R^6$, $C(X)R^7$, $S(O)_mR^9$ and $S(O)_2NR^{11}R^{12}$.

More preferably, each $R^1$ is independently halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $S(O)_mR^9$ and $S(O)_2NR^{11}R^{12}$.

Especially preferably, each $R^1$ is independently hydrogen, chlorine, bromine, $C_1$-$C_4$-alkyl (particularly methyl, isopropyl or t-butyl), trifluoromethyl, pentafluoroethyl or $SCH_3$.

$R^2$ preferably is H, halogen, cyano, nitro, $OR^4$, $NR^5R^6$, $C_1$-$C_6$-alkyl, $C_1$-$C_4$-haloalkyl, $C_2$-$C_4$-alkenyl, $C_2$-$C_4$-haloalkenyl, $C_3$-$C_7$-cycloalkyl, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_6$-alkyl substituted with 1 to 4 substituents independently selected from the group consisting of cyano, $OR^4$, $NR^5R^6$, $S(O)_mR^9$ and $S(O)_2NR^{11}R^{12}$.

More preferably, $R^2$ is

H, halogen, cyano, $S(O)_mR^9$ or $S(O)_2NR^{11}R^{12}$;

or $C_3$-$C_6$-cycloalkyl, optionally substituted with 1 to 4 substituents independently selected from the group consisting of halogen, cyano, $C_1$-$C_4$-alkyl and $C_1$-$C_4$-haloalkyl;

or $C_1$-$C_4$-alkyl substituted with 1 to 2 substituents independently selected from the group consisting of cyano, $OR^4$ and $S(O)_mR^9$.

Especially preferably, $R^2$ is hydrogen, methyl, chlorine, bromine or iodine.

$R^3$ preferably is

H, $C_1$-$C_6$-alkyl, $C_1$-$C_6$-haloalkyl, $C_2$-$C_4$-alkenyl, $C_2$-$C_4$-haloalkenyl, $C_2$-$C_4$-alkynyl, $C_2$-$C_4$-haloalkynyl, $C(X)R^7$, $C(O)OR^8$ or $C(O)NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $OR^{4a}$ and $S(O)_mR^{9a}$;

or $C_1$-$C_4$-alkyl substituted with 1 to 4 substituents independently selected from the group consisting of cyano, $OR^4$, $C(X)R^7$ and $C(O)OR^8$;

or $C_1$-$C_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $C_1$-$C_4$-haloalkyl, $C_2$-$C_6$-alkoxyalkyl, $C(X)R^7$, $C(O)OR^8$, $S(O)_mR^9$ and $S(O)_2NR^{11}R^{12}$.

More preferably, $R^3$ is

H, $C_1$-$C_4$-alkyl, $C_2$-$C_3$-alkenyl, $C(X)R^7$ or $C(O)OR^8$;

or $C_1$-$C_2$-alkyl substituted with $OR^4$;

or $C_1$-$C_2$-alkyl substituted with phenyl.

Especially preferably, $R^3$ is hydrogen.

Q preferably is phenyl or a 5- or 6-membered heteroaromatic ring system, each optionally substituted with 1 to 5 substituents independently selected from the group consisting of halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

More preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OS(O)_2R^9$, $N(R^{10})C(O)R^7$, $N(R^{10})C(O)NR^{11}R^{12}$, $N(R^{10})S(O)_2R^9$, $N(R^{10})S(O)_2NR^{11}R^{12}$ and $R^{14}$;

Even more preferably, Q is phenyl or a 5- or 6-membered heteroaromatic ring system, each optionally substituted with 1 to 5 substituents independently selected from the group consisting of halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$, $OS(O)_2R^9$ and $R^{14}$;

Especially preferably, Q is selected from the group consisting of (U-1) to (U-61), (U-81) to (U-87), (U-89) to (U-103) and (U-105) to (U-123).

Each $R^4$ preferably is independently

H, $C_1$-$C_4$-alkyl or $C_1$-$C_4$-haloalkyl;

or $C_3$-$C_7$-cycloalkyl or $C_4$-$C_8$-cycloalkylalkyl, each optionally substituted with 1 to 4 substituents independently selected from the group consisting of halogen.

More preferably, each $R^4$ is independently

H, $C_1$-$C_4$-alkyl or $C_1$-$C_4$-haloalkyl.

Especially preferably, each $R^4$ is methyl, ethyl, propyl, isopropyl, difluoromethyl or trifluoromethyl.

Each $R^{4a}$ preferably is independently

H, $C_1$-$C_6$-alkyl or $C_1$-$C_6$-haloalkyl.

More preferably, each $R^{4a}$ is independently $C_1$-$C_4$-alkyl or $C_1$-$C_4$-haloalkyl.

Especially preferably, each $R^{4a}$ is independently methyl or ethyl.

Each $R^5$ preferably is independently

H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_mR^{9a}$.

More preferably, each $R^5$ is independently

H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_mR^9$ or $S(O)_2NR^{11}R^{12}$.

Especially preferably, each $R^5$ is independently

H, methyl or ethyl.

Each $R^{5a}$ preferably is independently

H or $C_1$-$C_4$-alkyl.

More preferably, each $R^{5a}$ is independently

H or $C_1$-$C_2$-alkyl.

Especially preferably, each $R^{5a}$ is independently methyl or ethyl.

Each $R^6$ preferably is independently

H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_mR^{9a}$.

More preferably, each $R^6$ is independently

H, $C_1$-$C_4$-alkyl, $C_1$-$C_4$-haloalkyl, $C_2$-$C_4$-alkenyl or $C_2$-$C_4$-haloalkenyl;

or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.

Especially preferably, each $R^6$ is independently

H, methyl or ethyl.

Each $R^{6a}$ preferably is independently

H, $C_1$-$C_4$-alkyl, $C(O)R^{13}$ or $C(O)OR^{13}$.

More preferably, each $R^{6a}$ is independently

H or $C_1$-$C_4$-alkyl.

Especially preferably, each $R^{6a}$ is independently

H, methyl or ethyl.

Each $R^7$ preferably is independently

H, $C_1$-$C_6$-alkyl, $C_1$-$C_6$-haloalkyl, $C_2$-$C_6$-alkenyl or $C_2$-$C_6$-haloalkenyl;

or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_mR^{9a}$.

More preferably, each $R^7$ is independently

H, $C_1$-$C_4$-alkyl or $C_1$-$C_4$-haloalkyl;

or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.

Especially preferably, each $R^7$ is independently

H, methyl, ethyl or trifluoromethyl.

Each $R^{7a}$ preferably is independently $C_1$-$C_4$-alkyl or $C_1$-$C_4$-haloalkyl.

More preferably, each $R^{7a}$ is independently $C_1$-$C_4$-alkyl or $C_1$-$C_2$-haloalkyl.

Especially preferably, each $R^{7a}$ is independently methyl or ethyl.

Each $R^8$ preferably is independently

H, $C_1$-$C_4$-alkyl or $C_1$-$C_4$-haloalkyl.

More preferably, each $R^8$ is independently $C_1$-$C_2$-alkyl or $C_1$-$C_2$-haloalkyl.

Especially preferably, each $R^8$ is independently methyl or ethyl.

Each $R^{8a}$ preferably is independently $C_1$-$C_4$-alkyl or $C_1$-$C_4$-haloalkyl.

More preferably, each $R^{8a}$ is independently $C_1$-$C_4$-alkyl.

Especially preferably, each $R^{8a}$ is independently methyl or ethyl.

Each $R^9$ preferably is independently $C_1$-$C_4$-alkyl or $C_1$-$C_4$-haloalkyl.

More preferably, each $R^9$ is independently $C_1$-$C_3$-alkyl, $C_1$-$C_2$-haloalkyl.

Especially preferably, each $R^9$ is independently methyl, ethyl or isopropyl.

Each $R^{9a}$ preferably is independently $C_1$-$C_4$-alkyl or $C_1$-$C_4$-haloalkyl.

More preferably, each $R^{9a}$ is independently $C_1$-$C_4$-alkyl or $C_1$-$C_2$-haloalkyl.

Especially preferably, each $R^{9a}$ is independently methyl, ethyl or trifluoromethyl.

Each $R^{10}$ preferably is independently

H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.

More preferably, each $R^{10}$ is independently

H, $C_1$-$C_4$-alkyl, $C_2$-$C_3$-alkenyl or $C_3$-$C_7$-cycloalkyl.

Especially preferably, each $R^{10}$ is independently

H or methyl.

Each $R^{11}$ preferably is independently

H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.

More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.
Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently
methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_m R^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_m R^9$ or $S(O)_2 NR^{11}R^{12}$;
or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_m R^9$, $S(O)_2 NR^{11}R^{12}$, $OC(O)R^{7a}$ or $N(R^{10})C(O)R^{7a}$;
More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2 NR^{11}R^{12}$;
Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_m R^9$ or $S(O)_2 NR^{11}R^{12}$;

Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, $OR^4$, $NR^5R^6$, $C_1$-$C_4$-alkyl, $C(X)R^7$, $C(O)OR^8$, $C(O)NR^{11}R^{12}$, $S(O)_m R^9$ and $S(O)_2 NR^{11}R^{12}$.
More preferably, each $R^{15}$ is independently
$C_1$-$C_4$-alkyl or $C_1$-$C_4$-haloalkyl.
Especially preferably, each $R^{15}$ is independently
methyl.
X preferably is O or S. More preferably X is O. Especially preferably X is O.
Z preferably is O or S. More preferably Z is O. Especially preferably Z is O.
Preferably, each m is independently 0, 1 or 2. More preferably, each m is independently 0 or 2. Especially preferably, each m is independently 0 or 2.
In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently hydrogen, halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$, or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;

or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^v$ is independently hydrogen, halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OS(O)_2R^9$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

or $C_3$-$C_6$-cycloalkyl, each optionally substituted with 1 to 4 substituents independently selected from the group consisting of halogen or $C_1$-$C_4$-alkyl;

or phenyl optionally substituted with 1 to 2 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Even more preferably, each $R^v$ is independently hydrogen, halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$, $OS(O)_2R^9$;

or phenyl;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

Especially preferably, each $R^v$ is independently hydrogen, fluorine, chlorine, bromine, iodine, cyano, methyl, ethyl, isopropyl, t-butyl, trifluoromethyl, $OR^4$, C(O)CH$_3$, OSO$_2$CH$_3$, SCH$_3$, S-ethyl, S-isopropyl, SO$_2$CH$_3$, phenyl or CH$_2$-pyrazol-1-yl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 1, 2, 3 or 4. Especially preferably, r is 1, 2 or 3.

Embodiment 4

The compounds of the invention are defined in general terms by the formula (I). In a preferred embodiment, the compounds of the invention are defined by formula (Id):

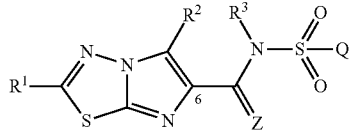

(Id)

wherein
R$^1$, R$^2$, R$^3$, R$^4$, R$^{4a}$, R$^5$, R$^{5a}$, R$^6$, R$^{6a}$, R$^7$, R$^{7a}$, R$^8$, R$^{8a}$, R$^9$, R$^{9a}$, R$^{10}$, R$^{11}$, R$^{11a}$, R$^{12}$, R$^{13}$, R$^{14}$, R$^{15}$, Z, Q, X and m are as defined above in the Summary of the Invention.

R$^1$ preferably is
H, halogen, cyano, nitro, OR$^4$, NR$^5$R$^6$, C$_1$-C$_6$-alkyl, C$_1$-C$_6$-haloalkyl, C$_2$-C$_6$-alkenyl, C$_2$-C$_6$-haloalkenyl, C(X)R$^7$, C(O)OR$^8$, C(O)NR$^{11}$R$^{12}$, S(O)$_m$R$^9$, S(O)$_2$NR$^{11}$R$^{12}$, N(R$^{10}$)C(O)R$^7$, N(R$^{10}$)C(O)NR$^{11}$R$^{12}$, N(R$^{10}$)S(O)$_2$R$^9$ or N(R$^{10}$)S(O)$_2$NR$^{11}$R$^{12}$;

or C$_3$-C$_7$-cycloalkyl, C$_4$-C$_8$-cycloalkylalkyl, C$_6$-C$_{14}$-cycloalkylcycloalkyl or C$_5$-C$_7$-cycloalkenyl, each optionally substituted with 1 to 4 substituents independently selected from the group consisting of halogen, cyano, nitro, C$_1$-C$_4$-alkyl, C$_1$-C$_4$-haloalkyl, OR$^{4a}$ and S(O)$_m$R$^{9a}$;

or C$_1$-C$_6$-alkyl substituted with 1 to 4 substituents independently selected from the group consisting of cyano, OR$^4$, NR$^5$R$^6$, C(X)R$^7$, S(O)$_m$R$^9$ and S(O)$_2$NR$^{11}$R$^{12}$.

More preferably, R$^1$ is
halogen, cyano, nitro, OR$^4$, NR$^5$R$^6$, C$_1$-C$_4$-alkyl, C$_1$-C$_4$-haloalkyl, C(X)R$^7$, C(O)OR$^8$, C(O)NR$^{11}$R$^{12}$, S(O)$_m$R$^9$ or S(O)$_2$NR$^{11}$R$^{12}$;

or C$_3$-C$_7$-cycloalkyl, optionally substituted with 1 to 4 substituents independently selected from the group consisting of halogen, cyano, C$_1$-C$_4$-alkyl and C$_1$-C$_4$-haloalkyl;

or C$_1$-C$_6$-alkyl substituted with 1 to 4 substituents independently selected from the group consisting of cyano, OR$^4$, S(O)$_m$R$^9$ and S(O)$_2$NR$^{11}$R$^{12}$.

Especially preferably, R$^1$ is
hydrogen, chlorine, bromine, C$_1$-C$_4$-alkyl (particularly methyl, isopropyl or t-butyl), trifluoromethyl, pentafluoroethyl or SCH$_3$.

R$^2$ preferably is
H, halogen, cyano, nitro, OR$^4$, NR$^5$R$^6$, C$_1$-C$_6$-alkyl, C$_1$-C$_4$-haloalkyl, C$_2$-C$_4$-alkenyl, C$_2$-C$_4$-haloalkenyl, C$_3$-C$_7$-cycloalkyl, S(O)$_m$R$^9$ or S(O)$_2$NR$^{11}$R$^{12}$;

or C$_3$-C$_6$-cycloalkyl, optionally substituted with 1 to 4 substituents independently selected from the group consisting of halogen, cyano, C$_1$-C$_4$-alkyl and C$_1$-C$_4$-haloalkyl;

or C$_1$-C$_6$-alkyl substituted with 1 to 4 substituents independently selected from the group consisting of cyano, OR$^4$, NR$^5$R$^6$, S(O)$_m$R$^9$ and S(O)$_2$NR$^{11}$R$^{12}$.

More preferably, R$^2$ is
H, halogen, cyano, S(O)$_m$R$^9$ or S(O)$_2$NR$^{11}$R$^{12}$;

or C$_3$-C$_6$-cycloalkyl, optionally substituted with 1 to 4 substituents independently selected from the group consisting of halogen, cyano, C$_1$-C$_4$-alkyl and C$_1$-C$_4$-haloalkyl;

or C$_1$-C$_4$-alkyl substituted with 1 to 2 substituents independently selected from the group consisting of cyano, OR$^4$ and S(O)$_m$R$^9$.

Especially preferably, R$^2$ is hydrogen, methyl, chlorine, bromine or iodine.

R$^3$ preferably is
H, C$_1$-C$_6$-alkyl, C$_1$-C$_6$-haloalkyl, C$_2$-C$_4$-alkenyl, C$_2$-C$_4$-haloalkenyl, C$_2$-C$_4$-alkynyl, C$_2$-C$_4$-haloalkynyl, C(X)R$^7$, C(O)OR$^8$ or C(O)NR$^{11}$R$^{12}$;

or C$_3$-C$_7$-cycloalkyl or C$_4$-C$_8$-cycloalkylalkyl, each optionally substituted with 1 to 4 substituents independently selected from the group consisting of halogen, cyano, OR$^{4a}$ and S(O)$_m$R$^{9a}$;

or C$_1$-C$_4$-alkyl substituted with 1 to 4 substituents independently selected from the group consisting of cyano, OR$^4$, C(X)R$^7$ and C(O)OR$^8$;

or C$_1$-C$_4$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, OR$^4$, C$_1$-C$_4$-haloalkyl, C$_2$-C$_6$-alkoxyalkyl, C(X)R$^7$, C(O)OR$^8$, S(O)$_m$R$^9$ and S(O)$_2$NR$^{11}$R$^{12}$.

More preferably, R$^3$ is
H, C$_1$-C$_4$-alkyl, C$_2$-C$_3$-alkenyl, C(X)R$^7$ or C(O)OR$^8$;

or C$_1$-C$_2$-alkyl substituted with OR$^4$;

or C$_1$-C$_2$-alkyl substituted with phenyl.

Especially preferably, R$^3$ is hydrogen.

Q preferably is
phenyl or a 5- or 6-membered heteroaromatic ring system, each optionally substituted with 1 to 5 substituents independently selected from the group consisting of halogen, cyano, nitro, Si(R$^{15}$)$_3$, OR$^4$, NR$^5$R$^6$, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C(X)R$^7$, C(O)OR$^8$, C(X)NR$^{11}$R$^{12}$, S(O)$_m$R$^9$, S(O)$_2$NR$^{11}$R$^{12}$, OC(O)R$^7$, OC(O)OR$^8$, OC(O)NR$^{11}$R$^{12}$, OS(O)$_2$R$^9$, OS(O)$_2$NR$^{11}$R$^{12}$, N(R$^{10}$)C(O)R$^7$, N(R$^{10}$)C(O)NR$^{11}$R$^{12}$, N(R$^{10}$)S(O)$_2$R$^9$, N(R$^{10}$)S(O)$_2$NR$^{11}$R$^{12}$ and R$^{14}$;

More preferably, Q is
phenyl or a 5- or 6-membered heteroaromatic ring system, each optionally substituted with 1 to 5 substituents independently selected from the group consisting of halogen, cyano, nitro, OR$^4$, C$_1$-C$_6$-alkyl, C$_1$-C$_6$-haloalkyl, C$_2$-C$_6$-alkenyl, C$_2$-C$_6$-haloalkenyl, C$_2$-C$_6$-alkynyl, C$_2$-C$_6$-haloalkynyl, C(X)R$^7$, C(O)OR$^8$, C(X)NR$^{11}$R$^{12}$, S(O)$_m$R$^9$, S(O)$_2$NR$^{11a}$R$^{12}$, OS(O)$_2$R$^9$, N(R$^{10}$)C(O)R$^7$, N(R$^{10}$)C(O)NR$^{11}$R$^{12}$, N(R$^{10}$)S(O)$_2$R$^9$, N(R$^{10}$)S(O)$_2$NR$^{11}$R$^{12}$ and R$^{14}$;

Even more preferably, Q is
phenyl or a 5- or 6-membered heteroaromatic ring system, each optionally substituted with 1 to 5 substituents independently selected from the group consisting of halogen, cyano, nitro, OR$^4$, C$_1$-C$_6$-alkyl, C$_1$-C$_6$-haloalkyl, C(X)R$^7$, C(O)OR$^8$, C(X)NR$^{11a}$R$^{12}$, S(O)$_m$R$^9$, S(O)$_2$NR$^{11}$R$^{12}$, OS(O)$_2$R$^9$ and R$^{14}$;

Especially preferably, Q is selected from the group consisting of (U-1) to (U-61), (U-81) to (U-87), (U-89) to (U-103) and (U-105) to (U-123).

Each R$^4$ preferably is independently
H, C$_1$-C$_4$-alkyl or C$_1$-C$_4$-haloalkyl;

or $C_3$-$C_7$-cycloalkyl or $C_4$-$C_8$-cycloalkylalkyl, each optionally substituted with 1 to 4 substituents independently selected from the group consisting of halogen.
More preferably, each $R^4$ is independently
H, $C_1$-$C_4$-alkyl or $C_1$-$C_4$-haloalkyl.
Especially preferably, each $R^4$ is methyl, ethyl, propyl, isopropyl, difluoromethyl or trifluoromethyl.
Each $R^{4a}$ preferably is independently
H, $C_1$-$C_6$-alkyl or $C_1$-$C_6$-haloalkyl.
More preferably, each $R^{4a}$ is independently
$C_1$-$C_4$-alkyl or $C_1$-$C_4$-haloalkyl.
Especially preferably, each $R^{4a}$ is independently methyl or ethyl.
Each $R^5$ preferably is independently
H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl; $C_1$-$C_4$-haloalkyl, $OR^{4a}$ and $S(O)_m R^{9a}$.
More preferably, each $R^5$ is independently
H, $C_1$-$C_4$-alkyl, $C_1$-$C_4$-haloalkyl, $C_2$-$C_6$-alkenyl, $C_2$-$C_6$-haloalkenyl, $C_2$-$C_6$-alkynyl, $C_2$-$C_6$-haloalkynyl, $S(O)_m R^9$ or $S(O)_2 NR^{11}R^{12}$.
Especially preferably, each $R^5$ is independently
H, methyl or ethyl.
Each $R^{5a}$ preferably is independently
H or $C_1$-$C_4$-alkyl.
More preferably, each $R^{5a}$ is independently
H or $C_1$-$C_2$-alkyl.
Especially preferably, each $R^{5a}$ is independently methyl or ethyl.
Each $R^6$ preferably is independently
H, $C_1$-$C_4$-alkyl, $C_1$-$C_4$-haloalkyl, $C_2$-$C_4$-alkenyl, $C_2$-$C_4$-haloalkenyl, $C_2$-$C_4$-alkynyl or $C_2$-$C_4$-haloalkynyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.
More preferably, each $R^6$ is independently
H, $C_1$-$C_4$-alkyl, $C_1$-$C_4$-haloalkyl, $C_2$-$C_4$-alkenyl or $C_2$-$C_4$-haloalkenyl;
or $C_3$-$C_7$-cycloalkyl optionally substituted with 1 to 4 substituents independently selected from the group consisting of halogen, cyano, $C_1$-$C_4$-alkyl and $C_1$-$C_4$-haloalkyl.
Especially preferably, each $R^6$ is independently
H, methyl or ethyl.
Each $R^{6a}$ preferably is independently
H, $C_1$-$C_4$-alkyl, $C(O)R^{13}$ or $C(O)OR^{13}$.
More preferably, each $R^{6a}$ is independently
H or $C_1$-$C_4$-alkyl.
Especially preferably, each $R^{6a}$ is independently
H, methyl or ethyl.
Each $R^7$ preferably is independently
H, $C_1$-$C_6$-alkyl, $C_1$-$C_6$-haloalkyl, $C_2$-$C_6$-alkenyl or $C_2$-$C_6$-haloalkenyl;
or $C_3$-$C_7$-cycloalkyl or $C_4$-$C_8$-cycloalkylalkyl, each optionally substituted with 1 to 4 substituents independently selected from the group consisting of halogen, cyano, $C_1$-$C_4$-alkyl, $C_1$-$C_4$-haloalkyl, $OR^{4a}$ and $S(O)_m R^{9a}$.
More preferably, each $R^7$ is independently
H, $C_1$-$C_4$-alkyl or $C_1$-$C_4$-haloalkyl;
or $C_3$-$C_7$-cycloalkyl optionally substituted with 1 to 4 substituents independently selected from the group consisting of halogen, cyano, $C_1$-$C_2$-alkyl and $C_1$-$C_2$-haloalkyl.
Especially preferably, each $R^7$ is independently
H, methyl, ethyl or trifluoromethyl.
Each $R^{7a}$ preferably is independently
$C_1$-$C_4$-alkyl or $C_1$-$C_4$-haloalkyl.
More preferably, each $R^{7a}$ is independently
$C_1$-$C_4$-alkyl or $C_1$-$C_2$-haloalkyl.
Especially preferably, each $R^{7a}$ is independently methyl or ethyl.
Each $R^8$ preferably is independently
H, $C_1$-$C_4$-alkyl or $C_1$-$C_4$-haloalkyl.
More preferably, each $R^8$ is independently
$C_1$-$C_2$-alkyl or $C_1$-$C_2$-haloalkyl.
Especially preferably, each $R^8$ is independently methyl or ethyl.
Each $R^{8a}$ preferably is independently
$C_1$-$C_4$-alkyl or $C_1$-$C_4$-haloalkyl.
More preferably, each $R^{8a}$ is independently
$C_1$-$C_4$-alkyl.
Especially preferably, each $R^{8a}$ is independently methyl or ethyl.
Each $R^9$ preferably is independently
$C_1$-$C_4$-alkyl or $C_1$-$C_4$-haloalkyl.
More preferably, each $R^9$ is independently
$C_1$-$C_3$-alkyl, $C_1$-$C_2$-haloalkyl.
Especially preferably, each $R^9$ is independently methyl, ethyl or isopropyl.
Each $R^{9a}$ preferably is independently
$C_1$-$C_4$-alkyl or $C_1$-$C_4$-haloalkyl.
More preferably, each $R^{9a}$ is independently
$C_1$-$C_4$-alkyl or $C_1$-$C_2$-haloalkyl.
Especially preferably, each $R^{9a}$ is independently methyl, ethyl or trifluoromethyl.
Each $R^{10}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl, $C_2$-$C_3$-haloalkynyl or $C_3$-$C_7$-cycloalkyl.
More preferably, each $R^{10}$ is independently
H, $C_1$-$C_4$-alkyl, $C_2$-$C_3$-alkenyl or $C_3$-$C_7$-cycloalkyl.
Especially preferably, each $R^{10}$ is independently
H or methyl.
Each $R^{11}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl or $C_3$-$C_7$-cycloalkyl.
More preferably, each $R^{11}$ is independently
H, $C_1$-$C_4$-alkyl, $C_1$-$C_4$-haloalkyl.
Especially preferably, each $R^{11}$ is independently
H, methyl or ethyl.
Each $R^{11a}$ preferably is independently
H, $C_1$-$C_4$-alkyl, $C_2$-$C_3$-alkenyl or $C_2$-$C_3$-alkynyl.
More preferably, each $R^{11a}$ is independently
H, $C_1$-$C_4$-alkyl, allyl or propargyl.
Especially preferably, each $R^{11a}$ is independently
H, methyl or ethyl.
Each $R^{12}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{12}$ is independently
H, $C_1$-$C_4$-alkyl or $C_1$-$C_4$-haloalkyl.
Especially preferably, each $R^{12}$ is independently
H, methyl or ethyl.

Each $R^{13}$ preferably is independently
H, $C_1$-$C_4$-alkyl, $C_1$-$C_4$-haloalkyl, $C_2$-$C_3$-alkenyl, $C_2$-$C_3$-haloalkenyl, $C_2$-$C_3$-alkynyl or $C_2$-$C_3$-haloalkynyl.
More preferably, each $R^{13}$ is independently
H, $C_1$-$C_4$-alkyl or $C_1$-$C_4$-haloalkyl.
Especially preferably, each $R^{13}$ is independently methyl.
Each $R^{14}$ preferably is independently
$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$;
or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;
  or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;
  or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;
More preferably, each $R^{14}$ is independently
$C_3$-$C_6$-cycloalkyl, each optionally substituted with 1 to 4 substituents independently selected from the group consisting of halogen or $C_1$-$C_4$-alkyl;
or $C_1$-$C_6$-alkyl, each substituted with 1 to 2 substituents independently selected from the group consisting of $OR^4$;
or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;
Especially preferably, each $R^{14}$ is independently
$C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;
Each $R^{15}$ preferably is independently
$C_1$-$C_4$-alkyl or $C_1$-$C_4$-haloalkyl;
or phenyl optionally substituted with 1 to 5 substituents independently selected from the group consisting of halogen, cyano, nitro, $OR^4$, $NR^5R^6$, $C_1$-$C_4$-alkyl, $C(X)R^7$, $C(O)OR^8$, $C(O)NR^{11}R^{12}$, $S(O)_mR^9$ and $S(O)_2NR^{11}R^{12}$.
More preferably, each $R^{15}$ is independently
$C_1$-$C_4$-alkyl or $C_1$-$C_4$-haloalkyl.
Especially preferably, each $R^{15}$ is independently methyl.
X preferably is O or S. More preferably X is O. Especially preferably X is O.

Z preferably is O or S. More preferably Z is O. Especially preferably Z is O.
Preferably, each m is independently 0, 1 or 2. More preferably, each m is independently 0 or 2. Especially preferably, each m is independently 0 or 2.
In an individual type of this embodiment, Q is U-1. In another individual type of this embodiment, Q is U-2. In another individual type of this embodiment, Q is U-3. In another individual type of this embodiment, Q is U-4. In another individual type of this embodiment, Q is U-5. In another individual type of this embodiment, Q is U-6. In another individual type of this embodiment, Q is U-7. In another individual type of this embodiment, Q is U-8. In another individual type of this embodiment, Q is U-9. In another individual type of this embodiment, Q is U-10. In another individual type of this embodiment, Q is U-11. In another individual type of this embodiment, Q is U-12. In another individual type of this embodiment, Q is U-13. In another individual type of this embodiment, Q is U-14. In another individual type of this embodiment, Q is U-15. In another individual type of this embodiment, Q is U-16. In another individual type of this embodiment, Q is U-17. In another individual type of this embodiment, Q is U-18. In another individual type of this embodiment, Q is U-19. In another individual type of this embodiment, Q is U-20. In another individual type of this embodiment, Q is U-21. In another individual type of this embodiment, Q is U-22. In another individual type of this embodiment, Q is U-23. In another individual type of this embodiment, Q is U-24. In another individual type of this embodiment, Q is U-25. In another individual type of this embodiment, Q is U-26. In another individual type of this embodiment, Q is U-27. In another individual type of this embodiment, Q is U-28. In another individual type of this embodiment, Q is U-29. In another individual type of this embodiment, Q is U-30. In another individual type of this embodiment, Q is U-31. In another individual type of this embodiment, Q is U-32. In another individual type of this embodiment, Q is U-33. In another individual type of this embodiment, Q is U-34. In another individual type of this embodiment, Q is U-35. In another individual type of this embodiment, Q is U-36. In another individual type of this embodiment, Q is U-37. In another individual type of this embodiment, Q is U-38. In another individual type of this embodiment, Q is U-39. In another individual type of this embodiment, Q is U-40. In another individual type of this embodiment, Q is U-41. In another individual type of this embodiment, Q is U-42. In another individual type of this embodiment, Q is U-43. In another individual type of this embodiment, Q is U-44. In another individual type of this embodiment, Q is U-45. In another individual type of this embodiment, Q is U-46. In another individual type of this embodiment, Q is U-47. In another individual type of this embodiment, Q is U-48. In another individual type of this embodiment, Q is U-49. In another individual type of this embodiment, Q is U-50. In another individual type of this embodiment, Q is U-51. In another individual type of this embodiment, Q is U-52. In another individual type of this embodiment, Q is U-53. In another individual type of this embodiment, Q is U-54. In another individual type of this embodiment, Q is U-55. In another individual type of this embodiment, Q is U-56. In another individual type of this embodiment, Q is U-57. In another individual type of this embodiment, Q is U-58. In another individual type of this embodiment, Q is U-59. In another individual type of this embodiment, Q is U-60. In another individual type of this embodiment, Q is U-61. In another individual type of this embodiment, Q is U-81. In another individual type of this embodiment, Q is U-82. In another individual type of this embodiment, Q is U-83. In another individual type of this embodiment, Q is U-84. In another individual type of this embodiment, Q is U-85. In another individual type of this embodiment, Q is U-86. In another individual type of this embodiment, Q is U-87. In another individual type of this embodiment, Q is U-89. In another individual type of this embodiment, Q is U-90. In another individual type of this embodiment, Q is U-91. In another individual type of this embodiment, Q is U-92. In another individual type of this embodiment, Q is U-93. In another individual type of this embodiment, Q is U-94. In another individual type of this embodiment, Q is U-95. In another individual type of this embodiment, Q is U-96. In another individual type of this embodiment, Q is U-97. In another individual type of this embodiment, Q is U-98. In another individual type of this embodiment, Q is U-99. In another individual type of this embodiment, Q is U-100. In another individual type of this embodiment, Q is U-101. In another individual type of this embodiment, Q is U-102. In another individual type of this embodiment, Q is U-103. In another individual type of this embodiment, Q is U-105. In another individual type of this embodiment, Q is U-106. In another individual type of this embodiment, Q is U-107. In another individual type of this embodiment, Q is U-108. In another individual type of this embodiment, Q is U-109. In another individual type of this embodiment, Q is U-110. In another individual type of this embodiment, Q is U-111. In another individual type of this embodiment, Q is U-112. In another individual type of this embodiment, Q is U-113. In another individual type of this embodiment, Q is U-114. In another individual type of this embodiment, Q is U-115. In another individual type of this embodiment, Q is U-116. In another individual type of this embodiment, Q is U-117. In another individual type of this embodiment, Q is U-118. In another individual type of this embodiment, Q is U-119. In another individual type of this embodiment, Q is U-120. In another individual type of this embodiment, Q is U-121. In another individual type of this embodiment, Q is U-122. In another individual type of this embodiment, Q is U-123.

In all cases with Q is defined to be one of (U-1) to (U-61), (U-81) to (U-87), (U-89) to (U-103) or (U-105) to (U-123), each $R^v$ preferably is independently hydrogen, halogen, cyano, nitro, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R$, $N(R^{10})C(O)NR^{11}R^{12}$, $N(R^{10})S(O)_2R^9$, $N(R^{10})S(O)_2NR^{11}R^{12}$;

$C_3$-$C_7$-cycloalkyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ or $S(O)_mR^{9a}$, or $C_1$-$C_6$-alkyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ or $S(O)_2NR^{11}R^{12}$;

or phenyl, or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

More preferably, each $R^v$ is independently hydrogen, halogen, cyano, nitro, $OR^4$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OS(O)_2R^9$, $N(R^{10})C(O)R^7$, $N(R^{10})C(O)NR^{11}R^{12}$, $N(R^{10})S(O)_2R^9$, $N(R^{10})S(O)_2NR^{11}R^{12}$;

or $C_3$-$C_6$-cycloalkyl, each optionally substituted with 1 to 4 substituents independently selected from the group consisting of halogen or $C_1$-$C_4$-alkyl;

or phenyl optionally substituted with 1 to 2 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ or $N(R^{10})C(O)R^{7a}$;

or $C_1$-$C_6$-alkyl, each substituted with 1 to 2 substituents independently selected from the group consisting of $OR^4$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$;

Even more preferably, each $R^v$ is independently hydrogen, halogen, cyano, nitro, $OR^4$, $C_1$-$C_6$-alkyl, $C_1$-$C_6$-haloalkyl, $C(X)R^7$, $C(O)OR^8$, $C(X)NR^{11}R^{12}$, $S(O)_mR^9$, $S(O)_2NR^{11}R^{12}$, $OS(O)_2R^9$;

or phenyl;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_1$-$C_4$-haloalkyl, $C(X)R^7$, $C(O)OR^8$, $C(O)NR^{11}R^{12}$, $S(O)_mR^9$ or $S(O)_2NR^{11}R^{12}$.

Especially preferably, each $R^v$ is independently hydrogen, fluorine, chlorine, bromine, iodine, cyano, methyl, ethyl, isopropyl, t-butyl, trifluoromethyl, $OR^4$, $C(O)CH_3$, $OSO_2CH_3$, $SCH_3$, S-ethyl, S-isopropyl, $SO_2CH_3$, phenyl or $CH_2$-pyrazol-1-yl.

In all cases with Q is defined to be one of (U-1) to (U-61), (U-81) to (U-87), (U-89) to (U-103) or (U-105) to (U-123), r preferably is 0, 1, 2, 3 or 4. More preferably, r is 1, 2, 3 or 4. Especially preferably, r is 1, 2 or 3.

The definitions of radicals, and explanations, that are given above in general or in ranges of preference may be combined arbitrarily with one another, thus including combinations between the respective ranges and ranges of preference. The definitions and explanations apply to the end products and also to the precursors and intermediates accordingly.

Preferred in accordance with the invention are the compounds of the formula (I) in which each structural element is defined as given above as being preferred ("preferably").

For those structural elements lacking the preferred definition, the definition in the summary of the invention shall apply.

Likewise preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (I) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (I) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (I) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (I) in which each structural element is defined as given above as being especially preferred (especially preferably). For those structural elements lacking the especially preferred definition, the definition in the summary of the invention shall apply.

Likewise especially preferred in accordance with the invention are the compounds of the formula (I) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 1 as defined above, the following applies:

Preferred in accordance with the invention are the compounds of the formula (Ia) in which each structural element is defined as given above as being preferred ("preferably"). For those structural elements lacking the preferred definition, the definition in the summary of the invention shall apply.

Likewise preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ia) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ia) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ia) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ia) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ia) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 2 as defined above, the following applies:

Preferred in accordance with the invention are the compounds of the formula (Ib) in which each structural element is defined as given above as being preferred ("preferably"). For those structural elements lacking the preferred definition, the definition in the summary of the invention shall apply.

Likewise preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ib) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ib) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ib) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ib) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ib) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 3 as defined above, the following applies:

Preferred in accordance with the invention are the compounds of the formula (Ic) in which each structural element is defined as given above as being preferred ("preferably"). For those structural elements lacking the preferred definition, the definition in the summary of the invention shall apply.

Likewise preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Ic) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Ic) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Ic) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Ic) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Ic) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

With regard to embodiment 4 as defined above, the following applies:

Preferred in accordance with the invention are the compounds of the formula (Id) in which each structural element is defined as given above as being preferred ("preferably"). For those structural elements lacking the preferred definition, the definition in the summary of the invention shall apply.

Likewise preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being preferred ("preferably"). For those structural elements lacking the preferred definition, the definition in the summary of the invention shall apply.

More preferred in accordance with the invention are the compounds of the formula (Id) in which each structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Likewise more preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being more preferred ("more preferably"). For those structural elements lacking the more preferred definition, the definition given above as being especially preferred ("especially preferably") shall apply with the proviso that for those structural elements lacking the especially preferred definition as well, the definition in the summary of the invention shall apply.

Even more preferred in accordance with the invention are the compounds of the formula (Id) in which each structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being more preferred ("more preferably") shall apply with the proviso that for those structural elements lacking the more preferred definition as well, the definition given above as being especially preferred ("especially preferably") shall apply with the proviso that for those structural elements lacking the especially preferred definition as well, the definition in the summary of the invention shall apply.

Alternatively, even more preferred in accordance with the invention are the compounds of the formula (Id) in which each structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Likewise even more preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being even more preferred ("even more preferably"). For those structural elements lacking the even more preferred definition, the definition given above as being especially preferred ("especially preferably") shall apply with the proviso that for those structural elements lacking the especially preferred definition as well, the definition in the summary of the invention shall apply.

Especially preferred in accordance with the invention are the compounds of the formula (Id) in which each structural element is defined as given above as being especially preferred (especially preferably). For those structural elements lacking the especially preferred definition, the definition in the summary of the invention shall apply.

Likewise especially preferred in accordance with the invention are the compounds of the formula (Id) in which Q is selected from the group consisting of (U-1) to (U-61), (U-81) to (U-87), (U-89) to (U-103) and (U-105) to (U-123) and in which each further structural element is defined as given above as being especially preferred (especially preferably). For those structural elements lacking the especially preferred definition, the definition in the summary of the invention shall apply.

Saturated or unsaturated hydrocarbon radicals such as alkyl, alkanediyl or alkenyl may in each case, both alone and in conjunction with heteroatoms, as in alkoxy, for example, be—where possible—either straight-chain or branched.

Any substituted radicals may, unless indicated otherwise, be substituted one or more times, and the substituents in the case of multiple substitutions may be alike or different.

In the definitions of radicals that are stated as being preferred, halogen (halo) is fluoro, chloro, bromo and iodo, very preferably fluoro, chloro and bromo, and especially preferably fluoro and chloro.

Further specific embodiments of the invention are described hereafter:

A specific embodiment of the invention are the compounds of the formula (I) in which
Z is O;
A is CH;
n is 1;
X is O;
Q is selected from the group consisting of U-1, U-2, U-3, U-27, U-49, U-50 and U-103;
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as preferred ("preferably") in embodiment 1.

A specific embodiment of the invention are the compounds of the formula (I) in which
Z is O;
A is CH;
n is 1;
X is O;

Q is selected from the group consisting of U-1, U-2, U-3, U-27, U-49, U-50 and U-103;
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as more preferred ("more preferably") in embodiment 1.

A specific embodiment of the invention are the compounds of the formula (I) in which
Z is O;
A is CH;
n is 1;
X is O;
Q is selected from the group consisting of U-1, U-2, U-3, U-27, U-49, U-50 and U-103;
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as especially preferred ("especially preferably") in embodiment 1.

A specific embodiment of the invention are the compounds of the formula (I) in which
Z is O;
A is CH;
n is 1;
X is O;
Q is selected from the group consisting of U-1, U-2 and U-27;
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as preferred ("preferably") in embodiment 1.

A specific embodiment of the invention are the compounds of the formula (I) in which
Z is O;
A is CH;
n is 1;
X is O;
Q is selected from the group consisting of U-1, U-2 and U-27;
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as more preferred ("more preferably") in embodiment 1.

A specific embodiment of the invention are the compounds of the formula (I) in which
Z is O;
A is CH;
n is 1;
X is O;
Q is selected from the group consisting of U-1, U-2 and U-27;
each m is independently 0 or 2;
$R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as especially preferred ("especially preferably") in embodiment 1.

A specific embodiment of the invention are the compounds of the formula (I) in which
Z is O;
A is $CR^1$;
n is 2;
X is O;
Q is selected from the group consisting of U-1, U-2, U-3, U-27, U-49, U-50 and U-103;
each m is independently 0 or 2;
Each $R^1$ is as defined as preferred ("preferably") in embodiment 3;
$R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as preferred ("preferably") in embodiment 3.

A specific embodiment of the invention are the compounds of the formula (I) in which
Z is O;
A is $CR^1$;
n is 2;
X is O;
Q is selected from the group consisting of U-1, U-2, U-3, U-27, U-49, U-50 and U-103;
each m is independently 0 or 2;
Each $R^1$ is as defined as more preferred ("more preferably") in embodiment 3;
$R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as more preferred ("more preferably") in embodiment 3.

A specific embodiment of the invention are the compounds of the formula (I) in which
Z is O;
A is $CR^1$;
n is 2;
X is O;
Q is selected from the group consisting of U-1, U-2, U-3, U-27, U-49, U-50 and U-103;
each m is independently 0 or 2;
Each $R^1$ is as defined as especially preferred ("especially preferably") in embodiment 3;
$R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as especially preferred ("especially preferably") in embodiment 3.

A specific embodiment of the invention are the compounds of the formula (I) in which
Z is O;
A is $CR^1$;
n is 2;
X is O;
Q is selected from the group consisting of U-1, U-2 and U-27;
each m is independently 0 or 2;
Each $R^1$ is as defined as preferred ("preferably") in embodiment 3;
$R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as preferred ("preferably") in embodiment 3.

A specific embodiment of the invention are the compounds of the formula (I) in which
Z is O;
A is $CR^1$;
n is 2;
X is O;
Q is selected from the group consisting of U-1, U-2 and U-27;
each m is independently 0 or 2;
Each $R^1$ is as defined as more preferred ("more preferably") in embodiment 3;
$R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as more preferred ("more preferably") in embodiment 3.

A specific embodiment of the invention are the compounds of the formula (I) in which
Z is O;
A is $CR^1$;
n is 2;

X is O;
Q is selected from the group consisting of U-1, U-2 and U-27;
each m is independently 0 or 2;
Each $R^1$ is as defined as especially preferred ("especially preferably") in embodiment 3;
$R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11}$, $R^{11a}$, $R^{12}$, $R^{13}$, $R^{14}$, $R^{15}$, $R^v$ and r are as defined as especially preferred ("especially preferably") in embodiment 3.

Of note is that compounds of this invention are characterized by favorable metabolic and/or soil residual patterns and exhibit activity controlling a spectrum of agronomic and nonagronomic parasitic nematodes.

Of particular note, for reasons of parasitic nematode control spectrum and economic importance, protection of agronomic crops from damage or injury caused by parasitic nematodes by controlling parasitic nematodes are embodiments of the invention. Compounds of this invention because of their favorable translocation properties or systemicity in plants also protect foliar or other plant parts which are not directly contacted with a compound of formula (I) or a composition comprising the compound.

Also noteworthy as embodiments of the present invention are compositions comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional active ingredient, preferably a mixing partner as described below.

Further noteworthy as embodiments of the present invention are compositions for controlling a parasitic nematode comprising a compound of any of the preceding Embodiments, as well as any other embodiments described herein, and any combinations thereof, and at least one additional component selected from the group consisting of a surfactant, a solid diluent and a liquid diluent, said compositions optionally further comprising at least one additional active ingredient, preferably a mixing partner as described below. Embodiments of the invention further include methods for controlling a parasitic nematode comprising contacting the parasitic nematode or its environment with a biologically effective amount of a compound of any of the preceding Embodiments (e.g., as a composition described herein).

Embodiments of the invention also include a composition comprising a compound of any of the preceding Embodiments, in the form of a soil drench liquid formulation. Embodiments of the invention further include methods for controlling a parasitic nematode comprising contacting the soil with a liquid composition as a soil drench comprising a biologically effective amount of a compound of any of the preceding Embodiments.

Embodiments of the invention also include a spray composition for controlling a parasitic nematode comprising a biologically effective amount of a compound of any of the preceding Embodiments and a propellant. Embodiments of the invention further include a bait composition for controlling a parasitic nematode comprising a biologically effective amount of a compound of any of the preceding Embodiments, one or more food materials, optionally an attractant, and optionally a humectant.

Embodiments of the invention also include methods for protecting a seed from a parasitic nematode comprising contacting the seed with a biologically effective amount of a compound of any of the preceding Embodiments.

Embodiments of the invention also include methods for controlling a parasitic nematode comprising contacting the parasitic nematode or its environment with a biologically effective amount of a compound of formula (I), an N-oxide, or a salt thereof, (e.g., as a composition described herein), provided that the methods are not methods of medical treatment of a human or animal body by therapy.

This invention also relates to such methods wherein the parasitic nematode or its environment is contacted with a composition comprising a biologically effective amount of a compound of formula (I), an N-oxide, or a salt thereof, and at least one additional component selected from the group consisting of surfactants, solid diluents and liquid diluents, said composition optionally further comprising a biologically effective amount of at least one additional active ingredient, preferably a mixing partner as described below, provided that the methods are not methods of medical treatment of a human or animal body by therapy.

Procedures and Methods

One or more of the following methods and variations as described in Schemes 1-8 can be used to prepare the compounds of formula (I). The definitions of A, Z, Q, n, $R^1$, $R^2$ and $R^3$ in the compounds of formulae (IA), (IB), (IC) and (II)-(XIII) below are as defined above in the Summary of the Invention unless otherwise noted. Formulae (IA)-(IC) are various subsets of formula (I), and all substituents for formulae (IA)-(IC) are as defined above for formula (I) unless otherwise noted. Room temperature is between about 20 and 25° C.

Compounds of formula (IA) (i.e. formula (I) wherein Z is oxygen and $R^3$ is H) can be prepared by the reaction of carboxylic acids of formula (II) with aryl or heteroaryl sulfonamides of formula (IIIA) as shown in Scheme 1. Typically, an amide coupling reagent and a catalyst such as N,N-dimethylaminopyridine (DMAP) are used in the method of Scheme 1. Amide coupling reagents include 1-ethyl-3-(3-dimethylaminopropyl)-carbodiimide hydrochloride (EDC), N,N'-dicyclohexylcarbodiimide (DCC) and 1,1'-carbonyldiimidazole (CDI). The reaction can be carried out at temperatures ranging from room temperature to the reflux temperature of the solvent. Typical solvents include alcohols, ethers, esters, amides and halogenated hydrocarbons. Step C of Synthesis Example 1 describes a particularly useful set of conditions utilizing EDC/DMAP in a 1:1 solvent mixture of t-butanol and dichloromethane.

Scheme 1:

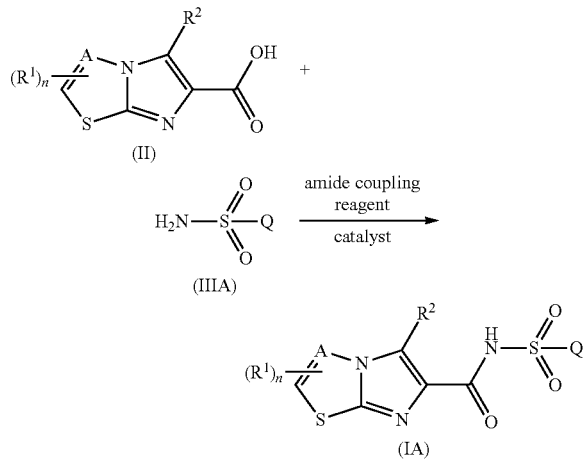

Compounds of formula (IA) can also be prepared by the reaction of carboxylic acid chlorides of formula (IV) with aryl or heteroaryl sulfonamides of formula (IIIA) as shown in Scheme 2. The reaction typically involves use of a base such as triethylamine or pyridine and optionally a catalyst such as DMAP in the presence of a solvent. The reaction can be carried out at temperatures ranging from room temperature to the reflux temperature of the solvent. Typical solvents include ethers, esters and halogenated hydrocarbons.

Scheme 2:

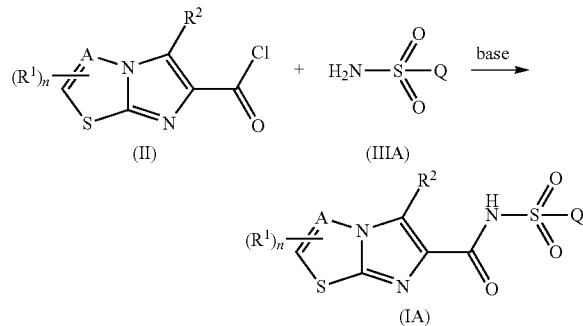

Compounds of formula (IB) wherein $R^3$ is optionally substituted alkyl, alkenyl, alkynyl or cycloalkylalkyl and Z is oxygen can be prepared by the reaction of compounds of formula (IA) with appropriately substituted alkyl, alkenyl, alkynyl or cycloalkylalkyl halides and base as shown in Scheme 3. Typical reaction conditions comprise potassium carbonate as the base and DMF as the solvent.

Scheme 3:

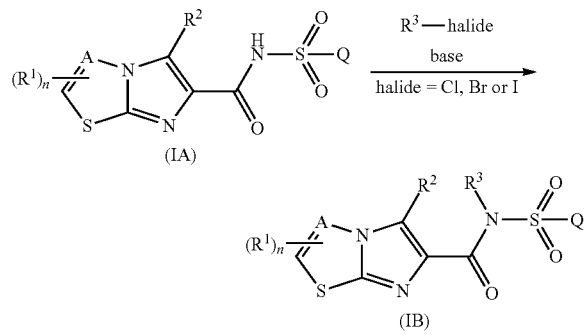

Compounds of formula (IB) wherein $R^3$ is $C(X)R^7$, $C(O)OR^8$, $C(O)NR^{11}R^{12}$, $S(O)_2R^9$ or $S(O)_2NR^{11}R^{12}$, can be prepared by the reaction of compounds of formula (IA) with acyl or sulfonyl halides (e.g., Cl—$C(X)R^7$, Cl—$C(O)OR^8$, Cl—$C(O)NR^{11}R^{12}$, Cl—$S(O)_2R^9$ or Cl—$S(O)_2NR^{11}R^{12}$) by acylation or sulfonylation methods well known in the art.

Compounds of formula (IB) wherein $R^3$ is optionally substituted alkyl, alkenyl, alkynyl, cycloalkyl or phenyl can be prepared by the reaction of acid chlorides of formula (IV) with sulfonamides of formula (IIIB) as shown in Scheme 4. Alternatively, compounds of formula (IB) wherein $R^3$ is optionally substituted alkyl, alkenyl, alkynyl, cycloalkyl or phenyl can be prepared by the reaction of carboxylic acids of formula (II) with sulfonamides of formula (IIIB) by the method of Scheme 1.

Scheme 4:

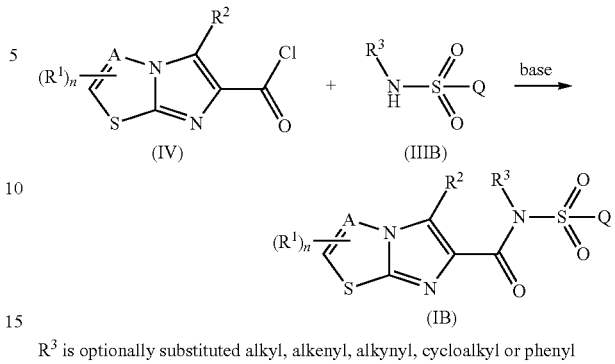

$R^3$ is optionally substituted alkyl, alkenyl, alkynyl, cycloalkyl or phenyl

Thioamides of formula (IC) (i.e. formula (I) wherein Z is sulfur) can be prepared by the reaction of compounds of formula (IA) or (IB) (i.e. formula (I) wherein Z is oxygen) with thiation reagents such as phosphorus pentasulfide or Lawesson's reagent as depicted in Scheme 5.

Scheme 5:

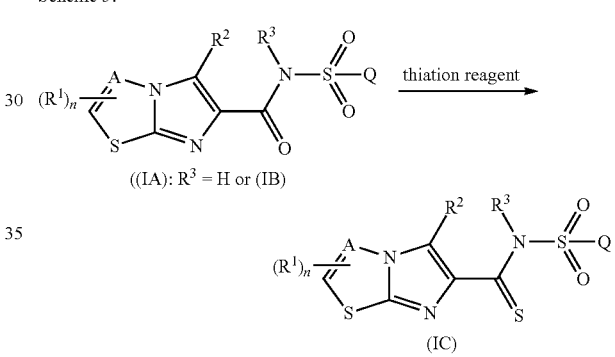

Compounds of formula (IIB) (i.e. formula (II) wherein $R^2$ is bromine) can be prepared by the reaction of compounds of formula (IIA) (i.e. formula (II) wherein $R^2$ is H) with bromine in acetic acid in the presence of sodium acetate as described in Chemistry of Heterocyclic Compounds (New York, N.Y., United States), 47(10), 1280-1285 (2012).

Scheme 6:

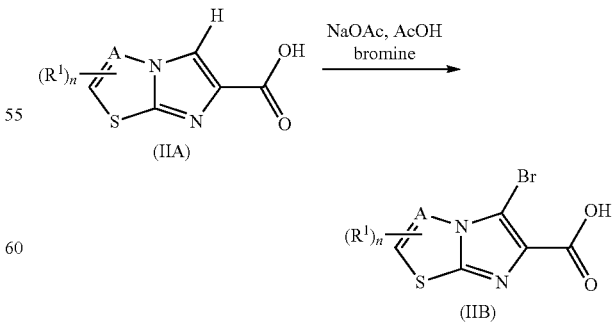

Compounds of formula (II) wherein $R^2$ is cyano can be prepared by reaction of compounds of formula (IIB) with CuCN by methods known in the art. Compounds of formula (II) wherein $R^2$ is nitro can be prepared by reaction of compounds of formula (IIA) with nitric acid/sulfuric acid as described in Heterocycles, 32(11), 2083-7 (1991). Compounds of formula (II) wherein $R^2$ is $OR^4$, $NR^5R^6$ or $SR^9$ can be prepared from compounds of formula (II) wherein $R^2$ is F by standard displacement reactions well known in the art. Compounds of formula (II) wherein $R^2$ is F can be prepared as described in Journal of Fluorine Chemistry, 131(10), 1044-1048 (2010).

Carboxylic acids of formula (II) and acid chlorides of Formula (IV) can be prepared by the reactions shown in Scheme 7. Reaction of a suitably substituted 2-aminothiazole of formula (V) with a 2-bromopyruvate of formula (VI) wherein $R^2$ is H, optionally substituted alkyl, alkenyl, alkynyl, $C(O)R^7$, $C(O)OR^8$ or $C(O)NR^{11}R^{12}$, or an optionally substituted phenyl, naphthalenyl or a 5- or 6-membered heteroaromatic ring at temperatures ranging from room temperature to the boiling temperature of the solvent affords the carboxylic ester of formula (VII) along with variable amounts of the alcohol of formula (VIII) (see, for example, Europ. J. Med. Chem. 1988. 23(4), pp. 385-389). Heating the reaction mixture to boiling in a solvent such as 1,2-dimethoxyethane results in complete conversion of alcohol (VIII) to ester (VII). Treatment of a mixture of esters (VII) and (VIII) with an aqueous hydroxide base such as sodium hydroxide in a water-miscible solvent such as ethanol results in ester hydrolysis to form the carboxylic acid of formula (II) after acidification with a strong acid such as hydrochloric acid. Furthermore, ester cleavage occurs in the presence of strong Lewis acids like $BBr_3$ in $CH_2Cl_2$, favorable in case of decarboxylation-sensitive carboxylic groups. This method is detailed in the experimental part. The carboxylic acid of formula (II) can be converted to the acid chloride of formula (IV) by well-known conventional means such as treatment with thionyl chloride or oxalyl chloride with a catalytic amount of N,N-dimethylformamide (DMF) in moderately polar, aprotic solvents including dichloromethane, dichloroethane, toluene and ethyl acetate. Intermediates of formula (VI) can be prepared by a variety of well-known synthetic methods, including the bromination of optionally substituted pyruvates or lactates (alpha-hydroxy esters). Typical reaction conditions include direct bromination with bromine (see, for example, JACS 1944, 66, pp. 1656-1659) or $CuBr_2$ in ethyl acetate/chloroform (see, for example, JOC 2002, 67(4), pp. 1102-1108), or reaction of a lactate with N-bromsuccinimide in $CCl_4$ (see, for example, JACS 1954, 76, pp. 5796-5797). Intermediates of formula (II), (IV) and (VI) can be prepared according well-known procedures, for example US 2010/0249071, wherein $R^1$ is H and $R^2$ is H or WO 2007/019416, wherein $R^1$ is 2-$NO_2$-phenyl and n=1, or European Journal of Medicinal Chemistry, 23(4), 385-9 (1988), wherein $R^1$ is methyl and n=1 or $R^1$=chlorine and n=1.

Scheme 7:

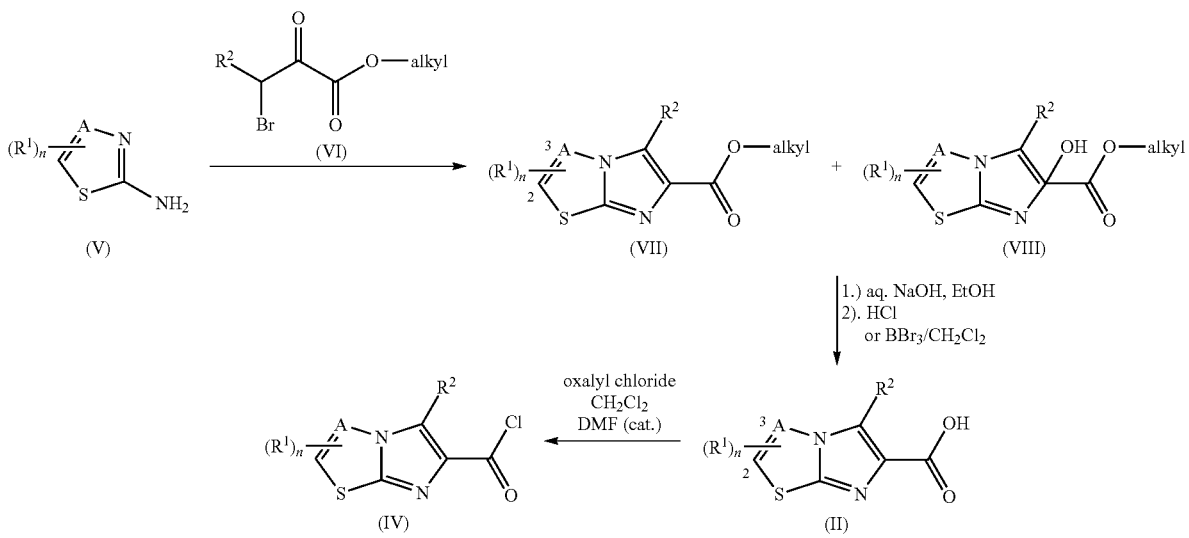

Examples for intermediates of formula (II) or (VII) are in several cases commercially available ("Comm. av.") or can be prepared according to well-known procedures, for example as indicated in table 1.

TABLE 1

| $R^1$ | n | A | $R^2$ | intermediate | remarks |
|---|---|---|---|---|---|
| H | 0 | CH | H | (II) | Comm. av. |
| 2-Me | 1 | CH | H | (II) | Comm. av. |
| 2-Me | 1 | CH | H | (VII) | Comm. av. |
| 3-Me | 1 | C-$R^1$ | H | (II) | Comm. av. |
| 3-Me | 1 | C-$R^1$ | H | (VII) | Comm. av. |
| H | 0 | CH | Me | (II) | Comm. av. |
| H | 0 | CH | Me | (VII) | Comm. av. |
| 2-CN | 1 | CH | H | (II) | Comm. av. |
| 2-Br | 1 | CH | H | (II) | Comm. av. |
| 2-Br | 1 | CH | H | (VII) | Comm. av. |
| 3-Et | 1 | C-$R^1$ | H | (II) | Comm. av. |
| 2-Me, 3-Me | 2 | C-$R^1$ | H | (II) | Comm. av. |
| 2-Me, 3-Me | 2 | C-$R^1$ | H | (VII) | Comm. av. |
| 2-Me | 1 | CH | Me | (II) | Comm. av. |
| 3-Isopropyl | 1 | C-$R^1$ | H | (II) | Comm. av. |
| 3-Me | 1 | C-$R^1$ | Me | (II) | Comm. av. |
| 3-tert.-butyl | 1 | C-$R^1$ | H | (II) | Comm. av. |
| 3-Cyclopropyl | 1 | C-$R^1$ | H | (II) | Comm. av. |
| 2-Me, 3-Et | 2 | C-$R^1$ | H | (II) | Comm. av. |
| H | 0 | CH | Br | (II) | Comm. av. |
| 3-Phenyl | 1 | C-$R^1$ | H | (II) | Comm. av. |
| 3-Cyclopentyl | 1 | C-$R^1$ | H | (II) | Comm. av. |
| 3-Cyclohexyl | 1 | C-$R^1$ | H | (II) | Comm. av. |
| 3-(4-Cl-Phenyl) | 1 | C-$R^1$ | H | (II) | Comm. av. |

TABLE 1-continued

| R$^1$ | n | A | R$^2$ | intermediate | remarks |
|---|---|---|---|---|---|
| 2-Cl | 1 | CH | H | (VII) | Comm. av. |
| 2-F | 1 | CH | H | (VII) | Comm. av. |
| 2-Br | 1 | N | H | (II) | Comm. av. |
| 2-Me | 1 | N | H | (II) | Comm. av. |
| 2-Et | 1 | N | H | (II) | Comm. av. |
| 2-Isopropyl | 1 | N | H | (II) | Comm. av. |
| 2-Isobutyl | 1 | N | H | (II) | Comm. av. |
| 2-tert.-butyl | 1 | N | H | (II) | Comm. av. |
| 2-CF$_3$ | 1 | N | H | (VII) | Comm. av. |

Aminothiazoles of formula (V) (A=C—R$^1$) containing fluoroalkyl groups like trifluoromethyl, pentafluorethyl and hexafluorisopropyl can be prepared according to published methods described in Journal of Fluorine Chemistry, 133(1), 115-119 (2012) and WO 2011/082660.

Sulfonamides of formulae (IIIA) and (IIIB) are known in the chemical literature or are available commercially. As shown in Scheme 8, sulfonamides of formula (IIIA) are readily prepared from the corresponding sulfonyl chlorides of formula (IX) by reaction with ammonia, while sulfonamides of formula (IIIB) are readily prepared from the corresponding sulfonyl chlorides of formula (IX) by reaction with R$^3$NH$_2$. The sulfonyl chloride intermediates are available commercially or can be prepared by a large variety of methods known in the literature. Three of the most common methods of sulfonyl chloride preparation are shown in Scheme 8, including (a) direct chlorosulfonylation of aromatic and heteroaromatic systems with chlorosulfonic acid, (b) oxidation of sulfides (for example with sodium hypochlorite) in the prescence of hydrochloric acid, and (c) diazotization and chlorosulfonylation of aromatic and heteroaromatic amines. These three methods are meant only to be illustrative; a large variety of other synthetic methods are available for the preparation of sulfonyl chlorides and sulfonamides.

Scheme 8:

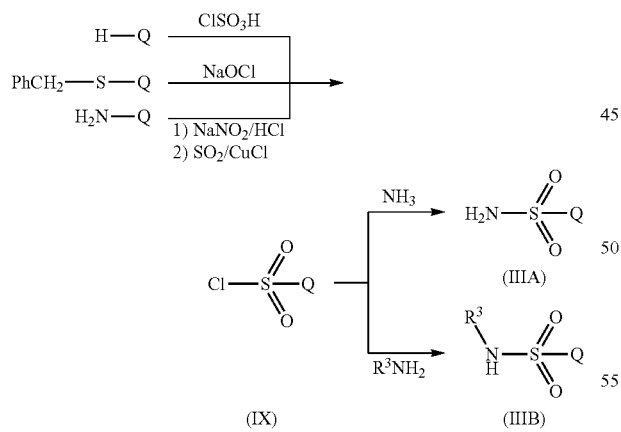

Aminothiazoles of general formula (V) or their salts with organic or inorganic acids like hydrochloric acid, are known in the chemical literature or are available commercially.

The compound according to the present invention can be prepared according to the processes described above. It will nevertheless be understood that, on the basis of his general knowledge and of available publications, the skilled worker will be able to adapt this method according to the specifics of each of the compounds, which it is desired to synthesize.

As exemplified above, important intermediates occur during the synthesis of the compounds of formula (I). Therefore, the invention is also directed to all intermediates described above. In particular, the invention is directed to a compound which is selected from the group consisting of:

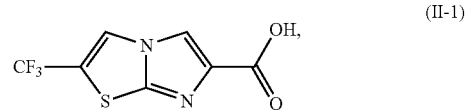
(II-1)

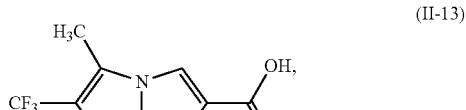
(II-13)

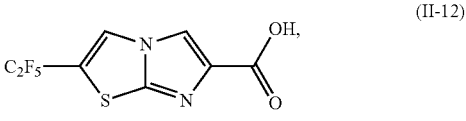
(II-12)

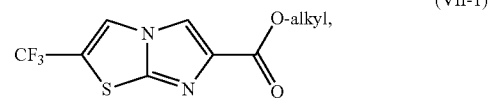
(VII-1)

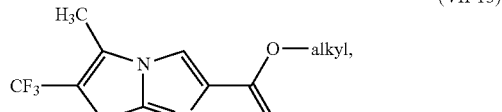
(VII-13)

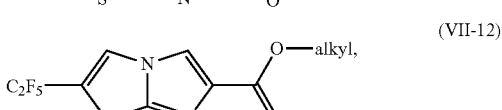
(VII-12)

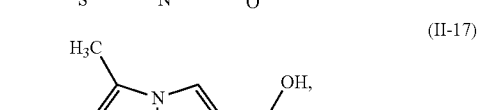
(II-17)

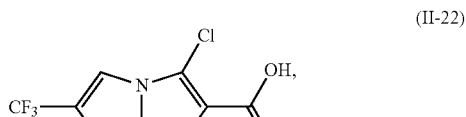
(II-22)

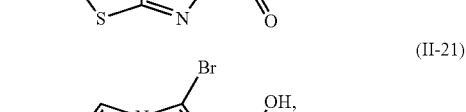
(II-21)

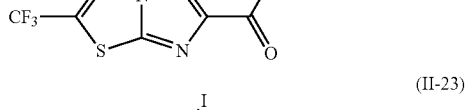
(II-23)

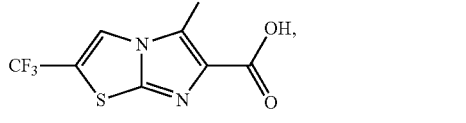
(II-24)

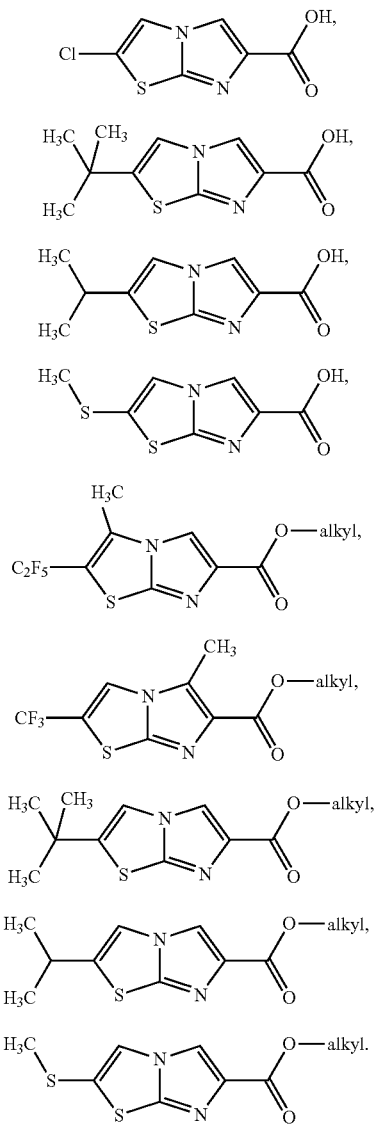

wherein alkyl is alkyl, preferably (C$_1$-C$_4$)alkyl and especially preferably ethyl.

The compounds of the invention can be used as nematicides and/or as insecticides.

A "nematicide" as used herein means that the compound is capable of controlling nematodes.

"Controlling nematodes" according to the invention shall mean to kill nematodes or to prevent their development or growth. The efficacy of the compositions or combinations according to the invention is assessed by comparing the mortality of nematodes, the development of galls, the formation of cysts, the concentration of nematodes per volume of soil, of cysts, the concentration of nematodes per root, the number of nematode eggs per volume of soil, the motility of the nematodes between a plant, a plant part or the soil treated with a composition or combination according to the invention and the untreated plant, plant part or soil (100%). Preferred is a reduction by 25-50% in comparison with the untreated plant, plant part or soil, very preferred a reduction by 51-79%, and particularly preferred the complete killing and the complete prevention of the development or growth by a reduction from 80% to 100% in comparison with the untreated plant, plant part or soil.

"Controlling nematodes" according to the invention shall mean the control of the reproduction of the nematodes (e.g. development of cysts or eggs). The compositions according to the invention can be used for keeping the plants healthy and can be used curatively, preventively or systemically for controlling nematodes.

The skilled person knows methods for determining the mortality of nematodes, the development of galls, the formation of cysts, the concentration of nematodes per volume of soil, of cysts, the concentration of nematodes per root, the number of nematode eggs per volume of soil, the motility of the nematodes between a plant, a plant part or the soil. The treatment according to the invention reduces the damages caused by nematodes to the plant and leads to an increase in yield.

"Nematodes" as used herein encompass all species of the phylum Nematoda and in particular species that are parasitic or cause health problems to plant or to fungi (for example species of the orders *Aphelenchida, Meloidogyne, Tylenchida* and others) or to humans and animals (for example species of the orders *Trichinellida, Tylenchida, Rhabditina,* and *Spirurida*) as well as other parasitic helminths. "Nematodes" as used herein, refer to plant nematodes meaning all nematodes that cause damage to plants. Plant nematodes encompass plant parasitic nematodes and nematodes living in the soil. Plant parasitic nematodes include, but are not limited to, ectoparasites such as *Xiphinema* spp., *Longidorus* spp., and *Trichodorus* spp.; semiparasites such as *Tylenchulus* spp.; migratory endoparasites such as *Pratylenchus* spp., *Radopholus* spp., and *Scutellonerna* spp.; sedentary parasites such as *Heterodera* spp., *Globodera* spp., and *Meloidogyne* spp., and stem and leaf endoparasites such as *Ditylenchus* spp., *Aphelenchoides* spp., and *Hirshmaniella* spp. Especially harmful root parasitic soil nematodes are such as cystforming nematodes of the genera *Heterodera* or *Globodera*, and/or root knot nematodes of the genus *Meloidogyne*. Harmful species of these genera are for example *Meloidogyne incognita, Heterodera glycines* (soybean cyst nematode), *Globodera pallida* and *Globodera rostochiensis* (potato cyst nematode), which species are effectively controlled with the compounds described herein. However, the use of the compounds described herein is in no way restricted to these genera or species, but also extends in the same manner to other nematodes.

Plant nematodes include but are not limited to e.g. *Aglenchus agricola, Anguina tritici, Aphelenchoides arachidis, Aphelenchoides fragaria* and the stem and leaf endoparasites *Aphelenchoides* spp. in general, *Belonolaimus gracilis, Belonolaimus longicaudatus, Belonolaimus nortoni, Bursaphelenchus cocophilus, Bursaphelenchus eremus, Bursaphelenchus xylophilus* and *Bursaphelenchus* spp. in general, *Cacopaurus pestis, Criconemella curvata, Criconemella onoensis, Criconemella ornata, Criconemella rusium, Criconemella xenoplax (=Mesocriconema xenoplax)* and *Criconemella* spp. in general, *Criconemoides ferniae, Criconemoides onoense, Criconemoides ornatum* and *Criconemoides* spp. in general, *Ditylenchus destructor, Ditylenchus dipsaci, Ditylenchus myceliophagus* and the stem and leaf endoparasites *Ditylenchus* spp. in general, *Dolichodorus heterocephalus, Globodera pallida (=Heterodera pallida), Globodera rostochiensis* (potato cyst nematode), *Globodera solanacearum, Globodera tabacum, Globodera virginia* and the sedentary, cyst forming parasites *Globodera* spp. in general, *Helicotylenchus digonicus, Helicotylenchus dihystera, Helicotylenchus erythrine, Helicoty-

*lenchus multicinctus, Helicotylenchus nannus, Helicotylenchus pseudorobustus* and *Helicotylenchus* spp. in general, *Hemicriconemoides, Hemicycliophora arenaria, Hemicycliophora nudata, Hemicycliophora parvana, Heterodera avenae, Heterodera cruciferae, Heterodera glycines* (soybean cyst nematode), *Heterodera oryzae, Heterodera schachtii, Heterodera zeae* and the sedentary, cyst forming parasites *Heterodera* spp. in general, *Hirschmaniella gracilis, Hirschmaniella oryzae Hirschmaniella spinicaudata* and the stem and leaf endoparasites *Hirschmaniella* spp. in general, *Hoplolaimus aegyptii, Hoplolaimus californicus, Hoplolaimus columbus, Hoplolaimus galeatus, Hoplolaimus indicus, Hoplolaimus magnistylus, Hoplolaimus pararobustus, Longidorus africanus, Longidorus breviannulatus, Longidorus elongatus, Longidorus laevicapitatus, Longidorus vineacola* and the ectoparasites *Longidorus* spp. in general, *Meloidogyne acronea, Meloidogyne africana, Meloidogyne arenaria, Meloidogyne arenaria thamesi, Meloidogyne artiella, Meloidogyne chitwoodi, Meloidogyne coffeicola, Meloidogyne ethiopica, Meloidogyne exigua, Meloidogyne fallax, Meloidogyne graminicola, Meloidogyne graminis, Meloidogyne hapla, Meloidogyne incognita, Meloidogyne incognita acrita, Meloidogyne javanica, Meloidogyne kikuyensis, Meloidogyne minor, Meloidogyne naasi, Meloidogyne paranaensis, Meloidogyne thamesi* and the sedentary parasites *Meloidogyne* spp. in general, *Meloinema* spp., *Nacobbus aberrans, Neotylenchus vigissi, Paraphelenchus pseudoparietinus, Paratrichodorus allius, Paratrichodorus lobatus, Paratrichodorus minor, Paratrichodorus nanus, Paratrichodorus porosus, Paratrichodorus teres* and *Paratrichodorus* spp. in general, *Paratylenchus hamatus, Paratylenchus minutus, Paratylenchus projectus* and *Paratylenchus* spp. in general, *Pratylenchus agilis, Pratylenchus alleni, Pratylenchus andinus, Pratylenchus brachyurus, Pratylenchus cerealis, Pratylenchus coffeae, Pratylenchus crenatus, Pratylenchus delattrei, Pratylenchus giibbicaudatus, Pratylenchus goodeyi, Pratylenchus hamatus, Pratylenchus hexincisus, Pratylenchus loosi, Pratylenchus neglectus, Pratylenchus penetrans, Pratylenchus pratensis, Pratylenchus scribneri, Pratylenchus teres, Pratylenchus thornei, Pratylenchus vulnus, Pratylenchus zeae* and the migratory endoparasites *Pratylenchus* spp. in general, *Pseudohalenchus minutus, Psilenchus magnidens, Psilenchus tumidus, Punctodera chalcoensis, Quinisulcius acutus, Radopholus citrophilus, Radopholus similis*, the migratory endoparasites *Radopholus* spp. in general, *Rotylenchulus borealis, Rotylenchulus parvus, Rotylenchulus reniformis* and *Rotylenchulus* spp. in general, *Rotylenchus laurentinus, Rotylenchus macrodoratus, Rotylenchus robustus, Rotylenchus uniformis* and *Rotylenchus* spp. in general, *Scutellonema brachyurum, Scutellonema bradys, Scutellonema clathricaudatum* and the migratory endoparasites *Scutellonema* spp. in general, *Subanguina radiciola, Tetylenchus nicotianae, Trichodorus cylindricus, Trichodorus minor, Trichodorus primitivus, Trichodorus proximus, Trichodorus similis, Trichodorus sparsus* and the ectoparasites *Trichodorus* spp. in general, *Tylenchorhynchus agri, Tylenchorhynchus brassicae, Tylenchorhynchus clarus, Tylenchorhynchus claytoni, Tylenchorhynchus digitatus, Tylenchorhynchus ebriensis, Tylenchorhynchus maximus, Tylenchorhynchus nudus, Tylenchorhynchus vulgaris* and *Tylenchorhynchus* spp. in general, *Tylenchulus semipenetrans* and the semiparasites *Tylenchulus* spp. in general, *Xiphinema americanum, Xiphinema brevicolle, Xiphinema dimorphicaudatum, Xiphinema index* and the ectoparasites *Xiphinema* spp. in general.

Examples of nematodes to which a nematicide of the present invention is applicable include, but are not limited to, nematodes of the genus *Meloidogyne* such as the southern root-knot nematode (*Meloidogyne incognita*), Javanese root-knot nematode (*Meloidogyne javanica*), northern root-knot nematode (*Meloidogyne hapla*), and peanut root-knot nematode (*Meloidogyne arenaria*); nematodes of the genus *Ditylenchus* such as the potato rot nematode (*Ditylenchus destructor*) and bulb and stem nematode (*Ditylenchus dipsaci*); nematodes of the genus *Pratylenchus* such as the cob root-lesion nematode (*Pratylenchus penetrans*), chrysanthemum root-lesion nematode (*Pratylenchus fallax*), coffee root-lesion nematode (*Pratylenchus coffeae*), tea root-lesion nematode (*Pratylenchus loosi*), and walnut root-lesion nematode (*Pratylenchus vulnus*); nematodes of the genus *Globodera* such as the golden nematode (*Globodera rostochiensis*) and potato cyst nematode (*Globodera pallida*); nematodes of the genus *Heterodera* such as the soybean cyst nematode (*Heterodera glycines*) and sugar beet cyst nematode (*Heterodera schachtii*); nematodes of the genus *Aphelenchoides* such as the rice white-tip nematode (*Aphelenchoides besseyi*), chrysanthemum foliar nematode (*Aphelenchoides ritzemabosi*), and strawberry nematode (*Aphelenchoides fragariae*); nematodes of the genus *Aphelenchus* such as the mycophagous nematode (*Aphelenchus avenae*); nematodes of the genus *Radopholus* such as the burrowing nematode (*Radopholus similis*); nematodes of the genus *Tylenchulus* such as the citrus nematode (*Tylenchulus semipenetrans*); nematodes of the genus *Rotylenchulus* such as the reniform nematode (*Rotylenchulus reniformis*); nematodes that occur in trees, such as the pine wood nematode (*Bursaphelenchus xylophilus*), and the like.

Plants for which a nematicide of the present invention can be used are not particularly limited; for example, plants such as cereals (for example, rice, barley, wheat, rye, oat, corn, and the like), beans (soybeans, azuki beans, broad beans, peas, peanuts and the like), fruit trees/fruits (apples, citrus species, pears, grapes, peaches, Japanese apricots, cherries, walnuts, almonds, bananas, strawberries and the like), vegetables (cabbage, tomato, spinach, broccoli, lettuce, onion, Welsh onion, pepper and the like), root crops (carrot, potato, sweet potato, radish, lotus root, turnip and the like), industrial crops (cotton, hemp, paper mulberry, mitsumata, rape, beet, hop, sugarcane, sugar beet, olive, rubber, palms, coffee, tobacco, tea and the like), pepos (pumpkin, cucumber, watermelon, melon and the like), pasture plants (orchard grass, sorghum, thimosy, clover, alfalfa and the like), lawn grasses (mascarene grass, bent grass and the like), crops for flavorings etc. (lavender, rosemary, thyme, parsley, pepper, ginger and the like), and flower plants (chrysanthemum, rose, orchids and the like) can be mentioned.

The compound(s) and compositions comprising the compound(s) of the present invention is/are particularly useful in controlling nematodes in coffee belonging to at least one species selected from the group of the phytoparasitic nematodes consisting of *Pratylenchus brachyurus, Pratylenchus coffeae, Meloidogyne exigua, Meloidogyne incognita, Meloidogyne coffeicola, Helicotylenchus* spp. and also consisting of *Meloidogyne paranaensis, Rotylenchus* spp., *Xiphinema* spp., *Tylenchorhynchus* spp., *Scutellonema* spp.

Compound(s) and compositions comprising compound(s) of the present invention is/are particularly useful in controlling nematodes in potato belonging to at least one species selected from the group of the phytoparasitic nematodes consisting of *Pratylenchus brachyurus, Pratylenchus pratensis, Pratylenchus scribneri, Pratylenchus penetrans, Pratylenchus coffeae, Ditylenchus dipsaci* and also consisting of

*Pratylenchus alleni, Pratylenchus andinus, Pratylenchus cerealis, Pratylenchus crenatus, Pratylenchus hexincisus, Pratylenchus loosi, Pratylenchus neglectus, Pratylenchus teres, Pratylenchus thornei, Pratylenchus vulnus, Belonolaimus longicaudatus, Trichodorus cylindricus, Trichodorus primitivus, Trichodorus proximus, Trichodorus similis, Trichodorus sparsus, Paratrichodorus minor, Paratrichodorus allius, Paratrichodorus nanus, Paratrichodorus teres, Meloidogyne arenaria, Meloidogyne fallax, Meloidogyne hapla, Meloidogyne thamesi, Meloidogyne incognita, Meloidogyne chitwoodi, Meloidogyne javanica, Nacobbus aberrans, Globodera rostochiensis, Globodera pallida, Ditylenchus destructor, Radopholus similis, Rotylenchulus reniformis, Neotylenchus vigissi, Paraphelenchus pseudoparietinus, Aphelenchoides fragariae, Meloinema* spp.

Compound(s) and compositions comprising the compound(s) of the present invention is/are particularly useful in controlling nematodes in tomato belonging to at least one species selected from the group of the phytoparasitic nematodes consisting of *Meloidogyne arenaria, Meloidogyne hapla, Meloidogyne javanica, Meloidogyne incognita, Pratylenchus penetrans* and also consisting of *Pratylenchus brachyurus, Pratylenchus coffeae, Pratylenchus scribneri, Pratylenchus vulnus, Paratrichodorus minor, Meloidogyne exigua, Nacobbus aberrans, Globodera solanacearum, Dolichodorus heterocephalus, Rotylenchulus reniformis.*

The compound(s) and compositions comprising the compound(s) of the present invention is/are particularly useful in controlling nematodes in cucurbits belonging to at least one species selected from the group of the phytoparasitic nematodes consisting of *Meloidogyne arenaria, Meloidogyne hapla, Meloidogyne javanica, Meloidogyne incognita, Rotylenchulus reniformis* and also consisting of *Pratylenchus thornei.*

The compound(s) and compositions comprising the compound(s) of the present invention is/are particularly useful in controlling nematodes in cotton belonging to at least one species selected from the group of the phytoparasitic nematodes consisting of *Belonolaimus longicaudatus, Meloidogyne incognita, Hoplolaimus columbus, Hoplolaimus galeatus, Rotylenchulus reniformis.*

The compound(s) and compositions comprising the compound(s) of the present invention is/are particularly useful in controlling nematodes in corn belonging to at least one species selected from the group of the phytoparasitic nematodes, especially consisting of *Belonolaimus longicaudatus, Paratrichodorus minor* and also consisting of *Pratylenchus brachyurus, Pratylenchus delattrei, Pratylenchus hexincisus, Pratylenchus penetrans, Pratylenchus zeae, (Belonolaimus gracilis), Belonolaimus nortoni, Longidorus breviannulatus, Meloidogyne arenaria, Meloidogyne arenaria thamesi, Meloidogyne graminis, Meloidogyne incognita, Meloidogyne incognita acrita, Meloidogyne javanica, Meloidogyne naasi, Heterodera avenae, Heterodera oryzae, Heterodera zeae, Punctodera chalcoensis, Ditylenchus dipsaci, Hoplolaimus aegyptii, Hoplolaimus magnistylus, Hoplolaimus galeatus, Hoplolaimus indicus, Helicotylenchus digonicus, Helicotylenchus dihystera, Helicotylenchus pseudorobustus, Xiphinema americanum, Dolichodorus heterocephalus, Criconemella ornata, Criconemella onoensis, Radopholus similis, Rotylenchulus borealis, Rotylenchulus parvus, Tylenchorhynchus agri, Tylenchorhynchus clarus, Tylenchorhynchus claytoni, Tylenchorhynchus maximus, Tylenchorhynchus nudus, Tylenchorhynchus vulgaris, Quinisulcius acutus, Paratylenchus minutus, Hemicycliophora parvana, Aglenchus agricola, Anguina tritici, Aphelenchoides arachidis, Scutellonema brachyurum, Subanguina radiciola.*

The compound(s) and compositions comprising the compound(s) of the present invention is/are particularly useful in controlling nematodes in soybean belonging to at least one species selected from the group of the phytoparasitic nematodes, especially consisting of *Pratylenchus brachyurus, Pratylenchus pratensis, Pratylenchus penetrans, Pratylenchus scribneri, Belonolaimus longicaudatus, Heterodera glycines, Hoplolaimus columbus* and also consisting of *Pratylenchus coffeae, Pratylenchus hexincisus, Pratylenchus neglectus, Pratylenchus crenatus, Pratylenchus alleni, Pratylenchus agilis, Pratylenchus zeae, Pratylenchus vulnus, (Belonolaimus gracilis), Meloidogyne arenaria, Meloidogyne incognita, Meloidogyne javanica, Meloidogyne hapla, Hoplolaimus columbus, Hoplolaimus galeatus, Rotylenchulus reniformis.*

The compound(s) and compositions comprising the compound(s) of the present invention is/are particularly useful in controlling nematodes in tobacco belonging to at least one species selected from the group of the phytoparasitic nematodes, especially consisting of *Meloidogyne incognita, Meloidogyne javanica* and also consisting of *Pratylenchus brachyurus, Pratylenchus pratensis, Pratylenchus hexincisus, Pratylenchus penetrans, Pratylenchus neglectus, Pratylenchus crenatus, Pratylenchus thornei, Pratylenchus vulnus, Pratylenchus zeae, Longidorus elongatu, Paratrichodorus lobatus, Trichodorus* spp., *Meloidogyne arenaria, Meloidogyne hapla, Globodera tabacum, Globodera solanacearum, Globodera virginiae, Ditylenchus dipsaci, Rotylenchus* spp., *Helicotylenchus* spp., *Xiphinema americanum, Criconemella* spp., *Rotylenchulus reniformis, Tylenchorhynchus claytoni, Paratylenchus* spp., *Tetylenchus nicotianae.*

The compound(s) and compositions comprising the compound(s) of the present invention is/are particularly useful in controlling nematodes in citrus belonging to at least one species selected from the group of the phytoparasitic nematodes, especially consisting of *Pratylenchus coffeae* and also consisting of *Pratylenchus brachyurus, Pratylenchus vulnus, Belonolaimus longicaudatus, Paratrichodorus minor, Paratrichodorus porosus, Trichodorus, Meloidogyne incognita, Meloidogyne incognita acrita, Meloidogyne javanica, Rotylenchus macrodoratus, Xiphinema americanum, Xiphinema brevicolle, Xiphinema index, Criconemella* spp., *Hemicriconemoides, Radopholus similisrespectively Radopholus citrophilus, Hemicycliophora arenaria, Hemicycliophora nudata, Tylenchulus semipenetrans.*

The compound(s) and compositions comprising the compound(s) of the present invention is/are particularly useful in controlling nematodes in banana belonging to at least one species selected from the group of the phytoparasitic nematodes, especially consisting of *Pratylenchus coffeae, Radopholus similis* and also consisting of *Pratylenchus giibbicaudatus, Pratylenchus loosi, Meloidogyne* spp., *Helicotylenchus multicinctus, Helicotylenchus dihystera, Rotylenchulus* spp.

The compound(s) and compositions comprising the compound(s) of the present invention is/are particularly useful in controlling nematodes in pine apple belonging to at least one species selected from the group of the phytoparasitic nematodes, especially consisting of *Pratylenchus zeae, Pratylenchus pratensis, Pratylenchus brachyurus, Pratylenchus goodeyi., Meloidogyne* spp., *Rotylenchulus reniformis* and also consisting of *Longidorus elongatus, Longidorus laevicapitatus, Trichodorus primitivus, Trichodorus minor, Het-* erodera spp., *Ditylenchus myceliophagus, Hoplolaimus californicus, Hoplolaimus pararobustus, Hoplolaimus indicus, Helicotylenchus dihystera, Helicotylenchus nannus, Helicotylenchus multicinctus, Helicotylenchus erythrine, Xiphinema dimorphicaudatum, Radopholus similis, Tylenchorhynchus digitatus, Tylenchorhynchus ebriensis, Paratylenchus minutus, Scutellonema clathricaudatum, Scutellonema bradys, Psilenchus tumidus, Psilenchus magnidens, Pseudohalenchus minutus, Criconemoides ferniae, Criconemoides onoense, Criconemoides ornatum.*

The compound(s) and compositions comprising the compound(s) of the present invention is/are particularly useful in controlling nematodes in grapes belonging to at least one species selected from the group of the phytoparasitic nematodes, especially consisting of *Pratylenchus vulnus, Meloidogyne arenaria, Meloidogyne incognita, Meloidogyne javanica, Xiphinema americanum, Xiphinema index* and also consisting of *Pratylenchus pratensis, Pratylenchus scribneri, Pratylenchus neglectus, Pratylenchus brachyurus, Pratylenchus thornei, Tylenchulus semipenetrans.*

The compound(s) and compositions comprising the compound(s) of the present invention is/are particularly useful in controlling nematodes in tree crops—pome fruits, belonging to at least one species selected from the group of the phytoparasitic nematodes, especially consisting of *Pratylenchus penetrans* and also consisting of *Pratylenchus vulnus, Longidorus elongatus, Meloidogyne incognita, Meloidogyne hapla.*

The compound(s) and compositions comprising the compound(s) of the present invention is/are particularly useful in controlling nematodes in tree crops—stone fruits, belonging to at least one species selected from the group of the phytoparasitic nematodes, especially consisting of *Pratylenchus penetrans, Pratylenchus vulnus, Meloidogyne arenaria, Meloidogyne hapla, Meloidogyne javanica, Meloidogyne incognita, Criconemella xenoplax* and also consisting of *Pratylenchus brachyurus, Pratylenchus coffeae, Pratylenchus scribneri, Pratylenchus zeae, Belonolaimus longicaudatus, Helicotylenchus dihystera, Xiphinema americanum, Criconemella curvata, Tylenchorhynchus claytoni, Paratylenchus hamatus, Paratylenchus projectus, Scutellonema brachyurum, Hoplolaimus galeatus.*

The compound(s) and compositions comprising the compound(s) of the present invention is/are particularly useful in controlling nematodes in tree crops—nuts, belonging to at least one species selected from the group of the phytoparasitic nematodes, especially consisting of *Trichodorus* spp., *Criconemella rusium* and also consisting of *Pratylenchus vulnus, Paratrichodorus* spp., *Meloidogyne incognita, Helicotylenchus* spp., *Tylenchorhynchus* spp., *Cacopaurus pestis.*

In a like manner, "nematodes" as used herein, refer to nematodes which cause damage to humans or animals.

Specific nematode species harmful to humans or animals are:

Trichinellida for example: *Trichuris* spp., *Capillaria* spp., *Trichomosoides* spp., *Trichinella* spp.

From the order of the Tylenchida for example: *Micronema* spp., *Strongyloides* spp.

From the order of the Rhabditina for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Many known nematicides are equally active against other parasitic helminths and are therefore used to control human and animal parasitic worms, which do not necessarily belong to the group of nematoda. Therefore, it is envisaged by the present invention that the compounds described herein may also be used as anthelmintic drugs in a more general meaning. Pathogenic endoparasitic helminths include platyhelmintha (e.g. monogenea, cestodes and trematodes), acanthocephala, and pentastoma. The following helminths may be mentioned by way of example and by way of preference—but without any limitation:

Monogenea: e.g.: *Gyrodactylus* spp., *Dactylogyrus* spp., *Polystoma* spp.

Cestodes: From the order of the Pseudophyllidea for example: *Diphyllobothrium* spp., *Spirometra* spp., *Schistocephalus* spp., *Ligula* spp., *Bothridium* spp., *Diplogonoporus* spp.

From the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: From the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp., *Metorchis* spp., *Heterophyes* spp., *Metagonimus* spp.

Acantocephala: From the order of the Oligacanthorhynchida z.B: *Macracanthorhynchus* spp., *Prosthenorchis* spp.; from the order of the Polymorphida for example: *Filicollis* spp.; from the order of the Moniliformida for example: *Moniliformis* spp., From the order of the Echinorhynchida for example *Acanthocephalus* spp., *Echinorhynchus* spp., *Leptorhynchoides* spp.

Pentastoma: From the order of the Porocephalida for example *Linguatula* spp.

In the veterinary field and in animal keeping, the administration of the active compounds according to the invention is carried out in the known manner directly or enterally, parenterally, dermally or nasally in the form of suitable preparations. Administration can be carried out prophylactically or therapeutically.

A further aspect of the invention are nematicidal compositions, comprising an effective amount of at least one compound as defined herein and at least one of the following: surfactant, solid or liquid diluent, characterized in that the surfactant or the diluent is normally used in nematicidal compositions. In an embodiment, said composition comprises at least two compounds as defined herein.

A related aspect of the invention is a method for preparing a nematicidal composition as described herein, comprising the step of mixing at least one compound as described herein with a surfactant or diluent normally used in nematicidal compositions. In an embodiment, said method comprises mixing least two compounds as defined herein with a surfactant or diluent normally used in nematicidal compositions.

In particular, the present invention relates to nematicidal composition developed to be used in agriculture or horticulture. These nematicidal compositions may be prepared in a manner known per se.

In the animal health field, i.e. in the field of veterinary medicine, the active compounds according to the present invention are active against animal parasites, in particular ectoparasites or endoparasites. The term endoparasite includes in particular helminths and protozoae, such as coccidia. Ectoparasites are typically and preferably arthropods, in particular insects and acarids. The compounds of formula (I) are preferably active against helminths.

In the field of veterinary medicine the compounds according to the invention are suitable, with favourable warm blood toxicity, for controlling parasites which occur in animal breeding and animal husbandry in livestock, breeding, zoo, laboratory, experimental and domestic animals. They are active against all or specific stages of development of the parasites.

Agricultural livestock include, for example mammals, such as, sheep, goats, horses, donkeys, camels, buffaloes, rabbits, reindeers, fallow deers, and in particular cattle and pigs; or poultry such as turkeys, ducks, geese, and in particular chickens; or fish or crustaceans e.g. in aquaculture; or as the case may be insects such as bees.

Domestic animals include, for example mammals, such as hamsters, guinea pigs, rats, mice, chinchillas, ferrets or in particular dogs, cats; cage birds; reptiles; amphibians or aquarium fish.

According to a preferred embodiment, the compounds according to the invention are administered to mammals.

According to another preferred embodiment, the compounds according to the invention are administered to birds, namely cage birds or in particular poultry.

By using the active compounds according to the invention to control animal parasites, it is intended to reduce or prevent illness, cases of deaths and performance reductions (in the case of meat, milk, wool, hides, eggs, honey and the like), so that more economical and simpler animal keeping is made possible and better animal well-being is achievable.

The term "control" or "controlling" as used herein with regard to the animal health field, means that the active compounds are effective in reducing the incidence of the respective parasite in an animal infected with such parasites to innocuous levels. More specifically, "controlling", as used herein, means that the active compound is effective in killing the respective parasite, inhibiting its growth, or inhibiting its proliferation.

Exemplary arthropods include, without any limitation: from the order of the Anoplurida, for example *Haematopinus* spp., *Linognathus* spp., *Pediculus* spp., *Phtirus* spp., *Solenopotes* spp.; from the order of the Mallophagida and the suborders Amblycerina and Ischnocerina, for example *Trimenopon* spp., *Menopon* spp., *Trinoton* spp., *Bovicola* spp., *Werneckiella* spp., *Lepikentron* spp., *Damalina* spp., *Trichodectes* spp., *Felicola* spp.; from the order of the Diptera and the suborders Nematocerina and Brachy ¬icerina, for example *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., *Odagmia* spp., *Wilhelmia* spp., *Hybomitra* spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp., *Melophagus* spp., *Rhinoestrus* spp., *Tipula* spp.; from the order of the Siphonapterida, for example *Pulex* spp., *Ctenocephalides* spp., *Tunga* spp., *Xenopsylla* spp., *Ceratophyllus* spp.; from the order of the Heteropterida, for example *Cimex* spp., *Triatoma* spp., *Rhodnius* spp., *Panstrongylus* spp.; as well as nuisance and hygiene pests from the order of the Blattarida.

Further, among the arthropods, the following acari may be mentioned by way of example, without any limitation: from the subclass of the Acari (Acarina) and the order of the Metastigmata, for example from the family of argasidae like *Argas* spp., *Ornithodorus* spp., *Otobius* spp., from the family of Ixodidae like *Ixodes* spp., *Amblyomma* spp., *Rhipicephalus* (*Boophilus*) spp *Dermacentor* spp., *Haemophysalis* spp., *Hyalomma* spp., *Rhipicephalus* spp. (the original genus of multi host ticks); from the order of mesostigmata like *Dermanyssus* spp., *Ornithonyssus* spp., *Pneumonyssus* spp., *Raillietia* spp., *Pneumonyssus* spp., *Sternostoma* spp., *Varroa* spp., *Acarapis* spp.; from the order of the Actinedida (Prostigmata), for example *Acarapis* spp., *Cheyletiella* spp., *Ornithocheyletia* spp., *Myobia* spp., *Psorergates* spp., *Demodex* spp., *Trombicula* spp., *Neotrombiculla* spp., *Listrophorus* spp.; and from the order of the Acaridida (Astigmata), for example *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp., *Laminosioptes* spp.

Exemplary parasitic protozoa include—, without any limitation:

Mastigophora (Flagellata), such as, for example, Trypanosomatidae, for example, *Trypanosoma b. brucei, T.b. gambiense, T.b. rhodesiense, T. congolense, T. cruzi, T. evansi, T. equinum, T. lewisi, T. percae, T. simiae, T. vivax, Leishmania brasiliensis, L. donovani, L. tropica*, such as, for example, Trichomonadidae, for example, *Giardia lamblia, G. canis*.

Sarcomastigophora (Rhizopoda), such as Entamoebidae, for example, *Entamoeba histolytica*, Hartmanellidae, for example, *Acanthamoeba* sp., *Harmanella* sp.

Apicomplexa (Sporozoa), such as Eimeridae, for example, *Eimeria acervulina, E. adenoides, E. alabamensis, E. anatis, E. anserina, E. arloingi, E. ashata, E. auburnensis, E. bovis, E. brunetti, E. canis, E. chinchillae, E. clupearum, E. columbae, E. contorta, E. crandalis, E. debliecki, E. dispersa, E. ellipsoidales, E. falciformis, E.

*faurei, E. flavescens, E. gallopavonis, E. hagani, E. intestinalis, E. iroquoina, E. irresidua, E. labbeana, E. leucarti, E. magna, E. maxima, E. media, E. meleagridis, E. meleagrimitis, E. mitis, E. necatrix, E. ninakohlyakimovae, E. ovis, E. parva, E. pavonis, E. perforans, E. phasani, E. piriformis, E. praecox, E. residua, E. scabra, E. spec., E. stiedai, E. suis, E. tenella, E. truncata, E. truttae, E. zuernii, Globidium* spec., *Isospora belli, I. canis, I. felis, I. ohioensis, I. rivolta, I.* spec., *I. suis, Cystisospora* spec., *Cryptosporidium* spec., in particular *C. parvum*; such as Toxoplasmadidae, for example, *Toxoplasma gondii, Hammondia heydornii, Neospora caninum, Besnoitia besnoitii*; such as Sarcocystidae, for example, *Sarcocystis bovicanis, S. bovihominis, S. ovicanis, S. ovifelis, S. neurona, S.* spec., *S. suihominis*, such as Leucozoidae, for example, *Leucozytozoon simondi*, such as Plasmodiidae, for example, *Plasmodium berghei, P. falciparum, P. malariae, P. ovale, P. vivax, P.* spec., such as Piroplasmea, for example, *Babesia argentina, B. bovis, B. canis, B.* spec., *Theileria parva, Theileria* spec., such as Adeleina, for example, *Hepatozoon canis, H.* spec.

Exemplary pathogenic endoparasites, which are helminths, include platyhelmintha (e.g. monogenea, cestodes and trematodes), nematodes, acanthocephala, and pentastoma. Additional exemplary helminths include—, without any limitation:

Monogenea: e.g.: *Gyrodactylus* spp., *Dactylogyrus* spp., *Polystoma* spp.

Cestodes: From the order of the Pseudophyllidea for example: *Diphyllobothrium* spp., *Spirometra* spp., *Schistocephalus* spp., *Ligula* spp., *Bothridium* spp., *Diplogonoporus* spp.

From the order of the Cyclophyllida for example: *Mesocestoides* spp., *Anoplocephala* spp., *Paranoplocephala* spp., *Moniezia* spp., *Thysanosoma* spp., *Thysaniezia* spp., *Avitellina* spp., *Stilesia* spp., *Cittotaenia* spp., *Andyra* spp., *Bertiella* spp., *Taenia* spp., *Echinococcus* spp., *Hydatigera* spp., *Davainea* spp., *Raillietina* spp., *Hymenolepis* spp., *Echinolepis* spp., *Echinocotyle* spp., *Diorchis* spp., *Dipylidium* spp., *Joyeuxiella* spp., *Diplopylidium* spp.

Trematodes: From the class of the Digenea for example: *Diplostomum* spp., *Posthodiplostomum* spp., *Schistosoma* spp., *Trichobilharzia* spp., *Ornithobilharzia* spp., *Austrobilharzia* spp., *Gigantobilharzia* spp., *Leucochloridium* spp., *Brachylaima* spp., *Echinostoma* spp., *Echinoparyphium* spp., *Echinochasmus* spp., *Hypoderaeum* spp., *Fasciola* spp., *Fasciolides* spp., *Fasciolopsis* spp., *Cyclocoelum* spp., *Typhlocoelum* spp., *Paramphistomum* spp., *Calicophoron* spp., *Cotylophoron* spp., *Gigantocotyle* spp., *Fischoederius* spp., *Gastrothylacus* spp., *Notocotylus* spp., *Catatropis* spp., *Plagiorchis* spp., *Prosthogonimus* spp., *Dicrocoelium* spp., *Eurytrema* spp., *Troglotrema* spp., *Paragonimus* spp., *Collyriclum* spp., *Nanophyetus* spp., *Opisthorchis* spp., *Clonorchis* spp. *Metorchis* spp., *Heterophyes* spp., *Metagonimus* spp.

Nematodes: Trichinellida for example: *Trichuris* spp., *Capillaria* spp., *Trichomosoides* spp., *Trichinella* spp.

From the order of the Tylenchida for example: *Micronema* spp., *Strongyloides* spp.

From the order of the Rhabditina for example: *Strongylus* spp., *Triodontophorus* spp., *Oesophagodontus* spp., *Trichonema* spp., *Gyalocephalus* spp., *Cylindropharynx* spp., *Poteriostomum* spp., *Cyclococercus* spp., *Cylicostephanus* spp., *Oesophagostomum* spp., *Chabertia* spp., *Stephanurus* spp., *Ancylostoma* spp., *Uncinaria* spp., *Bunostomum* spp., *Globocephalus* spp., *Syngamus* spp., *Cyathostoma* spp., *Metastrongylus* spp., *Dictyocaulus* spp., *Muellerius* spp., *Protostrongylus* spp., *Neostrongylus* spp., *Cystocaulus* spp., *Pneumostrongylus* spp., *Spicocaulus* spp., *Elaphostrongylus* spp. *Parelaphostrongylus* spp., *Crenosoma* spp., *Paracrenosoma* spp., *Angiostrongylus* spp., *Aelurostrongylus* spp., *Filaroides* spp., *Parafilaroides* spp., *Trichostrongylus* spp., *Haemonchus* spp., *Ostertagia* spp., *Marshallagia* spp., *Cooperia* spp., *Nematodirus* spp., *Hyostrongylus* spp., *Obeliscoides* spp., *Amidostomum* spp., *Ollulanus* spp.

From the order of the Spirurida for example: *Oxyuris* spp., *Enterobius* spp., *Passalurus* spp., *Syphacia* spp., *Aspiculuris* spp., *Heterakis* spp.; *Ascaris* spp., *Toxascaris* spp., *Toxocara* spp., *Baylisascaris* spp., *Parascaris* spp., *Anisakis* spp., *Ascaridia* spp.; *Gnathostoma* spp., *Physaloptera* spp., *Thelazia* spp., *Gongylonema* spp., *Habronema* spp., *Parabronema* spp., *Draschia* spp., *Dracunculus* spp.; *Stephanofilaria* spp., *Parafilaria* spp., *Setaria* spp., *Loa* spp., *Dirofilaria* spp., *Litomosoides* spp., *Brugia* spp., *Wuchereria* spp., *Onchocerca* spp.

Acantocephala: From the order of the Oligacanthorhynchida z.B: *Macracanthorhynchus* spp., *Prosthenorchis* spp.; from the order of the Polymorphida for example: *Filicollis* spp.; from the order of the Moniliformida for example: *Moniliformis* spp.

From the order of the Echinorhynchida for example *Acanthocephalus* spp., *Echinorhynchus* spp., *Leptorhynchoides* spp.

Pentastoma: From the order of the Porocephalida for example *Linguatula* spp.

In the veterinary field and in animal keeping, the administration of the active compounds according to the invention is carried out by methods generally known in the art, such as enterally, parenterally, dermally or nasally in the form of suitable preparations. Administration can be carried out prophylactically or therapeutically.

Thus, one embodiment of the present invention refers to compounds according to the invention for use as a medicament.

Another aspect refers to compounds according to the invention for use as an antiendoparasitical agent, in particular a helmithicidal agent or antiprotozoaic agent. For example, compounds according to the invention for use as an antiendoparasitical agent, in particular an helmithicidal agent or antiprotozoaic agent, e.g., in animal husbandry, in animal breeding, in animal housing, in the hygiene sector.

Yet another aspect refers to compounds according to the invention for use as an antiectoparasitical agent, in particular an arthropodicidal agent such as an insecticidal agent or acaricidal agent. For example, compounds according to the invention for use as an antiectoparasitical agent, in particular an arthropodicidal agent such as an insecticidal agent or acaricidal agent, e.g., in animal husbandry, in animal breeding, in animal housing, in the hygiene sector.

The present invention further provides formulations, and application forms prepared from them, as crop protection agents and/or pesticidal agents, such as drench, drip and spray liquors, comprising at least one of the active compounds of the invention. The application forms may comprise further crop protection agents and/or pesticidal agents, and/or activity-enhancing adjuvants such as penetrants, examples being vegetable oils such as, for example, rapeseed oil, sunflower oil, mineral oils such as, for example, liquid paraffins, alkyl esters of vegetable fatty acids, such as rapeseed oil or soybean oil methyl esters, or alkanol alkoxylates, and/or spreaders such as, for example, alkylsiloxanes and/or salts, examples being organic or inorganic ammonium or phosphonium salts, examples being ammonium sulphate or diammonium hydrogen phosphate, and/or retention promoters such as dioctyl sulphosuccinate or hydroxypropylguar polymers and/or humectants such as glycerol and/or fertilizers such as ammonium, potassium or phosphorous fertilizers, for example.

Examples of typical formulations include water-soluble liquids (SL), emulsifiable concentrates (EC), emulsions in water (EW), suspension concentrates (SC, SE, FS, OD), water-dispersible granules (WG), granules (GR) and capsule concentrates (CS); these and other possible types of formulation are described, for example, by Crop Life International and in Pesticide Specifications, Manual on development and use of FAO and WHO specifications for pesticides, FAO Plant Production and Protection Papers—173, prepared by the FAO/WHO Joint Meeting on Pesticide Specifications, 2004, ISBN: 9251048576. The formulations may comprise active agrochemical compounds other than one or more active compounds of the invention.

The formulations or application forms in question preferably comprise auxiliaries, such as extenders, solvents, spontaneity promoters, carriers, emulsifiers, dispersants, frost protectants, biocides, thickeners and/or other auxiliaries, such as adjuvants, for example. An adjuvant in this context is a component which enhances the biological effect of the formulation, without the component itself having a biological effect. Examples of adjuvants are agents which promote the retention, spreading, attachment to the leaf surface, or penetration.

These formulations are produced in a known manner, for example by mixing the active compounds with auxiliaries such as, for example, extenders, solvents and/or solid carriers and/or further auxiliaries, such as, for example, surfactants. The formulations are prepared in suitable plants or else before or during the application.

Suitable for use as auxiliaries are substances which are suitable for imparting to the formulation of the active compound or the application forms prepared from these formulations (such as, e.g., usable crop protection agents, such as spray liquors or seed dressings) particular properties such as certain physical, technical and/or biological properties.

Suitable extenders are, for example, water, polar and nonpolar organic chemical liquids, for example from the classes of the aromatic and non-aromatic hydrocarbons (such as paraffins, alkylbenzenes, alkylnaphthalenes, chlorobenzenes), the alcohols and polyols (which, if appropriate, may also be substituted, etherified and/or esterified), the ketones (such as acetone, cyclohexanone), esters (including fats and oils) and (poly)ethers, the unsubstituted and substituted amines, amides, lactams (such as N-alkylpyrrolidones) and lactones, the sulphones and sulphoxides (such as dimethyl sulphoxide).

If the extender used is water, it is also possible to employ, for example, organic solvents as auxiliary solvents. Essentially, suitable liquid solvents are: aromatics such as xylene, toluene or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

In principle it is possible to use all suitable solvents. Suitable solvents are, for example, aromatic hydrocarbons, such as xylene, toluene or alkylnaphthalenes, for example, chlorinated aromatic or aliphatic hydrocarbons, such as chlorobenzene, chloroethylene or methylene chloride, for example, aliphatic hydrocarbons, such as cyclohexane, for example, paraffins, petroleum fractions, mineral and vegetable oils, alcohols, such as methanol, ethanol, isopropanol, butanol or glycol, for example, and also their ethers and esters, ketones such as acetone, methyl ethyl ketone, methyl isobutyl ketone or cyclohexanone, for example, strongly polar solvents, such as dimethyl sulphoxide, and water.

All suitable carriers may in principle be used. Suitable carriers are in particular: for example, ammonium salts and ground natural minerals such as kaolins, clays, talc, chalk, quartz, attapulgite, montmorillonite or diatomaceous earth, and ground synthetic minerals, such as finely divided silica, alumina and natural or synthetic silicates, resins, waxes and/or solid fertilizers. Mixtures of such carriers may likewise be used. Carriers suitable for granules include the following: for example, crushed and fractionated natural minerals such as calcite, marble, pumice, sepiolite, dolomite, and also synthetic granules of inorganic and organic meals, and also granules of organic material such as sawdust, paper, coconut shells, maize cobs and tobacco stalks.

Liquefied gaseous extenders or solvents may also be used. Particularly suitable are those extenders or carriers which at standard temperature and under standard pressure are gaseous, examples being aerosol propellants, such as halogenated hydrocarbons, and also butane, propane, nitrogen and carbon dioxide.

Examples of emulsifiers and/or foam-formers, dispersants or wetting agents having ionic or nonionic properties, or mixtures of these surface-active substances, are salts of polyacrylic acid, salts of lignosulphonic acid, salts of phenolsulphonic acid or naphthalenesulphonic acid, polycondensates of ethylene oxide with fatty alcohols or with fatty acids or with fatty amines, with substituted phenols (preferably alkylphenols or arylphenols), salts of sulphosuccinic esters, taurine derivatives (preferably alkyltaurates), phosphoric esters of polyethoxylated alcohols or phenols, fatty acid esters of polyols, and derivatives of the compounds containing sulphates, sulphonates and phosphates, examples being alkylaryl polyglycol ethers, alkylsulphonates, alkyl sulphates, arylsulphonates, protein hydrolysates, lignin-sulphite waste liquors and methylcellulose. The presence of a surface-active substance is advantageous if one of the active compounds and/or one of the inert carriers is not soluble in water and if application takes place in water.

Further auxiliaries that may be present in the formulations and in the application forms derived from them include colorants such as inorganic pigments, examples being iron oxide, titanium oxide, Prussian Blue, and organic dyes, such as alizarin dyes, azo dyes and metal phthalocyanine dyes, and nutrients and trace nutrients, such as salts of iron, manganese, boron, copper, cobalt, molybdenum and zinc.

Stabilizers, such as low-temperature stabilizers, preservatives, antioxidants, light stabilizers or other agents which improve chemical and/or physical stability may also be present. Additionally present may be foam-formers or defoamers.

Furthermore, the formulations and application forms derived from them may also comprise, as additional auxiliaries, stickers such as carboxymethylcellulose, natural and synthetic polymers in powder, granule or latex form, such as gum arabic, polyvinyl alcohol, polyvinyl acetate, and also natural phospholipids, such as cephalins and lecithins, and synthetic phospholipids. Further possible auxiliaries include mineral and vegetable oils.

There may possibly be further auxiliaries present in the formulations and the application forms derived from them. Examples of such additives include fragrances, protective colloids, binders, adhesives, thickeners, thixotropic substances, penetrants, retention promoters, stabilizers, sequestrants, complexing agents, humectants and spreaders. Generally speaking, the active compounds may be combined with any solid or liquid additive commonly used for formulation purposes.

Suitable retention promoters include all those substances which reduce the dynamic surface tension, such as dioctyl sulphosuccinate, or increase the viscoelasticity, such as hydroxypropylguar polymers, for example.

Suitable penetrants in the present context include all those substances which are typically used in order to enhance the penetration of active agrochemical compounds into plants. Penetrants in this context are defined in that, from the (generally aqueous) application liquor and/or from the spray coating, they are able to penetrate the cuticle of the plant and thereby increase the mobility of the active compounds in the cuticle. This property can be determined using the method described in the literature (Baur et al., 1997, Pesticide Science 51, 131-152). Examples include alcohol alkoxylates such as coconut fatty ethoxylate (10) or isotridecyl ethoxylate (12), fatty acid esters such as rapeseed or soybean oil methyl esters, fatty amine alkoxylates such as tallowamine ethoxylate (15), or ammonium and/or phosphonium salts such as ammonium sulphate or diammonium hydrogen phosphate, for example.

The formulations preferably comprise between 0.00000001% and 98% by weight of active compound or, with particular preference, between 0.01% and 95% by weight of active compound, more preferably between 0.5% and 90% by weight of active compound, based on the weight of the formulation.

The active compound content of the application forms (crop protection products) prepared from the formulations may vary within wide ranges. The active compound concentration of the application forms may be situated typically between 0.00000001% and 95% by weight of active compound, preferably between 0.00001% and 1% by weight, based on the weight of the application form. Application takes place in a customary manner adapted to the application forms.

Preferred plants are those from the group of the useful plants, ornamentals, turfs, generally used trees which are employed as ornamentals in the public and domestic sectors, and forestry trees. Forestry trees comprise trees for the production of timber, cellulose, paper and products made from parts of the trees.

The term useful plants as used in the present context refers to crop plants which are employed as plants for obtaining foodstuffs, feedstuffs, fuels or for industrial purposes.

The useful plants which can be improved by applying the compounds of formula (I) include for example the following types of plants: turf, vines, cereals, for example wheat, barley, rye, oats, rice, maize and millet/sorghum; beet, for example sugar beet and fodder beet; fruits, for example pome fruit, stone fruit and soft fruit, for example apples, pears, plums, peaches, almonds, cherries and berries, for example strawberries, raspberries, blackberries; legumes, for example beans, lentils, peas and soybeans; oil crops, for example oilseed rape, mustard, poppies, olives, sunflowers, coconuts, castor oil plants, cacao and peanuts; cucurbits, for example pumpkin/squash, cucumbers and melons; fibre plants, for example cotton, flax, hemp and jute; citrus fruit, for example oranges, lemons, grapefruit and tangerines; vegetables, for example spinach, lettuce, asparagus, cabbage species, carrots, onions, tomatoes, potatoes and bell peppers; Lauraceae, for example avocado, Cinnamomum, camphor, or else plants such as tobacco, nuts, coffee, aubergine, sugar cane, tea, pepper, grapevines, hops, bananas, latex plants and ornamentals, for example flowers, shrubs, deciduous trees and coniferous trees. This enumeration is no limitation.

The following plants are considered to be particularly suitable target crops: cotton, aubergine, turf, pome fruit, stone fruit, soft fruit, maize, wheat, barley, cucumber, tobacco, vines, rice, cereals, pear, beans, soybeans, oilseed rape, tomato, bell pepper, melons, cabbage, potato and apple.

Examples of trees which can be improved in accordance with the method according to the invention are: *Abies* sp., *Eucalyptus* sp., *Picea* sp., *Pinus* sp., *Aesculus* sp., *Platanus* sp., *Tilia* sp., Acer sp., *Tsuga* sp., *Fraxinus* sp., *Sorbus* sp., *Betula* sp., *Crataegus* sp., *Ulmus* sp., *Quercus* sp., *Fagus* sp., *Salix* sp., *Populus* sp.

Preferred trees which can be improved in accordance with the method according to the invention are: from the tree species *Aesculus*: *A. hippocastanum, A. pariflora, A. carnea*; from the tree species *Platanus*: *P. aceriflora, P. occidentalis, P. racemosa*; from the tree species *Picea*: *P. abies*; from the tree species *Pinus*: *P. radiata, P. ponderosa, P. contorta, P. sylvestre, P. elliottii, P. montecola, P. albicaulis, P. resinosa, P. palustris, P. taeda, P. flexilis, P. jeffregi, P. baksiana, P. strobus*; from the tree species *Eucalyptus*: *E. grandis, E. globulus, E. camadentis, E. nitens, E. obliqua, E. regnans, E. pilularus*.

Especially preferred trees which can be improved in accordance with the method according to the invention are: from the tree species *Pinus*: *P. radiata, P. ponderosa, P. contorta, P. sylvestre, P. strobus*; from the tree species *Eucalyptus*: *E. grandis, E. globulus, E. camadentis*.

Very particularly preferred trees which can be improved in accordance with the method according to the invention are: horse chestnut, Platanaceae, linden tree, maple tree.

The present invention can also be applied to any turf grasses, including cool-season turf grasses and warm-season turf grasses. Examples of cold-season turf grasses are bluegrasses (*Poa* spp.), such as Kentucky bluegrass (*Poa pratensis* L.), rough bluegrass (*Poa trivialis* L.), Canada bluegrass (*Poa compressa* L.), annual bluegrass (*Poa annua* L.), upland bluegrass (*Poa glaucantha* Gaudin), wood bluegrass (*Poa nemoralis* L.) and bulbous bluegrass (*Poa bulbosa* L.); bentgrasses (*Agrostis* spp.) such as creeping bentgrass (*Agrostis palustris* Huds.), colonial bentgrass (*Agrostis tenuis* Sibth.), velvet bentgrass (*Agrostis canina* L.), South German mixed bentgrass (*Agrostis* spp. including *Agrostis tenuis* Sibth., *Agrostis canina* L., and *Agrostis palustris* Huds.), and redtop (*Agrostis alba* L.);

fescues (*Festuca* spp.), such as red fescue (*Festuca rubra* L. spp. *rubra*), creeping fescue (*Festuca rubra* L.), chewings fescue (*Festuca rubra commutata* Gaud.), sheep fescue (*Festuca ovina* L.), hard fescue (*Festuca longifolia* Thuill.), hair fescue (*Festucu capillata* Lam.), tall fescue (*Festuca arundinacea* Schreb.) and meadow fescue (*Festuca elanor* L.);

ryegrasses (*Lolium* spp.), such as annual ryegrass (*Lolium multiflorum* Lam.), perennial ryegrass (*Lolium perenne* L.) and Italian ryegrass (*Lolium multiflorum* Lam.);

and wheatgrasses (*Agropyron* spp.), such as fairway wheatgrass (*Agropyron cristatum* (L.) Gaertn.), crested wheatgrass (*Agropyron desertorum* (Fisch.) Schult.) and western wheatgrass (*Agropyron smithii* Rydb.).

Examples of further cool-season turf grasses are beachgrass (*Ammophila breviligulata* Fern.), smooth bromegrass (*Bromus inermis* Leyss.), cattails such as timothy (*Phleum pratense* L.), sand cattail (*Phleum subulatum* L.), orchardgrass (*Dactylis glomerata* L.), weeping alkaligrass (*Puccinellia distans* (L.) Parl.) and crested dog's-tail (*Cynosurus cristatus* L.).

Examples of warm-season turf grasses are Bermuda grass (*Cynodon* spp. L. C. Rich), zoysia grass (*Zoysia* spp. Willd.), St. Augustine grass (*Stenotaphrum secundatum* Walt Kuntze), centipede grass (*Eremochloa ophiuroides* Munro Hack.), carpetgrass (*Axonopus affinis* Chase), Bahia grass (*Paspalum notatum* Flugge), Kikuyu grass (*Pennisetum clandestinum* Hochst. ex Chiov.), buffalo grass (*Buchloe dactyloids* (Nutt.) Engelm.), blue grama (*Bouteloua gracilis* (H.B.K.) Lag. ex Griffiths), seashore paspalum (*Paspalum vaginatum* Swartz) and sideoats grama (*Bouteloua Curtipendula* (Michx. Torr.). Cool-season turf grasses are generally preferred for the use according to the invention. Especially preferred are bluegrass, benchgrass and redtop, fescues and ryegrasses. Bentgrass is especially preferred.

All plants and plant parts can be treated in accordance with the invention. In the present context, plants are understood as meaning all plants and plant populations, such as desired and undesired wild plants or crop plants (including naturally occurring crop plants). Crop plants can be plants which can be obtained by traditional breeding and optimization methods or by biotechnological and recombinant methods, or combinations of these methods, including the transgenic plants and including the plant varieties capable or not of being protected by Plant Breeders' Rights. Plant parts are understood as meaning all aerial and subterranean parts and organs of the plants, such as shoot, leaf, flower and root, examples which may be mentioned being leaves, needles, stalks, stems, flowers, fruiting bodies, fruits and seeds, and also roots, tubers and rhizomes. The plant parts also include crop material and vegetative and generative propagation material, for example cuttings, tubers, rhizomes, slips and seeds.

The control of animal pests by treating the seed of plants has been known for a long time and is a subject of continual improvements. Nevertheless, the treatment of seed entails a series of problems which cannot always be solved in a satisfactory manner. Thus, it is desirable to develop methods for protecting the seed and the germinating plant that remove the need for, or at least significantly reduce, the additional delivery of crop protection compositions in the course of storage, after sowing or after the emergence of the plants. It is desirable, furthermore, to optimize the amount of active ingredient employed in such a way as to provide the best-possible protection to the seed and the germinating plant from attack by animal pests, but without causing damage to the plant itself by the active ingredient employed. In particular, methods for treating seed ought also to take into consideration the intrinsic insecticidal and/or nematicidal properties of pest-resistant or pest-tolerant transgenic plants, in order to achieve optimum protection of the seed and of the germinating plant with a minimal use of crop protection compositions.

The present invention therefore also relates in particular to a method for protecting seed and germinating plants from attack by pests, by treating the seed with a compound of formula (I).

The invention likewise relates to the use of the compound of formula (I) for treating seed for the purpose of protecting the seed and the resultant plant against animal pests.

The invention relates, furthermore, to seed which for protection against animal pests has been treated with a compound of formula (I).

Furthermore, the invention relates to seed which, following treatment with a compound of formula (I) of the invention, is subjected to a film-coating process in order to prevent dust abrasion of the seed.

One of the advantages of the present invention is that, owing to the particular systemic properties of the compositions of the invention, the treatment of the seed with these compositions provides protection from animal pests not only to the seed itself but also to the plants originating from the seed, after they have emerged. In this way, it may not be necessary to treat the crop directly at the time of sowing or shortly thereafter.

A further advantage is to be seen in the fact that, through the treatment of the seed with a compound of formula (I) of the invention, germination and emergence of the treated seed may be promoted.

It is likewise considered to be advantageous that compound of formula (I) may also be used, in particular, on transgenic seed.

It is also stated that a compound of formula (I) may be used in combination with agents of the signalling technology, as a result of which, for example, colonization with symbionts is improved, such as rhizobia, mycorrhiza and/or endophytic bacteria, for example, is enhanced, and/or nitrogen fixation is optimized.

The compositions of the invention are suitable for protecting seed of any variety of plant which is used in agriculture, in greenhouses, in forestry or in horticulture. More particularly, the seed in question is that of cereals (e.g. wheat, barley, rye, oats and millet), maize, cotton, soybeans, rice, potatoes, sunflower, coffee, tobacco, canola, oilseed rape, beets (e.g. sugar beet and fodder beet), peanuts, vegetables (e.g. tomato, cucumber, bean, brassicas, onions and lettuce), fruit plants, lawns and ornamentals. Particularly important is the treatment of the seed of cereals (such as wheat, barley, rye and oats) maize, soybeans, cotton, canola, oilseed rape and rice.

As already mentioned above, the treatment of transgenic seed with a compound of formula (I) is particularly important. The seed in question here is that of plants which generally contain at least one heterologous gene that controls the expression of a polypeptide having, in particular, insecticidal and/or nematicidal properties. These heterologous genes in transgenic seed may come from microorganisms such as *Bacillus, Rhizobium, Pseudomonas, Serratia, Trichoderma, Clavibacter, Glomus* or *Gliocladium*. The present invention is particularly suitable for the treatment of transgenic seed which contains at least one heterologous gene from *Bacillus* sp. With particular preference, the heterologous gene in question comes from *Bacillus thuringiensis*.

For the purposes of the present invention, the compound of formula (I) of the invention is applied alone or in a suitable formulation to the seed. The seed is preferably treated in a condition in which its stability is such that no damage occurs in the course of the treatment. Generally speaking, the seed may be treated at any point in time between harvesting and sowing. Typically, seed is used which has been separated from the plant and has had cobs, hulls, stems, husks, hair or pulp removed. Thus, for example, seed may be used that has been harvested, cleaned and dried to a moisture content of less than 15% by weight. Alternatively, seed can also be used that after drying has been treated with water, for example, and then dried again.

When treating seed it is necessary, generally speaking, to ensure that the amount of the composition of the invention, and/or of other additives, that is applied to the seed is selected such that the germination of the seed is not adversely affected, and/or that the plant which emerges from the seed is not damaged. This is the case in particular with active ingredients which may exhibit phytotoxic effects at certain application rates.

The compositions of the invention can be applied directly, in other words without comprising further components and without having been diluted. As a general rule, it is preferable to apply the compositions in the form of a suitable formulation to the seed. Suitable formulations and methods for seed treatment are known to the skilled person and are described in, for example, the following documents: U.S. Pat. No. 4,272,417 A, U.S. Pat. No. 4,245,432 A, U.S. Pat. No. 4,808,430 A, U.S. Pat. No. 5,876,739 A, US 2003/0176428 A1, WO 2002/080675 A1, WO 2002/028186 A2.

The compound of formula (I) which can be used in accordance with the invention may be converted into the customary seed-dressing formulations, such as solutions, emulsions, suspensions, powders, foams, slurries or other coating compositions for seed, and also ULV formulations.

These formulations are prepared in a known manner, by mixing the compound of formula (I) with customary adjuvants, such as, for example, customary extenders and also solvents or diluents, colorants, wetters, dispersants, emulsifiers, antifoams, preservatives, secondary thickeners, stickers, gibberellins, and also water.

Colorants which may be present in the seed-dressing formulations which can be used in accordance with the invention include all colorants which are customary for such purposes. In this context it is possible to use not only pigments, which are of low solubility in water, but also water-soluble dyes. Examples include the colorants known under the designations Rhodamin B, C.I. Pigment Red 112 and C.I. Solvent Red 1.

Wetters which may be present in the seed-dressing formulations which can be used in accordance with the invention include all of the substances which promote wetting and which are customary in the formulation of active agrochemical ingredients. Use may be made preferably of alkylnaphthalene-sulphonates, such as diisopropyl- or diisobutyl-naphthalenesulphonates.

Dispersants and/or emulsifiers which may be present in the seed-dressing formulations which can be used in accordance with the invention include all of the nonionic, anionic and cationic dispersants that are customary in the formulation of active agrochemical ingredients. Use may be made preferably of nonionic or anionic dispersants or of mixtures of nonionic or anionic dispersants. Suitable nonionic dispersants are, in particular, ethylene oxide-propylene oxide block polymers, alkylphenol polyglycol ethers and also tristryrylphenol polyglycol ethers, and the phosphated or sulphated derivatives of these.

Suitable anionic dispersants are, in particular, lignosulphonates, salts of polyacrylic acid, and arylsulphonate-formaldehyde condensates.

Antifoams which may be present in the seed-dressing formulations which can be used in accordance with the invention include all of the foam inhibitors that are customary in the formulation of active agrochemical ingredients. Use may be made preferably of silicone antifoams and magnesium stearate.

Preservatives which may be present in the seed-dressing formulations which can be used in accordance with the invention include all of the substances which can be employed for such purposes in agrochemical compositions. Examples include dichlorophen and benzyl alcohol hemiformal.

Secondary thickeners which may be present in the seed-dressing formulations which can be used in accordance with the invention include all substances which can be used for such purposes in agrochemical compositions. Those contemplated with preference include cellulose derivatives, acrylic acid derivatives, xanthan, modified clays and highly disperse silica.

Stickers which may be present in the seed-dressing formulations which can be used in accordance with the invention include all customary binders which can be used in seed-dressing products. Preferred mention may be made of polyvinylpyrrolidone, polyvinyl acetate, polyvinyl alcohol and tylose.

Gibberellins which may be present in the seed-dressing formulations which can be used in accordance with the invention include preferably the gibberellins A1, A3 (=gibberellic acid), $A^4$ and A7, with gibberellic acid being used with particular preference. The gibberellins are known (cf. R. Wegler, "Chemie der Pflanzenschutz-und Schidlingsbekimpfungsmittel", Volume 2, Springer Verlag, 1970, pp. 401-412).

The seed-dressing formulations which can be used in accordance with the invention may be used, either directly or after prior dilution with water, to treat seed of any of a wide variety of types. Accordingly, the concentrates or the preparations obtainable from them by dilution with water may be employed to dress the seed of cereals, such as wheat, barley, rye, oats and triticale, and also the seed of maize, rice, oilseed rape, peas, beans, cotton, sunflowers and beets, or else the seed of any of a very wide variety of vegetables. The seed-dressing formulations which can be used in accordance with the invention, or their diluted preparations, may also be used to dress seed of transgenic plants. In that case, additional synergistic effects may occur in interaction with the substances formed through expression.

For the treatment of seed with the seed-dressing formulations which can be used in accordance with the invention, or with the preparations produced from them by addition of water, suitable mixing equipment includes all such equipment which can typically be employed for seed dressing. More particularly, the procedure when carrying out seed dressing is to place the seed in a mixer, to add the particular desired amount of seed-dressing formulations, either as such or following dilution with water beforehand, and to carry out mixing until the distribution of the formulation on the seed is uniform. This may be followed by a drying operation.

The application rate of the seed-dressing formulations which can be used in accordance with the invention may be varied within a relatively wide range. It is guided by the particular amount of the compound of formula (I) in the formulations, and by the seed. The application rates with regard to the compound of formula (I) are situated generally at between 0.001 and 50 g per kilogram of seed, preferably between 0.01 and 15 g per kilogram of seed.

As already mentioned above, it is possible to treat all plants and their parts in accordance with the invention. In a preferred embodiment, wild plant species and plant cultivars, or those obtained by conventional biological breeding methods, such as crossing or protoplast fusion, and also parts thereof, are treated. In a further preferred embodiment, transgenic plants and plant cultivars obtained by genetic engineering, if appropriate in combination with conventional methods (Genetically Modified Organisms), and parts thereof are treated. The terms "parts" or "parts of plants" or "plant parts" have been explained above.

More preferably, plants of the plant cultivars which are each commercially available or in use are treated in accordance with the invention. Plant cultivars are understood to mean plants having new properties ("traits") and which have been obtained by conventional breeding, by mutagenesis or by recombinant DNA techniques. They may be cultivars, biotypes and genotypes.

Depending on the plant species or plant cultivars, and the location and growth conditions (soils, climate, vegetation period, diet) thereof, the inventive treatment may also result in over additive ("synergistic") effects. For example, possibilities include reduced application rates and/or broadening of the activity spectrum and/or an increase in the activity of the compounds and compositions usable in accordance with the invention, better plant growth, increased tolerance to high or low temperatures, increased tolerance to drought or to levels of water or soil salinity, enhanced flowering performance, easier harvesting, accelerated ripening, higher yields, higher quality and/or higher nutritional value of the harvested products, increased storage life and/or processibility of the harvested products, which exceed the effects normally to be expected.

The transgenic plants or plant cultivars (those obtained by genetic engineering) which are to be treated with preference in accordance with the invention include all plants which, through the genetic modification, received genetic material which imparts particular advantageous useful properties ("traits") to these plants. Examples of such properties are better plant growth, increased tolerance to high or low temperatures, increased tolerance to drought or to levels of water or soil salinity, enhanced flowering performance, easier harvesting, accelerated ripening, higher yields, higher quality and/or a higher nutritional value of the harvested products, better storage life and/or processibility of the harvested products. Further and particularly emphasized examples of such properties are an improved defence of the plants against animal and microbial pests, such as against insects, mites, phytopathogenic fungi, bacteria and/or viruses, and also increased tolerance of the plants to certain herbicidally active ingredients. Examples of transgenic plants include the important crop plants, such as cereals (wheat, rice), maize, soya, potatoes, sugar beet, tomatoes, peas and other vegetable types, cotton, tobacco, oilseed rape, and also fruit plants (with the fruits of apples, pears, citrus fruits and grapes), particular emphasis being given to maize, soya, potatoes, cotton, tobacco and oilseed rape. Traits that are particularly emphasized are improved defence of the plants against insects, arachnids, nematodes, slugs and snails by toxins formed in the plants, especially those formed in the plants by the genetic material from *Bacillus thuringiensis* (for example by the genes CryIA(a), CryIA(b), CryIA(c), CryIIA, CryIIIA, CryIIIB2, Cry9c, Cry2Ab, Cry3Bb and CryIF, and also combinations thereof) (referred to hereinafter as "Bt plants"). Traits that are also particularly emphasized are the improved defence of plants against fungi, bacteria and viruses by systemic acquired resistance (SAR), systemin, phytoalexins, elicitors and also resistance genes and correspondingly expressed proteins and toxins. Traits that are additionally particularly emphasized are the increased tolerance of the plants to certain active herbicidal ingredients, for example imidazolinones, sulphonylureas, glyphosate or phosphinothricin (for example the "PAT" gene). The genes which impart the desired traits in question may also be present in combinations with one another in the transgenic plants. Examples of "Bt plants" include maize varieties, cotton varieties, soya varieties and potato varieties which are sold under the trade names YIELD GARD® (for example maize, cotton, soya), KnockOut® (for example maize), StarLink® (for example maize), Bollgard® (cotton), Nucotn® (cotton) and NewLeaf (potato). Examples of herbicide-tolerant plants include maize varieties, cotton varieties and soya varieties which are sold under the trade names Roundup Ready® (tolerance to glyphosate, for example maize, cotton, soya), Liberty Link® (tolerance to phosphinothricin, for example oilseed rape), IMI® (tolerance to imidazolinones) and STS® (tolerance to sulphonylureas, for example maize). Herbicide-resistant plants (plants bred in a conventional manner for herbicide tolerance) which may be mentioned include the varieties sold under the name Clearfield® (for example maize). Of course, these statements also apply to plant cultivars which have these genetic traits or genetic traits which are still to be developed and will be developed and/or marketed in the future.

The plants listed can be treated in accordance with the invention in a particularly advantageous manner with the compounds of the general formula (I) and/or the active ingredient mixtures according to the invention. The preferred ranges stated above for the active ingredients or mixtures also apply to the treatment of these plants. Particular emphasis is given to the treatment of plants with the compounds or mixtures specifically mentioned in the present text.

The treatment of the plants and plant parts with the compounds of formula (I) is carried out directly or by acting on the environment, habitat or storage space using customary treatment methods, for example by dipping, spraying, atomizing, misting, evaporating, dusting, fogging, scattering, foaming, painting on, spreading, injecting, drenching, trickle irrigation and, in the case of propagation material, in particular in the case of seed, furthermore by the dry seed treatment method, the wet seed treatment method, the slurry treatment method, by encrusting, by coating with one or more coats and the like. It is furthermore possible to apply the active substances by the ultra-low volume method or to inject the active substance preparation or the active substance itself into the soil.

A preferred direct treatment of the plants is the leaf application treatment, i.e. compounds of formula (I) or compositions containing them are applied to the foliage, it being possible for the treatment frequency and the application rate to be matched to the infection pressure.

In the case of systemically active compounds, compounds of formula (I) or compositions according to the invention reach the plants via the root system. In this case, the treatment of the plants is effected by allowing the compounds of formula (I) or compositions according to the invention to act on the environment of the plant. This can be done for example by drenching, incorporating in the soil or into the nutrient solution, i.e. the location of the plant (for example the soil or hydroponic systems) is impregnated with a liquid form of compounds of formula (I) or compositions according to the invention, or by soil application, i.e. the compounds of formula (I) or compositions according to the invention are incorporated into the location of the plants in solid form (for example in the form of granules). In the case of paddy rice cultures, this may also be done by metering the compounds of formula (I) or compositions according to the invention into a flooded paddy field in a solid use form (for example in the form of granules).

The inventive active ingredient may be present in its commercially available formulations and in the use forms, prepared from these formulations, as a mixture with other active ingredients, such as insecticides, attractants, sterilants, bactericides, acaricides, nematicides, fungicides, growth regulators, herbicides, safeners, fertilizers or semiochemicals. The mixtures thus obtained have a broadened spectrum of activity.

Mixtures with fungicides are particularly advantageous. Examples of suitable fungicide mixing partners can be selected from the list consisting of
1) Inhibitors of the ergosterol biosynthesis, for example (1.1) aldimorph, (1.2) azaconazole, (1.3) bitertanol, (1.4) bromuconazole, (1.5) cyproconazole, (1.6) diclobutrazole, (1.7) difenoconazole, (1.8) diniconazole, (1.9) diniconazole-M, (1.10) dodemorph, (1.11) dodemorph acetate, (1.12) epoxiconazole, (1.13) etaconazole, (1.14) fenarimol, (1.15) fenbuconazole, (1.16) fenhexamid, (1.17) fenpropidin, (1.18) fenpropimorph, (1.19) fluquinconazole, (1.20) flurprimidol, (1.21) flusilazole, (1.22) flutriafol, (1.23) furconazole, (1.24) furconazole-cis, (1.25) hexaconazole, (1.26) imazalil, (1.27) imazalil sulfate, (1.28) imibenconazole, (1.29) ipconazole, (1.30) metconazole, (1.31) myclobutanil, (1.32) naftifine, (1.33) nuarimol, (1.34) oxpoconazole, (1.35) paclobutrazol, (1.36) pefurazoate, (1.37) penconazole, (1.38) piperalin, (1.39) prochloraz, (1.40) propiconazole, (1.41) prothioconazole, (1.42) pyributicarb, (1.43) pyrifenox, (1.44) quinconazole, (1.45) simeconazole, (1.46) spiroxamine, (1.47) tebuconazole, (1.48) terbinafine, (1.49) tetraconazole, (1.50) triadimefon, (1.51) triadimenol, (1.52) tridemorph, (1.53) triflumizole, (1.54) triforine, (1.55) triticonazole, (1.56) uniconazole, (1.57) uniconazole-p, (1.58) viniconazole, (1.59) voriconazole, (1.60) 1-(4-chlorophenyl)-2-(1H-1,2,4-triazol-1-yl)cycloheptanol, (1.61) methyl 1-(2,2-dimethyl-2,3-dihydro-1H-inden-1-yl)-1H-imidazole-5-carboxylate, (1.62) N'-{5-(difluoromethyl)-2-methyl-4-[3-(trimethylsilyl)propoxy]phenyl}-N-ethyl-N-methylimidoformamide, (1.63) N-ethyl-N-methyl-N'-{2-methyl-5-(trifluoromethyl)-4-[3-(trimethylsilyl)propoxy]phenyl}imidoformamide, (1.64) O-[1-(4-methoxyphenoxy)-3,3-dimethylbutan-2-yl]1H-imidazole-1-carbothioate, (1.65) Pyrisoxazole.
2) Inhibitors of the respiratory chain at complex I or II, for example (2.1) bixafen, (2.2) boscalid, (2.3) carboxin, (2.4) diflumetorim, (2.5) fenfuram, (2.6) fluopyram, (2.7) flutolanil, (2.8) fluxapyroxad, (2.9) furametpyr, (2.10) furmecyclox, (2.11) isopyrazam (mixture of syn-epimeric racemate 1RS,4SR,9RS and anti-epimeric racemate 1RS,4SR,9SR), (2.12) isopyrazam (anti-epimeric racemate 1RS,4SR,9SR), (2.13) isopyrazam (anti-epimeric enantiomer 1R,4S,9S), (2.14) isopyrazam (anti-epimeric enantiomer 1S,4R,9R), (2.15) isopyrazam (syn epimeric racemate 1RS,4SR,9RS), (2.16) isopyrazam (syn-epimeric enantiomer 1R,4S,9R), (2.17) isopyrazam (syn-epimeric enantiomer 1S,4R,9S), (2.18) mepronil, (2.19) oxycarboxin, (2.20) penflufen, (2.21) penthiopyrad, (2.22) sedaxane, (2.23) thifluzamide, (2.24) 1-methyl-N-[2-(1,1,2,2-tetrafluoroethoxy)phenyl]-3-(trifluoromethyl)-1H-pyrazole-4-carboxamide, (2.25) 3-(difluoromethyl)-1-methyl-N-[2-(1,1,2,2-tetrafluoroethoxy)phenyl]-1H-pyrazole-4-carboxamide, (2.26) 3-(difluoromethyl)-N-[4-fluoro-2-(1,1,2,3,3,3-hexafluoropropoxy)phenyl]-1-methyl-1H-pyrazole-4-carboxamide, (2.27) N-[1-(2,4-dichlorophenyl)-1-methoxypropan-2-yl]-3-(difluoromethyl)-1-methyl-1H-pyrazole-4-carboxamide, (2.28) 5,8-difluoro-N-[2-(2-fluoro-4-{[4-(trifluoromethyl)pyridin-2-yl]oxy}phenyl)ethyl]quinazolin-4-amine, (2.29) benzovindiflupyr, (2.30) N-[(1S,4R)-9-(dichloromethylene)-1,2,3,4-tetrahydro-1,4-methanonaphthalen-5-yl]-3-(difluoromethyl)-1-methyl-1H-pyrazole-4-carboxamide, (2.31) N-[(1R,4S)-9-(dichloromethylene)-1,2,3,4-tetrahydro-1,4-methanonaphthalen-5-yl]-3-(difluoromethyl)-1-methyl-1H-pyrazole-4-carboxamide, (2.32) 3-(difluoromethyl)-1-methyl-N-(1,1,3-trimethyl-2,3-dihydro-1H-inden-4-yl)-1H-pyrazole-4-carboxamide, (2.33) 1,3,5-trimethyl-N-(1,1,3-trimethyl-2,3-dihydro-1H-inden-4-yl)-1H-pyrazole-4-carboxamide, (2.34) 1-methyl-3-(trifluoromethyl)-N-(1,1,3-trimethyl-2,3-dihydro-1H-inden-4-yl)-1H-pyrazole-4-carboxamide, (2.35) 1-methyl-3-(trifluoromethyl)-N-[(3R)-1,1,3-trimethyl-2,3-dihydro-1H-inden-4-yl]-1H-pyrazole-4-carboxamide, (2.36) 1-methyl-3-(trifluoromethyl)-N-[(3S)-1,1,3-trimethyl-2,3-dihydro-1H-inden-4-yl]-1H-pyrazole-4-carboxamide, (2.37) 3-(difluoromethyl)-1-methyl-N-[(3S)-1,1,3-trimethyl-2,3-dihydro-1H-inden-4-yl]-1H-pyrazole-4-carboxamide, (2.38) 3-(difluoromethyl)-1-methyl-N-[(3R)-1,1,3-trimethyl-2,3-dihydro-1H-inden-4-yl]-1H-pyrazole-4-carboxamide, (2.39) 1,3,5-trimethyl-N-[(3R)-1,1,3-trimethyl-2,3-dihydro-1H-inden-4-yl]-1H-pyrazole-4-carboxamide, (2.40) 1,3,5-trimethyl-N-[(3S)-1,1,3-trimethyl-2,3-dihydro-1H-inden-4-yl]-1H-pyrazole-4-carboxamide, (2.41) benodanil, (2.42) 2-chloro-N-(1,1,3-trimethyl-2,3-dihydro-1H-inden-4-yl)pyridine-3-carboxamide, (2.43) Isofetamid.
3) Inhibitors of the respiratory chain at complex III, for example (3.1) ametoctradin, (3.2) amisulbrom, (3.3) azoxystrobin, (3.4) cyazofamid, (3.5) coumethoxystrobin, (3.6) coumoxystrobin, (3.7) dimoxystrobin, (3.8) enoxastrobin, (3.9) famoxadone, (3.10) fenamidone, (3.11) flufenoxystrobin, (3.12) fluoxastrobin, (3.13) kresoxim-methyl, (3.14) metominostrobin, (3.15) orysastrobin, (3.16) picoxystrobin, (3.17) pyraclostrobin, (3.18) pyrametostrobin, (3.19) pyraoxystrobin, (3.20) pyribencarb, (3.21) triclopyricarb, (3.22) trifloxystrobin, (3.23) (2E)-2-(2-{[6-(3-chloro-2-methylphenoxy)-5-fluoropyrimidin-4-yl]oxy}phenyl)-2-(methoxyimino)-N-methylacetamide, (3.24) (2E)-2-(methoxyimino)-N-methyl-2-(2-{[({(1E)-1-[3-(trifluoromethyl)phenyl]ethylidene}amino)oxy]methyl}phenyl)acetamide, (3.25) (2E)-2-(methoxyimino)-N-methyl-2-{2-[(E)-({1-[3-(trifluoromethyl)phenyl]ethoxy}imino)methyl]phenyl}acetamide, (3.26) (2E)-2-{2-[({[(1E)-1-(3-{[(E)-1-fluoro-2-phenylvinyl]oxy}phenyl)ethylidene]amino}oxy)methyl]phenyl}-2-(methoxyimino)-N-methylacetamide, (3.27) Fenaminostrobin, (3.28) 5-methoxy-2-methyl-4-(2-{[({(1E)-1-[3-(trifluoromethyl)phenyl]ethylidene}amino)oxy]methyl}phenyl)-2,4-dihydro-3H-1,2,4-triazol-3-one, (3.29) methyl (2E)-2-{2-[({cyclopropyl[(4-methoxyphenyl)imino]methyl}sulfanyl)methyl]phenyl}-3-methoxyacrylate, (3.30) N-(3-ethyl-3,5,5-trimethylcyclohexyl)-3-formamido-2-hydroxybenzamide, (3.31) 2-{2-[(2,5-dimethylphenoxy)methyl]phenyl}-2-methoxy-N-methylacetamide, (3.32) 2-{2-[(2,5-dimethylphenoxy)methyl]phenyl}-2-methoxy-N-methylacetamide.
4) Inhibitors of the mitosis and cell division, for example (4.1) benomyl, (4.2) carbendazim, (4.3) chlorfenazole, (4.4) diethofencarb, (4.5) ethaboxam, (4.6) fluopicolide, (4.7) fuberidazole, (4.8) pencycuron, (4.9) thiabendazole, (4.10) thiophanate-methyl, (4.11) thiophanate, (4.12) zoxamide, (4.13) 5-chloro-7-(4-methylpiperidin-1-yl)-6-(2,4,6-trifluorophenyl)[1,2,4]triazolo[1,5-a]pyrimidine, (4.14) 3-chloro-5-(6-chloropyridin-3-yl)-6-methyl-4-(2,4,6-trifluorophenyl)pyridazine.
5) Compounds capable to have a multisite action, for example (5.1) bordeaux mixture, (5.2) captafol, (5.3) captan, (5.4) chlorothalonil, (5.5) copper hydroxide, (5.6) copper naphthenate, (5.7) copper oxide, (5.8) copper oxychloride, (5.9) copper (2+) sulfate, (5.10) dichlofluanid, (5.11) dithianon, (5.12) dodine, (5.13) dodine free base, (5.14) ferbam, (5.15) fluorofolpet, (5.16) folpet, (5.17) guazatine, (5.18) guazatine acetate, (5.19) iminoctadine, (5.20) iminoctadine albesilate, (5.21) iminoctadine triacetate, (5.22) mancopper, (5.23) mancozeb, (5.24) maneb, (5.25) metiram, (5.26) metiram zinc, (5.27) oxine-copper, (5.28) propamidine, (5.29) propineb, (5.30) sulfur and sulfur preparations including calcium polysulfide, (5.31) thiram, (5.32) tolylfluanid, (5.33) zineb, (5.34) ziram, (5.35) anilazine.

6) Compounds capable to induce a host defence, for example (6.1) acibenzolar-S-methyl, (6.2) isotianil, (6.3) probenazole, (6.4) tiadinil, (6.5) laminarin.

7) Inhibitors of the amino acid and/or protein biosynthesis, for example (7.1) andoprim, (7.2) blasticidin-S, (7.3) cyprodinil, (7.4) kasugamycin, (7.5) kasugamycin hydrochloride hydrate, (7.6) mepanipyrim, (7.7) pyrimethanil, (7.8) 3-(5-fluoro-3,3,4,4-tetramethyl-3,4-dihydroisoquinolin-1-yl)quinoline, (7.9) oxytetracycline, (7.10) streptomycin.

8) Inhibitors of the ATP production, for example (8.1) fentin acetate, (8.2) fentin chloride, (8.3) fentin hydroxide, (8.4) silthiofam.

9) Inhibitors of the cell wall synthesis, for example (9.1) benthiavalicarb, (9.2) dimethomorph, (9.3) flumorph, (9.4) iprovalicarb, (9.5) mandipropamid, (9.6) polyoxins, (9.7) polyoxorim, (9.8) validamycin A, (9.9) valifenalate, (9.10) polyoxin B.

10) Inhibitors of the lipid and membrane synthesis, for example (10.1) biphenyl, (10.2) chloroneb, (10.3) dicloran, (10.4) edifenphos, (10.5) etridiazole, (10.6) iodocarb, (10.7) iprobenfos, (10.8) isoprothiolane, (10.9) propamocarb, (10.10) propamocarb hydrochloride, (10.11) prothiocarb, (10.12) pyrazophos, (10.13) quintozene, (10.14) tecnazene, (10.15) tolclofos-methyl.

11) Inhibitors of the melanin biosynthesis, for example (11.1) carpropamid, (11.2) diclocymet, (11.3) fenoxanil, (11.4) phthalide, (11.5) pyroquilon, (11.6) tricyclazole, (11.7) 2,2,2-trifluoroethyl {3-methyl-1-[(4-methylbenzoyl)amino]butan-2-yl}carbamate.

12) Inhibitors of the nucleic acid synthesis, for example (12.1) benalaxyl, (12.2) benalaxyl-M (kiralaxyl), (12.3) bupirimate, (12.4) clozylacon, (12.5) dimethirimol, (12.6) ethirimol, (12.7) furalaxyl, (12.8) hymexazol, (12.9) metalaxyl, (12.10) metalaxyl-M (mefenoxam), (12.11) ofurace, (12.12) oxadixyl, (12.13) oxolinic acid, (12.14) octhilinone.

13) Inhibitors of the signal transduction, for example (13.1) chlozolinate, (13.2) fenpiclonil, (13.3) fludioxonil, (13.4) iprodione, (13.5) procymidone, (13.6) quinoxyfen, (13.7) vinclozolin, (13.8) proquinazid.

14) Compounds capable to act as an uncoupler, for example (14.1) binapacryl, (14.2) dinocap, (14.3) ferimzone, (14.4) fluazinam, (14.5) meptyldinocap.

15) Further compounds, for example (15.1) benthiazole, (15.2) bethoxazin, (15.3) capsimycin, (15.4) carvone, (15.5) chinomethionat, (15.6) pyriofenone (chlazafenone), (15.7) cufraneb, (15.8) cyflufenamid, (15.9) cymoxanil, (15.10) cyprosulfamide, (15.11) dazomet, (15.12) debacarb, (15.13) dichlorophen, (15.14) diclomezine, (15.15) difenzoquat, (15.16) difenzoquat metilsulfate, (15.17) diphenylamine, (15.18) ecomate, (15.19) fenpyrazamine, (15.20) flumetover, (15.21) fluoroimide, (15.22) flusulfamide, (15.23) flutianil, (15.24) fosetyl-aluminium, (15.25) fosetyl-calcium, (15.26) fosetyl-sodium, (15.27) hexachlorobenzene, (15.28) irumamycin, (15.29) methasulfocarb, (15.30) methyl isothiocyanate, (15.31) metrafenone, (15.32) mildiomycin, (15.33) natamycin, (15.34) nickel dimethyldithiocarbamate, (15.35) nitrothal-isopropyl, (15.37) oxamocarb, (15.38) oxyfenthiin, (15.39) pentachlorophenol and salts, (15.40) phenothrin, (15.41) phosphorous acid and its salts, (15.42) propamocarb-fosetylate, (15.43) propanosine-sodium, (15.44) pyrimorph, (15.45) (2E)-3-(4-tert-butyl-phenyl)-3-(2-chloropyridin-4-yl)-1-(morpholin-4-yl)prop-2-en-1-one, (15.46) (2Z)-3-(4-tert-butylphenyl)-3-(2-chloropyridin-4-yl)-1-(morpholin-4-yl)prop-2-en-1-one, (15.47) pyrrolnitrine, (15.48) tebufloquin, (15.49) tecloftalam, (15.50) tolnifanide, (15.51) triazoxide, (15.52) trichlamide, (15.53) zarilamid, (15.54) (3S,6S,7R,8R)-8-benzyl-3-[({3-[(isobutyryloxy)methoxy]-4-methoxypyridin-2-yl}carbonyl)amino]-6-methyl-4,9-dioxo-1,5-dioxonan-7-yl 2-methylpropanoate, (15.55) 1-(4-{4-[(5R)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.56) 1-(4-{4-[(5S)-5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.57) 1-(4-{4-[5-(2,6-difluorophenyl)-4,5-dihydro-1,2-oxazol-3-yl]-1,3-thiazol-2-yl}piperidin-1-yl)-2-[5-methyl-3-(trifluoromethyl)-1H-pyrazol-1-yl]ethanone, (15.58) 1-(4-methoxyphenoxy)-3,3-dimethylbutan-2-yl 1H-imidazole-1-carboxylate, (15.59) 2,3,5,6-tetrachloro-4-(methylsulfonyl)pyridine, (15.60) 2,3-dibutyl-6-chlorothieno[2,3-d]pyrimidin-4(3H)-one, (15.61) 2,6-dimethyl-1H,5H-[1,4]dithiino[2,3-c:5,6-c']dipyrrole-1,3,5,7(2H,6H)-tetrone, (15.62) 2-[5-methyl-3-(trifluoromethyl)-1H-pyrazol-1-yl]-1-(4-{4-[(5R)-5-phenyl-4,5-dihydro-1,2-oxazol-3-yl]-1,3-thiazol-2-yl}piperidin-1-yl)ethanone, (15.63) 2-[5-methyl-3-(trifluoromethyl)-1H-pyrazol-1-yl]-1-(4-{4-[(5S)-5-phenyl-4,5-dihydro-1,2-oxazol-3-yl]-1,3-thiazol-2-yl}piperidin-1-yl)ethanone, (15.64) 2-[5-methyl-3-(trifluoromethyl)-1H-pyrazol-1-yl]-1-{4-[4-(5-phenyl-4,5-dihydro-1,2-oxazol-3-yl)-1,3-thiazol-2-yl]piperidin-1-yl}ethanone, (15.65) 2-butoxy-6-iodo-3-propyl-4H-chromen-4-one, (15.66) 2-chloro-5-[2-chloro-1-(2,6-difluoro-4-methoxyphenyl)-4-methyl-1H-imidazol-5-yl]pyridine, (15.67) 2-phenylphenol and salts, (15.68) 3-(4,4,5-trifluoro-3,3-dimethyl-3,4-dihydroisoquinolin-1-yl)quinoline, (15.69) 3,4,5-trichloropyridine-2,6-dicarbonitrile, (15.70) 3-chloro-5-(4-chlorophenyl)-4-(2,6-difluorophenyl)-6-methylpyridazine, (15.71) 4-(4-chlorophenyl)-5-(2,6-difluorophenyl)-3,6-dimethylpyridazine, (15.72) 5-amino-1,3,4-thiadiazole-2-thiol, (15.73) 5-chloro-N'-phenyl-N'-(prop-2-yn-1-yl)thiophene-2-sulfonohydrazide, (15.74) 5-fluoro-2-[(4-fluorobenzyl)oxy]pyrimidin-4-amine, (15.75) 5-fluoro-2-[(4-methylbenzyl)oxy]pyrimidin-4-amine, (15.76) 5-methyl-6-octyl[1,2,4]triazolo[1,5-a]pyrimidin-7-amine, (15.77) ethyl (2Z)-3-amino-2-cyano-3-phenylacrylate, (15.78) N'-(4-{[3-(4-chlorobenzyl)-1,2,4-thiadiazol-5-yl]oxy}-2,5-dimethylphenyl)-N-ethyl-N-methylimidoformamide, (15.79) N-(4-chlorobenzyl)-3-[3-methoxy-4-(prop-2-yn-1-yloxy)phenyl]propanamide, (15.80) N-[(4-chlorophenyl)(cyano)methyl]-3-[3-methoxy-4-(prop-2-yn-1-yloxy)phenyl]propanamide, (15.81) N-[(5-bromo-3-chloropyridin-2-yl)methyl]-2,4-dichloronicotinamide, (15.82) N-[1-(5-bromo-3-chloropyridin-2-yl)ethyl]-2,4-dichloronicotinamide, (15.83) N-[1-(5-bromo-3-chloropyridin-2-yl)ethyl]-2-fluoro-4-iodonicotinamide, (15.84) N-{(E)-[(cyclopropylmethoxy)imino][6-(difluoromethoxy)-2,3-difluorophenyl]methyl}-2-phenylacetamide, (15.85) N—{(Z)-[(cyclopropylmethoxy)imino][6-(difluoromethoxy)-2,3-difluorophenyl]methyl}-2- phenylacetamide, (15.86) N'-{4-[(3-tert-butyl-4-cyano-1,2-thiazol-5-yl)oxy]-2-chloro-5-methylphenyl}-N-ethyl-N-methylimidoformamide, (15.87) N-methyl-2-(1-{[5-methyl-3-(trifluoromethyl)-1H-pyrazol-1-yl]acetyl}piperidin-4-yl)-N-(1,2,3,4-tetrahydronaphthalen-1-yl)-1,3-thiazole-4-carboxamide, (15.88) N-methyl-2-(1-{[5-methyl-3-(trifluoromethyl)-1H-pyrazol-1-yl]acetyl}piperidin-4-yl)-N-[(1R)-1,2,3,4-tetrahydronaphthalen-1-yl]-1,3-thiazole-4-carboxamide, (15.89) N-methyl-2-(1-{[5-methyl-3-(trifluoromethyl)-1H-pyrazol-1-yl]acetyacetyl}piperidin-4-yl)-N-[(1 S)-1,2,3,4-tetrahydronaphthalen-1-yl]-1,3-thiazole-4-carboxamide, (15.90) pentyl {6-[({1 [(1-methyl-1H-tetrazol-5-yl)(phenyl)methylene]amino}oxy)methyl]pyridin-2-yl}carbamate, (15.91) phenazine-1-carboxylic acid, (15.92) quinolin-8-ol, (15.93) quinolin-8-ol sulfate (2:1), (15.94) tert-butyl {6-[({[(1-methyl-1H-tetrazol-5-yl)(phenyl)methylene]amino}oxy)methyl]pyridin-2-yl}carbamate, (15.95) 1-methyl-3-(trifluoromethyl)-N-[2'-(trifluoromethyl)biphenyl-2-yl]-1H-pyrazole-4-carboxamide, (15.96) N-(4'-chlorobiphenyl-2-yl)-3-(difluoromethyl)-1-methyl-1H-pyrazole-4-carboxamide, (15.97) N-(2',4'-dichlorobiphenyl-2-yl)-3-(difluoromethyl)-1-methyl-1H-pyrazole-4-carboxamide, (15.98) 3-(difluoromethyl)-1-methyl-N-[4'-(trifluoromethyl)biphenyl-2-yl]-1H-pyrazole-4-carboxamide, (15.99) N-(2',5'-difluorobiphenyl-2-yl)-1-methyl-3-(trifluoromethyl)-1H-pyrazole-4-carboxamide, (15.100) 3-(difluoromethyl)-1-methyl-N-[4'-(prop-1-yn-1-yl)biphenyl-2-yl]-1H-pyrazole-4-carboxamide, (15.101) 5-fluoro-1,3-dimethyl-N-[4'-(prop-1-yn-1-yl)biphenyl-2-yl]-1H-pyrazole-4-carboxamide, (15.102) 2-chloro-N-[4'-(prop-1-yn-1-yl)biphenyl-2-yl]nicotinamide, (15.103) 3-(difluoromethyl)-N-[4'-(3,3-dimethylbut-1-yn-1-yl)biphenyl-2-yl]-1-methyl-1H-pyrazole-4-carboxamide, (15.104) N-[4'-(3,3-dimethylbut-1-yn-1-yl)biphenyl-2-yl]-5-fluoro-1,3-dimethyl-1H-pyrazole-4-carboxamide, (15.105) 3-(difluoromethyl)-N-(4'-ethynylbiphenyl-2-yl)-1-methyl-1H-pyrazole-4-carboxamide, (15.106) N-(4'-ethynylbiphenyl-2-yl)-5-fluoro-1,3-dimethyl-1H-pyrazole-4-carboxamide, (15.107) 2-chloro-N-(4'-ethynylbiphenyl-2-yl)nicotinamide, (15.108) 2-chloro-N-[4'-(3,3-dimethylbut-1-yn-1-yl)biphenyl-2-yl]nicotinamide, (15.109) 4-(difluoromethyl)-2-methyl-N-[4'-(trifluoromethyl)biphenyl-2-yl]-1,3-thiazole-5-carboxamide, (15.110) 5-fluoro-N-[4'-(3-hydroxy-3-methylbut-1-yn-1-yl)biphenyl-2-yl]-1,3-dimethyl-1H-pyrazole-4-carboxamide, (15.111) 2-chloro-N-[4'-(3-hydroxy-3-methylbut-1-yn-1-yl)biphenyl-2-yl]nicotinamide, (15.112) 3-(difluoromethyl)-N-[4'-(3-methoxy-3-methylbut-1-yn-1-yl)biphenyl-2-yl]-1-methyl-1H-pyrazole-4-carboxamide, (15.113) 5-fluoro-N-[4'-(3-methoxy-3-methylbut-1-yn-1-yl)biphenyl-2-yl]-1,3-dimethyl-1H-pyrazole-4-carboxamide, (15.114) 2-chloro-N-[4'-(3-methoxy-3-methylbut-1-yn-1-yl)biphenyl-2-yl]nicotinamide, (15.115) (5-bromo-2-methoxy-4-methylpyridin-3-yl)(2,3,4-trimethoxy-6-methylphenyl)methanone, (15.116) N-[2-(4-{[3-(4-chlorophenyl)prop-2-yn-1-yl]oxy}-3-methoxyphenyl)ethyl]-N2-(methylsulfonyl)valinamide, (15.117) 4-oxo-4-[(2-phenylethyl)amino]butanoic acid, (15.118) but-3-yn-1-yl {6-[({[(Z)-(1-methyl-1H-tetrazol-5-yl)(phenyl)methylene]amino}oxy)methyl]pyridin-2-yl}carbamate, (15.119) 4-amino-5-fluoropyrimidin-2-ol (tautomeric form: 4-amino-5-fluoropyrimidin-2(1H)-one), (15.120) propyl 3,4,5-trihydroxybenzoate, (15.121) 1,3-dimethyl-N-(1,1,3-trimethyl-2,3-dihydro-1H-inden-4-yl)-1H-pyrazole-4-carboxamide, (15.122) 1,3-dimethyl-N-[(3R)-1,1,3-trimethyl-2,3-dihydro-1H-inden-4-yl]-1H-pyrazole-4-carboxamide, (15.123) 1,3-dimethyl-N-[(3S)-1,1,3-trimethyl-2,3-dihydro-1H-inden-4-yl]-1H-pyrazole-4-carboxamide, (15.124) [3-(4-chloro-2-fluorophenyl)-5-(2,4-difluorophenyl)-1,2-oxazol-4-yl](pyridin-3-yl)methanol, (15.125) (S)-[3-(4-chloro-2-fluorophenyl)-5-(2,4-difluorophenyl)-1,2-oxazol-4-yl](pyridin-3-yl)methanol, (15.126) (R)-[3-(4-chloro-2-fluorophenyl)-5-(2,4-difluorophenyl)-1,2-oxazol-4-yl](pyridin-3-yl)methanol, (15.127) 2-{[3-(2-chlorophenyl)-2-(2,4-difluorophenyl)oxiran-2-yl]methyl}-2,4-dihydro-3H-1,2,4-triazole-3-thione, (15.128) 1-{[3-(2-chlorophenyl)-2-(2,4-difluorophenyl)oxiran-2-yl]methyl}-1H-1,2,4-triazol-5-yl thiocyanate, (15.129) 5-(allylsulfanyl)-1-{[3-(2-chlorophenyl)-2-(2,4-difluorophenyl)oxiran-2-yl]methyl}-1H-1,2,4-triazole, (15.130) 2-[1-(2,4-dichlorophenyl)-5-hydroxy-2,6,6-trimethylheptan-4-yl]-2,4-dihydro-3H-1,2,4-triazole-3-thione, (15.131) 2-{[rel (2R,3S)-3-(2-chlorophenyl)-2-(2,4-difluorophenyl)oxiran-2-yl]methyl}-2,4-dihydro-3H-1,2,4-triazole-3-thione, (15.132) 2-{[rel(2R,3R)-3-(2-chlorophenyl)-2-(2,4-difluorophenyl)oxiran-2-yl]methyl}-2,4-dihydro-3H-1,2,4-triazole-3-thione, (15.133) 1-{[rel(2R,3S)-3-(2-chlorophenyl)-2-(2,4-difluorophenyl)oxiran-2-yl]methyl}-1H-1,2,4-triazol-5-yl thiocyanate, (15.134) 1-{[rel(2R,3R)-3-(2-chlorophenyl)-2-(2,4-difluorophenyl)oxiran-2-yl]methyl}-1H-1,2,4-triazol-5-yl thiocyanate, (15.135) 5-(allylsulfanyl)-1-{[rel(2R,3S)-3-(2-chlorophenyl)-2-(2,4-difluorophenyl)oxiran-2-yl]methyl}-1H-1,2,4-triazole, (15.136) 5-(allylsulfanyl)-1-{[rel(2R,3R)-3-(2-chlorophenyl)-2-(2,4-difluorophenyl)oxiran-2-yl]methyl}-1H-1,2,4-triazole, (15.137) 2-[(2S,4S,5S)-1-(2,4-dichlorophenyl)-5-hydroxy-2,6,6-trimethylheptan-4-yl]-2,4-dihydro-3H-1,2,4-triazole-3-thione, (15.138) 2-[(2R,4S,5S)-1-(2,4-dichlorophenyl)-5-hydroxy-2,6,6-trimethylheptan-4-yl]-2,4-dihydro-3H-1,2,4-triazole-3-thione, (15.139) 2-[(2R,4R,5R)-1-(2,4-dichlorophenyl)-5-hydroxy-2,6,6-trimethylheptan-4-yl]-2,4-dihydro-3H-1,2,4-triazole-3-thione, (15.140) 2-[(2S,4R,5R)-1-(2,4-dichlorophenyl)-5-hydroxy-2,6,6-trimethylheptan-4-yl]-2,4-dihydro-3H-1,2,4-triazole-3-thione, (15.141) 2-[(2S,4S,5R)-1-(2,4-dichlorophenyl)-5-hydroxy-2,6,6-trimethylheptan-4-yl]-2,4-dihydro-3H-1,2,4-triazole-3-thione, (15.142) 2-[(2R,4S,5R)-1-(2,4-dichlorophenyl)-5-hydroxy-2,6,6-trimethylheptan-4-yl]-2,4-dihydro-3H-1,2,4-triazole-3-thione, (15.143) 2-[(2R,4R,5S)-1-(2,4-dichlorophenyl)-5-hydroxy-2,6,6-trimethylheptan-4-yl]-2,4-dihydro-3H-1,2,4-triazole-3-thione, (15.144) 2-[(2S,4R,5S)-1-(2,4-dichlorophenyl)-5-hydroxy-2,6,6-trimethylheptan-4-yl]-2,4-dihydro-3H-1,2,4-triazole-3-thione, (15.145) 2-fluoro-6-(trifluoromethyl)-N-(1,1,3-trimethyl-2,3-dihydro-1H-inden-4-yl)benzamide, (15.146) 2-(6-benzylpyridin-2-yl)quinazoline, (15.147) 2-[6-(3-fluoro-4-methoxyphenyl)-5-methylpyridin-2-yl]quinazoline, (15.148) 3-(4,4-difluoro-3,3-dimethyl-3,4-dihydroisoquinolin-1-yl)quinoline, (15.149) Abscisic acid, (15.150) 3-(difluoromethyl)-N-methoxy-1-methyl-N-[1-(2,4,6-trichlorophenyl)propan-2-yl]-1H-pyrazole-4-carboxamide, (15.151) N'-[5-bromo-6-(2,3-dihydro-1H-inden-2-yloxy)-2-methylpyridin-3-yl]-N-ethyl-N-methylimidoformamide, (15.152) N'-{5-bromo-6-[1-(3,5-difluorophenyl)ethoxy]-2-methylpyridin-3-yl}-N-ethyl-N-methylimidoformamide, (15.153) N'-{5-bromo-6-[(1R)-1-(3,5-difluorophenyl)ethoxy]-2-methylpyridin-3-yl}-N-ethyl-N-methylimidoformamide, (15.154) N'-{5-bromo-6-[(1S)-1-(3,5-difluorophenyl)ethoxy]-2- methylpyridin-3-yl}-N-ethyl-N-methylimidoformamide, (15.155) N'-{5-bromo-6-[(cis-4-isopropylcyclohexyl)oxy]-2-methylpyridin-3-yl}-N-ethyl-N-methylimidoformamide, (15.156) N'-{5-bromo-6-[(trans-4-isopropylcyclohexyl)oxy]-2-methylpyridin-3-yl}-N-ethyl-N-methylimidoformamide, (15.157) N-cyclopropyl-3-(difluoromethyl)-5-fluoro-N-(2-isopropylbenzyl)-1-methyl-1H-pyrazole-4-carboxamide, (15.158) N-cyclopropyl-N-(2-cyclopropylbenzyl)-3-(difluoromethyl)-5-fluoro-1-methyl-1H-pyrazole-4-carboxamide, (15.159) N-(2-tert-butylbenzyl)-N-cyclopropyl-3-(difluoromethyl)-5-fluoro-1-methyl-1H-pyrazole-4-carboxamide, (15.160) N-(5-chloro-2-ethylbenzyl)-N-cyclopropyl-3-(difluoromethyl)-5-fluoro-1-methyl-1H-pyrazole-4-carboxamide, (15.161) N-(5-chloro-2-isopropylbenzyl)-N-cyclopropyl-3-(difluoromethyl)-5-fluoro-1-methyl-1H-pyrazole-4-carboxamide, (15.162) N-cyclopropyl-3-(difluoromethyl)-N-(2-ethyl-5-fluorobenzyl)-5-fluoro-1-methyl-1H-pyrazole-4-carboxamide, (15.163) N-cyclopropyl-3-(difluoromethyl)-5-fluoro-N-(5-fluoro-2-isopropylbenzyl)-1-methyl-1H-pyrazole-4-carboxamide, (15.164) N-cyclopropyl-N-(2-cyclopropyl-5-fluorobenzyl)-3-(difluoromethyl)-5-fluoro-1-methyl-1H-pyrazole-4-carboxamide, (15.165) N-(2-cyclopentyl-5-fluorobenzyl)-N-cyclopropyl-3-(difluoromethyl)-5-fluoro-1-methyl-1H-pyrazole-4-carboxamide, (15.166) N-cyclopropyl-3-(difluoromethyl)-5-fluoro-N-(2-fluoro-6-isopropylbenzyl)-1-methyl-1H-pyrazole-4-carboxamide, (15.167) N-cyclopropyl-3-(difluoromethyl)-N-(2-ethyl-5-methylbenzyl)-5-fluoro-1-methyl-1H-pyrazole-4-carboxamide, (15.168) N-cyclopropyl-3-(difluoromethyl)-5-fluoro-N-(2-isopropyl-5-methylbenzyl)-1-methyl-1H-pyrazole-4-carboxamide, (15.169) N-cyclopropyl-N-(2-cyclopropyl-5-methylbenzyl)-3-(difluoromethyl)-5-fluoro-1-methyl-1H-pyrazole-4-carboxamide, (15.170) N-(2-tert-butyl-5-methylbenzyl)-N-cyclopropyl-3-(difluoromethyl)-5-fluoro-1-methyl-1H-pyrazole-4-carboxamide, (15.171) N-[5-chloro-2-(trifluoromethyl)benzyl]-N-cyclopropyl-3-(difluoromethyl)-5-fluoro-1-methyl-1H-pyrazole-4-carboxamide, (15.172) N-cyclopropyl-3-(difluoromethyl)-5-fluoro-1-methyl-N-[5-methyl-2-(trifluoromethyl)benzyl]-1H-pyrazole-4-carboxamide, (15.173) N-[2-chloro-6-(trifluoromethyl)benzyl]-N-cyclopropyl-3-(difluoromethyl)-5-fluoro-1-methyl-1H-pyrazole-4-carboxamide, (15.174) N-[3-chloro-2-fluoro-6-(trifluoromethyl)benzyl]-N-cyclopropyl-3-(difluoromethyl)-5-fluoro-1-methyl-1H-pyrazole-4-carboxamide, (15.175) N-cyclopropyl-3-(difluoromethyl)-N-(2-ethyl-4,5-dimethylbenzyl)-5-fluoro-1-methyl-1H-pyrazole-4-carboxamide, (15.176) N-cyclopropyl-3-(difluoromethyl)-5-fluoro-N-(2-isopropylbenzyl)-1-methyl-1H-pyrazole-4-carbothioamide, (15.177) 3-(difluoromethyl)-N-(7-fluoro-1,1,3-trimethyl-2,3-dihydro-1H-inden-4-yl)-1-methyl-1H-pyrazole-4-carboxamide, (15.178) 3-(difluoromethyl)-N-[(3R)-7-fluoro-1,1,3-trimethyl-2,3-dihydro-1H-inden-4-yl]-1-methyl-1H-pyrazole-4-carboxamide, (15.179) 3-(difluoromethyl)-N-[(3S)-7-fluoro-1,1,3-trimethyl-2,3-dihydro-1H-inden-4-yl]-1-methyl-H-pyrazole-4-carboxamide, (15.180) N'-(2,5-dimethyl-4-phenoxyphenyl)-N-ethyl-N-methylimidoformamide, (15.181) N'-{4-[(4,5-dichloro-1,3-thiazol-2-yl)oxy]-2,5-dimethylphenyl}-N-ethyl-N-methylimidoformamide, (15.182) N-(4-chloro-2,6-difluorophenyl)-4-(2-chloro-4-fluorophenyl)-1,3-dimethyl-1H-pyrazol-5-amine.

Mixtures with insecticides are also particularly advantageous. Examples of suitable insecticide mixing partners can be selected from the list consisting of (1) Acetylcholinesterase (AChE) inhibitors, for example carbamates, e.g. Alanycarb, Aldicarb, Bendiocarb, Benfuracarb, Butocarboxim, Butoxycarboxim, Carbaryl, Carbofuran, Carbosulfan, Ethiofencarb, Fenobucarb, Formetanate, Furathiocarb, Isoprocarb, Methiocarb, Methomyl, Metolcarb, Oxamyl, Pirimicarb, Propoxur, Thiodicarb, Thiofanox, Triazamate, Trimethacarb, XMC and Xylylcarb or organophosphates, e.g. Acephate, Azamethiphos, Azinphos-ethyl, Azinphos-methyl, Cadusafos, Chlorethoxyfos, Chlorfenvinphos, Chlormephos, Chlorpyrifos, Chlorpyrifos-methyl, Coumaphos, Cyanophos, Demeton-S-methyl, Diazinon, Dichlorvos/DDVP, Dicrotophos, Dimethoate, Dimethylvinphos, Disulfoton, EPN, Ethion, Ethoprophos, Famphur, Fenamiphos, Fenitrothion, Fenthion, Fosthiazate, Heptenophos, Imicyafos, Isofenphos, Isopropyl O-(methoxyaminothio-phosphoryl)salicylate, Isoxathion, Malathion, Mecarbam, Methamidophos, Methidathion, Mevinphos, Monocrotophos, Naled, Omethoate, Oxydemeton-methyl, Parathion, Parathion-methyl, Phenthoate, Phorate, Phosalone, Phosmet, Phosphamidon, Phoxim, Pirimiphos-methyl, Profenofos, Propetamphos, Prothiofos, Pyraclofos, Pyridaphenthion, Quinalphos, Sulfotep, Tebupirimfos, Temephos, Terbufos, Tetrachlorvinphos, Thiometon, Triazophos, Trichlorfon and Vamidothion.

(2) GABA-gated chloride channel antagonists, for example cyclodiene organochlorines, e.g. Chlordane and Endosulfan or phenylpyrazoles (fiproles), e.g. Ethiprole and Fipronil.

(3) Sodium channel modulators/voltage-dependent sodium channel blockers, for example pyrethroids, e.g. Acrinathrin, Allethrin, d-cis-trans Allethrin, d-trans Allethrin, Bifenthrin, Bioallethrin, Bioallethrin S-cyclopentenyl isomer, Bioresmethrin, Cycloprothrin, Cyfluthrin, beta-Cyfluthrin, Cyhalothrin, lambda-Cyhalothrin, gamma-Cyhalothrin, Cypermethrin, alpha-Cypermethrin, beta-Cypermethrin, theta-Cypermethrin, zeta-Cypermethrin, Cyphenothrin [(1R)-trans isomers], Deltamethrin, Empenthrin [(EZ)-(1R) isomers), Esfenvalerate, Etofenprox, Fenpropathrin, Fenvalerate, Flucythrinate, Flumethrin, tau-Fluvalinate, Halfenprox, Imiprothrin, Kadethrin, Permethrin, Phenothrin [(1R)-trans isomer), Prallethrin, Pyrethrine (pyrethrum), Resmethrin, Silafluofen, Tefluthrin, Tetramethrin, Tetramethrin [(1R) isomers)], Tralomethrin and Transfluthrin or DDT or Methoxychlor.

(4) Nicotinic acetylcholine receptor (nAChR) agonists, for example neonicotinoids, e.g. Acetamiprid, Clothianidin, Dinotefuran, Imidacloprid, Nitenpyram, Thiacloprid and Thiamethoxam or Nicotine or Sulfoxaflor.

(5) Nicotinic acetylcholine receptor (nAChR) allosteric activators, for example spinosyns, e.g. Spinetoram and Spinosad.

(6) Chloride channel activators, for example avermectins/milbemycins, e.g. Abamectin, Emamectin benzoate, Lepimectin and Milbemectin.

(7) Juvenile hormone mimics, for example juvenile hormon analogues, e.g. Hydroprene, Kinoprene and Methoprene or Fenoxycarb or Pyriproxyfen.

(8) Miscellaneous non-specific (multi-site) inhibitors, for example alkyl halides, e.g. Methyl bromide and other alkyl halides; or Chloropicrin or Sulfuryl fluoride or Borax or Tartar emetic.

(9) Selective homopteran feeding blockers, e.g. Pymetrozine or Flonicamid.

(10) Mite growth inhibitors, e.g. Clofentezine, Hexythiazox and Diflovidazin or Etoxazole.

(11) Microbial disruptors of insect midgut membranes, e.g. *Bacillus thuringiensis* subspecies *israelensis, Bacillus sphaericus, Bacillus thuringiensis* subspecies *aizawai, Bacillus thuringiensis* subspecies *kurstaki, Bacillus thuringiensis* subspecies *tenebrionis* and BT crop proteins: Cry1Ab, Cry1Ac, Cry1Fa, Cry2Ab, mCry3A, Cry3Ab, Cry3Bb, Cry34/35Ab1.

(12) Inhibitors of mitochondrial ATP synthase, for example Diafenthiuron or organotin miticides, e.g. Azocyclotin, Cyhexatin and Fenbutatin oxide or Propargite or Tetradifon.

(13) Uncouplers of oxidative phoshorylation via disruption of the proton gradient, for example Chlorfenapyr, DNOC and Sulfluramid.

(14) Nicotinic acetylcholine receptor (nAChR) channel blockers, for example Bensultap, Cartap hydrochloride, Thiocyclam and Thiosultap-sodium.

(15) Inhibitors of chitin biosynthesis, type 0, for example Bistrifluron, Chlorfluazuron, Diflubenzuron, Flucycloxuron, Flufenoxuron, Hexaflumuron, Lufenuron, Novaluron, Noviflumuron, Teflubenzuron and Triflumuron.

(16) Inhibitors of chitin biosynthesis, type 1, for example Buprofezin.

(17) Moulting disruptors, for example Cyromazine.

(18) Ecdysone receptor agonists, for example Chromafenozide, Halofenozide, Methoxyfenozide and Tebufenozide.

(19) Octopamine receptor agonists, for example Amitraz.

(20) Mitochondrial complex III electron transport inhibitors, for example Hydramethylnon or Acequinocyl or Fluacrypyrim.

(21) Mitochondrial complex I electron transport inhibitors, for example METI acaricides, e.g. Fenazaquin, Fenpyroximate, Pyrimidifen, Pyridaben, Tebufenpyrad and Tolfenpyrad or Rotenone (Derris).

(22) Voltage-dependent sodium channel blockers, e.g. Indoxacarb or Metaflumizone.

(23) Inhibitors of acetyl CoA carboxylase, for example tetronic and tetramic acid derivatives, e.g. Spirodiclofen, Spiromesifen and Spirotetramat.

(24) Mitochondrial complex IV electron transport inhibitors, for example phosphines, e.g. Aluminium phosphide, Calcium phosphide, Phosphine and Zinc phosphide or Cyanide.

(25) Mitochondrial complex II electron transport inhibitors, for example Cyenopyrafen and Cyflumetofen.

(28) Ryanodine receptor modulators, for example diamides, e.g. Chlorantraniliprole, Cyantraniliprole and Flubendiamide.

Further active ingredients with unknown or uncertain mode of action, for example Afidopyropen, Azadirachtin, Benclothiaz, Benzoximate, Bifenazate, Bromopropylate, Chinomethionat, Cryolite, Dicofol, Diflovidazin, Fluensulfone, Flometoquin, Flufenerim, Flufenoxystrobin, Flufiprole, Fluopyram, Flupyradifurone, Fufenozide, Heptafluthrin, Imidaclothiz, Iprodione, Meperfluthrin, Paichongding, Pyflubumide, Pyrifluquinazon, Pyriminostrobin, Tetramethylfluthrin and Iodomethane; furthermore products based on *Bacillus firmus* (including but not limited to strain CNCM 1-1582, such as, for example, VOTiVO™, BioNem) or one of the following known active compounds: 3-bromo-N-{2-bromo-4-chloro-6-[(1-cyclopropylethyl)carbamoyl]phenyl}-1-(3-chloropyridin-2-yl)-1H-pyrazole-5-carboxamide (known from WO2005/077934) and 1-{2-fluoro-4-methyl-5-[(2,2,2-trifluorethyl)sulfinyl]phenyl}-3-(trifluoromethyl)-1H-1,2,4-triazol-5-amine (known from WO2006/043635), {1'-[(2E)-3-(4-chlorophenyl)prop-2-en-1-yl]-5-fluorospiro [indole-3,4'-piperidin]-1(2H)-yl}(2-chloropyridin-4-yl) methanone (known from WO2003/106457), 2-chloro-N-[2-{1-[(2E)-3-(4-chlorophenyl)prop-2-en-1-yl]piperidin-4-yl}-4-(trifluoromethyl)phenyl]isonicotinamide (known from WO2006/003494), 3-(2,5-dimethylphenyl)-4-hydroxy-8-methoxy-1,8-diazaspiro[4.5]dec-3-en-2-one (known from WO2009/049851), 3-(2,5-dimethylphenyl)-8-methoxy-2-oxo-1,8-diazaspiro[4.5]dec-3-en-4-yl ethyl carbonate (known from WO2009/049851), 4-(but-2-yn-1-yloxy)-6-(3,5-dimethylpiperidin-1-yl)-5-fluoropyrimidine (known from WO2004/099160), 4-(but-2-yn-1-yloxy)-6-(3-chlorophenyl)pyrimidine (known from WO2003/076415), PF1364 (CAS-Reg. No. 1204776-60-2), 4-[5-(3,5-dichlorophenyl)-5-(trifluoromethyl)-4,5-dihydro-1,2-oxazol-3-yl]-2-methyl-N-{2-oxo-2-[(2,2,2-trifluoroethyl)amino]ethyl}benzamide (known from WO2005/085216), 4-{5-[3-chloro-5-(trifluoromethyl)phenyl]-5-(trifluoromethyl)-4,5-dihydro-1,2-oxazol-3-yl}-N-{2-oxo-2-[(2,2,2-trifluoroethyl)amino]ethyl}-1-naphthamide (known from WO2009/002809), methyl 2-[2-({[3-bromo-1-(3-chloropyridin-2-yl)-1H-pyrazol-5-yl]carbonyl}amino)-5-chloro-3-methylbenzoyl]-2-methylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-ethylhydrazinecarboxylate (known from WO2005/085216), methyl 2-[2-({[3-bromo-1-(3-chloropyridin-2-yl)-1H-pyrazol-5-yl]carbonyl}amino)-5-cyano-3-methylbenzoyl]-2-methylhydrazinecarboxylate (known from WO2005/085216), methyl 2-[3,5-dibromo-2-({[3-bromo-1-(3-chloropyridin-2-yl)-1H-pyrazol-5-yl]carbonyl}amino)benzoyl]-2-ethylhydrazinecarboxylate (known from WO2005/085216), 1-(3-chloropyridin-2-yl)-N-[4-cyano-2-methyl-6-(methylcarbamoyl) phenyl]-3-{[5-(trifluoromethyl)-2H-tetrazol-2-yl]methyl}-1H-pyrazole-5-carboxamide (known from WO2010/069502), N-[2-(5-amino-1,3,4-thiadiazol-2-yl)-4-chloro-6-methylphenyl]-3-bromo-1-(3-chloropyridin-2-yl)-1H-pyrazole-5-carboxamide (known from CN102057925), 3-chloro-N-(2-cyanopropan-2-yl)-N-[4-(1,1,1,2,3,3,3-heptafluoropropan-2-yl)-2-methylphenyl]phthalamide (known from WO2012/034472), 8-chloro-N-[(2-chloro-5-methoxyphenyl)sulfonyl]-6-(trifluoromethyl)imidazo[1,2-a]pyridine-2-carboxamide (known from WO2010/129500), 8-chloro-N-[(2-chloro-5-methoxyphenyl)sulfonyl]-6-(trifluoromethyl)imidazo[1,2-a]pyridine-2-carboxamide (known from WO2009/080250), N-[(2E)-1-[(6-chloropyridin-3-yl)methyl]pyridin-2(1H)-ylidene]-2,2,2-trifluoroacetamide (known from WO2012/029672), 1-[(2-chloro-1,3-thiazol-5-yl)methyl]-4-oxo-3-phenyl-4H-pyrido[1,2-a] pyrimidin-1-ium-2-olate (known from WO2009/099929), 1-[(6-chloropyridin-3-yl)methyl]-4-oxo-3-phenyl-4H-pyrido[1,2-a]pyrimidin-1-ium-2-olate (known from WO2009/099929), (5S,8R)-1-[(6-chloropyridin-3-yl) methyl]-9-nitro-2,3,5,6,7,8-hexahydro-1H-5,8-epoxyimidazo[1,2-a]azepine (known from WO2010/069266), (2E)-1-[(6-chloropyridin-3-yl)methyl]-N'-nitro-2-pentylidenehydrazinecarboximidamide (known from WO2010/060231), 4-(3-{2,6-dichloro-4-[(3,3-dichloroprop-2-en-1-yl)oxy]phenoxy}propoxy)-2-methoxy-6-(trifluoromethyl)pyrimidine (known from CN101337940), N-[2-(tert-butylcarbamoyl)-4-chloro-6-methylphenyl]-1-(3-chloropyridin-2-yl)-3-(fluoromethoxy)-1H-pyrazole-5-carboxamide (known from WO2008/134969).

Mixtures with nematicides are also particularly advantageous. Examples of suitable nematicide mixing partners can be selected from the list consisting of Dichloropropene, Metam sodium, Metam potassium, Chloropicrin, Oxamyl, Carbofuran, Fosthiazate, Aldicarb, Fenamiphos, Cadusafos, Abamectin, Cyanamide, Dazomet, Methylbromide, Terbufos, Ethoprophos, Ethylen dibromide, Phorate, Methylisothiocyanate, Thiodicarb, Sodium tetrathiocarbonate, Iprodione, Fluensulfone, Imicyafos, Dimethyl disulfide, Spirotetramate, Fluopyram, 1-{2-fluoro-4-methyl-5-[(2,2,2-trifluoroethyl)sulfinyl]phenyl}-3-(trifluoromethyl)-1H-1,2,4-triazol-5-amine, 8-chloro-N-[(2-chloro-5-methoxyphenyl)sulfonyl]-6-(trifluoromethyl)imidazo[1,2-a]pyridine-2-carboxamide, 8-chloro-N-[(4-cyano-2,5-dimethylphenyl) sulfonyl]-6-(trifluoromethyl)imidazo[1,2-a]pyridine-2-carboxamide, 2-(4-chlorophenyl)-5-(2-thienyl)-1,3,4-oxadiazole, 5-phenyl-2-(2-thienyl)-1,3-oxazole, 5-(4-chlorophenyl)-2-(2-thienyl)-1,3-oxazole, 5-(4-bromophenyl)-2-(2-thienyl)-1,3-oxazole or 2-(4-chlorophenyl)-5-(2-thienyl)-2H-tetrazole.

All named mixing partners can, if their functional groups enable this, optionally form salts with suitable bases or acids.

The active ingredients specified herein by their "common name" are known and described, for example, in the Pesticide Manual ("The Pesticide Manual", 14th Ed., British Crop Protection Council 2006) or can be searched in the internet (e.g. http://www.alanwood.net/pesticides).

The active substances, active substance combinations or compositions according to the invention can also be combined with microbials.

The microbials according to the invention, in combination with good plant tolerance and favourable toxicity to warm-blooded animals and being tolerated well by the environment, are suitable for protecting plants and plant organs, for increasing harvest yields, for improving the quality of the harvested material and for controlling animal pests, in particular insects, arachnids, helminths, nematodes and molluscs, which are encountered in agriculture, in horticulture, in animal husbandry, in forests, in gardens and leisure facilities, in the protection of stored products and of materials, and in the hygiene sector. They can be preferably employed as plant protection agents. They are active against normally sensitive and resistant species and against all or some stages of development. The abovementioned microbials include:

Microbials from the domain Bacteria, microbials from the domain Fungi, insecticidal microbials from the domain Protozoa, insecticidal microbials from the domain Viruses, and microbials from the domain of entomopathogenic nematodes.

The various aspects of the invention will now be illustrated with reference to the following production and use examples in a non limiting manner.

PREPARATION EXAMPLES

It is recognized that some reagents and reaction conditions described above for preparing compounds of formula (I) may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. Protective Groups in Organic Synthesis, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of formula (I). One skilled in the art will also recognize that it may be necessary to perform a combination of the steps illustrated in the above schemes in an order other than that implied by the particular sequence presented to prepare the compounds of formula (I).

One skilled in the art will also recognize that compounds of formula (I) and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Synthesis Examples are, therefore, to be construed as merely illustrative, and not limiting of the disclosure in any way whatsoever. Steps in the following Synthesis Examples illustrate a procedure for each step in an overall synthetic transformation, and the starting material for each step may not have necessarily been prepared by a particular preparative run whose procedure is described in other Examples or Steps.

$^1$H-NMR Data $^1$H-NMR-data were determined with a Bruker Avance 400 equipped with a flow cell (60 µl volume) or with a Bruker AVIII 400 equipped with 1.7 mm cryo-CPTCI probe head or with a Bruker AVII 600 (600.13 MHz) equipped with a cyroTCI probe head or with a Bruker AVIII 600 (601.6 MHz) equipped with a cryo CPMNP probe head with tetramethylsilane as reference (0.0) and the solvents $CD_3CN$, $CDCl_3$, $[D_6]$-DMSO.

$^1$H-NMR-data of selected examples are listed in classic format (chemical shift δ, multiplicity, number of hydrogen atoms) or as NMR-peak-lists.

$^1$H NMR spectra are reported in ppm downfield from tetramethylsilane.

"s" means singlet, "d" means doublet, "dd" means doublet of doublets, "t" means triplet, "q" means quartet, "br s" means broad singlet, "m" means multiplet.

NMR-Peak-Lists:

If NMR-data of selected examples are provided in form of $^1$H-NMR-peak lists, then for every peak first the chemical shift δ in ppm and then, separated by a blank, the intensity of the signal in round brackets is listed. Between the δ-value—signal intensity pairs are semicolons as delimiters.

The peak list of an example is therefore listed as: $δ_1$ (intensity$_1$); $δ_2$ (intensity$_2$); . . . ; $δ_i$ (intensity$_i$); . . . ; $δ_n$ (intensity$_n$).

Intensity of sharp signals correlates with the height of the signals in a printed example of a NMR spectrum in cm and shows the real relations of signal intensities. From broad signals several peaks or the middle of the signal and their relative intensity in comparison to the most intensive signal in the spectrum can be shown.

For calibrating chemical shift for 1H spectra, we use tetramethylsilane and/or the chemical shift of the solvent used, especially in the case of spectra measured in DMSO. Therefore in NMR peak lists, tetramethylsilane peak can occur but not necessarily.

The 1H-NMR peak lists are similar to classical 1H-NMR prints and contain therefore usually all peaks, which are listed at classical NMR-interpretation.

Additionally they can show like classical 1H-NMR prints signals of solvents, stereoisomers of the target compounds, which are also object of the invention, and/or peaks of impurities.

To show compound signals in the delta-range of solvents and/or water the usual peaks of solvents, for example peaks of DMSO in DMSO-$D_6$ and the peak of water are shown in our 1H-NMR peak lists and have usually on average a high intensity.

The peaks of stereoisomers of the target compounds and/or peaks of impurities have usually on average a lower intensity than the peaks of target compounds (for example with a purity >90%).

Such stereoisomers and/or impurities can be typical for the specific preparation process. Therefore their peaks can help to recognize the reproduction of our preparation process via "side-products-fingerprints".

An expert, who calculates the peaks of the target compounds with known methods (MestreC, ACD-simulation, but also with empirically evaluated expectation values) can isolate the peaks of the target compounds as needed optionally using additional intensity filters. This isolation would be similar to relevant peak picking at classical $^1$H-NMR interpretation.

Further details of NMR-data description with peak lists you find in the publication "Citation of NMR Peaklist Data within Patent Applications" of the Research Disclosure Database Number 564025.

The solvent, in which the NMR-spectrum was measured, is specified in squared brackets.

Synthesis Example 1

Preparation of N-[(2-chloro-5-methoxyphenyl)sulfonyl]-2-(trifluoromethyl)imidazo[2,1-b][1,3]thiazole-6-carboxamide (table 2, example (I-1-1))

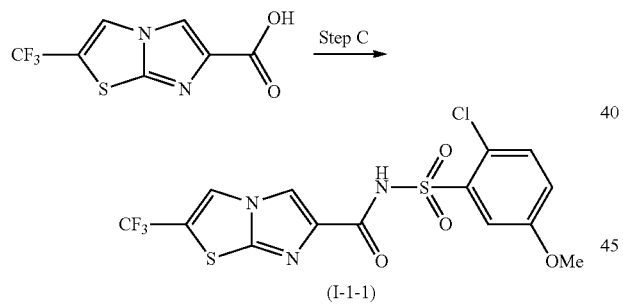

(I-1-1)

To 200 mg 2-(trifluoromethyl)imidazo[2,1-b][1,3]thiazole-6-carboxylic acid (0.84 mmol) was added a solution of 4-(dimethylamino)pyridine (310 mg, 2.54 mmol) and 1-(3-dimethyl-aminopropyl)-3-ethylcarbodiimide hydrochloride (487 mg, 2.54 mmol) in t-butanol (8 mL) and dichloromethane (16 mL). The reaction mixture was stirred for 15 min, 2-chloro-5-methoxybenzenesulfonamide (187 mg, 0.84 mmol) was added, and the reaction mixture was stirred at room temperature overnight. Dichloromethane (200 mL) was then added, the mixture was extracted with 1 N hydrochloric acid (3×100 mL), and the organic phase was separated over a Whatman filter cartridge. The solvent was evaporated and the remaining solid was rinsed with diethyl ether to afford 59 mg (14.6%) of the title compound, a compound of the present invention, as a colorless solid.

$^1$H-NMR, Solvent [$D_6$]-DMSO: δ=12.00 (br s, NH), 8.75 (s, 1H), 8.07 (s, 1H), 7.55 (d, 1H), 7.34 (d, 1H), 7.01-6.98 (dd, 1H), 3.79 (s, 3H).

Preparation of Intermediates of General Formula (VII)

Preparation of ethyl 2-(trifluoromethyl)imidazo[2,1-b][1,3]thiazole-6-carboxylate (VII-1)

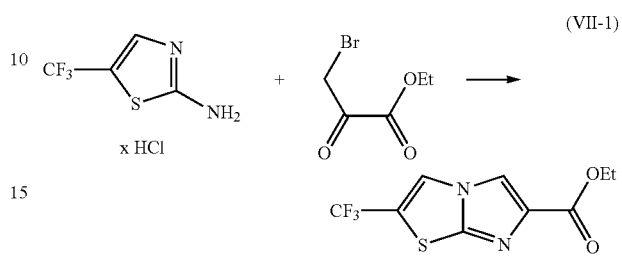

To a solution of 2-amino-5-(trifluoromethyl)thiazole hydrochloride (5 g, 24.4 mmol) in toluene (150 mL) at room temperature was added ethyl bromopyruvate (3.07 mL, 24.4 mmol) dropwise. The reaction mixture was boiled in a Dean-Stark apparatus overnight. The solvent was evaporated and the reaction mixture was then extracted with ethyl acetate (2×100 mL) and washed with water (2×100 mL). The combined ethyl acetate extracts were dried over magnesium sulfate and concentrated under reduced pressure to obtain a solid residue which was chromatographed with a cyclohexane/ethyl acetate gradient on silica gel.

Yield: 2.96 g (45.9%).

Starting from 2-aminothiazoles or 2-aminothiadiazoles of the general formula (V) the following intermediates of general formula (VII) can be made in an analogues manner. The following abbreviations are used in the tables which follow: Me means methyl, Et means ethyl and OMe means methoxy.

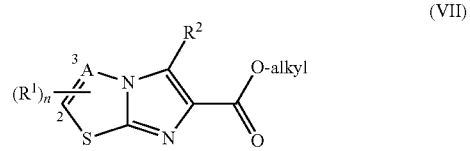

(VII)

| Example | $R^1$ | n | A | $R^2$ | alkyl | Remark |
|---|---|---|---|---|---|---|
| VII-1 | 2-$CF_3$ | 1 | CH | H | Et | NMR |
| VII-2 | 3-$CF_3$ | 1 | C-$R^1$ | H | Et | NMR |
| VII-3 | 2-$C_4H_9$-t | 1 | CH | H | Et | NMR |
| VII-4 | 2-Br | 1 | CH | H | Et | NMR |
| VII-5 | 2-Cl | 1 | CH | H | Et | NMR |
| VII-6 | 2-F | 1 | CH | H | Et | |
| VII-7 | 2-$CH_3$ | 1 | CH | H | Et | |
| VII-8 | 2-Et | 1 | CH | H | Et | |
| VII-9 | 2-Propyl | 1 | CH | H | Et | |
| VII-10 | 2-Isopropyl | 1 | CH | H | Et | NMR |
| VII-11 | 2-Cyclopropyl | 1 | CH | H | Et | |
| VII-12 | 2-$C_2F_5$ | 1 | CH | H | Et | NMR |
| VII-13 | 2-$CF_3$, 3-$CH_3$ | 2 | C-$R^1$ | H | Et | NMR |
| VII-14 | 2-$CF_3$, 3-Et | 2 | C-$R^1$ | H | Et | |
| VII-15 | 2-$CH_3$, 3-$CH_3$ | 2 | C-$R^1$ | H | Et | |
| VII-16 | 2-$CF_3$ | 1 | N | H | Et | |
| VII-17 | 2-$C_2F_5$, 3-$CH_3$ | 2 | C-$R^1$ | H | Et | NMR |
| VII-18 | H | 0 | CH | Br | Et | NMR |
| VII-19 | 2-$SCH_3$ | 1 | CH | H | Et | NMR |
| VII-20 | 2-Si($CH_3$)$_2$ | 1 | CH | H | Et | NMR |
| VII-21 | 2-$CF_3$ | 1 | CH | $CH_3$ | Et | NMR |

| Example | NMR data |
|---|---|
| VII-1 | ¹H-NMR, Solvent [D$_6$]-DMSO, spectrometer: 399.95 MHz: <br> δ = 8.81 (s, 1H), 8.45 (s, 1H), 4.32-4.26 (q, 2H), 1.30 (t, 3H). |
| VII-2 | ¹H-NMR, Solvent [D$_6$]-DMSO, spectrometer: 399.95 MHz: <br> δ = 8.49 (s, 1H), 8.42 (s, 1H), 4.32-4.24 (q, 2H), 1.30 (t, 3H). |
| VII-3 | ¹H-NMR, Solvent [D$_6$]-DMSO, spectrometer: 399.95 MHz: <br> δ = 8.580 (2.3); 7.039 (2.2); 4.307 (0.5); 4.289 (1.6); 4.271 (1.6); 4.253 (0.6); 3.329 (11.2); 2.502 (25.3); 1.397 (8.2); 1.391 (16.0); 1.323 (1.7); 1.306 (3.4); 1.288 (1.7); 1.236 (0.4); 1.219 (0.4); 1.187 (0.4); 0.000 (26.1) |
| VII-4 | ¹H-NMR, Solvent [D$_6$]-DMSO, spectrometer: 399.95 MHz: <br> δ = 9.032 (0.4); 8.934 (0.7); 8.648 (0.5); 8.585 (0.9); 8.382 (0.4); 8.372 (9.4); 8.361 (0.4); 8.317 (0.5); 8.301 (0.5); 8.254 (9.5); 7.656 (1.0); 7.627 (0.3); 7.480 (0.4); 7.460 (0.4); 7.118 (0.3); 6.995 (0.4); 6.015 (0.5); 4.901 (0.7); 4.424 (0.4); 4.407 (0.4); 4.397 (0.7); 4.380 (0.9); 4.375 (0.8); 4.362 (0.9); 4.357 (0.9); 4.344 (0.9); 4.338 (1.0); 4.320 (1.5); 4.303 (1.5); 4.291 (2.9); 4.273 (7.4); 4.256 (7.5); 4.238 (3.1); 4.221 (1.1); 4.204 (1.0); 4.182 (1.0); 4.174 (1.0); 4.153 (1.0); 4.135 (1.2); 4.117 (1.1); 4.099 (0.7); 4.086 (0.6); 4.067 (0.5); 4.038 (0.5); 4.021 (0.4); 3.590 (11.5); 2.676 (0.9); 2.671 (1.3); 2.667 (0.9); 2.542 (0.4); 2.511 (79.6); 2.507 (154.4); 2.502 (198.6); 2.498 (143.8); 2.425 (0.5); 2.334 (1.1); 2.329 (1.4); 2.325 (1.1); 2.300 (0.5); 2.287 (0.9); 1.355 (1.2); 1.350 (1.5); 1.337 (1.8); 1.332 (2.3); 1.328 (2.1); 1.310 (3.8); 1.303 (8.3); 1.292 (3.6); 1.285 (16.0); 1.267 (8.4); 1.245 (2.0); 1.234 (2.0); 1.229 (1.9); 1.216 (2.3); 1.198 (2.5); 1.180 (1.7); 1.159 (1.3); 1.155 (1.2); 1.141 (1.3); 1.136 (1.3); 1.125 (1.2); 1.108 (1.0); 1.091 (0.9); 1.086 (0.8); 1.075 (0.9); 1.063 (0.9); 1.057 (1.0); 1.046 (0.9); 1.039 (0.7); 1.028 (0.6); 1.008 (0.5); 0.871 (0.5); 0.855 (1.8); 0.839 (1.5); 0.834 (0.8); 0.824 (0.5); 0.816 (0.4); 0.808 (0.4); 0.146 (0.4); 0.008 (4.2); 0.000 (88.3); −0.008 (3.6); −0.150 (0.4) |
| VII-5 | ¹H-NMR, Solvent [D$_6$]-DMSO, spectrometer: 399.95 MHz: <br> δ = 9.032 (0.4); 8.934 (0.7); 8.648 (0.5); 8.585 (0.9); 8.382 (0.4); 8.372 (9.4); 8.361 (0.4); 8.317 (0.5); 8.301 (0.5); 8.254 (9.5); 7.656 (1.0); 7.627 (0.3); 7.480 (0.4); 7.460 (0.4); 7.118 (0.3); 6.995 (0.4); 6.015 (0.5); 4.901 (0.7); 4.424 (0.4); 4.407 (0.4); 4.397 (0.7); 4.380 (0.9); 4.375 (0.8); 4.362 (0.9); 4.357 (0.9); 4.344 (0.9); 4.338 (1.0); 4.320 (1.5); 4.303 (1.5); 4.291 (2.9); 4.273 (7.4); 4.256 (7.5); 4.238 (3.1); 4.221 (1.1); 4.204 (1.0); 4.182 (1.0); 4.174 (1.0); 4.153 (1.0); 4.135 (1.2); 4.117 (1.1); 4.099 (0.7); 4.086 (0.6); 4.067 (0.5); 4.038 (0.5); 4.021 (0.4); 3.590 (11.5); 2.676 (0.9); 2.671 (1.3); 2.667 (0.9); 2.542 (0.4); 2.511 (79.6); 2.507 (154.4); 2.502 (198.6); 2.498 (143.8); 2.425 (0.5); 2.334 (1.1); 2.329 (1.4); 2.325 (1.1); 2.300 (0.5); 2.287 (0.9); 1.355 (1.2); 1.350 (1.5); 1.337 (1.8); 1.332 (2.3); 1.328 (2.1); 1.310 (3.8); 1.303 (8.3); 1.292 (3.6); 1.285 (16.0); 1.267 (8.4); 1.245 (2.0); 1.234 (2.0); 1.229 (1.9); 1.216 (2.3); 1.198 (2.5); 1.180 (1.7); 1.159 (1.3); 1.155 (1.2); 1.141 (1.3); 1.136 (1.3); 1.125 (1.2); 1.108 (1.0); 1.091 (0.9); 1.086 (0.8); 1.075 (0.9); 1.063 (0.9); 1.057 (1.0); 1.046 (0.9); 1.039 (0.7); 1.028 (0.6); 1.008 (0.5); 0.871 (0.5); 0.855 (1.8); 0.839 (1.5); 0.834 (0.8); 0.824 (0.5); 0.816 (0.4); 0.808 (0.4); 0.146 (0.4); 0.008 (4.2); 0.000 (88.3); −0.008 (3.6); −0.150 (0.4) |
| VII-10 | ¹H-NMR, Solvent [D$_6$]-DMSO, spectrometer: 399.95 MHz: <br> δ = 8.279 (5.5); 7.725 (3.2); 7.722 (3.4); 4.277 (1.2); 4.259 (3.8); 4.241 (3.8); 4.224 (1.3); 3.330 (12.8); 3.164 (0.6); 3.161 (0.7); 3.147 (0.9); 3.144 (0.9); 3.130 (0.7); 3.127 (0.7); 2.526 (0.4); 2.508 (16.2); 2.504 (21.5); 2.499 (16.6); 1.301 (5.8); 1.297 (15.5); 1.284 (10.5); 1.280 (16.0); 1.266 (4.2); 1.257 (0.8); 1.181 (1.0); 1.164 (1.0); 0.964 (0.5); 0.947 (0.5); 0.008 (0.8); 0.000 (20.9) |
| VII-12 | ¹H-NMR, Solvent [D$_6$]-DMSO, spectrometer: 399.95 MHz: <br> δ = 8.826 (5.0); 8.437 (10.5); 4.324 (2.3); 4.306 (7.2); 4.288 (7.3); 4.270 (2.3); 3.334 (44.9); 2.509 (27.9); 2.505 (35.9); 2.500 (25.8); 1.321 (7.7); 1.304 (16.0); 1.286 (7.4); 0.008 (0.4); 0.000 (10.0); −0.008 (0.4) |
| VII-13 | ¹H-NMR, Solvent [D$_6$]-DMSO, spectrometer: 399.95 MHz: <br> δ = 9.475 (0.4); 8.696 (11.2); 7.526 (0.6); 7.519 (0.5); 6.765 (0.4); 6.751 (0.4); 6.741 (0.5); 6.715 (0.5); 6.645 (0.6); 6.622 (0.6); 6.594 (0.6); 5.903 (0.6); 4.327 (2.4); 4.310 (7.4); 4.292 (7.4); 4.274 (2.4); 2.729 (0.4); 2.725 (0.4); 2.675 (0.4); 2.646 (11.8); 2.642 (11.9); 2.637 (4.8); 2.514 (21.7); 2.510 (41.9); 2.506 (54.1); 2.501 (39.1); 2.497 (18.9); 2.333 (0.4); 2.292 (0.7); 2.227 (12.4); 2.222 (12.4); 2.218 (4.9); 1.360 (0.6); 1.342 (0.4); 1.327 (7.7); 1.309 (16.0); 1.291 (7.5); 0.000 (1.5) |
| VII-16 | ¹H-NMR, Solvent [D$_6$]-DMSO, spectrometer: 399.95 MHz: <br> δ = 9.107 (10.6); 4.345 (2.2); 4.327 (7.1); 4.310 (7.2); 4.292 (2.3); 3.336 (116.5); 3.316 (0.4); 2.672 (0.4); 2.526 (1.3); 2.521 (2.0); 2.512 (23.6); 2.508 (47.5); 2.503 (63.2); 2.499 (47.0); 2.494 (23.3); 2.330 (0.4); 1.332 (7.5); 1.314 (16.0); 1.296 (7.3); 0.008 (0.9); 0.000 (29.0); −0.009 (1.1) |
| VII-17 | ¹H-NMR, Solvent [D$_6$]-DMSO, spectrometer: 399.95 MHz: <br> δ = 8.692 (9.8); 4.331 (2.4); 4.313 (7.3); 4.295 (7.4); 4.277 (2.4); 3.331 (24.1); 2.624 (13.0); 2.508 (35.1); 2.504 (44.4); 2.500 (33.6); 1.398 (0.4); 1.328 (7.8); 1.310 (16.0); 1.292 (7.6); 0.000 (0.8) |
| VII-18 | ¹H-NMR, Solvent [D$_6$]-DMSO, spectrometer: 600 MHz: <br> δ = 7.952 (5.8); 7.944 (6.0); 7.582 (5.7); 7.574 (5.5); 4.304 (2.3); 4.292 (7.3); 4.280 (7.4); 4.268 (2.4); 3.330 (72.3); 2.523 (0.3); 2.520 (0.4); 2.511 (7.5); 2.508 (15.7); 2.505 (21.3); 2.502 (15.2); 2.499 (6.9); 1.320 (7.6); 1.308 (16.0); 1.296 (7.5) |
| VII-19 | ¹H-NMR, Solvent [D$_6$]-DMSO, spectrometer: 399.95 MHz: <br> δ = 8.316 (11.8); 8.079 (11.9); 5.760 (0.4); 4.288 (2.4); 4.270 (7.4); 4.253 (7.5); 4.235 (2.5); 2.672 (0.3); 2.567 (0.6); 2.555 (34.5); 2.527 (0.4); 2.513 (9.9); 2.509 (19.9); 2.505 (26.3); 2.500 (19.7); 2.496 (10.1); 2.423 (0.4); 1.304 (7.8); 1.287 (16.0); 1.269 (7.7); 1.238 (0.3); 1.220 (0.6); 1.203 (0.4); 0.008 (0.6); 0.000 (16.3); −0.008 (0.7) |
| VII-20 | ¹H-NMR, Solvent [D$_6$]-DMSO, spectrometer: 399.95 MHz: <br> δ = 8.332 (2.1); 7.944 (2.0); 4.289 (0.4); 4.271 (1.3); 4.253 (1.3); 4.235 (0.4); 3.326 (10.7); 2.511 (5.4); 2.507 (10.8); 2.503 (14.3); 2.498 (10.6); 2.494 (5.3); 1.309 (1.3); 1.291 (2.8); 1.273 (1.3); 0.353 (0.7); 0.345 (16.0); 0.336 (0.7); 0.000 (2.1) |

| Example | NMR data |
|---|---|
| VII-21 | ¹H-NMR, Solvent [D₆]-DMSO, spectrometer: 399.95 MHz: δ = 1.30 (t, 3H); 2.68 (s, 3H); 4.27 (q, 2H); 8.99 (s, 1H) ppm |

Preparation of Intermediates of General Formula (II)

Preparation of 2-(trifluoromethyl)imidazo[2,1-b][1,3]thiazole-6-carboxylic acid (II-1)

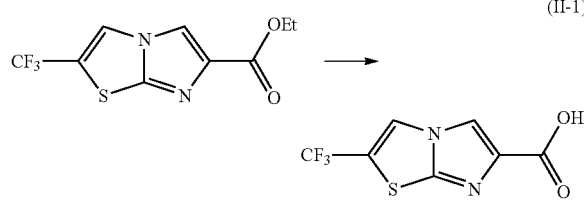

2.9 g (10.9 mmol) ethyl 2-(trifluoromethyl)imidazo[2,1-b][1,3]thiazole-6-carboxylate (VII-1) were dissolved in 65 mL dichloromethane and cooled to −10° C. 55 mL 1M BBr₃ solution in dichloromethane was added dropwise. The reaction mixture was allowed to get warmed to room temperature overnight and subsequently quenched with water. The organic layer was separated, dried over sodium sulfate and the solvent was evaporated. Yield: 430 mg (11.6%) of a solid which has been used for coupling reactions without further purification.

Starting from alkylesters of the general formula (VII) the following intermediates of general formula (II) can be made in an analogues manner:

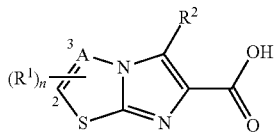

| Example | R¹ | n | A | R² | Remark |
|---|---|---|---|---|---|
| II-1 | 2-CF₃ | 1 | CH | H | NMR |
| II-2 | 3-CF₃ | 1 | C—R¹ | H | NMR |
| II-3 | 2-C₄H₉-t | 1 | CH | H | NMR |
| II-4 | 2-Br | 1 | CH | H | NMR |
| II-5 | 2-Cl | 1 | CH | H | NMR |
| II-6 | 2-F | 1 | CH | H | |
| II-7 | 2-CH₃ | 1 | CH | H | |
| II-8 | 2-Et | 1 | CH | H | |
| II-9 | 2-Propyl | 1 | CH | H | |
| II-10 | 2-Isopropyl | 1 | CH | H | NMR |
| II-11 | 2-Cyclopropyl | 1 | CH | H | |
| II-12 | 2-C₂F₅ | 1 | CH | H | NMR |
| II-13 | 2-CF₃, 3-CH₃ | 2 | C—R¹ | H | NMR |
| II-14 | 2-CF₃, 3-Et | 2 | C—R¹ | H | |
| II-15 | 2-CH₃, 3-CH₃ | 2 | C—R¹ | H | |
| II-16 | 2-CF₃ | 1 | N | H | NMR |
| II-17 | 2-C₂F₅, 3-CH₃ | 2 | C—R¹ | H | |
| II-18 | H | 0 | CH | Br | |
| II-19 | 2-SCH₃ | 1 | CH | H | NMR |
| II-20 | 2-Si(CH₃)₂ | 1 | CH | H | |
| II-21 | 2-CF₃ | 1 | CH | Br | NMR |
| II-22 | 2-CF₃ | 1 | CH | Cl | NMR |
| II-23 | 2-CF₃ | 1 | CH | I | NMR |
| II-24 | 2-CF₃ | 1 | CH | CH₃ | NMR |

| Example | NMR data |
|---|---|
| II-1 | ¹H-NMR, Solvent [D₆]-DMSO, spectrometer: 399.95 MHz: δ = 12.8 (br s, COOH), 8.81 (s, 1H), 8.38 (s, 1H). |
| II-2 | ¹H-NMR, Solvent [D₆]-DMSO, spectrometer: 399.95 MHz: δ = 12.88 (s, COOH), 8.41 (s, 2H). |
| II-3 | ¹H-NMR, Solvent [D₆]-DMSO, spectrometer: 399.95 MHz: δ = 8.566 (2.2); 7.053 (2.7); 2.509 (10.8); 2.505 (13.8); 2.500 (9.9); 2.480 (0.6); 2.462 (1.1); 2.445 (0.5); 1.577 (0.5); 1.559 (0.5); 1.391 (16.0); 1.252 (1.1); 0.983 (0.8); 0.965 (1.5); 0.946 (0.7); 0.008 (0.3); 0.000 (9.7); −0.009 (0.4) |
| II-4 | ¹H-NMR, Solvent [D₆]-DMSO, spectrometer: 399.95 MHz: δ = 20.009 (0.5); 8.320 (3.5); 8.192 (16.0); 7.811 (3.0); 3.328 (728.6); 2.675 (6.0); 2.671 (8.0); 2.667 (6.1); 2.506 (953.5); 2.502 (1242.8); 2.498 (907.6); 2.333 (6.0); 2.329 (8.0); 2.324 (6.0); 1.890 (0.5); 1.073 (0.6); 1.055 (1.0); 1.037 (0.5); 0.000 (23.2) |
| II-5 | ¹H-NMR, Solvent [D₆]-DMSO, spectrometer: 399.95 MHz: δ = 8.373 (0.5); 8.301 (16.0); 8.251 (16.0); 8.186 (0.3); 7.582 (0.3); 7.506 (0.4); 7.482 (0.5); 7.462 (0.6); 7.391 (0.4); 7.383 (0.4); 7.360 (0.4); 7.263 (0.6); 7.244 (0.4); 7.230 (0.5); 7.182 (0.4); 7.117 (0.5); 7.099 (0.5); 6.949 (0.9); 4.388 (0.4); 4.356 (0.4); 4.273 (0.8); 4.255 (0.9); 4.210 (0.8); 4.203 (0.8); 4.183 (0.8); 4.169 (0.7); 4.162 (0.7); 4.144 (0.7); 4.113 (0.7); 4.099 (0.6); 4.081 (0.6); 4.070 (0.5); 4.023 (0.5); 4.007 (0.5); 3.890 (0.5); 3.864 (0.5); 3.853 (0.5); 3.833 (0.5); 3.791 (0.6); 3.737 (0.8); 3.493 (4.1); 3.483 (4.0); 3.361 (1.6); 3.348 (1.4); 3.218 (0.5); 2.671 (1.5); 2.503 (287.8); 2.365 (0.9); 2.351 (0.9); 2.348 (1.0); 2.330 (2.3); 2.287 (1.6); 2.262 (0.5); 2.227 (0.5); 2.183 (0.5); 2.164 (0.4); 2.160 (0.4); 1.381 (0.5); 1.355 (1.9); 1.316 (0.9); 1.303 (1.1); 1.285 (1.4); 1.264 (1.2); 1.235 (1.2); 1.197 (1.1); 1.168 (1.0); 1.153 (1.0); 1.113 (0.9); 1.108 (0.9); 1.098 (0.9); 1.083 (0.8); 1.072 (0.8); 1.012 (0.5); 0.926 (0.3); 0.146 (1.5); 0.057 (0.4); 0.000 (308.3); −0.150 (1.9) |

-continued

| Example | NMR data |
|---|---|
| II-10 | $^1$H-NMR, Solvent [D$_6$]-DMSO, spectrometer: 399.95 MHz: δ = 8.320 (6.5); 7.816 (3.6); 7.813 (3.7); 7.037 (0.4); 7.034 (0.4); 3.196 (0.7); 3.193 (0.7); 3.179 (1.0); 3.176 (1.0); 3.161 (0.8); 3.159 (0.7); 2.530 (0.3); 2.517 (7.1); 2.512 (14.2); 2.508 (18.7); 2.503 (14.1); 2.499 (7.2); 1.306 (16.0); 1.289 (15.7); 1.209 (1.8); 1.192 (1.8); 0.008 (0.7); 0.000 (20.0); −0.008 (0.8) |
| II-12 | $^1$H-NMR, Solvent [D$_6$]-DMSO, spectrometer: 399.95 MHz: δ = 8.846 (9.3); 8.388 (16.0); 8.330 (0.4); 8.132 (0.3); 2.677 (0.3); 2.512 (41.0); 2.508 (55.6); 2.504 (44.8); 2.335 (0.3); 0.008 (0.7); 0.000 (15.1) |
| II-13 | $^1$H-NMR, Solvent [D$_6$]-DMSO, spectrometer: 399.95 MHz: δ = 8.615 (14.9); 4.039 (0.7); 4.021 (0.7); 3.433 (0.3); 3.415 (0.3); 2.640 (15.7); 2.635 (16.0); 2.631 (6.7); 2.527 (0.4); 2.513 (10.3); 2.509 (21.0); 2.504 (27.9); 2.500 (20.3); 2.496 (10.0); 1.990 (2.7); 1.910 (1.6); 1.194 (0.7); 1.176 (1.4); 1.158 (0.7); 0.008 (1.2); 0.000 (33.6); −0.009 (1.3) |
| II-16 | $^1$H-NMR, Solvent [D$_6$]-DMSO, spectrometer: 399.95 MHz: δ = 13.037 (1.5); 9.021 (16.0); 8.319 (1.3); 6.539 (1.3); 3.348 (63.7); 2.676 (2.7); 2.671 (3.7); 2.667 (2.8); 2.507 (427.1); 2.502 (552.1); 2.498 (417.1); 2.333 (2.7); 2.329 (3.7); 2.325 (2.8); 0.146 (0.4); 0.008 (3.8); 0.000 (90.2); −0.008 (5.0); −0.150 (0.4) |
| II-17 | $^1$H-NMR, Solvent [D$_6$]-DMSO, spectrometer: 399.95 MHz: δ = 8.615 (11.5); 6.871 (0.5); 3.618 (0.4); 3.603 (0.7); 3.587 (0.5); 3.458 (1.0); 3.410 (1.1); 3.393 (1.6); 3.375 (1.5); 3.358 (0.8); 2.673 (0.4); 2.619 (16.0); 2.509 (48.2); 2.505 (58.5); 2.331 (0.4); 2.184 (0.8); 1.761 (0.5); 1.356 (5.2); 1.110 (1.1); 1.092 (2.0); 1.075 (1.0); 0.000 (9.9) |
| II-19 | $^1$H-NMR, Solvent [D$_6$]-DMSO, spectrometer: 399.95 MHz: δ = 12.627 (1.2); 8.244 (16.0); 8.078 (16.0); 3.392 (0.3); 3.374 (0.4); 3.328 (21.3); 2.676 (0.6); 2.672 (0.9); 2.667 (0.6); 2.548 (49.7); 2.525 (2.2); 2.511 (47.9); 2.507 (97.7); 2.502 (130.0); 2.498 (95.5); 2.494 (47.1); 2.334 (0.6); 2.329 (0.8); 2.325 (0.6); 1.091 (0.5); 0.146 (0.8); 0.008 (6.1); 0.000 (168.9); −0.008 (6.4); −0.150 (0.8) |
| II-21 | $^1$H-NMR, Solvent [D$_6$]-DMSO, spectrometer: 399.95 MHz: δ = 8.947 (1.0); 8.943 (2.8); 8.939 (3.0); 7.953 (2.3); 3.376 (1.0); 2.892 (16.0); 2.881 (2.0); 2.733 (13.4); 2.732 (13.4); 2.721 (1.8); 2.566 (3.3); 2.555 (0.4); 2.526 (0.6); 2.512 (14.3); 2.508 (30.3); 2.504 (42.2); 2.499 (34.5); 2.495 (22.0); 0.008 (1.7); 0.000 (48.0); −0.009 (4.7); −0.011 (5.1) |
| II-22 | $^1$H-NMR, Solvent [D$_6$]-DMSO, spectrometer: 399.95 MHz: δ = 13.203 (2.2); 9.022 (6.7); 9.018 (16.0); 9.014 (15.5); 7.954 (0.7); 3.339 (24.8); 2.893 (4.9); 2.733 (4.1); 2.732 (4.1); 2.678 (0.6); 2.673 (0.9); 2.669 (0.6); 2.567 (1.0); 2.551 (0.6); 2.537 (0.6); 2.527 (2.3); 2.513 (53.0); 2.509 (104.4); 2.504 (135.8); 2.500 (99.6); 2.495 (49.1); 2.335 (0.7); 2.331 (0.9); 2.326 (0.6); 0.146 (0.5); 0.008 (4.6); 0.000 (114.2); −0.009 (4.3); −0.150 (0.5) |
| II-23 | $^1$H-NMR, Solvent [D$_6$]-DMSO, spectrometer: 399.95 MHz: δ = 12.987 (2.2); 8.943 (1.6); 8.939 (1.5); 8.830 (15.0); 8.826 (14.4); 7.954 (2.1); 3.410 (0.5); 3.392 (1.0); 3.374 (1.7); 3.333 (71.6); 2.892 (14.3); 2.733 (12.4); 2.677 (0.9); 2.673 (1.2); 2.669 (0.9); 2.567 (16.0); 2.508 (149.6); 2.504 (190.9); 2.500 (145.2); 2.335 (0.9); 2.331 (1.2); 2.326 (0.9); 1.109 (0.3); 1.092 (0.7); 1.074 (0.3); 0.146 (0.6); 0.000 (120.5); −0.008 (9.1); −0.150 (0.6) |
| II-24 | $^1$H-NMR, Solvent [D$_6$]-DMSO, spectrometer: 399.95 MHz: δ = 2.69 (s, 3H); 8.99 (s, 1H) ppm |

According to the method described above, the following compounds of general formula (I) have been prepared.

TABLE 2

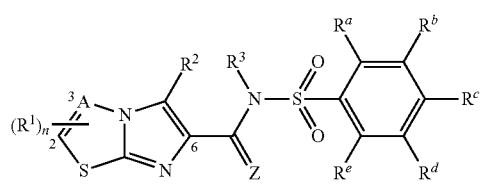

(I-1)

Z = O, R$^2$ and R$^3$ are H and Q = substituted aryl

| Example | R$^1$ | n | A | R$^a$ | R$^b$ | R$^c$ | R$^d$ | R$^e$ | Remarks |
|---|---|---|---|---|---|---|---|---|---|
| I-1-1 | 2-CF$_3$ | 1 | CH | Cl | H | H | OMe | H | NMR |
| I-1-2 | 3-CF$_3$ | 1 | C—R$^1$ | Cl | H | H | H | H | NMR |
| I-1-3 | 2-CF$_3$ | 1 | CH | Cl | H | H | H | H | NMR |
| I-1-4 | 2-CF$_3$ | 1 | CH | Cl | H | H | CF$_3$ | H | NMR |
| I-1-5 | 2-CF$_3$ | 1 | CH | Br | H | H | CF$_3$ | H | NMR |
| I-1-6 | 2-CF$_3$ | 1 | CH | Cl | H | H | Cl | H | NMR |
| I-1-7 | 2-CF$_3$ | 1 | CH | CH$_3$ | H | H | OCHF$_2$ | H | NMR |
| I-1-8 | 2-CF$_3$ | 1 | CH | CH$_3$ | H | H | Cl | H | NMR |
| I-1-9 | 2-CF$_3$ | 1 | CH | CH$_3$ | H | H | CH$_3$ | H | NMR |
| I-1-10 | 2-CF$_3$ | 1 | CH | Cl | H | H | H | Cl | NMR |

TABLE 2-continued (I-1)

Z = O, R² and R³ are H and Q = substituted aryl

| Example | R¹ | n | A | Rᵃ | Rᵇ | Rᶜ | Rᵈ | Rᵉ | Remarks |
|---|---|---|---|---|---|---|---|---|---|
| I-1-11 | 2-CF₃ | 1 | CH | F | H | H | H | F | NMR |
| I-1-12 | 2-CF₃ | 1 | CH | Cl | H | O—CF₂—O | | H | NMR |
| I-1-13 | 2-C₄H₉-t | 1 | CH | Cl | H | H | H | Cl | NMR |
| I-1-14 | 2-CF₃ | 1 | CH | CH₃ | H | Br | CH₃ | H | NMR |
| I-1-15 | 2-C₄H₉-t | 1 | CH | Cl | H | H | Cl | H | NMR |
| I-1-16 | 2-C₄H₉-t | 1 | CH | Cl | H | H | H | H | NMR |
| I-1-17 | 2-Cl | 1 | CH | Cl | H | H | H | H | NMR |
| I-1-18 | 2-Cl | 1 | CH | Cl | H | H | Cl | H | NMR |
| I-1-19 | 2-Cl | 1 | CH | Cl | H | H | OMe | H | NMR |
| I-1-20 | 2-Cl | 1 | CH | F | H | H | H | F | NMR |
| I-1-21 | 2-Cl | 1 | CH | Cl | H | H | CF₃ | H | NMR |
| I-1-22 | 2-Cl | 1 | CH | CH₃ | H | H | CH₃ | H | NMR |
| I-1-23 | 2-C₄H₉-t | 1 | CH | Cl | H | H | OMe | H | NMR |
| I-1-24 | 2-CF₃ | 1 | CH | CH₃ | H | CN | CH₃ | H | NMR |
| I-1-25 | 2-CF₃ | 1 | CH | CH₃ | H | H | COCH₃ | H | |
| I-1-26 | 2-CF₃ | 1 | CH | Cl | H | H | Et | H | |
| I-1-27 | 2-CF₃ | 1 | CH | F | H | H | OMe | H | NMR |
| I-1-28 | 2-CF₃ | 1 | CH | CH₃ | H | H | Cl | H | |
| I-1-29 | 3-CF₃ | 1 | C—R¹ | Cl | H | H | OMe | H | NMR |
| I-1-30 | 3-CF₃ | 1 | C—R¹ | Cl | H | H | H | Cl | NMR |
| I-1-31 | 3-CF₃ | 1 | C—R¹ | Cl | H | H | Cl | H | NMR |
| I-1-32 | 3-CF₃ | 1 | C—R¹ | Cl | H | H | CH₃ | H | |
| I-1-33 | 3-CF₃ | 1 | C—R¹ | Cl | H | H | Et | H | |
| I-1-34 | 3-CF₃ | 1 | C—R¹ | CH₃ | H | H | Cl | H | |
| I-1-35 | 3-CF₃ | 1 | C—R¹ | F | H | H | OMe | H | |
| I-1-36 | 3-CF₃ | 1 | C—R¹ | CH₃ | H | H | COCH₃ | H | |
| I-1-37 | 2-C₄H₉-t | 1 | CH | Cl | H | H | CH₃ | H | |
| I-1-38 | 2-C₄H₉-t | 1 | CH | CH₃ | H | CN | CH₃ | H | |
| I-1-39 | 2-C₄H₉-t | 1 | CH | Cl | H | H | Et | H | |
| I-1-40 | 2-C₄H₉-t | 1 | CH | F | H | H | OMe | H | |
| I-1-41 | 2-C₄H₉-t | 1 | CH | CH₃ | H | H | COCH₃ | H | |
| I-1-42 | 2-C₄H₉-t | 1 | CH | CH₃ | H | H | Cl | H | |
| I-1-43 | 2-Cl | 1 | CH | Cl | H | H | H | Cl | NMR |
| I-1-44 | 2-Cl | 1 | CH | Cl | H | H | CH₃ | H | |
| I-1-45 | 2-Cl | 1 | CH | CH₃ | H | CN | CH₃ | H | NMR |
| I-1-46 | 2-Cl | 1 | CH | Cl | H | H | Et | H | |
| I-1-47 | 2-Cl | 1 | CH | F | H | H | OMe | H | |
| I-1-48 | 2-Cl | 1 | CH | CH₃ | H | H | COCH₃ | H | |
| I-1-49 | 2-Cl | 1 | CH | CH₃ | H | H | Cl | H | |
| I-1-50 | 2-Cl | 1 | CH | H | Cl | H | H | H | NMR |
| I-1-51 | 2-Cl | 1 | CH | H | H | Cl | H | H | NMR |
| I-1-52 | 2-C₄H₉-t | 1 | CH | H | Cl | H | H | H | |
| I-1-53 | 2-C₄H₉-t | 1 | CH | H | H | Cl | H | H | |
| I-1-54 | 3-CF₃ | 1 | CH | H | Cl | | H | H | |
| I-1-55 | 3-CF₃ | 1 | CH | H | H | Cl | H | H | |
| I-1-56 | 2-CF₃ | 1 | CH | H | Cl | H | H | H | |
| I-1-57 | 2-CF₃ | 1 | CH | H | H | Cl | H | H | |
| I-1-58 | 2-Br | 1 | CH | H | Cl | H | H | H | |
| I-1-59 | 2-Br | 1 | CH | Cl | H | Cl | H | H | |
| I-1-60 | 2-Br | 1 | CH | Cl | H | H | OMe | H | NMR |
| I-1-61 | 2-Br | 1 | CH | Cl | H | H | H | Cl | |
| I-1-62 | 2-Br | 1 | CH | Cl | H | H | Cl | H | |
| I-1-63 | 2-Br | 1 | CH | Cl | H | H | CH₃ | H | |
| I-1-64 | 2-Br | 1 | CH | F | H | H | H | F | |
| I-1-65 | 2-Br | 1 | CH | CH₃ | H | CN | CH₃ | H | |
| I-1-66 | 2-Br | 1 | CH | Cl | H | H | Et | H | |
| I-1-67 | 2-Br | 1 | CH | F | H | H | OMe | H | |
| I-1-68 | 2-Br | 1 | CH | CH₃ | H | H | COCH₃ | H | |
| I-1-69 | 2-Br | 1 | CH | CH₃ | H | H | Cl | H | |
| I-1-70 | 2-F | 1 | CH | Cl | H | H | H | H | |
| I-1-71 | 2-F | 1 | CH | H | Cl | H | H | H | |
| I-1-72 | 2-F | 1 | CH | H | H | Cl | H | H | |
| I-1-73 | 2-F | 1 | CH | Cl | H | H | Cl | H | |
| I-1-74 | 2-F | 1 | CH | Cl | H | H | H | Cl | |
| I-1-75 | 2-F | 1 | CH | Cl | H | H | OMe | H | |
| I-1-76 | 2-F | 1 | CH | Cl | H | H | CH₃ | H | |
| I-1-77 | 2-F | 1 | CH | CH₃ | H | CN | CH₃ | H | |

TABLE 2-continued

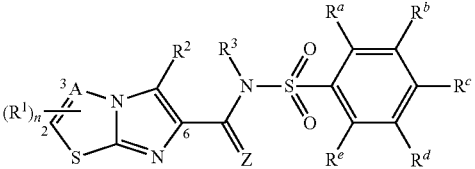

(I-1)

Z = O, R² and R³ are H and Q = substituted aryl

| Example | R¹ | n | A | Rᵃ | Rᵇ | Rᶜ | Rᵈ | Rᵉ | Remarks |
|---|---|---|---|---|---|---|---|---|---|
| I-1-78 | 2-F | 1 | CH | Cl | H | H | Et | H | |
| I-1-79 | 2-F | 1 | CH | F | H | H | OMe | H | |
| I-1-80 | 2-F | 1 | CH | CH₃ | H | H | COCH₃ | H | |
| I-1-81 | 2-F | 1 | CH | CH₃ | H | H | Cl | H | |
| I-1-82 | 2-CH₃ | 1 | CH | Cl | H | H | H | H | |
| I-1-83 | 2-CH₃ | 1 | CH | H | Cl | H | H | H | |
| I-1-84 | 2-CH₃ | 1 | CH | H | H | Cl | H | H | |
| I-1-85 | 2-CH₃ | 1 | CH | Cl | H | H | Cl | H | |
| I-1-86 | 2-CH₃ | 1 | CH | Cl | H | H | H | Cl | |
| I-1-87 | 2-CH₃ | 1 | CH | Cl | H | H | OMe | H | |
| I-1-88 | 2-CH₃ | 1 | CH | Cl | H | H | CH₃ | H | |
| I-1-89 | 2-CH₃ | 1 | CH | CH₃ | H | CN | CH₃ | H | |
| I-1-90 | 2-CH₃ | 1 | CH | Cl | H | H | Et | H | |
| I-1-91 | 2-CH₃ | 1 | CH | F | H | H | OMe | H | |
| I-1-92 | 2-CH₃ | 1 | CH | CH₃ | H | H | COCH₃ | H | |
| I-1-93 | 2-CH₃ | 1 | CH | CH₃ | H | H | Cl | H | |
| I-1-94 | 2-Et | 1 | CH | Cl | H | H | H | H | |
| I-1-95 | 2-Et | 1 | CH | H | Cl | H | H | H | |
| I-1-96 | 2-Et | 1 | CH | H | H | Cl | H | H | |
| I-1-97 | 2-Et | 1 | CH | Cl | H | H | Cl | H | |
| I-1-98 | 2-Et | 1 | CH | Cl | H | H | H | Cl | |
| I-1-99 | 2-Et | 1 | CH | Cl | H | H | OMe | H | |
| I-1-100 | 2-Et | 1 | CH | Cl | H | H | CH₃ | H | |
| I-1-101 | 2-Et | 1 | CH | CH₃ | H | CN | CH₃ | H | |
| I-1-102 | 2-Et | 1 | CH | Cl | H | H | Et | H | |
| I-1-103 | 2-Et | 1 | CH | F | H | H | OMe | H | |
| I-1-104 | 2-Et | 1 | CH | CH₃ | H | H | COCH₃ | H | |
| I-1-105 | 2-Et | 1 | CH | CH₃ | H | H | Cl | H | |
| I-1-106 | 2-Propyl | 1 | CH | Cl | H | H | H | H | |
| I-1-107 | 2-Propyl | 1 | CH | H | Cl | H | H | H | |
| I-1-108 | 2-Propyl | 1 | CH | H | H | Cl | H | H | |
| I-1-109 | 2-Propyl | 1 | CH | Cl | H | H | Cl | H | |
| I-1-110 | 2-Propyl | 1 | CH | Cl | H | H | H | Cl | |
| I-1-111 | 2-Propyl | 1 | CH | Cl | H | H | OMe | H | |
| I-1-112 | 2-Propyl | 1 | CH | Cl | H | H | CH₃ | H | |
| I-1-113 | 2-Propyl | 1 | CH | CH₃ | H | CN | CH₃ | H | |
| I-1-114 | 2-Propyl | 1 | CH | Cl | H | H | Et | H | |
| I-1-115 | 2-Propyl | 1 | CH | F | H | H | OMe | H | |
| I-1-116 | 2-Propyl | 1 | CH | CH₃ | H | H | COCH₃ | H | |
| I-1-117 | 2-Propyl | 1 | CH | CH₃ | H | H | Cl | H | |
| I-1-118 | 2-Isopropyl | 1 | CH | Cl | H | H | H | H | NMR |
| I-1-119 | 2-Isopropyl | 1 | CH | H | Cl | H | H | H | |
| I-1-120 | 2-Isopropyl | 1 | CH | H | H | Cl | H | H | |
| I-1-121 | 2-Isopropyl | 1 | CH | Cl | H | H | Cl | H | |
| I-1-122 | 2-Isopropyl | 1 | CH | Cl | H | H | H | Cl | |
| I-1-123 | 2-Isopropyl | 1 | CH | Cl | H | H | OMe | H | NMR |
| I-1-124 | 2-Isopropyl | 1 | CH | Cl | H | H | CH₃ | H | |
| I-1-125 | 2-Isopropyl | 1 | CH | CH₃ | H | CN | CH₃ | H | |
| I-1-126 | 2-Isopropyl | 1 | CH | Cl | H | H | Et | H | |
| I-1-127 | 2-Isopropyl | 1 | CH | F | H | H | OMe | H | |
| I-1-128 | 2-Isopropyl | 1 | CH | CH₃ | H | H | COCH₃ | H | |
| I-1-129 | 2-Isopropyl | 1 | CH | CH₃ | H | H | Cl | H | |
| I-1-130 | 2-Cyclopropyl | 1 | CH | Cl | H | H | H | H | |
| I-1-131 | 2-Cyclopropyl | 1 | CH | H | Cl | H | H | H | |
| I-1-132 | 2-Cyclopropyl | 1 | CH | H | H | Cl | H | H | |
| I-1-133 | 2-Cyclopropyl | 1 | CH | Cl | H | H | Cl | H | |
| I-1-134 | 2-Cyclopropyl | 1 | CH | Cl | H | H | H | Cl | |
| I-1-135 | 2-Cyclopropyl | 1 | CH | Cl | H | H | OMe | H | |
| I-1-136 | 2-Cyclopropyl | 1 | CH | Cl | H | H | CH₃ | H | |
| I-1-137 | 2-Cyclopropyl | 1 | CH | CH₃ | H | CN | CH₃ | H | |
| I-1-138 | 2-Cyclopropyl | 1 | CH | Cl | H | H | Et | H | |
| I-1-139 | 2-Cyclopropyl | 1 | CH | F | H | H | OMe | H | |
| I-1-140 | 2-Cyclopropyl | 1 | CH | CH₃ | H | H | COCH₃ | H | |
| I-1-141 | 2-Cyclopropyl | 1 | CH | CH₃ | H | H | Cl | H | |
| I-1-142 | 2-C₂F₅ | 1 | CH | Cl | H | H | H | H | NMR |
| I-1-143 | 2-C₂F₅ | 1 | CH | H | Cl | H | H | H | NMR |
| I-1-144 | 2-C₂F₅ | 1 | CH | H | H | Cl | H | H | NMR |

TABLE 2-continued

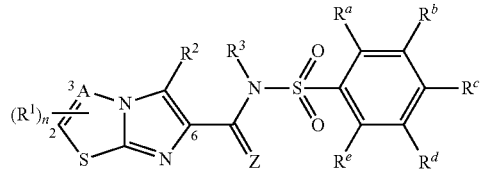
(I-1)

Z = O, $R^2$ and $R^3$ are H and Q = substituted aryl

| Example | $R^1$ | n | A | $R^a$ | $R^b$ | $R^c$ | $R^d$ | $R^e$ | Remarks |
|---|---|---|---|---|---|---|---|---|---|
| I-1-145 | 2-$C_2F_5$ | 1 | CH | Cl | H | H | Cl | H | NMR |
| I-1-146 | 2-$C_2F_5$ | 1 | CH | Cl | H | H | H | Cl | NMR |
| I-1-147 | 2-$C_2F_5$ | 1 | CH | Cl | H | H | OMe | H | NMR |
| I-1-148 | 2-$C_2F_5$ | 1 | CH | Cl | H | H | $CH_3$ | H | |
| I-1-149 | 2-$C_2F_5$ | 1 | CH | $CH_3$ | H | CN | $CH_3$ | H | |
| I-1-150 | 2-$C_2F_5$ | 1 | CH | Cl | H | H | Et | H | |
| I-1-151 | 2-$C_2F_5$ | 1 | CH | F | H | H | OMe | H | NMR |
| I-1-152 | 2-$C_2F_5$ | 1 | CH | $CH_3$ | H | H | $COCH_3$ | H | |
| I-1-153 | 2-$C_2F_5$ | 1 | CH | $CH_3$ | H | H | Cl | H | NMR |
| I-1-154 | 2-$CF_3$, 3-$CH_3$ | 2 | C—$R^1$ | Cl | H | H | H | H | NMR |
| I-1-155 | 2-$CF_3$, 3-$CH_3$ | 2 | C—$R^1$ | H | Cl | H | H | H | NMR |
| I-1-156 | 2-$CF_3$, 3-$CH_3$ | 2 | C—$R^1$ | H | H | Cl | H | H | NMR |
| I-1-157 | 2-$CF_3$, 3-$CH_3$ | 2 | C—$R^1$ | Cl | H | H | Cl | H | NMR |
| I-1-158 | 2-$CF_3$, 3-$CH_3$ | 2 | C—$R^1$ | Cl | H | H | H | Cl | NMR |
| I-1-159 | 2-$CF_3$, 3-$CH_3$ | 2 | C—$R^1$ | Cl | H | H | OMe | H | NMR |
| I-1-160 | 2-$CF_3$, 3-$CH_3$ | 2 | C—$R^1$ | Cl | H | H | $CH_3$ | H | |
| I-1-161 | 2-$CF_3$, 3-$CH_3$ | 2 | C—$R^1$ | $CH_3$ | H | CN | $CH_3$ | H | |
| I-1-162 | 2-$CF_3$, 3-$CH_3$ | 2 | C—$R^1$ | Cl | H | H | Et | H | |
| I-1-163 | 2-$CF_3$, 3-$CH_3$ | 2 | C—$R^1$ | F | H | H | OMe | H | |
| I-1-164 | 2-$CF_3$, 3-$CH_3$ | 2 | C—$R^1$ | $CH_3$ | H | H | $COCH_3$ | H | |
| I-1-165 | 2-$CF_3$, 3-$CH_3$ | 2 | C—$R^1$ | $CH_3$ | H | H | Cl | H | |
| I-1-166 | 2-$CF_3$, 3-$CH_3$ | 2 | C—$R^1$ | Cl | H | H | H | H | |
| I-1-167 | 2-$CF_3$, 3-$CH_3$ | 2 | C—$R^1$ | H | Cl | H | H | H | |
| I-1-168 | 2-$CF_3$, 3-$CH_3$ | 2 | C—$R^1$ | H | H | Cl | H | H | |
| I-1-169 | 2-$CF_3$, 3-$CH_3$ | 2 | C—$R^1$ | Cl | H | H | Cl | H | |
| I-1-170 | 2-$CF_3$, 3-Et | 2 | C—$R^1$ | Cl | H | H | H | Cl | |
| I-1-171 | 2-$CF_3$, 3-Et | 2 | C—$R^1$ | Cl | H | H | OMe | H | |
| I-1-172 | 2-$CF_3$, 3-Et | 2 | C—$R^1$ | Cl | H | H | $CH_3$ | H | |
| I-1-173 | 2-$CF_3$, 3-Et | 2 | C—$R^1$ | $CH_3$ | H | CN | $CH_3$ | H | |
| I-1-174 | 2-$CF_3$, 3-Et | 2 | C—$R^1$ | Cl | H | H | Et | H | |
| I-1-175 | 2-$CF_3$, 3-Et | 2 | C—$R^1$ | F | H | H | OMe | H | |
| I-1-176 | 2-$CF_3$, 3-Et | 2 | C—$R^1$ | $CH_3$ | H | H | $COCH_3$ | H | |
| I-1-177 | 2-$CF_3$, 3-Et | 2 | C—$R^1$ | $CH_3$ | H | H | Cl | H | |
| I-1-178 | 2-$CH_3$, 3-$CH_3$ | 2 | C—$R^1$ | Cl | H | H | H | H | |
| I-1-179 | 2-$CH_3$, 3-$CH_3$ | 2 | C—$R^1$ | H | Cl | H | H | H | |
| I-1-180 | 2-$CH_3$, 3-$CH_3$ | 2 | C—$R^1$ | H | H | Cl | H | H | |
| I-1-181 | 2-$CH_3$, 3-$CH_3$ | 2 | C—$R^1$ | Cl | H | H | Cl | H | |
| I-1-182 | 2-$CH_3$, 3-$CH_3$ | 2 | C—$R^1$ | Cl | H | H | H | Cl | |
| I-1-183 | 2-$CH_3$, 3-$CH_3$ | 2 | C—$R^1$ | Cl | H | H | OMe | H | |
| I-1-184 | 2-$CH_3$, 3-$CH_3$ | 2 | C—$R^1$ | Cl | H | H | $CH_3$ | H | |
| I-1-185 | 2-$CH_3$, 3-$CH_3$ | 2 | C—$R^1$ | $CH_3$ | H | CN | $CH_3$ | H | |
| I-1-186 | 2-$CH_3$, 3-$CH_3$ | 2 | C—$R^1$ | Cl | H | H | Et | H | |
| I-1-187 | 2-$CH_3$, 3-$CH_3$ | 2 | C—$R^1$ | F | H | H | OMe | H | |
| I-1-188 | 2-$CH_3$, 3-$CH_3$ | 2 | C—$R^1$ | $CH_3$ | H | H | $COCH_3$ | H | |
| I-1-189 | 2-$CH_3$, 3-$CH_3$ | 2 | C—$R^1$ | $CH_3$ | H | H | Cl | H | |
| I-1-190 | 2-$CF_3$ | 1 | CH | Cl | H | H | $CH_2$—pyrazol-1-yl | H | |
| I-1-191 | 2-$CF_3$ | 1 | CH | F | H | H | $CH_2$—pyrazol-1-yl | H | NMR |
| I-1-192 | 2-$CF_3$ | 1 | CH | Br | H | H | $CH_2$—pyrazol-1-yl | H | NMR |
| I-1-193 | 2-$CF_3$ | 1 | CH | $CH_3$ | H | H | $CH_2$—pyrazol-1-yl | H | |

TABLE 2-continued

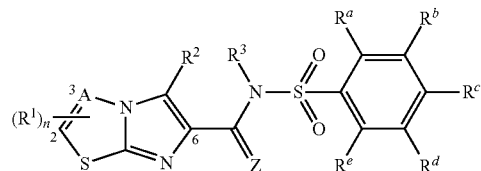

(I-1)

Z = O, R² and R³ are H and Q = substituted aryl

| Example | R¹ | n | A | Rᵃ | Rᵇ | Rᶜ | Rᵈ | Rᵉ | Remarks |
|---|---|---|---|---|---|---|---|---|---|
| I-1-194 | 2-CF₃ | 1 | CH | Et | H | H | CH₂—N(pyrazole) | H | NMR |
| I-1-195 | 2-CF₃ | 1 | CH | CF₃ | H | H | CH₂—N(pyrazole) | H | |
| I-1-196 | 2-CF₃ | 1 | CH | OCF₃ | H | H | CH₂—N(pyrazole) | H | NMR |
| I-1-197 | 2-CF₃ | 1 | CH | OMe | H | H | CH₂—N(pyrazole) | H | |
| I-1-198 | 2-CF₃ | 1 | CH | Cl | H | Cl | CH₂—N(pyrazole) | H | NMR |
| I-1-199 | 2-CF₃ | 1 | CH | Cl | H | F | CH₂—N(pyrazole) | H | |
| I-1-200 | 2-CF₃ | 1 | CH | F | H | Cl | CH₂—N(pyrazole) | H | NMR |
| I-1-201 | 2-CF₃ | 1 | CH | H | Cl | H | CH₂—N(pyrazole) | H | |
| I-1-202 | 2-CF₃ | 1 | N | Cl | H | H | H | H | NMR |
| I-1-203 | 2-CF₃ | 1 | N | Cl | H | H | H | Cl | NMR |
| I-1-204 | 2-CF₃ | 1 | CH | CH₃ | CH₃ | H | CH₂—N(pyrazole) | H | NMR |
| I-1-205 | 2-CF₃ | 1 | CH | Br | H | H | Cl | H | NMR |
| I-1-206 | 2-CF₃ | 1 | CH | Br | H | H | OMe | H | NMR |
| I-1-207 | 2-CF₃ | 1 | CH | Cl | H | H | OC₃H₇-n | H | NMR |
| I-1-208 | 2-CF₃ | 1 | CH | Cl | H | H | OC₃H₇-i | H | NMR |
| I-1-209 | 2-CF₃ | 1 | CH | Cl | H | H | Br | H | NMR |
| I-1-210 | 2-CF₃ | 1 | CH | I | H | H | H | H | NMR |
| I-1-211 | 2-CF₃ | 1 | CH | Br | H | H | H | H | NMR |
| I-1-212 | 2-CF₃ | 1 | CH | F | H | H | H | H | NMR |
| I-1-213 | 2-CF₃, 3-CH₃ | 2 | C—R¹ | OCF₃ | H | H | CH₂—N(pyrazole) | H | NMR |
| I-1-214 | 2-CF₃, 3-CH₃ | 2 | C—R¹ | F | H | Cl | CH₂—N(pyrazole) | H | NMR |

TABLE 2-continued (I-1)

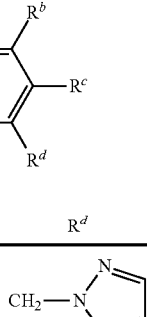

Z = O, R² and R³ are H and Q = substituted aryl

| Example | R¹ | n | A | Rᵃ | Rᵇ | Rᶜ | Rᵈ | Rᵉ | Remarks |
|---|---|---|---|---|---|---|---|---|---|
| I-1-215 | 2-CF₃, 3-CH₃ | 2 | C—R¹ | Cl | H | Cl | CH₂—pyrazolyl | H | NMR |
| I-1-216 | 2-CF₃, 3-CH₃ | 2 | C—R¹ | CH₃ | CH₃ | H | CH₂—pyrazolyl | H | NMR |
| I-1-217 | 2-CF₃, 3-CH₃ | 2 | C—R¹ | Et | H | H | CH₂—pyrazolyl | H | NMR |
| I-1-218 | 2-CF₃, 3-CH₃ | 2 | C—R¹ | F | H | H | CH₂—pyrazolyl | H | NMR |
| I-1-219 | 2-CF₃, 3-CH₃ | 2 | C—R¹ | H | H | Cl | CH₂—pyrazolyl | H | NMR |
| I-1-220 | 2-CF₃, 3-CH₃ | 2 | C—R¹ | H | H | OMe | CH₂—pyrazolyl | H | NMR |
| I-1-221 | 2-CF₃, 3-CH₃ | 2 | C—R¹ | Cl | H | H | CH₂—pyrazolyl | H | NMR |
| I-1-222 | 2-C₂F₅ | 1 | CH | F | H | H | H | F | NMR |
| I-1-223 | 2-C₂F₅ | 1 | CH | Br | H | H | CF₃ | H | NMR |
| I-1-224 | 2-C₂F₅ | 1 | CH | Cl | H | Cl | H | H | NMR |
| I-1-225 | 2-C₂F₅ | 1 | CH | CH₃ | H | H | CH₃ | H | NMR |
| I-1-226 | 2-C₂F₅ | 1 | CH | F | H | H | H | H | NMR |
| I-1-227 | 2-C₂F₅ | 1 | CH | Br | H | H | H | H | NMR |
| I-1-228 | 2-C₂F₅ | 1 | CH | Et | H | H | CH₂—pyrazolyl | H | NMR |
| I-1-229 | 2-C₂F₅ | 1 | CH | OCF₃ | H | H | CH₂—pyrazolyl | H | NMR |
| I-1-230 | 2-C₂F₅ | 1 | CH | Cl | H | Cl | CH₂—pyrazolyl | H | NMR |
| I-1-231 | 2-C₂F₅ | 1 | CH | F | H | Cl | CH₂—pyrazolyl | H | NMR |
| I-1-232 | 2-C₂F₅ | 1 | CH | CH₃ | CH₃ | H | CH₂—pyrazolyl | H | NMR |

TABLE 2-continued (I-1)

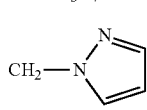

Z = O, R² and R³ are H and Q = substituted aryl

| Example | R¹ | n | A | Rᵃ | Rᵇ | Rᶜ | Rᵈ | Rᵉ | Remarks |
|---|---|---|---|---|---|---|---|---|---|
| I-1-233 | 2-C₂F₅ | 1 | CH | CH₃ | H | H | C₄H₉-t | H | NMR |
| I-1-234 | 2-C₂F₅ | 1 | CH | OCF₃ | H | H | H | H | NMR |
| I-1-235 | 2-C₂F₅ | 1 | CH | phenyl | H | H | H | H | NMR |
| I-1-236 | 2-C₂F₅ | 1 | CH | Cl | Cl | H | H | H | NMR |
| I-1-237 | 2-C₂F₅ | 1 | CH | Cl | H | H | Br | H | NMR |
| I-1-238 | 2-C₂F₅ | 1 | CH | Cl | H | H | OC₃H₇-n | H | NMR |
| I-1-239 | 2-C₂F₅ | 1 | CH | Cl | H | H | OC₃H₇-i | H | NMR |
| I-1-240 | 2-C₂F₅ | 1 | CH | F | H | H | 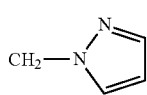 | H | NMR |
| I-1-241 | 2-C₂F₅ | 1 | CH | H | H | OMe | 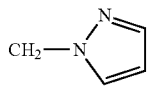 | H | NMR |
| I-1-242 | 2-C₂F₅ | 1 | CH | H | H | Cl | 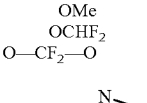 | H | NMR |
| I-1-243 | 2-C₂F₅ | 1 | CH | Br | H | H | OMe | H | NMR |
| I-1-244 | 2-C₂F₅ | 1 | CH | CH₃ | H | H | OCHF₂ | H | NMR |
| I-1-245 | 2-C₂F₅ | 1 | CH | Cl | H | O—CF₂—O | | H | NMR |
| I-1-246 | 2-C₂F₅ | 1 | CH | H | H | F | 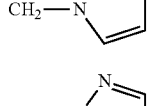 | H | NMR |
| I-1-247 | 2-C₂F₅ | 1 | CH | H | OMe | OMe | 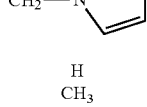 | H | NMR |
| I-1-248 | 2-C₂F₅ | 1 | CH | OMe | H | H | H | H | NMR |
| I-1-249 | 2-C₂F₅ | 1 | CH | O—SO₂Me | H | H | CH₃ | H | NMR |
| I-1-250 | 2-C₂F₅, 3-CH₃ | 2 | C—R¹ | H | Cl | H | H | H | NMR |
| I-1-251 | 2-C₂F₅, 3-CH₃ | 2 | C—R¹ | Cl | H | H | OMe | H | NMR |
| I-1-252 | 2-C₂F₅, 3-CH₃ | 2 | C—R¹ | F | H | H | H | F | NMR |
| I-1-253 | 2-C₂F₅, 3-CH₃ | 2 | C—R¹ | H | H | Cl | H | H | NMR |
| I-1-254 | 2-C₂F₅, 3-CH₃ | 2 | C—R¹ | Cl | H | H | H | Cl | NMR |
| I-1-255 | 2-C₂F₅, 3-CH₃ | 2 | C—R¹ | Cl | H | H | H | H | NMR |
| I-1-256 | 2-C₂F₅, 3-CH₃ | 2 | C—R¹ | OCF₃ | H | H | 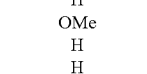 | H | NMR |
| I-1-257 | 2-C₂F₅, 3-CH₃ | 2 | C—R¹ | F | H | Cl | 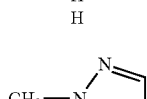 | H | NMR |
| I-1-258 | 2-C₂F₅, 3-CH₃ | 2 | C—R¹ | CH₃ | CH₃ | H | 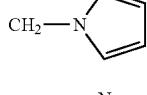 | H | NMR |
| I-1-259 | 2-C₂F₅, 3-CH₃ | 2 | C—R¹ | Cl | H | Cl | 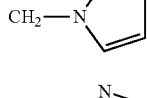 | H | NMR |

TABLE 2-continued

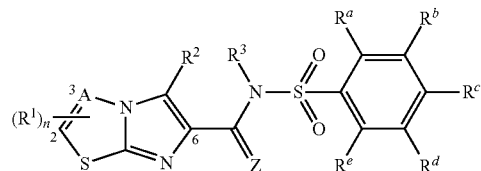

(I-1)

Z = O, R² and R³ are H and Q = substituted aryl

| Example | R¹ | n | A | Rᵃ | Rᵇ | Rᶜ | Rᵈ | Rᵉ | Remarks |
|---|---|---|---|---|---|---|---|---|---|
| I-1-260 | 2-C₂F₅, 3-CH₃ | 2 | C—R¹ | Et | H | H | CH₂—pyrazol-1-yl | H | NMR |
| I-1-261 | 2-C₂F₅, 3-CH₃ | 2 | C—R¹ | F | H | H | CH₂—pyrazol-1-yl | H | NMR |
| I-1-262 | 2-C₂F₅, 3-CH₃ | 2 | C—R¹ | H | H | Cl | CH₂—pyrazol-1-yl | H | NMR |
| I-1-263 | 2-C₂F₅, 3-CH₃ | 2 | C—R¹ | H | H | OMe | CH₂—pyrazol-1-yl | H | NMR |
| I-1-264 | 2-C₂F₅, 3-CH₃ | 2 | C—R¹ | Cl | H | H | CH₂—pyrazol-1-yl | H | NMR |
| I-1-265 | 2-Cl | 1 | CH | Et | H | H | CH₂—pyrazol-1-yl | H | NMR |
| I-1-266 | 2-Cl | 1 | CH | O—SO₂Me | H | H | CH₃ | H | NMR |
| I-1-267 | 2-Cl | 1 | CH | OCF₃ | H | H | CH₂—pyrazol-1-yl | H | NMR |
| I-1-268 | 2-Cl | 1 | CH | Cl | H | Cl | CH₂—pyrazol-1-yl | H | NMR |
| I-1-269 | 3-CF₃ | 1 | C—R¹ | Cl | H | H | CF₃ | H | NMR |
| I-1-270 | 3-CF₃ | 1 | C—R¹ | CH₃ | H | H | CH₃ | H | NMR |
| I-1-271 | 3-CF₃ | 1 | C—R¹ | Br | H | H | CF₃ | H | NMR |
| I-1-272 | 2-CF₃ | 1 | CH | H | Cl | H | H | H | |
| I-1-273 | 2-CF₃ | 1 | CH | H | OMe | OMe | CH₂—pyrazol-1-yl | H | NMR |
| I-1-274 | 2-CF₃ | 1 | CH | Cl | H | H | CH₂—pyrazol-1-yl | H | NMR |
| I-1-275 | 2-CF₃ | 1 | CH | H | H | Br | CH₂—pyrazol-1-yl | H | NMR |
| I-1-276 | 2-CF₃ | 1 | CH | H | H | Cl | CH₂—pyrazol-1-yl | H | NMR |

TABLE 2-continued

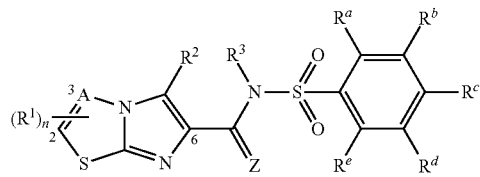
(I-1)

Z = O, R² and R³ are H and Q = substituted aryl

| Example | R¹ | n | A | Rᵃ | Rᵇ | Rᶜ | Rᵈ | Rᵉ | Remarks |
|---|---|---|---|---|---|---|---|---|---|
| I-1-277 | 2-CF₃, 3-CH₃ | 2 | C—R¹ | H | OMe | OMe | CH₂—pyrazole | H | NMR |
| I-1-278 | 2-C₂F₅, 3-CH₃ | 2 | C—R¹ | H | OMe | OMe | CH₂—pyrazole | H | NMR |
| I-1-279 | 2-CF₃ | 1 | CH | Cl | H | Cl | H | H | NMR |
| I-1-280 | 2-CF₃ | 1 | CH | H | H | Cl | H | H | NMR |
| I-1-281 | 2-CF₃ | 1 | CH | 2-OCF₃ | H | H | H | H | NMR |
| I-1-282 | 2-CF₃ | 1 | CH | Cl | Cl | CH | H | H | NMR |
| I-1-283 | 2-CF₃ | 1 | CH | H | H | OMe | CH₂—pyrazole | H | NMR |
| I-1-284 | 2-CF₃ | 1 | CH | H | H | F | CH₂—pyrazole | H | NMR |
| I-1-285 | 2-CF₃ | 1 | CH | OSO₂Me | H | H | Me | H | NMR |
| I-1-286 | 2-CF₃ | 1 | CH | Cl | H | H | OEt | H | NMR |
| I-1-287 | 2-CF₃ | 1 | CH | OMe | H | H | CH₂—pyrazole | H | NMR |
| I-1-288 | 2-CF₃ | 1 | CH | Me | H | H | CH₂—pyrazole | H | NMR |
| I-1-289 | 2-CF₃, 3-CH₃ | 2 | C—R¹ | Cl | H | H | CF₃ | H | NMR |
| I-1-290 | 2-CF₃, 3-CH₃ | 2 | C—R¹ | Me | H | H | Cl | H | NMR |
| I-1-291 | 2-CF₃, 3-CH₃ | 2 | C—R¹ | Me | H | H | Me | H | NMR |
| I-1-292 | 2-C₂F₅ | 1 | CH | Cl | H | H | CH₂—pyrazole | H | NMR |
| I-1-293 | 2-C₂F₅ | 1 | CH | H | H | Br | CH₂—pyrazole | H | NMR |
| I-1-294 | 2-C₂F₅ | 1 | CH | OMe | H | H | CH₂—pyrazole | H | NMR |
| I-1-295 | 2-C₂F₅ | 1 | CH | Me | H | H | CH₂—pyrazole | H | NMR |
| I-1-296 | 2-SCH₃ | 1 | CH | Cl | H | H | CF₃ | H | NMR |
| I-1-297 | 2-SCH₃ | 1 | CH | Cl | H | H | Cl | H | NMR |
| I-1-298 | 2-SCH₃ | 1 | CH | Cl | H | H | H | H | NMR |
| I-1-299 | 2-SCH₃ | 1 | CH | Cl | H | H | OMe | H | NMR |
| I-1-300 | 2-SCH₃ | 1 | CH | Cl | H | H | H | Cl | NMR |

TABLE 2-continued (I-1)

$Z = O$, $R^2$ and $R^3$ are H and Q = substituted aryl

| Example | $R^1$ | n | A | $R^a$ | $R^b$ | $R^c$ | $R^d$ | $R^e$ | Remarks |
|---|---|---|---|---|---|---|---|---|---|
| I-1-301 | 2-CF$_3$ | 1 | CH | Cl | H | H | CO—Me | H | NMR |
| I-1-302 | 2-CF$_3$, 3-CH$_3$ | 2 | C—R$^1$ | Cl | H | H | CO—Me | H | NMR |
| I-1-303 | 2-SCH$_3$ | 1 | CH | F | H | H | H | F | NMR |
| I-1-304 | 2-SCH$_3$ | 1 | CH | H | H | Cl | H | H | NMR |
| I-1-305 | 2-CF$_3$ | 1 | CH | Et | H | H | Et | H | NMR |
| I-1-306 | 2-CF$_3$ | 1 | CH | Me | H | H | Isopropyl | H | NMR |
| I-1-307 | 2-CF$_3$ | 1 | CH | Me | Me | Cl | H | H | NMR |
| I-1-308 | 2-CF$_3$ | 1 | CH | Cl | H | H | SMe | H | NMR |
| I-1-309 | 2-CF$_3$ | 1 | CH | Et | H | H | Cl | H | NMR |
| I-1-310 | 2-CF$_3$ | 1 | CH | Cl | H | H | CN | H | NMR |
| I-1-311 | 2-CF$_3$ | 1 | CH | Br | H | Me | Me | H | NMR |
| I-1-312 | 2-CF$_3$ | 1 | CH | Br | H | H | Br | H | NMR |
| I-1-313 | 2-CF$_3$ | 1 | CH | Opropyl | H | H | Cl | H | NMR |
| I-1-314 | 2-CF$_3$ | 1 | CH | OCHF$_2$ | H | H | Me | H | NMR |
| I-1-315 | 2-CF$_3$, 3-CH$_3$ | 2 | C—R$^1$ | Cl | H | H | CN | H | NMR |
| I-1-316 | 2-CF$_3$, 3-CH$_3$ | 2 | C—R$^1$ | Cl | H | H | SMe | H | NMR |
| I-1-317 | 2-CF$_3$, 3-CH$_3$ | 2 | C—R$^1$ | Br | H | H | Br | H | NMR |
| I-1-318 | 2-CF$_3$, 3-CH$_3$ | 2 | C—R$^1$ | OCHF$_2$ | H | H | Me | H | NMR |
| I-1-319 | 2-CF$_3$, 3-CH$_3$ | 2 | C—R$^1$ | Cl | H | H | OEt | H | NMR |
| I-1-320 | 2-CF$_3$, 3-CH$_3$ | 2 | C—R$^1$ | Et | H | H | Cl | H | NMR |
| I-1-321 | 2-CF$_3$ | 1 | CH | Isopropyl | H | H | Isopropyl | H | NMR |
| I-1-322 | 2-CF$_3$ | 1 | CH | Cl | H | H | SO$_2$Me | H | NMR |
| I-1-323 | 2-CF$_3$ | 1 | CH | OMe | H | H | H | H | NMR |
| I-1-324 | 2-CF$_3$ | 1 | CH | Phenyl | H | H | H | H | NMR |
| I-1-325 | 2-CF$_3$ | 1 | CH | CH$_3$ | H | H | Br | H | NMR |
| I-1-326 | 2-CF$_3$ | 1 | CH | CH$_3$ | H | H | Et | H | NMR |
| I-1-327 | 2-CF$_3$ | 1 | CH | F | H | H | H | Cl | NMR |
| I-1-328 | 2-CF$_3$ | 1 | CH | S-Isopropyl | H | H | H | Cl | NMR |
| I-1-329 | 2-CF$_3$ | 1 | CH | CH$_3$ | H | H | H | Cl | NMR |
| I-1-330 | 2-CF$_3$ | 1 | CH | S—CH$_3$ | H | H | H | Cl | NMR |
| I-1-331 | 2-CF$_3$ | 1 | CH | O-Isopropyl | H | H | H | Cl | NMR |
| I-1-332 | 2-CF$_3$ | 1 | CH | S—Et | H | H | H | Cl | NMR |

| Example | NMR data |
|---|---|
| I-1-1 | $^1$H-NMR, Solvent [D$_6$]-DMSO, spectrometer: 399.95 MHz: <br> δ = 12.00 (br s, NH), 8.75 (s, 1H), 8.07 (s, 1H), 7.55 (d, 1H), 7.34 (d, 1H), 7.01-6.98 (dd, 1H), 3.79 (s, 3H). |
| I-1-2 | $^1$H-NMR, Solvent [D$_6$]-DMSO, spectrometer: 399.95 MHz: <br> δ = 13.10-12.50 (br s, NH), 8.79 (s, 1H), 8.44 (s, 1H), 8.19 (s, 1H), 7.74-7.61 (m, 3H). |
| I-1-3 | $^1$H-NMR, Solvent [D$_6$]-DMSO, spectrometer: 399.95 MHz: <br> δ = 12.00 (br s, NH), 8.75 (s, 1H), 8.07 (s, 1H), 8.02 (d, 1H), 7.46-7.36 (m, 3H). |
| I-1-4 | $^1$H-NMR, Solvent [D$_6$]-DMSO, spectrometer: 399.95 MHz: <br> δ = 8.748 (2.8); 8.744 (6.6); 8.741 (6.3); 8.317 (0.9); 8.273 (5.1); 8.267 (5.1); 8.057 (16.0); 7.803 (2.4); 7.797 (2.3); 7.782 (3.3); 7.776 (3.1); 7.679 (5.2); 7.658 (3.7); 3.325 (177.8); 2.676 (1.4); 2.671 (1.9); 2.667 (1.3); 2.662 (0.7); 2.541 (1.2); 2.524 (6.0); 2.511 (110.0); 2.507 (214.3); 2.502 (276.3); 2.498 (195.6); 2.493 (91.5); 2.333 (1.3); 2.329 (1.8); 2.324 (1.3); 1.235 (0.7); 0.146 (2.2); 0.008 (21.9); 0.000 (471.8); −0.008 (16.7); −0.150 (2.2) |
| I-1-5 | $^1$H-NMR, Solvent [D$_6$]-DMSO, spectrometer: 399.95 MHz: <br> δ = 8.751 (7.7); 8.748 (7.3); 8.317 (0.6); 8.292 (6.3); 8.287 (6.4); 8.066 (16.0); 7.872 (4.9); 7.851 (6.1); 7.691 (3.8); 7.686 (3.8); 7.671 (3.1); 7.666 (3.0); 4.038 (0.9); 4.020 (0.9); 3.324 (88.9); 2.671 (1.4); 2.541 (0.8); 2.506 (171.5); 2.502 (214.2); 2.498 (156.2); 2.329 (1.4); 1.989 (3.8); 1.398 (0.3); 1.236 (0.4); 1.193 (1.0); 1.175 (2.0); 1.157 (1.0); 1.073 (0.3); 1.056 (0.7); 1.038 (0.3); 0.146 (1.6); 0.000 (314.0); −0.150 (1.6). |
| I-1-6 | $^1$H-NMR, Solvent [D$_6$]-DMSO, spectrometer: 399.95 MHz: <br> δ = 8.754 (6.0); 8.751 (5.6); 8.083 (11.3); 7.972 (5.9); 7.966 (5.8); 7.515 (2.1); 7.509 (1.9); 7.494 (5.4); 7.488 (5.4); 7.469 (8.8); 7.448 (3.0); 4.056 (1.2); 4.038 (3.7); 4.020 (3.8); 4.003 (1.3); 3.330 (9.2); 2.672 (0.3); 2.508 (40.9); 2.503 (50.1); 2.499 (35.9); 1.989 (16.0); 1.397 (3.4); 1.236 (0.4); 1.193 (4.4); 1.175 (8.7); 1.157 (4.3); 0.146 (0.4); 0.008 (6.7); 0.000 (86.4); −0.009 (4.1); −0.150 (0.4) |
| I-1-7 | $^1$H-NMR, Solvent [D$_6$]-DMSO, spectrometer: 399.95 MHz: <br> δ = 8.761 (2.9); 8.758 (2.7); 8.317 (0.5); 8.041 (1.6); 7.698 (2.6); 7.693 (2.5); 7.298 (1.7); 7.290 (1.1); 7.268 (1.2); 7.106 (2.8); 7.062 (1.7); 7.042 (1.4); 6.914 (1.4); 4.055 (0.7); |

| Example | NMR data |
|---|---|
| | 4.038 (2.1); 4.020 (2.1); 4.002 (0.7); 3.324 (74.0); 2.680 (0.5); 2.675 (0.9); 2.671 (1.2); 2.666 (0.9); 2.662 (0.4); 2.541 (0.7); 2.524 (3.2); 2.511 (69.7); 2.506 (136.7); 2.502 (175.6); 2.497 (122.4); 2.493 (55.8); 2.322 (16.0); 1.989 (9.6); 1.398 (4.2); 1.193 (2.6); 1.175 (5.2); 1.157 (2.6); 0.146 (1.3); 0.008 (14.9); 0.000 (318.1); −0.009 (10.3); −0.150 (1.3) |
| I-1-8 | $^1$H-NMR, Solvent [D$_6$]-DMSO, spectrometer: 399.95 MHz: δ = 8.751 (0.6); 8.747 (0.7); 8.740 (1.3); 8.736 (3.1); 8.733 (2.9); 8.072 (6.5); 8.065 (1.0); 7.854 (2.8); 7.849 (2.9); 7.828 (0.5); 7.823 (0.5); 7.380 (1.4); 7.374 (1.4); 7.359 (1.9); 7.353 (1.8); 7.303 (0.4); 7.283 (0.7); 7.232 (2.8); 7.212 (2.1); 4.056 (1.2); 4.038 (3.7); 4.020 (3.7); 4.002 (1.2); 3.328 (11.6); 2.523 (14.3); 2.512 (14.3); 2.507 (28.4); 2.503 (36.8); 2.498 (26.0); 2.494 (12.1); 2.324 (2.6); 1.989 (16.0); 1.397 (2.2); 1.235 (1.0); 1.193 (4.3); 1.175 (8.6); 1.157 (4.2); 0.008 (2.8); 0.000 (67.6); −0.009 (2.3) |
| I-1-9 | $^1$H-NMR, Solvent [D$_6$]-DMSO, spectrometer: 399.95 MHz: δ = 8.745 (2.9); 8.316 (0.4); 8.091 (0.8); 7.710 (3.2); 7.146 (0.9); 7.130 (1.5); 7.089 (2.1); 7.070 (1.2); 4.056 (0.6); 4.038 (1.9); 4.020 (2.0); 4.002 (0.7); 3.323 (61.0); 2.675 (0.8); 2.671 (1.1); 2.666 (0.8); 2.541 (0.8); 2.524 (3.3); 2.506 (136.3); 2.502 (160.4); 2.497 (112.9); 2.493 (54.1); 2.333 (0.8); 2.329 (1.1); 2.324 (0.9); 2.319 (0.6); 2.302 (16.0); 1.989 (8.4); 1.398 (1.7); 1.235 (0.7); 1.193 (2.2); 1.175 (4.4); 1.157 (2.2); 0.146 (0.9); 0.008 (7.7); 0.000 (199.6); −0.008 (7.7); −0.150 (0.9) |
| I-1-10 | $^1$H-NMR, Solvent [D$_6$]-DMSO, spectrometer: 399.95 MHz: δ = 8.745 (6.8); 8.742 (6.3); 8.317 (0.4); 8.043 (8.3); 7.414 (8.0); 7.395 (13.9); 7.317 (4.6); 7.299 (4.1); 7.295 (3.6); 7.277 (2.3); 4.056 (1.2); 4.038 (3.7); 4.020 (3.7); 4.002 (1.3); 3.326 (46.2); 2.676 (0.8); 2.671 (1.0); 2.667 (0.8); 2.541 (0.9); 2.506 (120.9); 2.502 (150.8); 2.498 (108.3); 2.333 (0.7); 2.329 (0.9); 2.325 (0.7); 1.989 (16.0); 1.259 (0.4); 1.236 (1.8); 1.193 (4.3); 1.175 (8.5); 1.157 (4.2); 0.000 (30.2); −0.008 (1.3) |
| I-1-11 | $^1$H-NMR, Solvent [D$_6$]-DMSO, spectrometer: 399.95 MHz: δ = 8.756 (3.3); 8.052 (3.8); 7.466 (0.4); 7.450 (0.9); 7.445 (0.9); 7.430 (1.5); 7.415 (1.0); 7.410 (0.9); 7.394 (0.4); 7.038 (2.3); 7.017 (4.1); 6.996 (2.0); 4.056 (1.2); 4.038 (3.6); 4.020 (3.7); 4.002 (1.2); 3.327 (69.3); 3.012 (0.5); 2.676 (0.5); 2.671 (0.6); 2.667 (0.5); 2.541 (0.4); 2.524 (2.0); 2.511 (39.8); 2.507 (78.0); 2.502 (100.1); 2.498 (70.8); 2.493 (33.5); 2.333 (0.5); 2.329 (0.7); 2.324 (0.5); 1.989 (16.0); 1.907 (0.4); 1.398 (0.8); 1.236 (0.8); 1.193 (4.3); 1.175 (8.5); 1.157 (4.2); 1.073 (0.4); 1.056 (0.9); 1.038 (0.4); 0.008 (0.8); 0.000 (19.2); −0.008 (0.7) |
| I-1-12 | $^1$H-NMR, Solvent [D$_6$]-DMSO, spectrometer: 399.95 MHz: δ = 8.744 (7.0); 8.740 (6.6); 8.316 (0.7); 8.049 (16.0); 7.908 (14.6); 7.635 (14.4); 4.056 (0.5); 4.038 (1.6); 4.020 (1.6); 4.002 (0.5); 3.324 (162.4); 2.675 (1.2); 2.671 (1.7); 2.666 (1.2); 2.541 (1.1); 2.524 (4.8); 2.511 (101.7); 2.506 (198.9); 2.502 (255.5); 2.497 (181.7); 2.493 (86.9); 2.333 (1.2); 2.329 (1.6); 2.324 (1.2); 1.989 (6.9); 1.398 (1.7); 1.236 (0.7); 1.193 (1.9); 1.175 (3.7); 1.157 (1.8); 0.008 (2.1); 0.000 (51.6); −0.009 (2.2) |
| I-1-13 | $^1$H-NMR, Solvent [D$_6$]-DMSO, spectrometer: 399.95 MHz: δ = 8.001 (0.7); 7.399 (1.3); 7.381 (1.6); 7.298 (0.6); 7.281 (0.6); 6.897 (1.4); 3.408 (0.5); 3.392 (0.9); 3.374 (1.4); 3.329 (17.2); 2.671 (0.6); 2.502 (76.3); 2.329 (0.5); 1.423 (2.6); 1.382 (16.0); 1.109 (0.5); 1.091 (0.8); 1.074 (0.4); 0.147 (0.5); 0.000 (82.8); −0.149 (0.5) |
| I-1-14 | $^1$H-NMR, Solvent [D$_6$]-DMSO, spectrometer: 399.95 MHz: δ = 8.719 (3.5); 8.715 (3.4); 8.316 (1.5); 8.002 (7.6); 7.782 (5.2); 7.387 (5.0); 3.480 (1.0); 3.408 (0.4); 3.323 (610.4); 2.712 (0.3); 2.675 (3.6); 2.670 (4.9); 2.666 (3.7); 2.630 (0.5); 2.540 (3.4); 2.523 (13.6); 2.510 (282.1); 2.506 (559.9); 2.501 (731.4); 2.497 (525.3); 2.493 (252.5); 2.471 (15.5); 2.335 (16.0); 2.328 (5.7); 2.324 (3.6); 1.398 (0.6); 1.236 (0.5); 1.075 (0.7); 1.058 (0.7); 0.146 (4.9); 0.085 (0.4); 0.077 (0.3); 0.053 (0.4); 0.007 (38.8); 0.000 (1001.4); −0.009 (37.1); −0.042 (0.3); −0.150 (4.8). |
| I-1-15 | $^1$H-NMR, Solvent [D$_6$]-DMSO, spectrometer: 399.95 MHz: δ = 8.028 (1.9); 7.967 (1.2); 7.961 (1.2); 7.613 (0.4); 7.607 (0.4); 7.493 (0.5); 7.487 (0.4); 7.472 (1.1); 7.466 (1.2); 7.448 (1.8); 7.427 (0.6); 7.401 (0.5); 6.904 (2.6); 3.392 (0.5); 3.374 (0.6); 3.356 (0.3); 3.324 (39.5); 2.675 (0.6); 2.671 (0.8); 2.541 (0.5); 2.506 (57.9); 2.502 (71.9); 2.497 (52.0); 2.332 (0.4); 2.328 (0.5); 2.324 (0.3); 1.384 (16.0); 1.108 (0.5); 1.091 (1.0); 1.073 (0.5); 0.146 (0.6); 0.000 (115.8); −0.008 (5.9); −0.150 (0.6) |
| I-1-16 | $^1$H-NMR, Solvent [D$_6$]-DMSO, spectrometer: 399.95 MHz: δ = 8.040 (0.4); 8.021 (0.7); 8.003 (0.6); 7.414 (1.1); 6.921 (1.4); 3.328 (8.7); 2.502 (37.6); 1.389 (16.0); 1.254 (0.4); 1.234 (0.5); 0.000 (24.1) |
| I-1-17 | $^1$H-NMR, Solvent [D$_6$]-DMSO, spectrometer: 399.95 MHz: δ = 8.316 (1.0); 8.195 (0.6); 8.181 (16.0); 8.005 (4.1); 8.001 (2.4); 7.990 (4.1); 7.985 (3.4); 7.967 (11.6); 7.414 (4.5); 7.410 (6.2); 7.401 (9.2); 7.397 (6.8); 7.390 (4.5); 7.383 (2.5); 7.380 (2.5); 7.377 (2.7); 7.372 (3.2); 7.364 (2.2); 7.358 (1.4); 7.350 (1.0); 4.038 (0.9); 4.020 (0.9); 4.002 (0.3); 3.324 (358.7); 2.675 (2.1); 2.671 (2.8); 2.666 (2.1); 2.541 (2.2); 2.506 (332.1); 2.502 (426.0); 2.497 (310.3); 2.333 (2.0); 2.328 (2.7); 2.324 (2.1); 1.989 (3.8); 1.259 (0.4); 1.236 (1.1); 1.192 (1.1); 1.175 (2.1); 1.157 (1.0); 0.146 (1.2); 0.008 (13.0); 0.000 (269.0); −0.008 (12.4); −0.150 (1.3) |
| I-1-18 | $^1$H-NMR, Solvent [D$_6$]-DMSO, spectrometer: 399.95 MHz: δ = 8.316 (1.8); 8.181 (16.0); 7.971 (12.7); 7.956 (7.9); 7.950 (8.2); 7.526 (0.4); 7.499 (2.7); 7.493 (2.5); 7.478 (6.5); 7.471 (6.7); 7.452 (10.8); 7.431 (3.9); 7.284 (0.5); 7.261 (0.4); 4.552 (1.5); 3.497 (0.3); 3.477 (0.3); 3.471 (0.4); 3.457 (0.4); 3.427 (0.6); 3.424 (0.6); 3.325 (612.9); 2.675 (4.0); 2.671 (5.4); 2.667 (4.3); 2.615 (0.6); 2.541 (4.5); 2.506 (623.5); 2.502 (802.2); 2.498 (615.4); 2.333 (3.8); 2.329 (5.0); 2.324 (4.3); 2.117 (4.3); 1.651 (0.5); 1.398 (2.1); 1.298 (0.4); 1.236 (3.9); 1.140 (10.0); 0.867 (0.5); 0.854 (0.7); 0.838 (0.5); 0.146 (1.3); 0.008 (15.5); 0.000 (283.0); −0.150 (1.3) |
| I-1-19 | $^1$H-NMR, Solvent [D$_6$]-DMSO, spectrometer: 399.95 MHz: δ = 8.317 (0.9); 8.181 (5.3); 7.955 (3.0); 7.534 (2.8); 7.527 (2.8); 7.317 (2.1); 7.295 (2.3); 6.992 (1.2); 6.984 (1.3); 6.970 (1.2); 6.963 (1.1); 4.554 (1.4); 3.780 (16.0); 3.762 (0.4); |

| Example | NMR data |
|---|---|
| | 3.348 (3.1); 3.327 (409.3); 3.301 (0.7); 2.675 (1.8); 2.671 (2.5); 2.540 (2.5); 2.506 (307.1); 2.502 (402.8); 2.497 (294.6); 2.453 (0.4); 2.328 (2.5); 2.324 (1.9); 2.117 (4.0); 1.257 (0.5); 1.235 (2.3); 1.139 (9.2); 0.852 (0.3); 0.146 (0.4); 0.008 (3.5); 0.000 (84.0); −0.151 (0.4) |
| I-1-20 | $^1$H-NMR, Solvent [D$_6$]-DMSO, spectrometer: 399.95 MHz: δ = 8.317 (1.7); 8.183 (12.3); 7.942 (10.2); 7.448 (0.6); 7.428 (1.4); 7.412 (2.4); 7.397 (1.4); 7.392 (1.6); 7.376 (0.8); 7.021 (4.2); 7.000 (7.6); 6.979 (3.6); 4.554 (2.4); 4.487 (0.5); 3.763 (1.6); 3.434 (0.6); 3.398 (0.8); 3.380 (1.1); 3.327 (1022.1); 3.247 (0.4); 2.703 (0.4); 2.675 (4.4); 2.671 (6.0); 2.666 (4.4); 2.646 (0.6); 2.624 (0.5); 2.620 (0.7); 2.615 (0.7); 2.550 (2.2); 2.506 (710.3); 2.502 (930.2); 2.497 (682.0); 2.426 (0.5); 2.416 (0.6); 2.402 (0.5); 2.365 (0.5); 2.328 (5.6); 2.117 (7.4); 2.085 (0.6); 1.240 (0.7); 1.237 (0.7); 1.140 (16.0); 0.146 (1.9); 0.070 (0.5); 0.035 (0.5); 0.008 (19.6); 0.000 (442.0); −0.008 (17.7); −0.150 (2.0) |
| I-1-21 | $^1$H-NMR, Solvent [D$_6$]-DMSO, spectrometer: 399.95 MHz: δ = 8.316 (0.9); 8.270 (4.7); 8.265 (5.0); 8.182 (16.0); 7.978 (13.8); 7.802 (2.2); 7.796 (2.2); 7.781 (3.1); 7.775 (3.1); 7.681 (4.8); 7.660 (3.5); 4.555 (2.1); 3.329 (635.4); 3.220 (0.5); 2.676 (1.9); 2.671 (2.6); 2.667 (1.9); 2.524 (8.4); 2.511 (147.2); 2.507 (295.6); 2.502 (389.2); 2.498 (282.9); 2.493 (138.3); 2.480 (5.6); 2.333 (1.8); 2.329 (2.5); 2.324 (1.8); 2.117 (5.6); 2.086 (0.9); 1.398 (1.5); 1.236 (1.2); 1.140 (12.8); 0.000 (9.3) |
| I-1-22 | $^1$H-NMR, Solvent [D$_6$]-DMSO, spectrometer: 399.95 MHz: δ = 8.316 (0.8); 8.166 (6.4); 7.950 (2.6); 7.690 (3.8); 7.118 (1.3); 7.098 (2.4); 7.067 (3.1); 7.048 (1.5); 4.552 (0.4); 3.382 (0.5); 3.325 (272.9); 2.671 (2.6); 2.506 (353.6); 2.502 (433.1); 2.497 (310.9); 2.423 (0.6); 2.406 (0.4); 2.384 (0.5); 2.333 (2.3); 2.328 (2.9); 2.291 (16.0); 2.254 (0.4); 2.250 (0.3); 2.117 (1.2); 1.235 (0.8); 1.140 (2.9); 0.000 (8.0) |
| I-1-23 | $^1$H-NMR, Solvent [D$_6$]-DMSO, spectrometer: 399.95 MHz: δ = 8.316 (0.5); 7.563 (0.4); 7.039 (0.4); 3.801 (1.5); 3.425 (0.3); 3.407 (0.4); 3.326 (32.3); 2.675 (1.0); 2.671 (1.4); 2.666 (1.0); 2.506 (170.7); 2.502 (220.9); 2.497 (159.7); 2.333 (1.0); 2.328 (1.4); 2.324 (1.0); 2.117 (0.5); 1.989 (1.3); 1.386 (16.0); 1.323 (0.4); 1.305 (0.6); 1.287 (0.4); 1.258 (0.5); 1.235 (3.0); 1.192 (0.5); 1.175 (1.0); 1.157 (0.4); 1.139 (1.4); 0.854 (0.3); 0.146 (0.8); 0.008 (6.6); 0.000 (176.5); −0.008 (7.4); −0.150 (0.8) |
| I-1-24 | $^1$H-NMR, Solvent [D$_6$]-DMSO, spectrometer: 399.95 MHz: δ = 8.745 (13.2); 8.316 (3.8); 8.158 (0.5); 8.102 (3.8); 8.099 (3.7); 7.914 (16.0); 7.683 (0.3); 7.626 (10.0); 7.582 (0.4); 3.719 (0.3); 3.688 (0.3); 3.639 (0.3); 3.625 (0.4); 3.614 (0.4); 3.603 (0.4); 3.541 (0.5); 3.324 (155.5); 3.204 (0.9); 3.198 (0.5); 3.165 (0.6); 3.132 (0.5); 3.071 (0.4); 3.059 (0.4); 3.001 (0.4); 2.988 (0.4); 2.969 (0.4); 2.955 (0.3); 2.942 (0.3); 2.906 (0.3); 2.899 (0.4); 2.894 (0.4); 2.887 (0.4); 2.858 (0.4); 2.834 (0.4); 2.818 (0.4); 2.803 (0.4); 2.793 (0.5); 2.770 (0.5); 2.738 (0.7); 2.716 (0.6); 2.675 (6.5); 2.671 (8.9); 2.666 (6.9); 2.628 (0.9); 2.554 (3.8); 2.524 (94.1); 2.506 (942.1); 2.502 (1265.6); 2.497 (981.0); 2.493 (568.7); 2.362 (0.4); 2.333 (5.8); 2.329 (8.3); 2.324 (6.2); 1.988 (0.9); 1.654 (0.3); 1.351 (0.6); 1.335 (0.6); 1.313 (0.4); 1.298 (1.9); 1.259 (2.8); 1.236 (6.4); 1.193 (0.6); 1.188 (0.5); 1.175 (0.8); 1.156 (0.4); 1.087 (0.3); 0.884 (0.4); 0.867 (0.9); 0.854 (1.4); 0.836 (1.1); 0.146 (5.8); 0.076 (0.4); 0.047 (0.7); 0.031 (1.2); 0.008 (45.1); 0.000 (1183.1); −0.008 (67.8); −0.150 (5.6) |
| I-1-27 | $^1$H-NMR, Solvent [D$_6$]-DMSO, spectrometer: 399.95 MHz: δ = 8.778 (2.2); 8.142 (0.5); 7.344 (1.2); 7.336 (1.5); 7.330 (1.5); 7.322 (1.3); 7.168 (0.4); 7.145 (0.9); 7.125 (0.6); 7.055 (0.8); 3.773 (16.0); 3.325 (6.3); 2.671 (0.6); 2.506 (70.0); 2.502 (90.2); 2.498 (71.3); 2.329 (0.6); 1.989 (0.3); 1.398 (1.1); 1.259 (0.4); 1.236 (1.0); 0.146 (0.4); 0.000 (76.6); −0.150 (0.4) |
| I-1-29 | $^1$H-NMR, Solvent [D$_6$]-DMSO, spectrometer: 399.95 MHz: δ = 8.301 (2.2); 8.298 (2.2); 7.913 (1.7); 7.545 (2.8); 7.537 (2.8); 7.319 (2.2); 7.297 (2.5); 6.996 (1.2); 6.989 (1.2); 6.975 (1.1); 6.967 (1.1); 4.552 (0.3); 3.798 (0.5); 3.782 (16.0); 3.325 (26.4); 2.671 (0.3); 2.524 (0.8); 2.511 (18.6); 2.507 (37.7); 2.502 (50.1); 2.498 (36.8); 2.493 (18.0); 2.481 (0.9); 2.117 (0.9); 2.086 (2.7); 1.398 (3.0); 1.236 (0.6); 1.140 (2.1); 0.008 (2.1); 0.000 (58.0); −0.009 (2.2) |
| I-1-30 | $^1$H-NMR, Solvent [D$_6$]-DMSO, spectrometer: 399.95 MHz: δ = 8.300 (6.2); 8.297 (6.2); 7.913 (4.9); 7.432 (0.4); 7.412 (8.2); 7.392 (14.5); 7.314 (4.9); 7.296 (4.0); 7.293 (3.7); 7.275 (2.5); 4.553 (0.9); 4.056 (1.2); 4.038 (3.7); 4.020 (3.7); 4.002 (1.2); 3.327 (47.7); 2.676 (0.4); 2.671 (0.6); 2.667 (0.5); 2.525 (1.4); 2.511 (35.4); 2.507 (72.3); 2.502 (96.9); 2.498 (71.4); 2.493 (34.9); 2.480 (2.3); 2.334 (0.5); 2.329 (0.6); 2.325 (0.5); 2.118 (2.6); 2.086 (0.4); 1.989 (16.0); 1.351 (0.5); 1.259 (0.6); 1.236 (3.9); 1.193 (4.4); 1.175 (8.6); 1.157 (4.3); 1.140 (6.1); 0.854 (0.6); 0.836 (0.4); 0.146 (0.4); 0.008 (3.2); 0.000 (95.1); −0.009 (3.5); −0.150 (0.4) |
| I-1-31 | $^1$H-NMR, Solvent [D$_6$]-DMSO, spectrometer: 399.95 MHz: δ = 8.384 (0.4); 8.317 (0.7); 8.304 (9.1); 8.301 (9.2); 8.222 (0.5); 8.096 (0.4); 8.090 (0.4); 7.968 (9.1); 7.962 (9.4); 7.942 (9.1); 7.919 (0.4); 7.523 (0.4); 7.510 (3.2); 7.503 (2.9); 7.488 (8.0); 7.482 (8.1); 7.462 (14.2); 7.441 (5.2); 7.429 (0.3); 7.194 (0.9); 7.188 (0.8); 4.553 (1.1); 4.284 (0.8); 4.270 (0.3); 3.327 (128.5); 2.676 (0.9); 2.672 (1.5); 2.667 (0.9); 2.565 (0.6); 2.507 (149.7); 2.502 (195.9); 2.498 (147.0); 2.333 (1.0); 2.329 (1.3); 2.325 (1.0); 2.117 (3.2); 2.086 (0.5); 1.398 (16.0); 1.351 (0.8); 1.303 (0.7); 1.299 (0.6); 1.288 (1.0); 1.270 (0.7); 1.259 (1.1); 1.235 (5.7); 1.210 (0.5); 1.140 (7.3); 0.868 (0.5); 0.854 (0.9); 0.836 (0.5); 0.146 (0.4); 0.008 (3.6); 0.000 (93.4); −0.008 (4.4); −0.150 (0.5) |
| I-1-43 | $^1$H-NMR, Solvent [D$_6$]-DMSO, spectrometer: 399.95 MHz: δ = 8.316 (0.6); 8.186 (5.9); 7.965 (1.6); 7.914 (1.5); 7.625 (1.1); 7.606 (2.3); 7.536 (0.9); 7.518 (0.7); 7.514 (0.6); 7.496 (0.5); 7.415 (3.6); 7.395 (5.3); 7.317 (1.6); 7.298 (1.9); 7.279 (1.0); 3.509 (0.4); 3.330 (38.5); 2.675 (1.0); 2.671 (1.5); 2.666 (1.0); 2.524 (2.6); 2.510 (89.9); 2.506 (181.7); 2.502 (237.8); 2.497 (172.8); 2.493 (85.0); 2.333 (1.3); 2.328 (1.7); 2.324 (1.3); 2.179 (0.4); 2.117 (0.5); 1.397 (2.1); 1.351 (0.9); 1.335 (0.6); 1.298 (2.7); 1.258 (4.2); 1.235 (16.0); 1.187 (0.8); 1.169 (0.8); 1.140 (1.4); |

| Example | NMR data |
| --- | --- |
| | 1.119 (0.5); 0.884 (0.7); 0.867 (1.3); 0.854 (2.5); 0.836 (1.3); 0.146 (0.4); 0.007 (3.3); −0.001 (91.0); −0.009 (3.5); −0.150 (0.4) |
| I-1-45 | $^1$H-NMR, Solvent [$D_6$]-DMSO, spectrometer: 399.95 MHz: <br> δ = 8.317 (0.7); 8.165 (8.5); 7.964 (4.7); 7.890 (5.1); 7.595 (4.7); 4.055 (0.6); 4.038 (2.0); 4.020 (2.0); 4.002 (0.7); 3.326 (99.1); 2.676 (1.2); 2.671 (1.5); 2.667 (1.1); 2.521 (20.5); 2.511 (84.9); 2.507 (166.8); 2.502 (217.8); 2.498 (158.8); 2.476 (16.0); 2.333 (1.0); 2.329 (1.4); 2.324 (1.0); 1.989 (8.4); 1.298 (0.4); 1.259 (0.6); 1.236 (1.0); 1.193 (2.3); 1.175 (4.5); 1.157 (2.2); 0.008 (1.2); 0.000 (30.4); −0.008 (1.2) |
| I-1-50 | $^1$H-NMR, Solvent [$D_6$]-DMSO, spectrometer: 399.95 MHz: <br> δ = 8.317 (2.1); 8.182 (16.0); 7.961 (12.6); 7.839 (2.5); 7.816 (7.6); 7.789 (1.4); 7.769 (1.8); 7.751 (4.8); 7.732 (5.3); 7.708 (1.0); 7.687 (1.5); 7.638 (1.7); 7.618 (2.2); 7.598 (0.9); 7.518 (4.2); 7.504 (3.1); 7.484 (5.8); 7.461 (5.9); 7.442 (6.7); 7.422 (2.4); 6.896 (0.5); 6.717 (0.4); 3.974 (0.4); 3.447 (0.5); 3.327 (631.0); 2.749 (0.5); 2.715 (0.6); 2.671 (6.7); 2.506 (811.2); 2.502 (959.4); 2.329 (6.0); 1.909 (0.9); 1.351 (4.5); 1.336 (2.2); 1.298 (2.8); 1.259 (4.4); 1.249 (4.2); 1.235 (10.4); 1.188 (0.6); 0.869 (0.7); 0.854 (1.4); 0.835 (0.9); 0.816 (0.4); 0.146 (4.2); 0.000 (844.3); −0.149 (4.1) |
| I-1-51 | $^1$H-NMR, Solvent [$D_6$]-DMSO, spectrometer: 399.95 MHz: <br> δ = 8.317 (1.0); 8.188 (16.0); 7.970 (11.0); 7.837 (11.6); 7.816 (12.8); 7.647 (0.3); 7.566 (0.3); 7.518 (0.4); 7.505 (0.5); 7.483 (12.2); 7.461 (10.4); 4.055 (0.5); 4.038 (1.4); 4.020 (1.4); 4.002 (0.5); 3.329 (262.6); 2.676 (1.9); 2.671 (2.4); 2.667 (1.8); 2.541 (1.1); 2.507 (291.3); 2.502 (367.5); 2.498 (269.6); 2.333 (1.8); 2.329 (2.4); 1.989 (6.0); 1.398 (0.4); 1.351 (0.7); 1.298 (1.8); 1.259 (2.4); 1.235 (2.7); 1.193 (1.8); 1.175 (3.3); 1.157 (1.7); 0.854 (0.4); 0.000 (20.4) |
| I-1-60 | $^1$H-NMR, Solvent [$D_6$]-DMSO, spectrometer: 399.95 MHz: <br> δ = 8.317 (0.8); 8.199 (4.6); 7.963 (1.9); 7.536 (2.8); 7.529 (2.9); 7.325 (1.5); 7.304 (1.7); 7.256 (0.3); 7.248 (0.4); 7.235 (0.3); 7.214 (0.4); 6.999 (0.9); 6.991 (0.9); 6.976 (0.8); 6.969 (0.8); 3.781 (16.0); 3.722 (2.1); 3.330 (248.1); 2.676 (1.4); 2.671 (1.9); 2.667 (1.4); 2.511 (116.1); 2.507 (227.3); 2.502 (293.4); 2.498 (209.9); 2.333 (1.4); 2.329 (1.8); 2.325 (1.3); 1.351 (0.4); 1.298 (1.2); 1.259 (1.8); 1.235 (4.1); 0.854 (0.5); 0.146 (0.6); 0.008 (5.9); 0.000 (147.1); −0.008 (5.6); −0.150 (0.7) |
| I-1-118 | $^1$H-NMR, Solvent [$D_6$]-DMSO, spectrometer: 399.95 MHz: <br> δ = 1.28 (d, 6H); 3.16 (m, 1H); 7.58-7.73 (m, 3H); 7.89 (m, 1H); 8.14 (d, 1H); 8.40 (s, 1H) ppm |
| I-1-123 | $^1$H-NMR, Solvent [$D_6$]-DMSO, spectrometer: 399.95 MHz: <br> δ = 1.28 (d, 6H); 3.08 (m, 1H); 3.78 (s, 3H); 6.97 (br. d, 1H); 7.30 (d, 1H); 7.53 (d, 1H); 7.67 (s, 1H); 7.89 (s, 1H) ppm |
| I-1-142 | $^1$H-NMR, Solvent [$D_6$]-DMSO, spectrometer: 399.95 MHz: <br> δ = 8.941 (8.5); 8.937 (14.2); 8.637 (16.0); 8.318 (0.8); 8.180 (7.1); 8.176 (7.4); 8.161 (7.8); 8.157 (7.7); 7.992 (1.4); 7.989 (1.4); 7.973 (1.5); 7.969 (1.5); 7.734 (1.9); 7.730 (2.0); 7.714 (5.5); 7.696 (6.4); 7.692 (6.1); 7.675 (9.0); 7.672 (11.3); 7.655 (5.5); 7.652 (4.6); 7.643 (5.6); 7.638 (5.8); 7.634 (3.0); 7.622 (8.1); 7.608 (5.1); 7.605 (5.7); 7.588 (0.8); 7.584 (0.7); 7.541 (1.1); 7.537 (1.1); 7.522 (1.3); 7.518 (1.3); 7.504 (0.7); 7.500 (0.6); 3.343 (12.7); 2.676 (2.1); 2.672 (2.7); 2.667 (2.0); 2.542 (1.3); 2.525 (7.2); 2.511 (156.4); 2.507 (311.5); 2.503 (404.7); 2.498 (288.0); 2.494 (135.8); 2.334 (1.8); 2.329 (2.5); 2.325 (1.8); 0.146 (0.6); 0.008 (5.1); 0.000 (136.1); −0.009 (4.6); −0.150 (0.6) |
| I-1-143 | $^1$H-NMR, Solvent [$D_6$]-DMSO, spectrometer: 399.95 MHz: <br> δ = 8.912 (10.9); 8.529 (16.0); 8.318 (0.4); 7.992 (9.7); 7.988 (7.3); 7.964 (5.4); 7.944 (5.9); 7.827 (4.1); 7.825 (4.1); 7.807 (5.3); 7.804 (5.5); 7.771 (0.3); 7.706 (5.8); 7.686 (8.9); 7.666 (3.7); 7.639 (0.3); 7.619 (0.4); 7.521 (0.7); 5.758 (0.4); 3.359 (2.6); 3.188 (1.1); 2.673 (1.3); 2.504 (179.5); 2.330 (1.1); 2.087 (1.2); 0.000 (50.1) |
| I-1-144 | $^1$H-NMR, Solvent [$D_6$]-DMSO, spectrometer: 399.95 MHz: <br> δ = 8.907 (10.7); 8.764 (0.3); 8.516 (15.5); 8.318 (0.6); 8.260 (0.6); 8.006 (13.5); 7.984 (16.0); 7.814 (0.4); 7.736 (15.5); 7.714 (13.2); 7.669 (0.3); 7.570 (0.4); 7.548 (0.4); 7.470 (0.3); 7.377 (0.5); 7.355 (0.4); 3.341 (18.1); 3.186 (0.9); 3.030 (0.4); 2.802 (1.0); 2.794 (1.1); 2.768 (0.4); 2.758 (0.4); 2.676 (1.7); 2.672 (2.3); 2.667 (1.7); 2.507 (265.9); 2.503 (342.9); 2.498 (254.4); 2.334 (1.6); 2.329 (2.1); 2.325 (1.6); 1.039 (0.4); 1.021 (0.7); 1.002 (0.4); 0.146 (0.4); 0.000 (93.5); −0.150 (0.4) |
| I-1-145 | $^1$H-NMR, Solvent [$D_6$]-DMSO, spectrometer: 399.95 MHz: <br> δ = 8.774 (7.2); 8.771 (12.3); 8.318 (0.8); 8.076 (14.9); 7.966 (11.4); 7.960 (11.6); 7.515 (3.6); 7.509 (3.2); 7.494 (8.7); 7.488 (8.9); 7.467 (16.0); 7.446 (6.0); 4.038 (0.6); 4.020 (0.6); 3.333 (167.8); 2.676 (1.5); 2.672 (2.0); 2.667 (1.4); 2.663 (0.8); 2.525 (6.0); 2.512 (118.3); 2.507 (236.1); 2.503 (306.9); 2.498 (219.2); 2.494 (104.3); 2.334 (1.5); 2.330 (1.9); 2.325 (1.4); 1.990 (2.7); 1.351 (0.6); 1.298 (0.4); 1.259 (0.7); 1.250 (0.7); 1.236 (2.2); 1.193 (0.8); 1.175 (1.4); 1.157 (0.7); 0.854 (0.5); 0.836 (0.3); 0.008 (0.3); 0.000 (8.6) |
| I-1-146 | $^1$H-NMR, Solvent [$D_6$]-DMSO, spectrometer: 399.95 MHz: <br> δ = 8.771 (9.0); 8.318 (1.0); 8.056 (3.8); 7.420 (8.3); 7.401 (12.3); 7.323 (3.6); 7.304 (3.9); 7.283 (1.7); 4.055 (1.2); 4.038 (3.7); 4.020 (3.7); 4.002 (1.2); 3.330 (97.8); 2.676 (2.2); 2.671 (2.9); 2.667 (2.2); 2.511 (181.8); 2.507 (354.9); 2.502 (458.1); 2.498 (330.3); 2.494 (159.8); 2.334 (2.1); 2.329 (2.9); 2.325 (2.2); 1.989 (16.0); 1.398 (1.6); 1.298 (0.5); 1.259 (0.8); 1.249 (0.5); 1.235 (1.4); 1.193 (4.4); 1.175 (8.9); 1.157 (4.3); 0.008 (0.4); 0.000 (10.7); −0.008 (0.4) |
| I-1-147 | $^1$H-NMR, Solvent [$D_6$]-DMSO, spectrometer: 600 MHz: <br> δ = 8.736 (2.9); 8.096 (2.3); 7.576 (2.6); 7.571 (2.7); 7.325 (2.2); 7.310 (2.5); 7.002 (1.2); 6.997 (1.2); 6.987 (1.1); 6.982 (1.1); 3.783 (16.0); 3.191 (2.5); 2.499 (7.1); 2.496 (15.0); 2.493 (21.4); 2.490 (16.0); 2.487 (8.2); 1.979 (1.2); 1.401 (1.0); 1.243 (0.4); 1.177 (0.6); 0.000 (1.3) |

| Example | NMR data |
|---|---|
| I-1-151 | $^1$H-NMR, Solvent [D$_6$]-DMSO, spectrometer: 399.95 MHz:<br>δ = 8.935 (2.7); 8.611 (4.2); 7.662 (0.7); 7.414 (1.7); 7.406 (1.4); 7.400 (1.3); 7.391 (2.8); 7.367 (1.4); 7.354 (0.4); 7.331 (0.9); 7.323 (1.3); 7.314 (0.8); 7.309 (0.6); 7.300 (0.7); 7.292 (0.4); 5.756 (0.4); 3.832 (16.0); 3.793 (2.9); 3.355 (0.6); 3.329 (0.5); 3.187 (0.5); 2.672 (0.4); 2.507 (37.7); 2.503 (50.9); 2.498 (38.9); 0.008 (1.7); 0.000 (48.3); −0.008 (2.4) |
| I-1-153 | $^1$H-NMR, Solvent [D$_6$]-DMSO, spectrometer: 399.95 MHz:<br>δ = 8.922 (2.2); 8.918 (4.1); 8.551 (5.6); 7.986 (3.3); 7.980 (3.6); 7.688 (1.5); 7.682 (1.6); 7.667 (1.9); 7.661 (1.9); 7.458 (2.8); 7.438 (2.3); 3.387 (0.6); 3.355 (0.6); 2.672 (0.7); 2.667 (0.5); 2.581 (16.0); 2.525 (1.4); 2.511 (29.4); 2.507 (61.0); 2.503 (82.4); 2.498 (62.3); 2.494 (32.0); 2.417 (0.8); 2.334 (0.4); 2.329 (0.5); 2.325 (0.4); 0.008 (1.0); 0.000 (29.9); −0.008 (1.3) |
| I-1-154 | $^1$H-NMR, Solvent [D$_6$]-DMSO, spectrometer: 399.95 MHz:<br>δ = 8.755 (11.0); 8.183 (3.5); 8.180 (3.4); 8.164 (3.7); 8.161 (3.5); 7.736 (1.1); 7.732 (1.1); 7.716 (3.1); 7.698 (3.4); 7.695 (3.1); 7.672 (5.5); 7.656 (2.7); 7.645 (2.8); 7.625 (3.7); 7.607 (1.8); 5.757 (1.8); 3.498 (0.7); 3.420 (1.0); 3.401 (0.9); 3.377 (0.9); 3.290 (1.1); 3.273 (0.7); 3.187 (0.6); 3.144 (0.4); 3.113 (0.5); 3.094 (0.4); 3.035 (0.4); 2.770 (0.5); 2.672 (0.5); 2.614 (16.0); 2.611 (15.4); 2.507 (52.2); 2.503 (60.7); 2.330 (0.4); 0.000 (29.6) |
| I-1-155 | $^1$H-NMR, Solvent [D$_6$]-DMSO, spectrometer: 399.95 MHz:<br>δ = 8.716 (10.8); 8.316 (0.4); 8.007 (3.6); 8.002 (6.0); 7.998 (4.0); 7.966 (3.3); 7.946 (3.7); 7.817 (2.5); 7.815 (2.4); 7.797 (3.3); 7.795 (3.3); 7.699 (3.9); 7.679 (6.1); 7.659 (2.5); 5.756 (1.9); 3.587 (0.4); 3.356 (2.5); 3.187 (0.7); 2.675 (1.1); 2.671 (1.4); 2.667 (1.1); 2.652 (0.3); 2.610 (16.0); 2.606 (16.0); 2.506 (137.8); 2.502 (174.3); 2.498 (131.4); 2.333 (0.9); 2.329 (1.2); 2.324 (0.9); 0.146 (0.5); 0.027 (0.5); 0.007 (7.4); 0.000 (100.6); −0.150 (0.5) |
| I-1-156 | $^1$H-NMR, Solvent [D$_6$]-DMSO, spectrometer: 399.95 MHz:<br>δ = 8.705 (14.9); 8.021 (1.3); 8.014 (10.7); 8.010 (12.6); 7.997 (3.9); 7.993 (12.6); 7.986 (1.5); 7.814 (0.4); 7.743 (1.7); 7.736 (12.2); 7.731 (3.7); 7.719 (3.5); 7.715 (10.4); 7.708 (1.2); 5.756 (3.6); 3.357 (1.3); 3.188 (0.4); 2.676 (0.6); 2.671 (0.8); 2.667 (0.6); 2.610 (15.9); 2.606 (16.0); 2.542 (0.4); 2.524 (2.0); 2.511 (40.4); 2.507 (79.0); 2.502 (103.2); 2.498 (75.4); 2.494 (36.5); 2.334 (0.5); 2.329 (0.7); 2.325 (0.5); 0.146 (0.3); 0.008 (2.8); 0.000 (73.8); −0.009 (2.8); −0.150 (0.3) |
| I-1-157 | $^1$H-NMR, Solvent [D$_6$]-DMSO, spectrometer: 399.95 MHz:<br>δ = 8.751 (11.1); 8.106 (5.7); 8.100 (6.0); 7.828 (2.7); 7.822 (2.6); 7.807 (4.0); 7.800 (4.0); 7.724 (7.2); 7.703 (4.8); 5.758 (12.2); 2.673 (0.5); 2.616 (16.0); 2.613 (16.0); 2.503 (78.1); 2.330 (0.6); 0.000 (3.5) |
| I-1-158 | $^1$H-NMR, Solvent [D$_6$]-DMSO, spectrometer: 399.95 MHz:<br>δ = 8.720 (5.5); 7.660 (4.8); 7.642 (11.3); 7.604 (4.0); 7.587 (2.7); 7.581 (2.2); 7.564 (1.3); 5.757 (0.6); 3.683 (0.4); 3.671 (0.4); 3.657 (0.4); 3.580 (0.5); 3.418 (0.6); 3.392 (0.5); 3.375 (0.5); 3.273 (0.5); 3.187 (0.4); 2.671 (0.5); 2.667 (0.5); 2.616 (16.0); 2.612 (15.9); 2.507 (80.2); 2.502 (100.5); 2.498 (75.2); 2.449 (0.4); 2.329 (0.7); 0.000 (58.2) |
| I-1-159 | $^1$H-NMR, Solvent [D$_6$]-DMSO, spectrometer: 399.95 MHz:<br>δ = 8.749 (4.7); 7.616 (3.2); 7.609 (3.2); 7.577 (2.6); 7.555 (2.9); 7.301 (1.8); 7.294 (1.8); 7.279 (1.6); 7.272 (1.4); 5.756 (0.6); 3.858 (16.0); 3.816 (0.4); 3.674 (0.4); 3.634 (0.4); 3.562 (0.7); 3.358 (3.5); 3.277 (2.2); 3.187 (0.9); 3.138 (0.6); 3.109 (0.5); 3.059 (0.4); 3.036 (0.3); 2.778 (0.4); 2.670 (0.9); 2.614 (9.8); 2.502 (111.1); 2.329 (0.8); 0.000 (34.4) |
| I-1-191 | $^1$H-NMR, Solvent [D$_6$]-DMSO, spectrometer: 399.95 MHz:<br>δ = 8.760 (2.6); 8.756 (6.6); 8.753 (6.4); 8.320 (0.3); 8.075 (0.6); 8.055 (11.7); 7.845 (6.2); 7.840 (6.2); 7.757 (2.5); 7.751 (2.8); 7.740 (2.7); 7.734 (2.7); 7.475 (5.8); 7.471 (5.9); 7.392 (0.4); 7.365 (0.4); 7.309 (1.2); 7.303 (1.3); 7.297 (1.4); 7.288 (1.8); 7.281 (1.8); 7.276 (1.8); 7.271 (1.7); 7.179 (3.1); 7.155 (3.6); 7.134 (2.3); 6.283 (4.7); 6.278 (7.7); 6.273 (4.7); 5.358 (16.0); 4.814 (0.7); 3.334 (115.7); 2.676 (0.4); 2.672 (0.6); 2.667 (0.5); 2.525 (1.4); 2.520 (2.2); 2.512 (30.8); 2.507 (63.8); 2.503 (85.9); 2.498 (63.6); 2.494 (31.0); 2.334 (0.4); 2.329 (0.5); 2.325 (0.4); 1.989 (1.1); 1.352 (0.8); 1.337 (0.4); 1.299 (5.5); 1.259 (7.6); 1.235 (2.8); 1.193 (0.4); 1.175 (0.7); 1.157 (0.4); 0.854 (0.5); 0.000 (0.3) |
| I-1-192 | $^1$H-NMR, Solvent [D$_6$]-DMSO, spectrometer: 399.95 MHz:<br>δ = 5.48 (s, 2H); 6.31 (m, 1H); 7.35 (d, 1H); 7.51 (br. s, 1H); 7.80 (d, 1H); 7.89 (br. s, 1H); 8.06 (br. s, 1H); 8.63 (s, 1H); 8.92 (s, 1H) ppm |
| I-1-194 | $^1$H-NMR, Solvent [D$_6$]-DMSO, spectrometer: 399.95 MHz:<br>δ = 8.743 (2.3); 8.739 (6.0); 8.736 (5.9); 8.041 (12.3); 7.847 (5.4); 7.843 (5.7); 7.815 (5.9); 7.810 (5.9); 7.456 (5.6); 7.452 (5.6); 7.238 (2.9); 7.218 (6.7); 7.193 (4.0); 7.189 (4.0); 7.174 (1.7); 7.169 (1.8); 6.269 (4.3); 6.264 (7.2); 6.259 (4.4); 5.328 (15.7); 4.055 (1.1); 4.038 (3.3); 4.020 (3.3); 4.002 (1.1); 3.335 (124.2); 3.072 (1.7); 3.054 (5.6); 3.035 (5.8); 3.016 (1.9); 2.676 (0.4); 2.672 (0.5); 2.667 (0.4); 2.525 (1.1); 2.512 (26.5); 2.507 (55.2); 2.503 (75.0); 2.498 (56.5); 2.494 (28.8); 2.334 (0.3); 2.329 (0.5); 2.325 (0.4); 1.989 (14.5); 1.352 (0.4); 1.336 (0.6); 1.299 (1.9); 1.259 (2.6); 1.250 (1.1); 1.235 (1.6); 1.193 (3.9); 1.175 (7.6); 1.157 (3.8); 1.131 (7.5); 1.112 (16.0); 1.093 (7.4) |
| I-1-196 | δ = 8.925 (5.4); 8.921 (5.3); 8.601 (9.4); 7.987 (5.5); 7.916 (5.3); 7.911 (5.6); 7.613 (0.7); 7.587 (8.0); 7.562 (0.7); 7.513 (5.0); 7.510 (5.4); 6.315 (3.6); 6.310 (6.1); 6.305 (3.8); 5.514 (16.0); 3.511 (0.5); 3.467 (0.6); 3.450 (0.7); 3.432 (0.8); 3.415 (0.7); 3.376 (0.7); 3.357 (0.7); 3.223 (0.4); 3.213 (0.4); 3.187 (0.6); 2.672 (0.6); 2.668 (0.5); 2.507 (70.8); 2.503 (93.2); 2.499 (72.2); 2.334 (0.5); 2.330 (0.6); 2.326 (0.5); 0.146 (0.6); 0.008 (5.7); 0.000 (114.4); −0.150 (0.6) |

-continued

| Example | NMR data |
|---|---|
| I-1-198 | $^1$H-NMR, Solvent [D$_6$]-DMSO, spectrometer: 399.95 MHz:<br>δ = 8.752 (5.8); 8.749 (5.7); 8.318 (0.5); 8.025 (12.8); 7.834 (5.7); 7.829 (5.7); 7.724 (10.0); 7.632 (10.6); 7.492 (5.6); 7.489 (5.7); 6.296 (4.1); 6.291 (6.7); 6.286 (4.2); 5.465 (16.0); 3.326 (127.2); 2.676 (0.7); 2.671 (1.0); 2.667 (0.8); 2.568 (0.4); 2.524 (2.7); 2.511 (48.5); 2.507 (97.7); 2.502 (131.1); 2.498 (100.6); 2.494 (53.7); 2.334 (0.5); 2.329 (0.8); 2.325 (0.6); 1.352 (0.6); 1.336 (1.5); 1.298 (3.0); 1.259 (4.1); 1.250 (2.4); 1.235 (2.7); 0.854 (0.5); 0.146 (0.7); 0.008 (5.6); 0.000 (144.2); −0.008 (9.0); −0.150 (0.7) |
| I-1-200 | $^1$H-NMR, Solvent [D$_6$]-DMSO, spectrometer: 399.95 MHz:<br>δ = 8.762 (6.0); 8.759 (6.1); 8.034 (12.5); 7.827 (6.2); 7.822 (6.3); 7.572 (4.7); 7.553 (4.8); 7.502 (5.3); 7.491 (6.9); 7.487 (7.0); 7.478 (5.8); 6.296 (4.1); 6.291 (6.9); 6.286 (4.4); 6.256 (0.8); 6.251 (1.4); 6.247 (0.9); 5.444 (16.0); 5.419 (0.3); 4.056 (1.1); 4.038 (3.3); 4.020 (3.4); 4.002 (1.2); 3.331 (107.5); 2.672 (0.5); 2.507 (61.6); 2.503 (80.7); 2.498 (63.8); 2.329 (0.5); 1.989 (13.9); 1.352 (0.5); 1.334 (0.6); 1.299 (1.4); 1.259 (1.8); 1.250 (0.7); 1.235 (1.3); 1.193 (3.8); 1.175 (7.4); 1.157 (3.7); 0.000 (6.3); −0.009 (0.6) |
| I-1-202 | $^1$H-NMR, Solvent [D$_6$]-DMSO, spectrometer: 399.95 MHz:<br>δ = 9.115 (0.4); 8.686 (3.9); 8.316 (0.4); 8.057 (6.7); 8.039 (7.5); 7.603 (0.5); 7.471 (9.3); 7.462 (16.0); 7.448 (5.9); 7.437 (4.2); 7.428 (4.4); 7.417 (3.8); 7.406 (1.7); 3.323 (6.1); 2.675 (0.9); 2.671 (1.2); 2.666 (0.9); 2.524 (4.0); 2.511 (65.7); 2.506 (130.8); 2.502 (173.0); 2.497 (128.9); 2.493 (66.4); 2.333 (0.8); 2.329 (1.1); 2.324 (0.8); 1.299 (0.8); 1.259 (1.1); 1.250 (0.4); 1.245 (0.4); 1.234 (0.3); 0.000 (8.1); −0.008 (0.4) |
| I-1-203 | $^1$H-NMR, Solvent [D$_6$]-DMSO, spectrometer: 399.95 MHz:<br>δ = 8.806 (0.7); 8.316 (1.6); 7.911 (1.4); 7.625 (1.3); 7.606 (2.5); 7.535 (4.4); 7.517 (5.6); 7.514 (5.7); 7.496 (2.2); 7.437 (2.0); 7.372 (0.3); 7.344 (0.4); 7.211 (0.4); 7.083 (0.5); 7.060 (0.3); 6.955 (0.4); 4.496 (0.4); 4.393 (0.4); 4.055 (1.3); 4.038 (3.7); 4.020 (3.8); 4.002 (1.4); 3.596 (0.4); 3.571 (0.5); 3.326 (24.3); 2.675 (4.3); 2.670 (6.0); 2.666 (4.6); 2.523 (19.9); 2.510 (322.8); 2.506 (642.2); 2.501 (853.4); 2.497 (643.2); 2.493 (338.7); 2.333 (4.0); 2.328 (5.6); 2.324 (4.2); 1.989 (16.0); 1.372 (2.9); 1.298 (0.6); 1.258 (0.8); 1.236 (0.5); 1.193 (4.2); 1.175 (8.3); 1.157 (4.1); 0.008 (1.1); 0.000 (31.0); −0.008 (1.7) |
| I-1-204 | $^1$H-NMR, Solvent [D$_6$]-DMSO, spectrometer: 399.95 MHz:<br>δ = 8.732 (4.2); 8.729 (4.3); 8.051 (7.3); 7.788 (4.1); 7.783 (4.3); 7.730 (4.3); 7.447 (4.1); 7.445 (4.3); 7.089 (4.2); 6.260 (2.6); 6.255 (4.5); 6.250 (2.9); 5.277 (10.9); 3.331 (84.2); 2.672 (0.4); 2.502 (55.1); 2.459 (15.7); 2.329 (0.4); 2.196 (16.0); 1.989 (1.0); 1.175 (0.5); 0.000 (3.5) |
| I-1-205 | $^1$H-NMR, Solvent [D$_6$]-DMSO, spectrometer: 399.95 MHz:<br>δ = 8.764 (16.0); 8.317 (3.1); 8.180 (0.4); 8.112 (5.3); 8.050 (0.4); 8.032 (0.3); 8.025 (0.4); 8.017 (0.5); 7.998 (15.0); 7.992 (15.3); 7.656 (8.7); 7.634 (10.2); 7.429 (6.2); 7.409 (5.2); 7.376 (0.3); 4.055 (1.0); 4.038 (2.7); 4.020 (2.7); 4.002 (0.9); 3.724 (0.3); 3.704 (0.3); 3.662 (0.4); 3.638 (0.5); 3.615 (0.5); 3.602 (0.5); 3.565 (0.6); 3.528 (0.8); 3.517 (0.9); 3.480 (1.3); 3.331 (104.6); 3.238 (2.8); 3.135 (0.7); 3.106 (0.6); 3.047 (0.4); 3.025 (0.4); 3.009 (0.3); 3.005 (0.4); 2.993 (0.4); 2.809 (0.4); 2.745 (0.4); 2.736 (0.3); 2.675 (5.9); 2.671 (7.8); 2.667 (6.0); 2.651 (0.5); 2.630 (0.5); 2.601 (0.8); 2.585 (1.0); 2.506 (883.0); 2.502 (1158.3); 2.498 (875.0); 2.437 (0.8); 2.333 (5.6); 2.329 (7.5); 2.325 (5.7); 1.989 (11.4); 1.657 (0.5); 1.617 (0.4); 1.398 (4.1); 1.352 (1.0); 1.335 (1.1); 1.312 (0.4); 1.298 (1.1); 1.259 (2.0); 1.249 (2.6); 1.236 (8.3); 1.193 (3.3); 1.175 (2.5); 1.157 (3.2); 1.150 (0.5); 1.117 (0.5); 0.885 (0.5); 0.867 (1.1); 0.854 (1.8); 0.836 (1.3); 0.146 (7.2); 0.051 (0.7); 0.038 (1.1); 0.008 (62.4); 0.000 (1448.7); −0.008 (75.2); −0.065 (0.5); −0.150 (7.2) |
| I-1-206 | $^1$H-NMR, Solvent [D$_6$]-DMSO, spectrometer: 399.95 MHz:<br>δ = 8.800 (1.6); 8.317 (0.6); 7.607 (2.8); 7.600 (2.9); 7.566 (0.7); 7.548 (0.7); 6.998 (0.6); 4.038 (0.3); 4.020 (0.4); 3.804 (16.0); 3.327 (6.7); 2.676 (0.7); 2.671 (1.0); 2.667 (0.7); 2.524 (2.3); 2.511 (50.8); 2.507 (104.2); 2.502 (140.1); 2.498 (104.8); 2.493 (53.2); 2.333 (0.7); 2.329 (0.9); 2.324 (0.7); 1.989 (1.4); 1.298 (0.6); 1.259 (0.9); 1.249 (0.5); 1.235 (2.0); 1.193 (0.5); 1.175 (0.8); 1.157 (0.4); 0.854 (0.4); 0.146 (0.9); 0.008 (7.2); 0.000 (203.9); −0.009 (9.2); −0.150 (0.9) |
| I-1-207 | $^1$H-NMR, Solvent [D$_6$]-DMSO, spectrometer: 399.95 MHz:<br>δ = 8.810 (2.6); 8.316 (0.5); 8.264 (0.4); 7.562 (4.2); 7.554 (4.4); 7.393 (1.0); 7.374 (1.1); 7.092 (0.9); 4.038 (0.6); 4.020 (0.6); 4.002 (0.3); 3.985 (2.9); 3.969 (6.0); 3.953 (3.1); 3.324 (1.7); 2.676 (0.5); 2.671 (0.6); 2.667 (0.5); 2.524 (1.6); 2.511 (35.7); 2.507 (72.9); 2.502 (97.9); 2.498 (74.3); 2.493 (38.9); 2.333 (0.5); 2.329 (0.7); 2.324 (0.5); 1.989 (2.5); 1.793 (0.5); 1.775 (2.1); 1.759 (4.2); 1.740 (4.4); 1.723 (2.3); 1.706 (0.6); 1.398 (1.4); 1.259 (0.4); 1.249 (0.4); 1.236 (1.4); 1.193 (0.7); 1.175 (1.3); 1.157 (0.7); 1.006 (7.8); 0.988 (16.0); 0.969 (7.2); 0.146 (0.4); 0.008 (3.6); 0.000 (100.4); −0.008 (5.4); −0.150 (0.5) |
| I-1-208 | $^1$H-NMR, Solvent [D$_6$]-DMSO, spectrometer: 399.95 MHz:<br>δ = 8.783 (1.2); 8.316 (0.4); 7.525 (2.1); 7.517 (2.2); 7.333 (0.5); 7.315 (0.5); 7.021 (0.4); 4.624 (0.6); 4.609 (0.9); 4.594 (0.7); 3.323 (8.8); 2.675 (0.6); 2.671 (0.9); 2.667 (0.6); 2.524 (2.4); 2.506 (96.8); 2.502 (128.8); 2.497 (98.5); 2.333 (0.6); 2.328 (0.8); 2.324 (0.7); 1.294 (16.0); 1.279 (16.0); 1.259 (0.6); 1.249 (0.4); 1.236 (1.1); 0.146 (0.6); 0.008 (5.0); 0.000 (124.5); −0.008 (7.4); −0.150 (0.6) |
| I-1-209 | $^1$H-NMR, Solvent [D$_6$]-DMSO, spectrometer: 399.95 MHz:<br>δ = 8.758 (8.9); 8.755 (9.1); 8.316 (0.6); 8.107 (13.1); 8.101 (16.0); 7.646 (3.4); 7.640 (3.5); 7.625 (4.1); 7.619 (4.1); 7.409 (7.9); 7.388 (6.7); 3.508 (0.7); 3.504 (0.7); 3.498 (0.5); 3.490 (0.7); 3.476 (0.4); 3.435 (1.0); 3.427 (0.9); 3.422 (1.2); 3.411 (1.2); 3.332 (7.4); 3.238 (2.9); 2.675 (0.9); 2.671 (1.2); 2.667 (0.9); 2.506 (138.2); 2.502 (183.4); 2.498 (141.0); 2.333 (0.9); 2.329 (1.2); 2.324 (1.0); 1.989 (0.5); 1.398 (0.6); 1.351 (0.6); |

| Example | NMR data |
|---|---|
| | 1.336 (0.4); 1.298 (0.9); 1.259 (1.5); 1.235 (4.2); 1.193 (0.4); 1.187 (0.3); 1.175 (0.4); 0.867 (0.6); 0.853 (1.0); 0.836 (0.7); 0.146 (0.8); 0.008 (6.8); 0.000 (159.7); −0.008 (9.8); −0.150 (0.8) |
| I-1-210 | $^1$H-NMR, Solvent [D$_6$]-DMSO, spectrometer: 399.95 MHz: δ = 8.935 (11.5); 8.931 (11.9); 8.651 (16.0); 8.316 (0.5); 8.207 (6.5); 8.204 (7.3); 8.188 (7.4); 8.184 (7.8); 8.138 (8.1); 8.118 (8.7); 8.099 (0.4); 7.680 (4.1); 7.662 (7.9); 7.644 (4.1); 7.642 (4.4); 7.500 (0.6); 7.390 (3.5); 7.386 (4.0); 7.370 (6.4); 7.367 (7.0); 7.352 (3.3); 7.348 (3.4); 3.467 (1.7); 3.449 (3.6); 3.432 (3.9); 3.414 (2.3); 3.356 (1.8); 2.671 (1.3); 2.667 (1.0); 2.507 (152.1); 2.502 (203.1); 2.498 (162.6); 2.334 (1.0); 2.329 (1.4); 1.073 (2.7); 1.056 (5.4); 1.038 (2.7); 0.146 (0.6); 0.007 (6.3); 0.000 (133.6); −0.150 (0.7) |
| I-1-211 | $^1$H-NMR, Solvent [D$_6$]-DMSO, spectrometer: 399.95 MHz: δ = 8.807 (0.5); 8.770 (16.0); 8.316 (5.1); 8.274 (0.3); 8.240 (0.5); 8.216 (0.5); 8.164 (1.2); 8.111 (3.0); 8.093 (2.3); 8.064 (10.3); 8.045 (10.5); 7.795 (0.4); 7.641 (6.8); 7.623 (7.3); 7.585 (0.8); 7.565 (0.6); 7.538 (0.4); 7.473 (4.3); 7.456 (7.4); 7.438 (5.1); 7.415 (1.3); 7.340 (5.7); 7.270 (0.4); 7.264 (0.5); 4.056 (0.5); 4.038 (1.2); 4.020 (1.3); 4.002 (0.4); 3.802 (0.4); 3.671 (0.3); 3.644 (0.4); 3.632 (0.4); 3.609 (0.4); 3.593 (0.4); 3.587 (0.5); 3.575 (0.5); 3.542 (0.5); 3.501 (0.7); 3.496 (0.7); 3.462 (1.0); 3.437 (1.4); 3.326 (434.0); 3.239 (1.7); 3.192 (0.8); 3.169 (0.6); 3.153 (0.5); 3.150 (0.5); 3.125 (0.4); 3.103 (0.4); 3.071 (0.4); 2.940 (0.3); 2.819 (0.7); 2.742 (0.3); 2.735 (0.4); 2.724 (0.4); 2.676 (7.2); 2.671 (10.3); 2.666 (7.9); 2.662 (4.1); 2.607 (0.8); 2.604 (0.8); 2.524 (22.9); 2.520 (35.3); 2.511 (531.1); 2.506 (1117.7); 2.502 (1521.5); 2.497 (1150.0); 2.493 (595.5); 2.338 (3.1); 2.333 (6.9); 2.329 (9.7); 2.324 (7.3); 2.244 (0.5); 1.989 (5.2); 1.654 (0.4); 1.617 (0.5); 1.398 (2.6); 1.351 (1.2); 1.336 (1.2); 1.298 (3.2); 1.259 (5.0); 1.249 (3.0); 1.236 (10.5); 1.193 (2.0); 1.175 (3.2); 1.157 (1.7); 1.117 (0.5); 1.083 (0.3); 0.941 (0.3); 0.910 (0.4); 0.884 (0.7); 0.868 (1.3); 0.854 (2.4); 0.836 (1.5); 0.807 (0.8); 0.800 (0.5); 0.787 (0.4); 0.146 (6.4); 0.033 (0.6); 0.025 (0.9); 0.008 (48.7); 0.000 (1531.5); −0.008 (81.0); −0.045 (0.9); −0.053 (0.6); −0.075 (0.4); −0.142 (0.4); −0.150 (6.6) |
| I-1-212 | $^1$H-NMR, Solvent [D$_6$]-DMSO, spectrometer: 399.95 MHz: δ = 8.915 (9.6); 8.911 (9.8); 8.604 (16.0); 8.317 (0.7); 8.015 (2.3); 8.011 (2.8); 7.995 (4.7); 7.992 (5.1); 7.977 (2.8); 7.972 (2.9); 7.803 (1.4); 7.799 (1.5); 7.791 (1.5); 7.784 (2.9); 7.766 (2.9); 7.760 (1.9); 7.751 (1.6); 7.747 (1.5); 7.658 (0.8); 7.477 (5.3); 7.474 (4.3); 7.459 (8.0); 7.452 (4.1); 7.450 (4.2); 7.446 (4.8); 7.441 (4.8); 7.425 (3.3); 7.362 (0.4); 5.757 (1.9); 3.527 (0.5); 3.467 (0.8); 3.449 (1.2); 3.432 (1.4); 3.414 (1.1); 3.367 (1.2); 3.352 (1.2); 3.308 (1.0); 3.187 (0.8); 3.164 (0.3); 2.676 (1.1); 2.671 (1.5); 2.667 (1.1); 2.525 (3.3); 2.511 (81.7); 2.507 (168.5); 2.502 (228.2); 2.498 (173.6); 2.494 (91.7); 2.334 (1.1); 2.329 (1.5); 2.325 (1.2); 1.073 (0.5); 1.056 (1.1); 1.038 (0.6); 0.146 (0.7); 0.008 (5.2); 0.000 (155.2); −0.008 (8.0); −0.150 (0.7) |
| I-1-213 | $^1$H-NMR, Solvent [D$_6$]-DMSO, spectrometer: 601.6 MHz: δ = 8.736 (9.0); 8.000 (5.2); 7.997 (5.5); 7.917 (5.7); 7.914 (5.8); 7.636 (0.3); 7.609 (1.2); 7.595 (4.2); 7.592 (4.6); 7.584 (4.1); 7.569 (1.1); 7.545 (0.4); 7.515 (5.9); 7.512 (6.1); 6.316 (3.9); 6.312 (6.7); 6.309 (4.0); 5.516 (16.0); 5.448 (0.6); 4.035 (0.6); 4.023 (0.6); 3.435 (0.4); 3.188 (1.0); 2.614 (13.6); 2.611 (13.8); 2.507 (50.7); 2.504 (69.1); 2.501 (53.2); 2.389 (0.5); 1.991 (2.5); 1.187 (0.6); 1.176 (1.3); 1.164 (0.7); 0.000 (45.6) |
| I-1-214 | $^1$H-NMR, Solvent [D$_6$]-DMSO, spectrometer: 601.6 MHz: δ = 8.735 (9.9); 7.887 (6.3); 7.884 (6.2); 7.825 (4.1); 7.809 (4.1); 7.788 (0.4); 7.627 (4.1); 7.615 (4.2); 7.531 (6.6); 7.529 (6.5); 6.333 (4.5); 6.329 (6.9); 6.326 (4.4); 5.533 (15.7); 5.483 (0.4); 4.034 (0.3); 4.023 (0.4); 3.434 (0.3); 3.187 (0.7); 2.615 (15.8); 2.613 (16.0); 2.506 (61.3); 2.504 (78.7); 2.501 (62.5); 2.388 (0.6); 1.991 (1.0); 1.175 (0.6); 0.000 (43.9) |
| I-1-215 | $^1$H-NMR, Solvent [D$_6$]-DMSO, spectrometer: 399.95 MHz: δ = 8.318 (0.3); 8.214 (10.9); 7.835 (5.5); 7.829 (5.7); 7.747 (10.4); 7.635 (10.3); 7.489 (5.6); 7.485 (5.8); 6.292 (4.2); 6.287 (6.8); 6.281 (4.2); 5.465 (16.0); 3.333 (240.3); 2.676 (0.5); 2.672 (0.7); 2.667 (0.6); 2.624 (13.2); 2.619 (13.3); 2.525 (1.5); 2.511 (38.8); 2.507 (79.3); 2.503 (104.8); 2.498 (76.1); 2.494 (37.1); 2.334 (0.5); 2.329 (0.7); 2.325 (0.5); 1.299 (0.5); 1.259 (0.6); 1.235 (0.6); 0.000 (8.1) |
| I-1-216 | $^1$H-NMR, Solvent [D$_6$]-DMSO, spectrometer: 399.95 MHz: δ = 8.224 (5.5); 7.793 (4.1); 7.788 (4.3); 7.741 (3.8); 7.444 (4.0); 7.440 (4.2); 7.098 (3.6); 6.258 (2.9); 6.253 (5.1); 6.248 (3.1); 5.277 (10.5); 4.055 (0.3); 4.038 (1.0); 4.020 (1.3); 4.002 (0.4); 3.333 (127.0); 2.676 (0.4); 2.671 (0.5); 2.667 (0.4); 2.622 (9.5); 2.618 (9.8); 2.525 (1.2); 2.511 (25.2); 2.507 (52.9); 2.502 (71.5); 2.498 (53.7); 2.494 (27.3); 2.474 (15.6); 2.329 (0.5); 2.325 (0.4); 2.203 (16.0); 1.989 (4.5); 1.298 (1.5); 1.259 (2.0); 1.250 (0.5); 1.235 (1.1); 1.193 (1.2); 1.175 (2.4); 1.157 (1.2); 0.000 (5.6) |
| I-1-217 | $^1$H-NMR, Solvent [D$_6$]-DMSO, spectrometer: 399.95 MHz: δ = 8.319 (0.4); 8.223 (7.9); 7.859 (5.5); 7.855 (5.6); 7.818 (5.8); 7.813 (5.8); 7.452 (5.6); 7.449 (5.7); 7.237 (2.5); 7.217 (6.5); 7.197 (4.0); 7.192 (4.0); 7.177 (1.6); 7.173 (1.6); 6.267 (4.3); 6.262 (7.0); 6.257 (4.3); 5.326 (15.5); 4.056 (0.5); 4.038 (1.5); 4.020 (1.5); 4.002 (0.5); 3.332 (165.7); 3.083 (1.8); 3.064 (5.7); 3.046 (5.8); 3.027 (1.9); 2.676 (0.5); 2.671 (0.7); 2.667 (0.5); 2.619 (13.2); 2.615 (13.4); 2.525 (1.5); 2.520 (2.2); 2.511 (34.5); 2.507 (71.9); 2.502 (96.1); 2.498 (70.7); 2.493 (34.8); 2.334 (0.4); 2.329 (0.6); 2.324 (0.5); 1.989 (6.6); 1.298 (1.7); 1.259 (2.4); 1.235 (1.2); 1.193 (1.9); 1.175 (3.7); 1.157 (1.9); 1.134 (7.6); 1.115 (16.0); 1.097 (7.3); 0.000 (6.1) |
| I-1-218 | $^1$H-NMR, Solvent [D$_6$]-DMSO, spectrometer: 399.95 MHz: δ = 8.739 (11.7); 7.893 (8.1); 7.888 (8.8); 7.875 (3.2); 7.870 (3.0); 7.585 (1.3); 7.580 (1.5); 7.574 (1.7); 7.565 (2.1); 7.558 (2.1); 7.553 (2.0); 7.548 (1.7); 7.502 (5.8); 7.498 (6.1); 7.445 (2.8); 7.420 (3.5); 7.398 (2.2); 6.304 (3.8); 6.299 (6.6); 6.295 (4.3); |

| Example | NMR data |
|---|---|
| | 5.460 (16.0); 3.547 (0.3); 3.477 (0.4); 3.467 (0.5); 3.450 (0.6); 3.433 (0.6); 3.415 (0.5); 3.359 (0.4); 3.340 (0.4); 3.316 (0.3); 3.187 (0.7); 3.170 (3.2); 2.672 (0.6); 2.612 (15.2); 2.608 (15.8); 2.506 (51.8); 2.502 (67.3); 2.498 (54.2); 2.329 (0.5); 1.056 (0.5); 0.000 (53.0) |
| I-1-219 | $^1$H-NMR, Solvent [D$_6$]-DMSO, spectrometer: 399.95 MHz: δ = 8.698 (12.7); 8.225 (0.4); 8.207 (0.4); 7.966 (2.5); 7.961 (2.7); 7.945 (3.2); 7.940 (3.4); 7.888 (5.8); 7.883 (5.9); 7.791 (6.6); 7.770 (5.3); 7.727 (0.4); 7.527 (6.0); 7.522 (8.8); 7.515 (5.7); 7.477 (0.5); 6.992 (0.6); 6.973 (0.6); 6.337 (4.0); 6.332 (6.8); 6.327 (4.3); 5.541 (16.0); 5.517 (0.9); 3.568 (0.4); 3.485 (0.7); 3.479 (0.7); 3.378 (1.1); 3.367 (1.1); 3.342 (1.1); 3.324 (0.9); 3.186 (6.4); 3.169 (2.5); 2.764 (0.4); 2.753 (0.4); 2.676 (0.5); 2.672 (0.7); 2.667 (0.6); 2.613 (13.4); 2.608 (14.0); 2.507 (64.2); 2.502 (85.7); 2.498 (66.5); 2.458 (0.3); 2.334 (0.4); 2.329 (0.5); 2.325 (0.4); 1.234 (0.3); 0.008 (2.3); 0.000 (61.3) |
| I-1-220 | $^1$H-NMR, Solvent [D$_6$]-DMSO, spectrometer: 399.95 MHz: δ = 8.675 (5.9); 8.226 (0.4); 8.206 (0.4); 7.987 (1.4); 7.981 (1.5); 7.965 (1.5); 7.959 (1.6); 7.784 (3.1); 7.778 (3.3); 7.472 (3.1); 7.468 (3.3); 7.448 (2.7); 7.442 (2.8); 7.272 (2.8); 7.249 (2.6); 7.213 (0.3); 6.992 (0.4); 6.973 (0.6); 6.288 (2.2); 6.283 (3.9); 6.278 (2.4); 5.339 (8.6); 3.922 (16.0); 3.903 (0.9); 3.341 (1.3); 3.186 (4.4); 2.756 (0.5); 2.671 (0.4); 2.667 (0.3); 2.609 (7.1); 2.604 (7.4); 2.524 (0.8); 2.511 (18.4); 2.507 (37.7); 2.502 (51.1); 2.498 (39.1); 2.494 (20.7); 2.329 (0.3); 0.008 (1.4); 0.000 (41.1); −0.008 (2.2) |
| I-1-221 | $^1$H-NMR, Solvent [D$_6$]-DMSO, spectrometer: 399.95 MHz: δ = 8.750 (12.6); 8.048 (5.3); 8.042 (5.5); 7.903 (5.6); 7.898 (5.7); 7.644 (5.1); 7.624 (6.6); 7.605 (0.3); 7.513 (5.4); 7.509 (5.6); 7.482 (3.1); 7.477 (3.1); 7.461 (2.4); 7.456 (2.5); 6.315 (3.8); 6.310 (6.6); 6.305 (3.8); 5.495 (16.0); 5.422 (0.4); 3.488 (0.4); 3.451 (0.4); 3.436 (0.4); 3.415 (0.4); 3.382 (0.4); 3.341 (0.4); 3.186 (0.5); 3.169 (5.6); 2.676 (0.4); 2.671 (0.5); 2.667 (0.4); 2.612 (13.3); 2.608 (13.6); 2.507 (55.2); 2.502 (72.8); 2.498 (53.8); 2.333 (0.4); 2.329 (0.5); 2.325 (0.4); 0.000 (7.6) |
| I-1-222 | $^1$H-NMR, Solvent [D$_6$]-DMSO, spectrometer: 399.95 MHz: δ = 8.770 (7.8); 8.317 (1.3); 8.039 (16.0); 7.457 (0.8); 7.442 (1.7); 7.437 (1.6); 7.427 (1.2); 7.421 (3.0); 7.406 (1.7); 7.400 (1.8); 7.386 (0.7); 7.030 (5.4); 7.008 (9.8); 6.988 (4.6); 6.980 (1.0); 3.447 (0.3); 3.434 (0.4); 3.393 (0.7); 3.354 (4.5); 3.332 (774.0); 3.306 (1.6); 2.975 (1.0); 2.676 (2.3); 2.671 (3.0); 2.667 (2.2); 2.561 (0.5); 2.525 (8.9); 2.511 (191.0); 2.507 (374.3); 2.502 (478.1); 2.498 (337.1); 2.494 (157.4); 2.334 (2.2); 2.329 (3.0); 2.325 (2.2); 1.236 (1.8); 0.146 (1.6); 0.022 (1.0); 0.008 (15.5); 0.000 (387.8); −0.009 (13.0); −0.026 (0.5); −0.150 (1.7) |
| I-1-223 | $^1$H-NMR, Solvent [D$_6$]-DMSO, spectrometer: 399.95 MHz: δ = 8.940 (5.7); 8.936 (10.1); 8.614 (16.0); 8.375 (6.8); 8.370 (7.0); 8.316 (0.7); 8.126 (4.9); 8.105 (6.9); 8.006 (4.2); 8.001 (4.1); 7.985 (3.1); 7.980 (3.0); 7.875 (0.6); 7.869 (0.8); 7.815 (0.5); 7.794 (0.6); 7.664 (0.4); 7.658 (0.4); 4.187 (0.3); 4.168 (0.4); 4.148 (0.4); 4.122 (0.4); 4.076 (0.4); 3.991 (0.5); 3.932 (0.6); 3.895 (0.6); 3.864 (0.6); 3.831 (0.6); 3.765 (0.6); 3.691 (0.6); 3.678 (0.6); 3.558 (0.5); 3.531 (0.5); 3.454 (0.5); 3.358 (0.4); 3.321 (0.3); 3.293 (0.3); 3.188 (4.0); 2.772 (0.5); 2.760 (0.5); 2.677 (0.9); 2.672 (1.3); 2.667 (0.9); 2.663 (0.5); 2.525 (3.2); 2.512 (64.9); 2.507 (132.6); 2.503 (176.2); 2.498 (127.6); 2.494 (61.3); 2.339 (0.4); 2.334 (0.9); 2.330 (1.2); 2.325 (0.9); 2.320 (0.4); 1.336 (1.7); 1.260 (0.8); 1.250 (1.1); 1.235 (0.5); 0.988 (0.3); 0.146 (0.5); 0.008 (3.6); 0.000 (110.6); −0.009 (4.0); −0.150 (0.5) |
| I-1-224 | $^1$H-NMR, Solvent [D$_6$]-DMSO, spectrometer: 399.95 MHz: δ = 8.766 (15.3); 8.316 (3.3); 8.059 (7.2); 8.004 (14.8); 7.983 (16.0); 7.562 (8.8); 7.558 (9.1); 7.498 (7.6); 7.494 (6.6); 7.477 (6.8); 7.472 (5.9); 4.552 (1.2); 3.589 (0.3); 3.567 (0.4); 3.543 (0.4); 3.526 (0.4); 3.465 (0.6); 3.325 (316.3); 3.258 (0.5); 3.245 (0.4); 2.805 (0.3); 2.773 (0.4); 2.736 (0.5); 2.705 (0.5); 2.680 (2.6); 2.676 (4.9); 2.671 (6.5); 2.666 (4.8); 2.662 (2.5); 2.634 (0.8); 2.620 (0.9); 2.524 (19.6); 2.511 (341.4); 2.506 (680.6); 2.502 (891.5); 2.497 (634.3); 2.493 (293.6); 2.338 (1.6); 2.333 (3.8); 2.329 (5.4); 2.324 (3.7); 2.320 (1.5); 2.117 (3.3); 1.351 (0.3); 1.259 (0.5); 1.236 (2.3); 1.140 (8.4); 0.869 (0.4); 0.854 (0.6); 0.850 (0.4); 0.837 (0.4); 0.146 (2.0); 0.008 (15.8); 0.000 (453.7); −0.009 (14.4); −0.150 (1.9) |
| I-1-225 | $^1$H-NMR, Solvent [D$_6$]-DMSO, spectrometer: 399.95 MHz: δ = 8.756 (3.5); 8.317 (0.6); 8.063 (1.1); 7.702 (3.3); 7.133 (1.0); 7.115 (1.7); 7.078 (2.5); 7.059 (1.3); 4.056 (0.6); 4.038 (1.8); 4.020 (1.8); 4.002 (0.6); 3.327 (182.0); 2.680 (0.4); 2.676 (0.9); 2.671 (1.2); 2.667 (0.9); 2.662 (0.5); 2.525 (3.3); 2.520 (5.3); 2.511 (66.8); 2.507 (137.9); 2.502 (191.7); 2.498 (130.2); 2.493 (59.7); 2.338 (0.5); 2.333 (0.9); 2.329 (1.2); 2.324 (0.9); 2.320 (0.5); 2.298 (16.0); 1.989 (8.0); 1.398 (0.6); 1.259 (0.3); 1.236 (0.8); 1.193 (2.2); 1.175 (4.5); 1.157 (2.2); 0.146 (0.3); 0.008 (2.9); 0.000 (90.1); −0.009 (2.7); −0.150 (0.3) |
| I-1-226 | $^1$H-NMR, Solvent [D$_6$]-DMSO, spectrometer: 399.95 MHz: δ = 8.935 (10.9); 8.611 (16.0); 8.316 (0.7); 8.016 (2.3); 8.012 (2.7); 7.996 (4.7); 7.993 (5.0); 7.977 (2.7); 7.973 (2.8); 7.824 (0.4); 7.819 (0.5); 7.805 (1.8); 7.801 (2.0); 7.793 (1.6); 7.786 (3.2); 7.769 (2.9); 7.762 (2.0); 7.754 (1.6); 7.750 (1.4); 7.658 (2.3); 7.642 (0.4); 7.637 (0.3); 7.479 (5.2); 7.475 (4.5); 7.461 (7.6); 7.454 (4.6); 7.452 (4.5); 7.448 (5.0); 7.443 (5.3); 7.427 (3.2); 7.398 (0.4); 7.383 (0.6); 7.380 (0.5); 7.364 (0.9); 7.345 (0.4); 7.342 (0.4); 3.689 (0.3); 3.345 (9.5); 3.187 (2.2); 3.072 (0.5); 3.055 (0.5); 3.040 (0.5); 3.022 (0.5); 3.005 (0.5); 2.990 (0.4); 2.770 (0.7); 2.758 (0.7); 2.676 (1.5); 2.671 (1.9); 2.667 (1.5); 2.507 (208.3); 2.502 (273.7); 2.498 (211.8); 2.334 (1.3); 2.329 (1.7); 2.325 (1.4); 1.234 (0.9); 0.987 (0.5); 0.146 (0.4); 0.008 (4.2); 0.000 (100.2); −0.150 (0.4) |
| I-1-227 | $^1$H-NMR, Solvent [D$_6$]-DMSO, spectrometer: 399.95 MHz: δ = 8.773 (15.5); 8.317 (1.0); 8.069 (16.0); 8.050 (8.2); 8.046 (8.3); 8.030 (8.8); 8.026 (8.4); 7.618 (8.5); 7.601 (9.2); 7.599 (9.5); 7.448 (4.3); 7.430 (8.8); 7.413 (5.2); 7.410 (5.2); 7.330 (4.7); 7.326 (4.8); 7.311 (7.1); 7.307 (7.0); 7.292 (3.2); 7.288 (3.1); |

| Example | NMR data |
|---|---|
| | 4.056 (1.2); 4.038 (3.6); 4.020 (3.6); 4.002 (1.2); 3.326 (237.4); 2.676 (1.7); 2.671 (2.3); 2.667 (1.7); 2.506 (260.5); 2.502 (336.2); 2.498 (246.8); 2.333 (1.6); 2.329 (2.1); 2.325 (1.6); 1.989 (15.4); 1.398 (3.2); 1.336 (0.4); 1.298 (0.6); 1.259 (0.9); 1.249 (0.7); 1.236 (1.8); 1.193 (4.3); 1.175 (8.5); 1.157 (4.2); 0.854 (0.4); 0.146 (1.9); 0.008 (19.4); 0.000 (421.8); −0.008 (17.3); −0.031 (0.4); −0.150 (1.9) |
| I-1-228 | $^1$H-NMR, Solvent [D$_6$]-DMSO, spectrometer: 399.95 MHz: □ = 8.925 (6.6); 8.561 (9.2); 8.226 (0.7); 8.209 (0.7); 7.931 (7.3); 7.867 (6.1); 7.863 (5.9); 7.480 (6.3); 7.422 (15.6); 6.993 (0.8); 6.974 (0.8); 6.284 (6.3); 5.428 (16.0); 5.361 (0.4); 3.391 (1.7); 3.374 (2.2); 3.357 (2.4); 3.187 (6.5); 3.036 (2.2); 3.018 (6.1); 2.999 (6.3); 2.981 (2.3); 2.672 (0.6); 2.503 (85.0); 2.330 (0.6); 1.189 (0.3); 1.137 (6.9); 1.119 (13.9); 1.100 (6.8); 1.074 (0.5); 0.146 (0.3); 0.000 (64.2); −0.150 (0.4) |
| I-1-229 | $^1$H-NMR, Solvent [D$_6$]-DMSO, spectrometer: 399.95 MHz: δ = 8.948 (3.6); 8.945 (6.3); 8.603 (9.4); 8.317 (0.4); 7.990 (4.8); 7.986 (5.1); 7.916 (5.4); 7.911 (5.3); 7.614 (0.7); 7.587 (7.1); 7.561 (0.6); 7.514 (5.1); 7.510 (5.0); 6.315 (4.0); 6.310 (6.5); 6.305 (3.8); 5.757 (0.4); 5.514 (16.0); 3.603 (0.3); 3.467 (1.2); 3.450 (2.1); 3.432 (2.2); 3.415 (1.3); 3.404 (1.0); 3.388 (1.0); 3.377 (1.0); 3.187 (1.1); 2.676 (0.6); 2.672 (0.8); 2.668 (0.6); 2.525 (1.9); 2.512 (43.6); 2.507 (87.0); 2.503 (113.8); 2.498 (81.8); 2.494 (38.9); 2.334 (0.5); 2.330 (0.8); 2.325 (0.6); 1.074 (1.3); 1.056 (2.6); 1.039 (1.2); 0.146 (0.4); 0.008 (3.0); 0.000 (84.4); −0.009 (2.9); −0.150 (0.4) |
| I-1-230 | $^1$H-NMR, Solvent [D$_6$]-DMSO, spectrometer: 399.95 MHz: δ = 8.930 (6.6); 8.605 (8.8); 7.938 (8.4); 7.899 (6.3); 7.895 (6.1); 7.730 (9.0); 7.700 (0.4); 7.538 (6.3); 6.333 (6.2); 5.556 (16.0); 5.499 (0.6); 3.874 (0.3); 3.844 (0.4); 3.426 (1.4); 3.409 (1.5); 3.392 (1.7); 3.375 (1.7); 3.357 (1.4); 3.334 (1.2); 3.207 (0.8); 3.187 (3.0); 3.104 (0.5); 3.057 (0.7); 3.019 (0.3); 3.001 (0.3); 2.672 (0.7); 2.503 (89.0); 2.331 (0.7); 1.235 (0.4); 1.109 (0.4); 1.092 (0.7); 1.074 (0.4); 0.855 (0.5); 0.838 (0.4); 0.146 (0.4); 0.000 (77.9); −0.150 (0.4) |
| I-1-231 | $^1$H-NMR, Solvent [D$_6$]-DMSO, spectrometer: 399.95 MHz: δ = 8.935 (3.9); 8.931 (7.1); 8.584 (11.9); 8.316 (0.3); 7.889 (6.2); 7.883 (6.2); 7.827 (5.0); 7.802 (5.1); 7.615 (4.7); 7.596 (4.8); 7.531 (6.2); 7.527 (6.1); 6.331 (4.6); 6.326 (7.6); 6.321 (4.6); 5.756 (4.6); 5.531 (16.0); 3.709 (0.4); 3.481 (0.8); 3.467 (1.3); 3.450 (2.3); 3.432 (2.3); 3.415 (1.3); 3.209 (0.4); 3.187 (1.0); 2.891 (0.4); 2.732 (0.3); 2.676 (0.5); 2.672 (0.7); 2.667 (0.5); 2.525 (1.2); 2.512 (39.2); 2.507 (80.7); 2.503 (107.6); 2.498 (78.4); 2.494 (38.2); 2.334 (0.6); 2.329 (0.8); 2.325 (0.6); 1.233 (0.7); 1.074 (1.5); 1.056 (3.0); 1.039 (1.4); 0.146 (0.4); 0.008 (2.7); 0.000 (84.8); −0.009 (3.1); −0.150 (0.4) |
| I-1-232 | $^1$H-NMR, Solvent [D$_6$]-DMSO, spectrometer: 399.95 MHz: δ = 8.928 (4.7); 8.557 (8.9); 8.226 (0.4); 8.208 (0.4); 7.847 (4.0); 7.842 (4.2); 7.824 (4.3); 7.640 (0.4); 7.474 (4.0); 7.471 (4.1); 7.457 (0.5); 7.454 (0.5); 7.364 (0.7); 7.336 (3.8); 7.275 (0.4); 6.993 (0.6); 6.974 (0.6); 6.282 (2.9); 6.277 (4.8); 6.272 (3.1); 6.261 (0.4); 5.378 (10.7); 5.310 (1.1); 4.038 (0.4); 4.020 (0.4); 3.409 (1.0); 3.392 (1.7); 3.374 (2.2); 3.357 (2.0); 3.187 (6.6); 3.040 (0.3); 3.006 (0.4); 2.758 (1.1); 2.747 (1.1); 2.672 (0.4); 2.507 (51.0); 2.503 (65.5); 2.498 (49.9); 2.464 (16.0); 2.451 (2.5); 2.334 (0.4); 2.330 (0.5); 2.325 (0.4); 2.276 (1.8); 2.250 (16.0); 1.989 (1.8); 1.352 (0.3); 1.259 (0.4); 1.234 (0.7); 1.193 (0.6); 1.186 (0.7); 1.175 (1.0); 1.157 (0.5); 1.109 (0.6); 1.106 (0.7); 1.091 (0.8); 1.074 (0.4); 1.005 (0.5); 0.987 (0.9); 0.969 (0.5); 0.855 (1.3); 0.838 (1.0); 0.146 (0.4); 0.008 (5.1); 0.000 (84.0); −0.008 (4.9); −0.150 (0.4) |
| I-1-233 | $^1$H-NMR, Solvent [D$_6$]-DMSO, spectrometer: 399.95 MHz: δ = 7.951 (0.4); 3.325 (33.4); 2.671 (0.4); 2.520 (3.8); 2.511 (22.0); 2.506 (44.8); 2.502 (59.3); 2.497 (42.2); 2.493 (19.8); 2.329 (0.4); 1.287 (16.0); 1.236 (0.6); 0.008 (1.7); 0.000 (51.7); −0.009 (1.6) |
| I-1-234 | $^1$H-NMR, Solvent [D$_6$]-DMSO, spectrometer: 399.95 MHz: δ = 8.946 (6.6); 8.943 (11.7); 8.610 (16.0); 8.317 (1.1); 8.151 (5.9); 8.147 (6.2); 8.131 (6.5); 8.127 (6.5); 7.957 (1.2); 7.952 (1.3); 7.936 (1.4); 7.933 (1.4); 7.868 (2.5); 7.863 (2.6); 7.847 (4.9); 7.844 (4.8); 7.828 (3.6); 7.824 (3.4); 7.756 (0.6); 7.752 (0.6); 7.737 (1.2); 7.734 (1.0); 7.732 (0.9); 7.717 (0.9); 7.713 (0.9); 7.659 (4.2); 7.657 (4.5); 7.638 (10.2); 7.620 (3.4); 7.618 (3.5); 7.601 (4.3); 7.580 (3.6); 7.568 (1.6); 7.564 (0.9); 7.560 (1.0); 7.557 (0.8); 7.550 (1.7); 7.543 (0.7); 7.540 (0.7); 7.532 (1.0); 5.757 (0.8); 3.361 (4.4); 3.280 (2.6); 3.187 (2.2); 3.111 (0.6); 3.095 (0.5); 3.072 (0.5); 3.055 (0.8); 3.040 (0.8); 3.031 (0.6); 3.023 (0.8); 3.008 (0.8); 3.005 (0.8); 2.991 (0.7); 2.971 (0.4); 2.804 (0.5); 2.793 (0.5); 2.768 (2.4); 2.756 (2.4); 2.676 (1.6); 2.672 (2.2); 2.667 (1.6); 2.662 (0.8); 2.525 (5.7); 2.511 (121.4); 2.507 (243.9); 2.503 (320.1); 2.498 (230.1); 2.494 (109.0); 2.338 (0.7); 2.334 (1.5); 2.329 (2.1); 2.325 (1.5); 1.335 (0.6); 1.298 (0.4); 1.259 (0.6); 1.235 (0.5); 1.005 (0.9); 0.988 (1.9); 0.970 (0.5); 0.146 (1.9); 0.028 (0.4); 0.008 (16.2); 0.000 (447.8); −0.009 (15.5); −0.150 (2.0) |
| I-1-235 | $^1$H-NMR, Solvent [D$_6$]-DMSO, spectrometer: 399.95 MHz: δ = 8.816 (7.7); 8.316 (1.5); 8.102 (5.8); 8.099 (5.6); 8.083 (6.4); 8.079 (6.1); 7.789 (2.1); 7.440 (9.6); 7.424 (10.0); 7.277 (1.5); 7.269 (4.0); 7.258 (7.6); 7.245 (16.0); 7.242 (14.7); 7.164 (4.1); 7.146 (3.7); 4.056 (0.8); 4.038 (2.4); 4.020 (2.5); 4.002 (0.8); 3.395 (0.4); 3.326 (334.9); 2.680 (1.0); 2.675 (2.0); 2.671 (2.7); 2.666 (1.9); 2.524 (7.3); 2.511 (151.5); 2.506 (306.0); 2.502 (403.7); 2.497 (289.9); 2.493 (137.5); 2.338 (0.9); 2.333 (1.9); 2.329 (2.6); 2.324 (1.9); 2.320 (0.9); 1.989 (10.8); 1.398 (1.9); 1.351 (0.5); 1.336 (0.5); 1.298 (0.8); 1.259 (1.3); 1.250 (1.0); 1.236 (2.5); 1.193 (2.9); 1.175 (5.8); 1.157 (2.8); 0.854 (0.6); 0.836 (0.3); 0.146 (1.4); 0.008 (12.0); 0.000 (338.9); −0.008 (11.6); −0.150 (1.5) |
| I-1-236 | $^1$H-NMR, Solvent [D$_6$]-DMSO, spectrometer: 399.95 MHz: δ = 8.773 (11.5); 8.093 (16.0); 8.015 (6.2); 8.011 (6.7); 7.995 (6.9); 7.991 (7.1); 7.786 (0.4); 7.711 (5.6); 7.708 (5.9); 7.691 (6.8); 7.688 (6.6); 7.447 (6.5); 7.427 (11.4); 7.407 (5.4); 5.757 (8.2); 4.039 (0.5); 4.021 (0.5); 3.337 (21.6); 2.678 (0.4); 2.673 (0.5); |

| Example | NMR data |
|---|---|
| | 2.669 (0.4); 2.526 (1.3); 2.513 (28.8); 2.509 (59.2); 2.504 (78.9); 2.500 (58.1); 2.495 (29.0); 2.335 (0.4); 2.331 (0.5); 2.326 (0.4); 2.181 (0.3); 1.990 (2.2); 1.260 (0.3); 1.236 (5.1); 1.194 (0.6); 1.176 (1.2); 1.158 (0.6); 0.854 (0.5); 0.000 (8.8); −0.009 (0.4) |
| I-1-237 | $^1$H-NMR, Solvent [D$_6$]-DMSO, spectrometer: 399.95 MHz: δ = 8.933 (11.7); 8.618 (16.0); 8.316 (0.6); 8.214 (10.8); 8.208 (11.7); 8.067 (0.7); 8.061 (0.7); 7.943 (5.2); 7.937 (5.3); 7.922 (6.1); 7.916 (6.1); 7.846 (0.4); 7.840 (0.4); 7.825 (0.4); 7.818 (0.4); 7.786 (1.1); 7.647 (11.4); 7.625 (10.1); 7.609 (0.8); 3.831 (0.4); 3.811 (0.4); 3.793 (0.4); 3.781 (0.4); 3.670 (0.5); 3.658 (0.5); 3.641 (0.5); 3.565 (0.6); 3.538 (0.6); 3.510 (0.6); 3.469 (0.5); 3.442 (0.5); 3.414 (0.5); 3.398 (0.5); 3.378 (0.5); 3.367 (0.5); 3.277 (0.4); 3.187 (0.7); 3.180 (0.4); 3.151 (0.3); 2.751 (0.3); 2.739 (0.3); 2.676 (1.1); 2.672 (1.5); 2.668 (1.1); 2.507 (159.0); 2.503 (212.4); 2.498 (166.7); 2.334 (1.1); 2.330 (1.5); 2.325 (1.2); 1.234 (0.6); 0.146 (0.9); 0.007 (8.2); 0.000 (195.5); −0.150 (1.0) |
| I-1-238 | $^1$H-NMR, Solvent [D$_6$]-DMSO, spectrometer: 399.95 MHz: δ = 8.940 (2.8); 8.936 (5.4); 8.637 (6.8); 8.316 (0.4); 7.605 (5.3); 7.598 (5.7); 7.558 (4.5); 7.536 (5.4); 7.292 (2.6); 7.284 (2.5); 7.270 (2.2); 7.262 (2.2); 4.038 (3.6); 4.022 (7.6); 4.006 (3.8); 3.467 (0.5); 3.450 (0.7); 3.432 (0.7); 3.414 (0.7); 3.361 (0.8); 2.676 (0.5); 2.672 (0.8); 2.667 (0.6); 2.525 (1.6); 2.520 (2.6); 2.512 (39.1); 2.507 (82.4); 2.503 (112.6); 2.498 (86.0); 2.494 (45.2); 2.334 (0.5); 2.329 (0.7); 2.325 (0.6); 1.810 (0.5); 1.792 (1.9); 1.775 (4.0); 1.757 (4.2); 1.740 (2.1); 1.722 (0.6); 1.056 (0.4); 1.016 (7.6); 0.998 (16.0); 0.979 (7.1); 0.146 (0.4); 0.008 (3.1); 0.000 (97.2); −0.008 (5.4); −0.150 (0.4) |
| I-1-239 | $^1$H-NMR, Solvent [D$_6$]-DMSO, spectrometer: 399.95 MHz: δ = 8.942 (1.6); 8.938 (3.1); 8.642 (4.0); 7.582 (2.7); 7.574 (3.0); 7.543 (2.5); 7.521 (3.0); 7.277 (1.4); 7.269 (1.4); 7.254 (1.2); 7.247 (1.2); 4.726 (0.4); 4.710 (1.1); 4.695 (1.4); 4.680 (1.1); 4.665 (0.4); 3.450 (0.5); 3.432 (0.5); 3.415 (0.5); 3.363 (0.5); 2.672 (0.3); 2.525 (0.7); 2.512 (17.7); 2.507 (37.3); 2.503 (50.8); 2.498 (38.8); 2.494 (20.5); 2.329 (0.3); 1.317 (16.0); 1.302 (16.0); 1.056 (0.4); 0.008 (1.3); 0.000 (40.1); −0.008 (2.2) |
| I-1-240 | $^1$H-NMR, Solvent [D$_6$]-DMSO, spectrometer: 399.95 MHz: δ = 8.772 (6.9); 8.050 (12.2); 7.844 (6.0); 7.839 (6.1); 7.755 (2.6); 7.750 (2.8); 7.738 (2.7); 7.733 (2.7); 7.473 (5.7); 7.469 (5.9); 7.304 (1.2); 7.298 (1.4); 7.293 (1.5); 7.284 (2.0); 7.277 (2.0); 7.272 (1.9); 7.267 (1.6); 7.174 (2.9); 7.150 (3.6); 7.128 (2.1); 6.281 (3.9); 6.276 (6.7); 6.271 (3.9); 5.357 (16.0); 3.329 (70.1); 2.672 (0.7); 2.668 (0.5); 2.507 (72.1); 2.502 (94.1); 2.498 (72.1); 2.329 (0.6); 2.325 (0.5); 1.989 (0.5); 1.299 (1.3); 1.259 (1.6); 1.250 (0.4); 1.236 (1.1); 0.146 (0.3); 0.008 (2.8); 0.000 (67.0); −0.150 (0.3) |
| I-1-241 | $^1$H-NMR, Solvent [D$_6$]-DMSO, spectrometer: 399.95 MHz: δ = 8.909 (0.9); 8.505 (1.5); 7.985 (0.4); 7.979 (0.4); 7.963 (0.4); 7.957 (0.4); 7.790 (0.8); 7.785 (0.8); 7.475 (0.8); 7.471 (0.8); 7.414 (0.7); 7.409 (0.7); 7.276 (0.7); 7.254 (0.7); 6.288 (0.5); 6.283 (0.9); 6.278 (0.6); 5.342 (2.1); 3.926 (3.9); 3.341 (0.4); 3.187 (0.5); 3.170 (16.0); 2.507 (9.4); 2.503 (12.3); 2.499 (9.9); 0.000 (8.2) |
| I-1-242 | $^1$H-NMR, Solvent [D$_6$]-DMSO, spectrometer: 399.95 MHz: □ = 8.919 (2.4); 8.915 (4.4); 8.518 (8.2); 7.964 (1.7); 7.958 (1.8); 7.943 (2.1); 7.937 (2.3); 7.893 (3.8); 7.888 (4.0); 7.794 (4.4); 7.773 (3.5); 7.529 (3.7); 7.526 (4.0); 7.488 (3.3); 7.483 (3.5); 6.337 (2.7); 6.332 (4.6); 6.327 (2.9); 5.543 (10.5); 5.518 (0.5); 3.187 (1.7); 3.170 (16.0); 2.525 (0.7); 2.508 (33.5); 2.503 (45.5); 2.499 (35.5); 0.008 (1.4); 0.000 (39.6) |
| I-1-243 | $^1$H-NMR, Solvent [D$_6$]-DMSO, spectrometer: 399.95 MHz: δ = 8.851 (1.6); 8.317 (1.0); 7.619 (3.1); 7.612 (3.4); 7.050 (0.6); 3.817 (16.0); 3.443 (0.4); 3.325 (16.8); 2.675 (1.8); 2.671 (2.5); 2.666 (2.0); 2.524 (6.4); 2.510 (131.1); 2.506 (267.1); 2.502 (361.2); 2.497 (279.7); 2.333 (1.6); 2.329 (2.3); 2.324 (1.7); 1.351 (0.4); 1.298 (0.4); 1.259 (0.7); 1.236 (3.0); 1.140 (0.7); 0.867 (0.4); 0.854 (0.6); 0.836 (0.4); 0.146 (1.2); 0.008 (9.4); 0.000 (250.5); −0.008 (17.6); −0.150 (1.1) |
| I-1-244 | $^1$H-NMR, Solvent [D$_6$]-DMSO, spectrometer: 399.95 MHz: δ = 8.949 (4.1); 8.609 (3.1); 7.854 (3.0); 7.850 (3.3); 7.574 (1.4); 7.553 (1.7); 7.417 (1.8); 7.304 (2.4); 7.283 (2.1); 7.235 (3.8); 7.052 (1.8); 3.331 (5.7); 2.675 (0.6); 2.671 (0.9); 2.667 (0.7); 2.506 (102.5); 2.502 (138.0); 2.497 (106.9); 2.398 (16.0); 2.329 (0.9); 2.324 (0.7); 0.146 (0.8); 0.007 (6.0); 0.000 (155.7); −0.150 (0.8) |
| I-1-245 | $^1$H-NMR, Solvent [D$_6$]-DMSO, spectrometer: 399.95 MHz: δ = 8.932 (9.9); 8.619 (14.6); 8.316 (0.4); 8.181 (16.0); 7.961 (0.6); 7.933 (15.6); 7.908 (0.5); 7.754 (0.5); 3.809 (0.3); 3.800 (0.3); 3.774 (0.4); 3.748 (0.4); 3.636 (0.5); 3.523 (0.6); 3.491 (0.6); 3.476 (0.6); 3.467 (0.7); 3.462 (0.9); 3.450 (0.9); 3.432 (0.9); 3.415 (0.7); 3.389 (0.5); 3.385 (0.5); 3.367 (0.5); 3.340 (0.5); 3.333 (0.5); 3.300 (0.5); 3.292 (0.4); 3.261 (0.4); 3.211 (0.4); 3.206 (0.4); 3.188 (0.4); 2.672 (1.2); 2.507 (139.8); 2.503 (181.0); 2.499 (139.9); 2.329 (1.2); 2.326 (1.0); 1.074 (0.4); 1.056 (0.7); 1.039 (0.4); 0.000 (38.9) |
| I-1-246 | $^1$H-NMR, Solvent [D$_6$]-DMSO, spectrometer: 399.95 MHz: δ = 8.909 (7.2); 8.512 (11.1); 8.038 (1.4); 8.032 (1.7); 8.027 (1.8); 8.017 (2.1); 8.010 (2.0); 8.005 (1.9); 7.999 (1.6); 7.871 (6.1); 7.866 (6.4); 7.764 (2.7); 7.759 (2.9); 7.748 (3.0); 7.742 (2.7); 7.537 (2.7); 7.514 (4.5); 7.490 (8.0); 7.486 (7.1); 6.303 (4.2); 6.297 (7.2); 6.293 (4.6); 5.498 (16.0); 3.335 (4.6); 3.187 (1.2); 2.672 (0.8); 2.667 (0.6); 2.507 (93.2); 2.503 (123.9); 2.498 (98.5); 2.333 (0.7); 2.329 (0.8); 0.000 (23.8) |
| I-1-247 | $^1$H-NMR, Solvent [D$_6$]-DMSO, spectrometer: 399.95 MHz: δ = 9.091 (0.7); 8.915 (3.4); 8.518 (4.5); 8.031 (0.4); 7.810 (3.0); 7.805 (3.0); 7.606 (2.8); 7.602 (2.8); 7.461 (3.0); 7.458 (3.0); 7.288 (0.4); 7.235 (2.8); 7.231 (2.7); 6.282 (2.1); 6.277 (3.2); 6.272 (2.0); 5.384 (8.0); 5.360 (0.7); 3.881 (13.8); 3.791 (16.0); 3.765 (1.2); 3.337 (3.1); 3.187 (0.7); 3.169 (0.4); 2.672 (0.5); 2.507 (59.1); 2.503 (74.3); |

| Example | NMR data |
|---|---|
| | 2.499 (58.7); 2.329 (0.5); 1.352 (0.4); 1.298 (0.4); 1.259 (0.6); 1.235 (1.8); 1.087 (1.9); 1.037 (1.0); 0.883 (0.3); 0.865 (0.7); 0.854 (0.5); 0.847 (0.6); 0.839 (0.8); 0.822 (0.7); 0.000 (20.9) |
| I-1-248 | $^1$H-NMR, Solvent [D$_6$]-DMSO, spectrometer: 399.95 MHz: δ = 12.059 (0.3); 8.951 (1.7); 8.947 (3.1); 8.646 (5.6); 7.919 (1.6); 7.915 (1.7); 7.899 (1.7); 7.895 (1.8); 7.718 (0.3); 7.693 (0.7); 7.689 (0.8); 7.672 (1.4); 7.654 (0.9); 7.649 (0.9); 7.238 (2.0); 7.217 (2.0); 7.193 (0.4); 7.173 (1.1); 7.171 (1.1); 7.153 (2.0); 7.134 (1.0); 7.133 (1.0); 7.051 (1.1); 3.900 (3.3); 3.849 (16.0); 3.329 (3.3); 2.525 (0.5); 2.512 (10.6); 2.508 (21.3); 2.503 (28.2); 2.499 (20.9); 2.495 (10.5) |
| I-1-249 | $^1$H-NMR, Solvent [D$_6$]-DMSO, spectrometer: 399.95 MHz: δ = 8.925 (2.8); 8.530 (5.1); 7.907 (2.0); 7.902 (2.1); 7.612 (0.9); 7.608 (0.9); 7.591 (1.2); 7.587 (1.2); 7.474 (2.7); 7.453 (2.1); 3.564 (16.0); 3.466 (1.6); 3.449 (1.4); 3.432 (1.4); 3.414 (0.8); 3.386 (0.5); 3.372 (0.4); 3.355 (0.3); 2.676 (0.3); 2.671 (0.4); 2.667 (0.3); 2.507 (53.3); 2.502 (68.8); 2.498 (51.2); 2.423 (10.0); 2.380 (0.7); 2.333 (0.4); 2.329 (0.5); 2.325 (0.4); 1.073 (0.9); 1.056 (1.7); 1.038 (0.9); 0.146 (0.5); 0.008 (5.8); 0.000 (112.2); −0.008 (6.1); −0.150 (0.6) |
| I-1-250 | $^1$H-NMR, Solvent [D$_6$]-DMSO, spectrometer: 399.95 MHz: δ = 8.717 (11.6); 8.316 (0.4); 8.004 (3.7); 8.000 (6.9); 7.995 (4.6); 7.965 (3.4); 7.944 (3.8); 7.818 (2.5); 7.816 (2.4); 7.798 (3.3); 7.796 (3.3); 7.700 (4.1); 7.680 (6.3); 7.660 (2.7); 5.756 (1.5); 3.355 (2.1); 2.676 (0.8); 2.671 (1.0); 2.667 (0.8); 2.588 (16.0); 2.525 (2.5); 2.511 (56.5); 2.507 (113.0); 2.502 (149.4); 2.498 (110.1); 2.494 (55.0); 2.333 (0.8); 2.329 (1.0); 2.325 (0.8); 0.008 (1.4); 0.000 (39.8); −0.008 (1.7) |
| I-1-251 | $^1$H-NMR, Solvent [D$_6$]-DMSO, spectrometer: 399.95 MHz: δ = 8.232 (4.2); 7.547 (2.8); 7.540 (2.8); 7.329 (2.4); 7.307 (2.8); 7.003 (1.6); 6.995 (1.5); 6.981 (1.4); 6.973 (1.3); 4.038 (0.6); 4.020 (0.6); 3.783 (16.0); 3.324 (64.6); 2.671 (0.6); 2.608 (7.1); 2.506 (67.1); 2.502 (82.2); 2.329 (0.5); 1.989 (2.4); 1.237 (0.4); 1.193 (0.7); 1.175 (1.3); 1.157 (0.6); 0.000 (14.2) |
| I-1-252 | $^1$H-NMR, Solvent [D$_6$]-DMSO, spectrometer: 399.95 MHz: δ = 8.316 (0.6); 8.239 (12.8); 7.463 (0.8); 7.448 (1.7); 7.442 (1.6); 7.433 (1.1); 7.427 (3.1); 7.421 (1.1); 7.412 (1.6); 7.406 (1.9); 7.391 (0.8); 7.042 (1.2); 7.036 (5.6); 7.014 (10.0); 6.993 (4.7); 6.986 (1.0); 4.055 (0.4); 4.038 (1.2); 4.020 (1.2); 4.002 (0.4); 3.325 (323.1); 2.675 (1.2); 2.671 (1.6); 2.666 (1.2); 2.662 (0.6); 2.605 (16.0); 2.524 (3.7); 2.511 (81.6); 2.506 (166.6); 2.502 (220.3); 2.497 (157.9); 2.493 (74.5); 2.338 (0.5); 2.333 (1.0); 2.329 (1.4); 2.324 (1.0); 2.320 (0.5); 1.989 (5.2); 1.398 (0.4); 1.259 (0.4); 1.236 (0.7); 1.193 (1.4); 1.175 (2.8); 1.157 (1.4); 0.008 (0.6); 0.000 (20.2); −0.009 (0.6) |
| I-1-253 | $^1$H-NMR, Solvent [D$_6$]-DMSO, spectrometer: 399.95 MHz: δ = 8.702 (12.7); 8.011 (9.6); 7.990 (11.4); 7.735 (11.2); 7.714 (9.5); 5.757 (1.7); 3.347 (2.4); 2.676 (0.6); 2.672 (0.8); 2.667 (0.6); 2.588 (16.0); 2.507 (88.6); 2.503 (113.8); 2.498 (83.1); 2.334 (0.6); 2.330 (0.8); 2.325 (0.6); 0.008 (0.5); 0.000 (11.9); −0.008 (0.5) |
| I-1-254 | $^1$H-NMR, Solvent [D$_6$]-DMSO, spectrometer: 399.95 MHz: δ = 8.316 (0.8); 8.205 (6.9); 7.411 (7.7); 7.392 (13.1); 7.313 (4.2); 7.295 (3.6); 7.292 (3.4); 7.273 (2.1); 4.056 (0.6); 4.038 (1.7); 4.020 (1.7); 4.002 (0.6); 3.326 (262.2); 2.675 (1.4); 2.671 (1.8); 2.666 (1.4); 2.601 (16.0); 2.524 (4.7); 2.511 (103.3); 2.506 (205.5); 2.502 (268.2); 2.497 (193.9); 2.493 (94.1); 2.333 (1.3); 2.329 (1.7); 2.324 (1.2); 1.989 (7.2); 1.398 (1.2); 1.298 (0.3); 1.258 (0.5); 1.249 (0.4); 1.236 (1.4); 1.193 (1.9); 1.175 (3.8); 1.157 (1.9); 0.146 (1.4); 0.008 (11.9); 0.000 (309.5); −0.009 (12.5); −0.028 (0.5); −0.150 (1.5) |
| I-1-255 | $^1$H-NMR, Solvent [D$_6$]-DMSO, spectrometer: 399.95 MHz: δ = 8.238 (7.5); 8.024 (3.4); 8.006 (3.2); 7.419 (5.3); 7.410 (9.9); 7.388 (2.6); 7.382 (2.7); 7.374 (1.7); 7.360 (0.7); 4.038 (0.4); 4.020 (0.4); 3.325 (168.3); 2.671 (1.2); 2.608 (16.0); 2.502 (175.0); 2.328 (1.2); 1.989 (1.8); 1.397 (3.0); 1.258 (0.4); 1.248 (0.3); 1.235 (0.8); 1.192 (0.6); 1.174 (1.0); 1.157 (0.5); 0.146 (0.6); 0.000 (118.7); −0.001 (118.9); −0.150 (0.7) |
| I-1-256 | $^1$H-NMR, Solvent [D$_6$]-DMSO, spectrometer: 601.6 MHz: δ = 19.972 (0.4); 8.733 (7.2); 7.996 (5.4); 7.917 (5.5); 7.914 (5.6); 7.607 (1.1); 7.590 (4.4); 7.582 (4.0); 7.568 (1.1); 7.515 (5.3); 7.513 (5.5); 6.316 (3.5); 6.312 (6.2); 6.309 (3.8); 5.515 (16.0); 5.447 (0.4); 3.425 (0.4); 3.188 (0.8); 2.616 (0.7); 2.592 (13.5); 2.507 (73.2); 2.504 (101.7); 2.501 (79.4); 2.388 (0.7); 0.096 (0.5); 0.000 (119.9); −0.100 (0.6) |
| I-1-257 | $^1$H-NMR, Solvent [D$_6$]-DMSO, spectrometer: 601.6 MHz: δ = 19.969 (0.4); 8.733 (8.5); 7.888 (6.0); 7.884 (6.1); 7.824 (3.8); 7.808 (3.9); 7.625 (4.0); 7.613 (4.1); 7.532 (6.0); 7.530 (6.1); 6.333 (4.2); 6.330 (7.1); 6.326 (4.3); 5.762 (0.4); 5.533 (16.0); 4.034 (0.8); 4.022 (0.8); 4.011 (0.4); 3.458 (1.2); 3.446 (2.2); 3.434 (2.3); 3.423 (1.2); 3.187 (1.3); 2.615 (0.8); 2.593 (14.5); 2.522 (1.0); 2.519 (1.1); 2.506 (80.5); 2.504 (111.5); 2.501 (84.7); 2.388 (0.7); 1.990 (2.9); 1.187 (0.8); 1.175 (1.6); 1.163 (0.8); 1.067 (1.6); 1.056 (3.2); 1.044 (1.6); 0.096 (0.6); 0.005 (4.9); 0.000 (136.0); −0.006 (5.5); −0.100 (0.6) |
| I-1-258 | $^1$H-NMR, Solvent [D$_6$]-DMSO, spectrometer: 601.6 MHz: δ = 8.226 (4.0); 7.799 (4.2); 7.796 (4.1); 7.743 (3.7); 7.445 (4.4); 7.442 (4.3); 7.099 (3.6); 6.257 (2.8); 6.254 (4.6); 6.251 (2.7); 5.279 (10.0); 4.034 (0.6); 4.022 (0.7); 3.344 (88.2); 2.602 (9.4); 2.506 (56.5); 2.503 (75.2); 2.500 (55.2); 2.470 (14.9); 2.388 (0.5); 2.201 (16.0); 1.990 (3.0); 1.299 (1.1); 1.259 (1.5); 1.235 (0.7); 1.187 (0.8); 1.175 (1.5); 1.163 (0.8); 0.000 (49.8) |
| I-1-259 | $^1$H-NMR, Solvent [D$_6$]-DMSO, spectrometer: 601.6 MHz: δ = 8.222 (6.7); 7.841 (5.9); 7.837 (5.8); 7.744 (9.2); 7.645 (8.4); 7.491 (6.2); 7.489 (6.2); 6.292 (4.0); 6.288 (6.6); 6.285 (3.9); 5.468 (16.0); 4.034 (0.9); 4.022 (0.9); |

| Example | NMR data |
|---|---|
| | 3.345 (134.8); 2.604 (13.9); 2.522 (1.1); 2.519 (1.1); 2.507 (71.6); 2.504 (96.7); 2.501 (70.6); 2.388 (0.6); 1.990 (3.7); 1.351 (0.6); 1.336 (0.6); 1.299 (2.8); 1.259 (3.8); 1.249 (0.9); 1.234 (1.4); 1.187 (1.2); 1.175 (2.0); 1.163 (1.0); 0.854 (0.5); 0.000 (66.5); −0.006 (2.6) |
| I-1-260 | $^1$H-NMR, Solvent [$D_6$]-DMSO, spectrometer: 399.95 MHz: δ = 8.700 (9.9); 7.942 (6.7); 7.864 (5.3); 7.859 (5.7); 7.481 (5.1); 7.477 (5.6); 7.419 (14.8); 6.290 (3.5); 6.285 (6.0); 6.280 (3.9); 5.427 (16.0); 3.450 (0.5); 3.433 (0.7); 3.339 (2.7); 3.187 (0.4); 3.035 (1.9); 3.017 (5.8); 2.998 (6.0); 2.979 (2.0); 2.672 (0.5); 2.589 (14.3); 2.507 (56.7); 2.503 (73.3); 2.499 (59.7); 2.330 (0.5); 1.132 (6.7); 1.114 (14.1); 1.095 (6.6); 0.000 (43.2) |
| I-1-261 | $^1$H-NMR, Solvent [$D_6$]-DMSO, spectrometer: 399.95 MHz: δ = 8.742 (12.5); 7.894 (7.4); 7.890 (8.3); 7.875 (2.9); 7.870 (2.8); 7.586 (1.2); 7.580 (1.4); 7.574 (1.5); 7.565 (1.9); 7.559 (1.9); 7.553 (1.9); 7.547 (1.6); 7.503 (5.6); 7.499 (6.0); 7.444 (2.8); 7.419 (3.4); 7.397 (2.2); 6.305 (4.0); 6.300 (6.9); 6.295 (4.2); 5.461 (16.0); 3.468 (0.6); 3.450 (1.6); 3.433 (1.6); 3.415 (0.7); 3.187 (0.4); 2.677 (0.4); 2.672 (0.5); 2.667 (0.4); 2.591 (14.9); 2.507 (54.3); 2.503 (72.0); 2.498 (55.6); 2.334 (0.4); 2.330 (0.5); 2.325 (0.4); 1.074 (1.4); 1.057 (2.8); 1.039 (1.4); 0.008 (2.8); 0.000 (65.9) |
| I-1-262 | $^1$H-NMR, Solvent [$D_6$]-DMSO, spectrometer: 399.95 MHz: δ = 8.696 (9.7); 7.963 (2.6); 7.958 (2.9); 7.942 (3.4); 7.937 (3.7); 7.888 (5.9); 7.883 (6.2); 7.791 (5.6); 7.770 (4.6); 7.525 (7.2); 7.517 (6.8); 7.512 (6.5); 6.332 (6.3); 5.757 (0.4); 5.541 (15.8); 3.531 (0.4); 3.495 (0.5); 3.467 (1.0); 3.450 (1.7); 3.433 (1.8); 3.415 (1.1); 3.368 (0.7); 3.349 (0.7); 3.337 (0.7); 3.326 (0.6); 3.187 (1.1); 2.672 (0.6); 2.591 (16.0); 2.503 (67.6); 2.426 (0.4); 2.329 (0.5); 1.233 (0.6); 1.074 (1.2); 1.056 (2.3); 1.039 (1.2); 0.000 (34.5) |
| I-1-263 | $^1$H-NMR, Solvent [$D_6$]-DMSO, spectrometer: 399.95 MHz: δ = 8.679 (6.7); 8.226 (0.3); 8.207 (0.3); 7.986 (1.5); 7.981 (1.6); 7.964 (1.6); 7.958 (1.7); 7.784 (3.2); 7.779 (3.3); 7.473 (3.3); 7.469 (3.4); 7.444 (2.9); 7.439 (2.8); 7.274 (2.9); 7.252 (2.8); 7.214 (0.5); 6.993 (0.4); 6.974 (0.4); 6.288 (2.2); 6.283 (3.7); 6.278 (2.2); 5.340 (8.7); 3.923 (16.0); 3.903 (1.2); 3.345 (3.9); 3.187 (4.3); 2.773 (0.4); 2.752 (0.5); 2.682 (0.5); 2.677 (0.5); 2.672 (0.4); 2.587 (7.6); 2.507 (42.4); 2.503 (54.7); 2.498 (41.6); 2.330 (0.3); 1.356 (1.4); 1.234 (0.5); 0.987 (0.4); 0.008 (1.8); 0.000 (41.7) |
| I-1-264 | $^1$H-NMR, Solvent [$D_6$]-DMSO, spectrometer: 399.95 MHz: δ = 8.751 (11.1); 8.048 (5.2); 8.043 (5.5); 7.904 (5.6); 7.899 (5.9); 7.643 (5.0); 7.622 (6.4); 7.605 (0.4); 7.514 (5.4); 7.510 (5.7); 7.481 (3.0); 7.476 (3.1); 7.461 (2.4); 7.456 (2.4); 6.315 (3.8); 6.310 (6.5); 6.305 (3.9); 5.758 (0.7); 5.495 (16.0); 5.421 (0.4); 3.187 (1.5); 3.169 (7.5); 2.672 (0.6); 2.667 (0.5); 2.590 (13.6); 2.507 (64.6); 2.503 (84.5); 2.498 (62.9); 2.329 (0.5); 2.325 (0.4); 1.356 (0.4); 0.008 (0.4); 0.000 (9.5) |
| I-1-265 | $^1$H-NMR, Solvent [$D_6$]-DMSO, spectrometer: 399.95 MHz: δ = 8.326 (0.4); 8.180 (9.6); 7.954 (7.7); 7.845 (4.4); 7.825 (5.4); 7.820 (5.4); 7.458 (6.0); 7.455 (6.2); 7.222 (2.5); 7.202 (5.3); 7.173 (4.0); 7.170 (3.9); 7.153 (2.0); 7.150 (2.0); 6.270 (3.9); 6.265 (6.5); 6.261 (4.0); 5.332 (13.4); 3.340 (148.2); 3.061 (1.8); 3.043 (5.6); 3.024 (5.8); 3.005 (2.1); 2.676 (0.7); 2.672 (1.5); 2.668 (0.7); 2.525 (2.5); 2.512 (59.9); 2.507 (121.2); 2.503 (158.6); 2.499 (113.8); 2.494 (54.5); 2.334 (0.8); 2.330 (1.1); 2.325 (0.8); 1.759 (16.0); 1.298 (0.4); 1.272 (0.4); 1.258 (0.7); 1.233 (2.9); 1.187 (0.4); 1.121 (7.4); 1.102 (15.1); 1.084 (7.3); 1.073 (1.4); 1.055 (1.6); 1.038 (0.9); 0.876 (0.4); 0.863 (0.4); 0.853 (0.6); 0.836 (0.4); 0.008 (0.8); 0.000 (22.3); −0.008 (0.8) |
| I-1-266 | $^1$H-NMR, Solvent [$D_6$]-DMSO, spectrometer: 399.95 MHz: δ = 8.317 (0.9); 8.184 (7.7); 7.967 (4.9); 7.753 (3.2); 7.749 (3.2); 7.311 (1.4); 7.307 (1.4); 7.291 (1.9); 7.204 (3.5); 7.183 (2.5); 4.037 (0.8); 4.020 (0.8); 3.436 (22.2); 3.411 (1.1); 3.384 (0.8); 3.332 (391.7); 2.676 (1.5); 2.671 (1.9); 2.667 (1.4); 2.507 (248.0); 2.502 (307.8); 2.498 (221.4); 2.425 (0.3); 2.343 (16.0); 2.329 (2.7); 2.325 (2.0); 1.989 (3.4); 1.298 (0.4); 1.259 (0.5); 1.250 (0.4); 1.235 (0.8); 1.193 (1.0); 1.175 (1.9); 1.157 (0.9); 0.147 (0.6); 0.008 (7.7); 0.000 (141.1); −0.008 (7.3); −0.149 (0.7) |
| I-1-267 | $^1$H-NMR, Solvent [$D_6$]-DMSO, spectrometer: 399.95 MHz: δ = 8.285 (0.4); 8.210 (6.8); 8.198 (0.4); 7.924 (3.8); 7.874 (3.6); 7.866 (3.8); 7.861 (3.5); 7.486 (3.0); 7.483 (2.9); 7.482 (2.9); 7.473 (0.7); 7.333 (5.8); 6.293 (2.3); 6.288 (3.5); 6.283 (2.4); 6.274 (0.6); 5.406 (8.6); 4.056 (1.2); 4.038 (3.7); 4.020 (3.8); 4.002 (1.3); 3.326 (42.5); 2.671 (0.4); 2.511 (21.8); 2.507 (40.9); 2.502 (54.3); 2.497 (41.5); 2.493 (22.9); 2.329 (0.4); 1.989 (16.0); 1.974 (0.8); 1.336 (0.4); 1.298 (1.3); 1.274 (0.4); 1.259 (1.8); 1.250 (0.8); 1.235 (1.3); 1.193 (4.5); 1.175 (8.9); 1.157 (4.5); 1.143 (0.3); 0.146 (0.3); 0.008 (4.3); 0.000 (74.8); −0.009 (4.6); −0.015 (3.7); −0.150 (0.3) |
| I-1-268 | $^1$H-NMR, Solvent [$D_6$]-DMSO, spectrometer: 601.6 MHz: δ = 19.976 (0.4); 8.323 (0.4); 8.293 (0.6); 8.201 (12.0); 7.952 (7.0); 7.834 (5.7); 7.830 (5.6); 7.763 (0.6); 7.710 (10.3); 7.650 (7.2); 7.620 (0.3); 7.494 (6.0); 7.491 (6.0); 7.482 (0.7); 6.294 (3.8); 6.291 (6.4); 6.287 (3.8); 5.461 (16.0); 4.046 (0.7); 4.034 (2.0); 4.022 (2.1); 4.010 (0.7); 3.344 (106.2); 2.615 (0.9); 2.524 (1.3); 2.521 (1.5); 2.518 (1.6); 2.506 (97.7); 2.503 (134.7); 2.500 (100.1); 2.387 (0.9); 1.990 (8.6); 1.351 (0.4); 1.298 (2.0); 1.277 (0.5); 1.258 (2.7); 1.235 (2.5); 1.187 (2.6); 1.175 (4.6); 1.163 (2.3); 0.854 (0.5); 0.097 (0.7); 0.005 (5.4); 0.000 (159.4); −0.006 (6.0); −0.100 (0.7) |
| I-1-269 | $^1$H-NMR, Solvent [$D_6$]-DMSO, spectrometer: 399.95 MHz: δ = 8.738 (16.0); 8.438 (15.8); 8.369 (13.0); 8.365 (13.9); 8.317 (0.7); 8.211 (0.4); 8.135 (6.2); 8.130 (6.4); 8.114 (7.8); 8.110 (7.9); 7.954 (11.8); 7.933 (9.7); 7.897 (0.8); 5.757 (3.0); 4.364 (0.3); 4.344 (0.4); 4.288 (0.4); 4.207 (0.4); 4.204 (0.5); 4.172 (0.5); 4.164 (0.5); 4.150 (0.5); 4.081 (0.6); 4.018 (0.7); 3.998 (0.8); 3.984 (0.7); 3.895 (0.8); 3.860 (0.8); 3.857 (0.8); 3.830 (0.8); 3.790 (0.9); 3.766 (0.9); 3.750 (0.9); 3.702 (0.9); 3.674 (0.9); 3.622 (0.9); 3.618 (0.8); 3.553 (0.8); 3.426 (0.7); 3.412 (0.6); 3.362 (0.6); 3.262 (0.5); 3.187 (0.8); 3.125 (0.3); 2.672 (1.7); 2.507 (211.1); 2.503 (275.8); 2.499 (225.1); 2.330 (2.2); 2.232 (0.3); 0.000 (18.1) |

| Example | NMR data |
|---|---|
| I-1-270 | ¹H-NMR, Solvent [D$_6$]-DMSO, spectrometer: 399.95 MHz:<br>δ = 8.317 (0.7); 8.303 (3.6); 7.982 (0.4); 7.918 (0.7); 7.700 (3.3); 7.127 (1.0); 7.108 (1.7); 7.073 (2.4); 7.054 (1.2); 3.326 (82.0); 2.676 (2.4); 2.672 (62.0); 2.667 (0.7); 2.662 (0.4); 2.541 (0.6); 2.524 (2.9); 2.511 (52.6); 2.507 (105.8); 2.502 (148.2); 2.498 (102.1); 2.493 (46.8); 2.338 (0.4); 2.333 (0.7); 2.329 (0.9); 2.324 (0.7); 2.320 (0.4); 2.294 (16.0); 1.398 (0.8); 1.340 (0.5); 1.259 (0.4); 1.236 (0.7); 0.008 (0.6); 0.000 (16.4); −0.009 (0.5) |
| I-1-271 | ¹H-NMR, Solvent [D$_6$]-DMSO, spectrometer: 399.95 MHz:<br>δ = 8.313 (15.0); 8.311 (15.2); 8.306 (16.0); 8.300 (13.8); 7.997 (4.6); 7.889 (7.8); 7.869 (9.7); 7.712 (6.2); 7.709 (6.1); 7.691 (5.1); 3.349 (12.2); 2.676 (1.0); 2.672 (1.4); 2.668 (1.0); 2.525 (3.2); 2.512 (81.7); 2.507 (162.4); 2.503 (211.8); 2.499 (153.6); 2.494 (74.4); 2.482 (3.8); 2.334 (1.1); 2.330 (1.4); 2.325 (1.1); 2.118 (3.3); 2.087 (13.2); 1.398 (8.9); 1.259 (0.5); 1.236 (2.3); 1.141 (7.8); 0.868 (0.4); 0.854 (0.6); 0.837 (0.4); 0.146 (0.5); 0.008 (4.2); 0.000 (122.2); −0.008 (4.7); −0.150 (0.6) |
| I-1-272 | ¹H-NMR, Solvent [D$_6$]-DMSO, spectrometer: 399.95 MHz:<br>δ = 8.890 (9.1); 8.887 (8.6); 8.532 (16.0); 7.998 (5.5); 7.994 (8.9); 7.989 (6.1); 7.965 (4.7); 7.945 (5.3); 7.826 (3.6); 7.824 (3.4); 7.806 (4.8); 7.803 (4.8); 7.705 (5.3); 7.685 (8.2); 7.665 (3.4); 7.518 (0.4); 3.348 (11.2); 3.187 (1.7); 3.091 (0.7); 3.001 (0.4); 2.676 (1.5); 2.672 (1.8); 2.507 (215.4); 2.503 (262.0); 2.498 (201.0); 2.329 (1.7); 2.325 (1.3); 1.056 (0.4); 0.146 (0.5); 0.000 (112.0); −0.150 (0.5) |
| I-1-273 | ¹H-NMR, Solvent [D$_6$]-DMSO, spectrometer: 399.95 MHz:<br>δ = 8.770 (2.2); 8.766 (2.1); 8.244 (0.6); 8.020 (4.3); 7.765 (2.2); 7.759 (2.2); 7.530 (2.3); 7.525 (2.4); 7.434 (2.3); 7.431 (2.3); 7.140 (2.3); 7.135 (2.3); 6.262 (1.7); 6.256 (2.8); 6.251 (1.7); 5.311 (6.4); 3.830 (12.0); 3.712 (16.0); 3.328 (51.9); 2.676 (0.4); 2.671 (0.5); 2.666 (0.4); 2.524 (1.5); 2.511 (31.9); 2.507 (64.1); 2.502 (84.1); 2.498 (61.5); 2.493 (30.0); 2.333 (0.4); 2.329 (0.5); 2.324 (0.4); 1.989 (0.9); 1.336 (0.4); 1.298 (0.9); 1.259 (1.2); 1.249 (0.7); 1.235 (0.6); 1.175 (0.5); 0.008 (1.7); 0.000 (52.1); −0.009 (1.8) |
| I-1-274 | ¹H-NMR, Solvent [D$_6$]-DMSO, spectrometer: 399.95 MHz:<br>δ = 8.918 (5.5); 8.914 (5.6); 8.627 (10.1); 8.038 (5.2); 8.033 (5.7); 7.905 (5.7); 7.899 (5.9); 7.648 (5.0); 7.627 (6.5); 7.513 (5.6); 7.508 (5.8); 7.479 (2.9); 7.474 (3.1); 7.458 (2.4); 7.453 (2.5); 6.314 (4.1); 6.309 (7.0); 6.304 (4.3); 5.494 (16.0); 3.572 (0.3); 3.564 (0.4); 3.467 (0.8); 3.449 (1.0); 3.432 (1.2); 3.414 (1.1); 3.354 (1.3); 3.187 (0.5); 3.170 (0.4); 2.676 (0.6); 2.671 (0.9); 2.667 (0.7); 2.525 (2.2); 2.511 (50.1); 2.507 (102.6); 2.502 (136.6); 2.498 (101.5); 2.494 (51.0); 2.333 (0.6); 2.329 (0.9); 2.325 (0.7); 1.056 (0.5); 0.146 (1.1); 0.008 (8.3); 0.000 (233.4); −0.009 (9.7); −0.150 (1.1) |
| I-1-275 | ¹H-NMR, Solvent [D$_6$]-DMSO, spectrometer: 399.95 MHz:<br>δ = 8.923 (5.6); 8.920 (5.8); 8.639 (9.3); 8.066 (5.3); 8.061 (5.8); 7.900 (5.6); 7.895 (5.9); 7.822 (5.1); 7.802 (5.8); 7.509 (5.6); 7.506 (6.0); 7.372 (2.8); 7.367 (3.0); 7.352 (2.6); 7.347 (2.7); 6.311 (3.9); 6.306 (6.7); 6.301 (4.2); 5.477 (16.0); 5.405 (0.4); 3.584 (0.4); 3.510 (0.7); 3.466 (1.5); 3.449 (2.6); 3.432 (2.8); 3.414 (2.0); 3.369 (1.8); 3.360 (1.8); 3.251 (0.9); 3.187 (0.6); 3.169 (0.6); 3.162 (0.5); 3.139 (0.4); 3.126 (0.3); 2.671 (1.1); 2.507 (128.0); 2.502 (167.6); 2.498 (129.6); 2.333 (0.8); 2.329 (1.1); 2.325 (0.9); 1.073 (1.6); 1.056 (3.2); 1.038 (1.6); 0.146 (1.2); 0.008 (12.8); 0.000 (255.5); −0.034 (0.5); −0.150 (1.3) |
| I-1-276 | ¹H-NMR, Solvent [D$_6$]-DMSO, spectrometer: 399.95 MHz:<br>δ = 8.893 (5.7); 8.890 (5.7); 8.516 (9.8); 7.963 (2.6); 7.957 (2.7); 7.942 (3.3); 7.936 (3.4); 7.893 (6.2); 7.887 (6.2); 7.792 (5.9); 7.770 (4.7); 7.727 (0.6); 7.528 (6.3); 7.525 (6.3); 7.491 (5.6); 7.486 (5.7); 7.382 (0.5); 7.377 (0.4); 6.337 (4.2); 6.332 (6.8); 6.327 (4.2); 5.541 (16.0); 5.517 (1.5); 3.526 (0.5); 3.450 (1.2); 3.343 (3.7); 3.186 (0.9); 2.671 (0.9); 2.506 (120.9); 2.502 (148.8); 2.421 (0.5); 2.329 (1.1); 0.146 (1.0); 0.047 (0.4); 0.000 (191.6); −0.150 (1.1) |
| I-1-277 | ¹H-NMR, Solvent [D$_6$]-DMSO, spectrometer: 399.95 MHz:<br>δ = 8.715 (5.3); 7.808 (2.4); 7.804 (2.4); 7.627 (2.3); 7.622 (2.5); 7.462 (2.5); 7.459 (2.6); 7.290 (0.3); 7.264 (2.4); 7.259 (2.4); 6.285 (1.8); 6.280 (2.9); 6.275 (1.9); 5.382 (6.8); 5.360 (0.7); 3.876 (12.6); 3.785 (16.0); 3.765 (1.4); 3.363 (1.6); 3.186 (2.6); 3.169 (3.4); 2.671 (0.4); 2.667 (0.4); 2.613 (5.6); 2.609 (5.8); 2.507 (38.1); 2.502 (49.4); 2.498 (37.8); 0.146 (0.4); 0.008 (4.7); 0.000 (75.6); −0.008 (4.2); −0.150 (0.4) |
| I-1-278 | ¹H-NMR, Solvent [D$_6$]-DMSO, spectrometer: 399.95 MHz:<br>δ = 8.712 (4.8); 7.808 (2.2); 7.803 (2.2); 7.625 (2.2); 7.620 (2.3); 7.462 (2.2); 7.458 (2.2); 7.260 (2.2); 7.255 (2.2); 6.284 (1.7); 6.279 (2.8); 6.274 (1.6); 5.382 (6.5); 3.875 (12.4); 3.785 (16.0); 3.765 (0.6); 3.341 (1.9); 3.187 (2.1); 3.169 (0.3); 2.591 (5.0); 2.525 (0.9); 2.511 (17.8); 2.507 (36.1); 2.502 (47.7); 2.498 (34.9); 2.494 (17.1); 1.356 (0.4); 0.146 (0.4); 0.014 (0.3); 0.008 (3.3); 0.000 (88.6); −0.009 (3.4); −0.150 (0.4) |
| I-1-279 | ¹H-NMR, Solvent [D$_6$]-DMSO, spectrometer: 399.95 MHz:<br>δ = 8.914 (9.8); 8.911 (9.5); 8.618 (16.0); 8.317 (0.5); 8.226 (0.4); 8.208 (0.4); 8.165 (11.2); 8.143 (12.4); 7.893 (9.7); 7.888 (10.3); 7.738 (6.7); 7.732 (6.4); 7.716 (6.1); 7.711 (6.1); 7.687 (1.6); 7.538 (1.3); 7.532 (1.4); 7.393 (0.9); 7.387 (0.8); 7.371 (0.8); 7.366 (0.7); 6.993 (0.8); 6.974 (0.7); 3.741 (0.4); 3.698 (0.5); 3.662 (0.6); 3.467 (1.8); 3.449 (2.9); 3.432 (2.9); 3.414 (2.0); 3.392 (1.6); 3.375 (1.6); 3.357 (1.5); 3.213 (0.8); 3.187 (9.6); 3.118 (0.5); 3.112 (0.5); 3.083 (0.4); 3.073 (0.4); 3.043 (0.3); 3.036 (0.3); 3.010 (0.3); 2.676 (1.6); 2.671 (2.2); 2.667 (1.6); 2.579 (0.4); 2.525 (6.4); 2.511 (119.8); 2.507 (239.0); 2.502 (313.4); 2.498 (230.9); 2.494 (115.0); 2.334 (1.5); 2.329 (2.1); 2.325 (1.6); 1.234 (2.0); 1.073 (1.5); 1.056 (2.9); 1.038 (1.4); 0.146 (1.6); 0.008 (13.2); 0.000 (350.6); −0.009 (14.4); −0.150 (1.6) |
| I-1-280 | ¹H-NMR, Solvent [D$_6$]-DMSO, spectrometer: 399.95 MHz:<br>δ = 8.885 (8.9); 8.881 (8.6); 8.515 (12.4); 8.317 (1.0); 8.012 (1.6); 8.006 (13.6); 8.001 (4.5); 7.989 (4.8); 7.984 (16.0); 7.978 (1.9); 7.841 (0.3); 7.835 (3.3); 7.830 (1.1); |

| Example | NMR data |
|---|---|
| | 7.819 (1.2); 7.814 (4.2); 7.808 (0.5); 7.739 (2.0); 7.733 (14.6); 7.728 (4.8); 7.716 (4.2); 7.711 (12.4); 7.674 (0.5); 7.668 (4.4); 7.663 (1.2); 7.651 (1.1); 7.647 (3.2); 7.640 (0.3); 7.466 (3.4); 5.757 (1.0); 3.336 (18.1); 3.187 (0.7); 2.676 (2.7); 2.671 (3.8); 2.667 (2.7); 2.524 (9.6); 2.511 (211.1); 2.507 (425.7); 2.502 (560.2); 2.498 (406.0); 2.493 (196.9); 2.338 (1.3); 2.333 (2.7); 2.329 (3.7); 2.324 (2.7); 1.234 (0.8); 1.148 (0.3); 0.146 (1.4); 0.008 (10.2); 0.000 (300.0); −0.009 (10.3); −0.150 (1.4) |
| I-1-281 | $^1$H-NMR, Solvent [D$_6$]-DMSO, spectrometer: 399.95 MHz: δ = 8.926 (9.0); 8.618 (16.0); 8.153 (4.9); 8.135 (5.3); 7.874 (2.1); 7.872 (2.1); 7.853 (4.9); 7.834 (3.1); 7.664 (4.0); 7.644 (7.0); 7.625 (3.3); 7.608 (4.3); 7.587 (3.6); 3.543 (0.4); 3.520 (0.5); 3.451 (0.5); 3.435 (0.5); 3.414 (0.5); 3.397 (0.5); 3.374 (0.5); 3.288 (0.8); 3.242 (0.4); 3.209 (0.4); 3.190 (0.5); 2.780 (0.4); 2.674 (0.8); 2.504 (115.7); 2.331 (0.8); 0.147 (0.4); 0.001 (67.2); 0.000 (73.8); −0.149 (0.4) |
| I-1-282 | $^1$H-NMR, Solvent [D$_6$]-DMSO, spectrometer: 399.95 MHz: δ = 8.918 (9.2); 8.631 (16.0); 8.179 (5.5); 8.159 (6.1); 8.019 (5.4); 7.999 (6.1); 7.785 (0.6); 7.675 (4.7); 7.655 (8.5); 7.635 (4.0); 3.878 (0.3); 3.817 (0.4); 3.806 (0.4); 3.771 (0.4); 3.662 (0.5); 3.652 (0.6); 3.569 (0.7); 3.563 (0.7); 3.556 (0.7); 3.550 (0.7); 3.543 (0.7); 3.540 (0.7); 3.490 (0.7); 3.480 (0.7); 3.454 (0.7); 3.415 (0.7); 3.401 (0.7); 3.383 (0.6); 3.337 (0.6); 3.323 (0.6); 3.284 (0.5); 3.197 (0.4); 3.188 (0.5); 2.672 (1.2); 2.503 (169.5); 2.330 (1.2); 0.146 (0.5); −0.001 (103.4); −0.150 (0.6) |
| I-1-283 | $^1$H-NMR, Solvent [D$_6$]-DMSO, spectrometer: 399.95 MHz: δ = 8.891 (1.1); 8.887 (2.8); 8.884 (2.8); 8.500 (4.7); 8.241 (0.6); 7.983 (1.4); 7.977 (1.4); 7.961 (1.5); 7.955 (1.5); 7.790 (2.8); 7.784 (2.8); 7.474 (2.9); 7.471 (2.8); 7.470 (2.9); 7.416 (2.5); 7.410 (2.5); 7.273 (2.7); 7.251 (2.5); 6.289 (2.3); 6.283 (3.7); 6.278 (2.3); 5.340 (7.8); 3.924 (16.0); 3.902 (0.4); 3.331 (17.0); 2.676 (0.4); 2.671 (0.6); 2.666 (0.5); 2.525 (1.6); 2.520 (2.4); 2.511 (35.2); 2.507 (72.7); 2.502 (97.1); 2.497 (71.1); 2.493 (34.7); 2.333 (0.4); 2.329 (0.6); 2.324 (0.5); 1.055 (0.5); 0.000 (11.1); −0.009 (0.4) |
| I-1-284 | $^1$H-NMR, Solvent [D$_6$]-DMSO, spectrometer: 399.95 MHz: δ = 8.745 (2.5); 8.742 (2.5); 7.985 (4.7); 7.859 (0.7); 7.853 (0.7); 7.846 (0.7); 7.838 (1.0); 7.831 (3.2); 7.825 (3.2); 7.653 (1.1); 7.648 (1.1); 7.635 (1.1); 7.630 (1.1); 7.452 (2.7); 7.448 (2.7); 7.253 (1.2); 7.228 (1.6); 7.206 (1.2); 6.270 (1.9); 6.265 (3.3); 6.260 (1.8); 5.408 (6.6); 3.341 (45.7); 3.168 (0.5); 2.676 (0.6); 2.672 (0.7); 2.667 (0.6); 2.525 (2.1); 2.511 (44.3); 2.507 (86.5); 2.503 (112.2); 2.498 (82.7); 2.334 (0.5); 2.329 (0.7); 2.325 (0.5); 1.730 (16.0); 1.259 (0.4); 1.233 (0.7); 0.008 (0.4); 0.000 (11.6); −0.008 (0.4) |
| I-1-285 | $^1$H-NMR, Solvent [D$_6$]-DMSO, spectrometer: 399.95 MHz: δ = 8.901 (2.5); 8.898 (2.5); 8.523 (4.1); 7.904 (2.2); 7.899 (2.3); 7.607 (1.0); 7.603 (1.0); 7.586 (1.3); 7.581 (1.3); 7.468 (2.6); 7.447 (2.0); 3.562 (16.0); 3.467 (0.6); 3.449 (0.7); 3.431 (0.8); 3.414 (0.6); 3.383 (0.8); 3.373 (0.8); 3.356 (0.8); 3.275 (0.4); 2.671 (0.4); 2.667 (0.3); 2.506 (51.2); 2.502 (66.7); 2.498 (50.0); 2.421 (11.0); 2.329 (0.5); 2.325 (0.4); 1.073 (0.4); 1.056 (0.7); 1.038 (0.4); 0.000 (31.5); −0.008 (1.3) |
| I-1-286 | $^1$H-NMR, Solvent [D$_6$]-DMSO, spectrometer: 399.95 MHz: δ = 8.919 (6.1); 8.917 (6.1); 8.640 (10.8); 7.598 (5.9); 7.590 (6.4); 7.564 (5.3); 7.542 (6.2); 7.287 (3.2); 7.280 (3.3); 7.265 (2.9); 7.258 (2.9); 4.149 (2.4); 4.132 (7.3); 4.115 (7.5); 4.097 (2.5); 3.602 (0.3); 3.550 (0.4); 3.450 (0.9); 3.432 (1.0); 3.414 (1.0); 3.386 (1.0); 3.368 (1.0); 2.672 (0.7); 2.503 (99.6); 2.330 (0.7); 1.381 (7.8); 1.363 (16.0); 1.346 (7.7); 0.146 (0.3); 0.000 (67.3); −0.150 (0.3) |
| I-1-287 | $^1$H-NMR, Solvent [D$_6$]-DMSO, spectrometer: 399.95 MHz: δ = 8.762 (4.0); 8.013 (4.8); 7.789 (4.3); 7.771 (4.0); 7.443 (4.1); 7.255 (1.9); 7.236 (2.1); 6.985 (2.8); 6.964 (2.4); 6.250 (3.9); 5.310 (0.7); 5.281 (9.2); 3.836 (0.6); 3.698 (15.1); 3.648 (0.6); 3.335 (19.4); 2.672 (1.1); 2.502 (141.3); 2.329 (0.9); 1.989 (0.4); 1.735 (16.0); 1.258 (0.5); 1.232 (1.0); 0.852 (0.4); 0.000 (41.7) |
| I-1-288 | $^1$H-NMR, Solvent [D$_6$]-DMSO, spectrometer: 399.95 MHz: δ = 8.723 (5.2); 8.720 (5.3); 8.320 (0.4); 8.009 (8.9); 7.812 (8.5); 7.806 (6.3); 7.455 (5.5); 7.451 (5.6); 7.135 (1.3); 7.115 (7.3); 7.110 (6.5); 7.090 (1.2); 7.086 (1.2); 6.267 (3.8); 6.262 (6.3); 6.257 (4.0); 5.327 (14.8); 4.038 (0.9); 4.020 (0.9); 4.002 (0.3); 3.333 (59.6); 2.671 (1.2); 2.507 (159.4); 2.502 (186.9); 2.498 (145.6); 2.329 (1.3); 1.989 (4.0); 1.725 (16.0); 1.298 (0.6); 1.259 (0.9); 1.232 (1.4); 1.193 (1.2); 1.175 (2.1); 1.157 (1.2); 0.873 (0.4); 0.854 (0.5); 0.835 (0.4); 0.808 (0.4); 0.000 (43.1) |
| I-1-289 | $^1$H-NMR, Solvent [D$_6$]-DMSO, spectrometer: 399.95 MHz: δ = 8.737 (11.2); 8.361 (5.1); 8.357 (5.8); 8.317 (0.4); 8.120 (2.3); 8.115 (2.5); 8.099 (3.1); 8.094 (3.2); 7.942 (4.9); 7.921 (4.1); 5.757 (4.7); 2.671 (0.8); 2.667 (0.5); 2.610 (14.7); 2.606 (16.0); 2.507 (137.9); 2.502 (190.3); 2.498 (150.9); 2.329 (1.7); 2.324 (1.4); 2.220 (0.4); 2.202 (0.3); 0.146 (0.9); 0.008 (6.7); 0.000 (229.4); −0.088 (0.4); −0.104 (0.3); −0.150 (1.3) |
| I-1-290 | $^1$H-NMR, Solvent [D$_6$]-DMSO, spectrometer: 399.95 MHz: δ = 8.751 (0.4); 8.718 (5.1); 7.992 (3.1); 7.986 (3.5); 7.686 (1.5); 7.681 (1.7); 7.666 (1.8); 7.660 (2.0); 7.528 (0.5); 7.457 (2.7); 7.436 (2.3); 3.462 (0.8); 3.448 (1.0); 3.431 (1.1); 3.364 (1.4); 2.671 (1.0); 2.611 (10.0); 2.607 (10.5); 2.582 (16.0); 2.556 (1.1); 2.502 (124.1); 2.417 (1.3); 2.329 (0.9); 1.055 (0.4); 0.146 (0.4); 0.000 (69.8); −0.150 (0.4) |
| I-1-291 | $^1$H-NMR, Solvent [D$_6$]-DMSO, spectrometer: 399.95 MHz: δ = 8.697 (6.9); 7.842 (3.9); 7.393 (1.7); 7.374 (2.3); 7.280 (3.5); 7.260 (2.5); 3.449 (2.0); 3.432 (0.4); 3.414 (0.4); 3.330 (3.9); 2.676 (0.5); 2.671 (0.6); 2.667 (0.5); 2.609 (10.2); 2.605 (10.6); 2.548 (16.9); 2.525 (2.1); 2.507 (66.3); 2.502 (87.5); 2.498 (67.2); 2.366 (16.0); 2.325 (0.9); 1.056 (0.5); 0.008 (2.6); 0.000 (62.9) |
| I-1-292 | $^1$H-NMR, Solvent [D$_6$]-DMSO, spectrometer: 399.95 MHz: δ = 8.935 (6.2); 8.626 (7.3); 8.374 (0.4); 8.037 (5.3); 8.032 (5.6); 7.905 (5.8); 7.899 (6.0); 7.878 (0.4); 7.873 (0.4); 7.842 (0.4); 7.837 (0.4); 7.645 (4.3); 7.625 (5.7); |

| Example | NMR data |
|---|---|
| | 7.605 (1.2); 7.513 (5.8); 7.509 (5.9); 7.491 (0.5); 7.486 (0.6); 7.477 (2.6); 7.472 (2.9); 7.457 (2.1); 7.452 (2.3); 6.993 (0.4); 6.974 (0.4); 6.315 (3.8); 6.309 (6.6); 6.304 (4.0); 6.293 (0.5); 5.493 (16.0); 5.422 (1.2); 3.467 (1.7); 3.450 (2.3); 3.432 (2.7); 3.359 (4.0); 3.187 (4.6); 3.169 (1.4); 3.100 (0.4); 3.055 (0.3); 2.676 (0.6); 2.672 (0.9); 2.668 (0.7); 2.507 (97.6); 2.503 (128.4); 2.499 (97.2); 2.334 (0.6); 2.330 (0.8); 2.325 (0.6); 1.074 (0.4); 1.056 (0.7); 1.039 (0.4); 0.146 (0.5); 0.008 (4.1); 0.000 (107.5); −0.008 (4.9); −0.150 (0.5) |
| I-1-293 | $^1$H-NMR, Solvent [D$_6$]-DMSO, spectrometer: 399.95 MHz: δ = 8.943 (6.6); 8.643 (8.4); 8.066 (5.5); 8.061 (5.7); 7.901 (5.8); 7.895 (5.9); 7.882 (0.6); 7.876 (0.7); 7.871 (0.4); 7.822 (5.0); 7.802 (5.8); 7.783 (0.5); 7.578 (0.6); 7.510 (5.8); 7.506 (5.8); 7.491 (0.5); 7.373 (2.8); 7.368 (2.9); 7.352 (2.6); 7.347 (2.7); 6.312 (4.1); 6.307 (6.8); 6.302 (4.1); 6.293 (0.7); 5.757 (1.0); 5.477 (16.0); 5.404 (1.0); 3.467 (1.2); 3.449 (1.5); 3.432 (1.8); 3.415 (1.8); 3.357 (2.3); 3.187 (3.1); 3.169 (1.6); 2.676 (0.7); 2.672 (0.9); 2.667 (0.7); 2.507 (109.9); 2.503 (140.1); 2.498 (106.4); 2.334 (0.7); 2.329 (0.9); 2.325 (0.7); 1.056 (0.6); 0.146 (0.6); 0.000 (14.3); −0.150 (0.6) |
| I-1-294 | $^1$H-NMR, Solvent [D$_6$]-DMSO, spectrometer: 399.95 MHz: δ = 8.810 (0.4); 8.783 (3.3); 8.024 (4.0); 7.951 (0.4); 7.796 (3.2); 7.791 (3.2); 7.773 (2.7); 7.769 (2.7); 7.445 (3.8); 7.441 (3.8); 7.264 (1.5); 7.259 (1.5); 7.243 (1.7); 7.237 (1.7); 6.992 (2.5); 6.971 (2.1); 6.255 (2.6); 6.250 (4.5); 6.245 (2.7); 5.311 (0.4); 5.283 (8.9); 3.835 (0.7); 3.700 (16.0); 3.649 (0.5); 3.332 (29.2); 3.242 (0.4); 2.676 (0.7); 2.671 (0.9); 2.667 (0.7); 2.525 (2.6); 2.511 (53.6); 2.507 (110.5); 2.502 (148.0); 2.498 (109.5); 2.493 (54.3); 2.333 (0.7); 2.329 (0.9); 2.325 (0.7); 1.989 (0.6); 1.755 (14.0); 1.233 (0.6); 0.146 (0.6); 0.008 (4.1); 0.000 (127.7); −0.009 (4.7); −0.150 (0.6) |
| I-1-295 | $^1$H-NMR, Solvent [D$_6$]-DMSO, spectrometer: 399.95 MHz: δ = 8.746 (7.0); 8.044 (12.0); 7.820 (6.0); 7.808 (6.0); 7.802 (6.1); 7.456 (5.8); 7.452 (6.1); 7.174 (1.8); 7.154 (7.0); 7.144 (5.1); 7.141 (4.9); 7.125 (1.2); 7.121 (1.3); 6.268 (4.2); 6.263 (7.2); 6.258 (4.4); 5.327 (16.0); 3.329 (124.2); 2.676 (0.7); 2.671 (0.9); 2.667 (0.7); 2.533 (24.8); 2.520 (4.0); 2.511 (49.2); 2.507 (100.5); 2.502 (133.9); 2.498 (100.4); 2.333 (0.6); 2.329 (0.8); 2.325 (0.6); 1.336 (0.4); 1.299 (1.1); 1.259 (1.4); 1.250 (0.6); 1.235 (0.6); 0.146 (0.6); 0.008 (4.1); 0.000 (120.8); −0.008 (4.5); −0.150 (0.6) |
| I-1-296 | $^1$H-NMR, Solvent [D$_6$]-DMSO, spectrometer: 399.95 MHz: δ = 8.429 (11.7); 8.348 (5.0); 8.343 (5.2); 8.160 (16.0); 8.119 (2.3); 8.114 (2.4); 8.098 (2.9); 8.093 (2.9); 7.942 (4.6); 7.921 (3.7); 5.758 (1.6); 2.677 (0.4); 2.672 (0.5); 2.668 (0.4); 2.557 (48.0); 2.526 (1.5); 2.512 (35.7); 2.508 (71.5); 2.503 (94.1); 2.499 (70.6); 2.495 (36.3); 2.378 (0.5); 2.335 (0.6); 2.330 (0.7); 2.326 (0.6); 1.057 (0.4); 0.008 (0.5); 0.000 (14.4); −0.008 (0.7) |
| I-1-297 | $^1$H-NMR, Solvent [D$_6$]-DMSO, spectrometer: 399.95 MHz: δ = 8.439 (10.6); 8.159 (16.0); 8.088 (7.3); 8.081 (7.4); 7.818 (2.9); 7.812 (2.8); 7.797 (4.2); 7.790 (4.2); 7.716 (7.8); 7.694 (5.1); 4.208 (0.4); 4.169 (0.4); 4.144 (0.4); 4.130 (0.4); 4.092 (0.5); 4.069 (0.5); 4.052 (0.5); 4.014 (0.5); 3.988 (0.6); 3.960 (0.6); 3.938 (0.6); 3.923 (0.6); 3.917 (0.6); 3.900 (0.7); 3.863 (0.7); 3.855 (0.8); 3.812 (0.7); 3.788 (0.8); 3.777 (0.8); 3.771 (0.8); 3.760 (0.8); 3.756 (0.7); 3.745 (0.8); 3.735 (0.8); 3.721 (0.7); 3.716 (0.7); 3.711 (0.7); 3.690 (0.7); 3.684 (0.7); 3.679 (0.7); 3.639 (0.7); 3.606 (0.6); 3.566 (0.5); 3.505 (0.5); 3.476 (0.4); 3.468 (0.4); 3.449 (0.5); 3.432 (0.4); 3.413 (0.4); 3.391 (0.3); 3.282 (0.5); 3.187 (0.7); 2.780 (0.4); 2.731 (0.4); 2.676 (0.8); 2.672 (1.1); 2.667 (0.8); 2.556 (49.6); 2.511 (60.5); 2.507 (115.1); 2.503 (147.9); 2.498 (110.0); 2.376 (0.3); 2.334 (0.7); 2.329 (1.0); 2.325 (0.7); 0.008 (0.9); 0.000 (20.5); −0.008 (1.0) |
| I-1-298 | $^1$H-NMR, Solvent [D$_6$]-DMSO, spectrometer: 399.95 MHz: δ = 8.450 (10.2); 8.165 (3.8); 8.157 (16.0); 8.145 (4.0); 8.141 (4.0); 7.726 (0.9); 7.723 (1.0); 7.705 (2.8); 7.703 (2.8); 7.689 (3.1); 7.685 (3.3); 7.668 (4.3); 7.665 (5.9); 7.648 (2.4); 7.645 (2.1); 7.634 (2.8); 7.630 (2.5); 7.613 (3.6); 7.611 (3.5); 7.596 (1.6); 7.593 (1.6); 5.757 (2.4); 3.685 (0.4); 3.467 (1.1); 3.449 (1.2); 3.432 (1.3); 3.414 (1.3); 3.397 (1.3); 3.389 (1.3); 3.379 (1.2); 3.187 (0.7); 3.149 (0.5); 3.077 (0.3); 2.676 (0.7); 2.671 (0.9); 2.667 (0.7); 2.553 (47.2); 2.525 (2.2); 2.507 (108.7); 2.502 (143.5); 2.498 (108.5); 2.374 (0.5); 2.334 (0.8); 2.329 (1.1); 2.325 (0.8); 0.008 (0.7); 0.000 (19.8); −0.008 (1.0) |
| I-1-299 | $^1$H-NMR, Solvent [D$_6$]-DMSO, spectrometer: 399.95 MHz: δ = 8.452 (4.9); 8.159 (5.8); 7.605 (2.9); 7.597 (3.0); 7.574 (2.5); 7.552 (2.9); 7.297 (1.6); 7.289 (1.5); 7.275 (1.4); 7.267 (1.3); 3.855 (16.0); 3.450 (0.4); 3.432 (0.4); 2.554 (18.2); 2.507 (31.9); 2.503 (40.0); 2.499 (31.3); 1.056 (0.6); 0.000 (4.7) |
| I-1-300 | $^1$H-NMR, Solvent [D$_6$]-DMSO, spectrometer: 399.95 MHz: δ = 8.434 (8.4); 8.161 (16.0); 7.915 (0.4); 7.668 (4.2); 7.663 (5.6); 7.646 (13.6); 7.628 (0.4); 7.626 (0.5); 7.609 (5.2); 7.593 (3.1); 7.586 (2.6); 7.570 (1.6); 5.757 (3.9); 3.969 (0.3); 3.496 (2.7); 3.187 (0.6); 3.131 (0.4); 2.676 (0.9); 2.671 (1.3); 2.667 (0.9); 2.555 (51.5); 2.525 (2.3); 2.511 (76.1); 2.507 (154.7); 2.502 (205.7); 2.498 (154.2); 2.494 (79.1); 2.375 (0.6); 2.333 (1.2); 2.329 (1.6); 2.325 (1.2); 0.008 (0.8); 0.000 (29.6); −0.008 (1.3) |
| I-1-301 | $^1$H-NMR, Solvent [D$_6$]-DMSO, spectrometer: 399.95 MHz: δ = 8.912 (2.6); 8.908 (2.6); 8.618 (5.3); 8.600 (3.1); 8.594 (3.1); 8.270 (1.5); 8.265 (1.5); 8.250 (1.7); 8.244 (1.6); 7.860 (3.0); 7.839 (2.8); 3.467 (0.8); 3.449 (2.3); 3.432 (2.3); 3.414 (0.9); 2.663 (16.0); 2.629 (0.4); 2.525 (0.6); 2.511 (17.5); 2.507 (35.5); 2.503 (47.3); 2.498 (35.9); 2.494 (18.6); 2.329 (0.3); 1.073 (2.2); 1.056 (4.3); 1.038 (2.1) |

| Example | NMR data |
|---|---|
| I-1-302 | $^1$H-NMR, Solvent [D$_6$]-DMSO, spectrometer: 399.95 MHz: δ = 8.739 (5.2); 8.600 (3.0); 8.595 (3.1); 8.456 (0.4); 8.266 (1.5); 8.261 (1.5); 8.245 (1.6); 8.240 (1.6); 7.855 (3.0); 7.834 (2.8); 7.789 (0.5); 3.449 (0.8); 3.431 (0.8); 3.414 (0.3); 2.662 (16.0); 2.628 (1.9); 2.613 (6.7); 2.609 (6.9); 2.506 (42.5); 2.502 (55.3); 2.498 (42.4); 2.440 (0.4); 2.436 (0.4); 2.329 (0.4); 1.073 (0.7); 1.056 (1.3); 1.038 (0.6) |
| I-1-303 | $^1$H-NMR, Solvent [D$_6$]-DMSO, spectrometer: 399.95 MHz: δ = 8.439 (15.1); 8.162 (16.0); 7.988 (1.3); 7.806 (0.8); 7.790 (1.8); 7.785 (1.9); 7.769 (3.3); 7.754 (1.9); 7.748 (2.0); 7.732 (0.9); 7.669 (0.4); 7.338 (5.7); 7.315 (9.1); 7.292 (5.5); 7.266 (1.0); 7.244 (0.5); 5.757 (1.1); 3.467 (0.5); 3.449 (1.0); 3.432 (0.9); 3.415 (0.4); 3.279 (0.4); 3.186 (0.4); 2.672 (1.1); 2.559 (49.1); 2.503 (172.5); 2.380 (0.5); 2.329 (1.3); 1.073 (0.7); 1.055 (1.4); 1.038 (0.7); 0.000 (5.9) |
| I-1-304 | $^1$H-NMR, Solvent [D$_6$]-DMSO, spectrometer: 399.95 MHz: δ = 8.361 (16.0); 8.125 (16.0); 8.010 (1.4); 8.003 (10.0); 7.998 (3.5); 7.986 (3.7); 7.981 (11.8); 7.975 (1.5); 7.737 (1.7); 7.731 (11.7); 7.726 (3.8); 7.714 (3.4); 7.709 (9.9); 7.702 (1.2); 5.758 (0.8); 3.593 (0.3); 3.589 (0.3); 3.576 (0.4); 3.524 (0.5); 3.450 (0.7); 3.433 (0.7); 3.411 (0.7); 3.392 (0.7); 3.374 (0.7); 3.357 (0.7); 3.352 (0.7); 3.344 (0.7); 3.291 (0.6); 3.274 (0.5); 3.202 (0.4); 3.187 (0.4); 2.677 (0.5); 2.672 (0.6); 2.668 (0.5); 2.553 (47.2); 2.525 (1.8); 2.512 (31.5); 2.508 (61.1); 2.503 (79.6); 2.499 (59.0); 2.494 (29.4); 2.335 (0.4); 2.330 (0.5); 2.326 (0.4); 0.000 (0.6) |
| I-1-305 | $^1$H-NMR, Solvent [D$_6$]-DMSO, spectrometer: 399.95 MHz: δ = 8.899 (5.3); 8.896 (5.3); 8.559 (9.0); 7.854 (5.5); 7.486 (2.3); 7.470 (3.1); 7.466 (3.2); 7.368 (5.0); 7.349 (3.7); 3.429 (0.4); 3.332 (9.7); 3.031 (1.9); 3.012 (5.7); 2.993 (5.9); 2.975 (2.0); 2.707 (1.9); 2.688 (5.9); 2.669 (6.7); 2.650 (2.2); 2.507 (98.1); 2.502 (124.6); 2.498 (98.1); 2.329 (0.8); 1.221 (7.7); 1.203 (16.0); 1.184 (7.6); 1.151 (6.8); 1.133 (14.3); 1.114 (6.7); 0.146 (0.3); 0.000 (73.0); −0.150 (0.4) |
| I-1-306 | $^1$H-NMR, Solvent [D$_6$]-DMSO, spectrometer: 399.95 MHz: δ = 8.901 (2.7); 8.898 (2.9); 8.816 (0.3); 8.561 (5.3); 8.464 (0.7); 7.888 (2.8); 7.884 (3.0); 7.479 (1.3); 7.475 (1.4); 7.460 (1.6); 7.456 (1.6); 7.321 (2.4); 7.301 (1.8); 3.825 (1.9); 3.467 (0.6); 3.449 (1.7); 3.432 (1.8); 3.414 (0.8); 3.331 (5.1); 3.011 (0.4); 2.994 (1.0); 2.976 (1.3); 2.959 (1.0); 2.942 (0.4); 2.672 (0.4); 2.560 (12.6); 2.535 (0.4); 2.507 (48.0); 2.503 (62.4); 2.498 (48.6); 2.369 (0.4); 2.334 (0.4); 2.329 (0.4); 2.325 (0.4); 1.230 (16.0); 1.213 (16.0); 1.073 (2.0); 1.056 (3.9); 1.038 (1.9); 0.000 (38.8) |
| I-1-307 | $^1$H-NMR, Solvent [D$_6$]-DMSO, spectrometer: 399.95 MHz: δ = 8.898 (3.5); 8.895 (3.4); 8.545 (6.6); 7.926 (2.7); 7.904 (3.1); 7.567 (2.9); 7.546 (2.6); 5.757 (4.3); 3.467 (0.6); 3.449 (1.1); 3.432 (1.3); 3.414 (1.1); 3.338 (5.6); 2.676 (0.5); 2.672 (0.7); 2.667 (0.5); 2.576 (15.6); 2.559 (1.9); 2.511 (42.5); 2.507 (84.2); 2.503 (109.0); 2.498 (78.8); 2.494 (38.7); 2.380 (0.7); 2.371 (0.7); 2.348 (16.0); 2.334 (0.9); 2.329 (0.9); 2.325 (0.7); 2.311 (0.8); 2.209 (0.6); 1.234 (0.5); 1.073 (0.8); 1.056 (1.5); 1.038 (0.8); 0.146 (0.4); 0.008 (3.2); 0.000 (82.0); −0.009 (3.0); −0.149 (0.4) |
| I-1-308 | $^1$H-NMR, Solvent [D$_6$]-DMSO, spectrometer: 399.95 MHz: δ = 8.920 (2.5); 8.916 (2.4); 8.633 (4.6); 7.909 (2.5); 7.905 (2.4); 7.605 (0.5); 7.584 (4.4); 7.577 (2.6); 7.560 (0.4); 7.555 (0.4); 3.449 (0.5); 3.432 (0.5); 3.414 (0.5); 3.385 (0.5); 3.367 (0.5); 3.311 (0.4); 2.672 (0.4); 2.565 (16.0); 2.507 (41.5); 2.503 (51.7); 2.498 (37.8); 2.330 (0.3); 0.008 (2.1); 0.000 (35.2); −0.008 (1.6) |
| I-1-309 | $^1$H-NMR, Solvent [D$_6$]-DMSO, spectrometer: 399.95 MHz: δ = 8.901 (5.2); 8.898 (5.3); 8.560 (10.8); 7.987 (5.7); 7.981 (5.9); 7.733 (2.7); 7.727 (2.6); 7.712 (3.3); 7.706 (3.2); 7.514 (5.3); 7.493 (4.4); 3.542 (0.5); 3.449 (1.1); 3.432 (1.2); 3.376 (1.5); 3.366 (1.5); 3.236 (0.7); 3.055 (2.0); 3.037 (6.1); 3.018 (6.3); 3.000 (2.1); 2.677 (0.5); 2.673 (0.6); 2.668 (0.5); 2.526 (1.6); 2.512 (33.2); 2.508 (64.6); 2.504 (83.0); 2.499 (60.8); 2.335 (0.4); 2.330 (0.6); 2.326 (0.4); 2.209 (0.3); 1.202 (0.3); 1.156 (7.3); 1.138 (16.0); 1.119 (7.2); 0.008 (2.3); 0.000 (60.0); −0.008 (2.4) |
| I-1-310 | $^1$H-NMR, Solvent [D$_6$]-DMSO, spectrometer: 399.95 MHz: δ = 8.918 (2.7); 8.915 (7.1); 8.911 (7.0); 8.611 (16.0); 8.530 (8.3); 8.525 (8.6); 8.215 (4.6); 8.210 (4.5); 8.194 (5.3); 8.189 (5.2); 7.934 (9.0); 7.913 (7.9); 4.370 (0.3); 4.301 (0.4); 4.283 (0.5); 4.266 (0.5); 4.246 (0.5); 4.234 (0.5); 4.003 (0.8); 3.921 (0.8); 3.914 (0.8); 3.900 (0.8); 3.880 (0.8); 3.852 (0.8); 3.810 (0.8); 3.676 (0.6); 3.467 (0.7); 3.450 (1.5); 3.432 (1.5); 3.415 (0.7); 2.677 (0.4); 2.673 (0.6); 2.669 (0.5); 2.526 (1.3); 2.513 (34.1); 2.508 (70.6); 2.504 (93.9); 2.499 (68.6); 2.495 (33.9); 2.455 (0.4); 2.335 (0.5); 2.331 (0.7); 2.326 (0.5); 1.074 (1.2); 1.056 (2.4); 1.039 (1.2); 0.008 (2.2); 0.000 (73.0); −0.009 (2.7); −0.150 (0.3) |
| I-1-311 | $^1$H-NMR, Solvent [D$_6$]-DMSO, spectrometer: 399.95 MHz: δ = 8.775 (1.1); 7.812 (1.3); 7.414 (0.6); 3.333 (107.4); 2.676 (0.8); 2.671 (1.1); 2.667 (0.8); 2.662 (0.4); 2.525 (2.7); 2.511 (58.8); 2.507 (118.9); 2.502 (157.1); 2.498 (115.5); 2.493 (57.2); 2.333 (0.8); 2.329 (1.0); 2.325 (0.8); 2.225 (16.0); 1.989 (1.0); 1.398 (1.9); 1.351 (0.4); 1.259 (0.5); 1.249 (0.4); 1.235 (1.3); 1.175 (0.6); 0.146 (0.6); 0.008 (4.5); 0.000 (134.3); −0.009 (5.4); −0.150 (0.6) |
| I-1-312 | $^1$H-NMR, Solvent [D$_6$]-DMSO, spectrometer: 399.95 MHz: δ = 8.924 (8.8); 8.920 (8.9); 8.635 (16.0); 8.238 (9.3); 8.233 (9.8); 7.842 (2.0); 7.837 (1.6); 7.821 (8.5); 7.816 (9.5); 7.808 (14.9); 7.787 (3.1); 5.759 (7.5); 4.021 (0.4); 3.994 (0.4); 3.948 (0.4); 3.881 (0.5); 3.807 (0.5); 3.713 (0.5); 3.699 (0.6); 3.656 (0.6); 3.634 (0.6); 3.564 (0.5); 3.519 (0.5); 3.507 (0.5); 3.467 (0.5); 3.450 (0.5); 3.432 (0.5); 3.416 (0.5); 3.400 (0.4); 3.312 (0.3); 2.677 (0.7); 2.673 (0.9); 2.669 (0.7); 2.508 (95.7); 2.504 (124.8); 2.499 (93.5); 2.335 (0.7); 2.330 (0.9); 2.326 (0.7); 0.146 (0.5); 0.008 (4.5); 0.000 (118.2); −0.008 (5.5); −0.150 (0.6) |
| I-1-313 | $^1$H-NMR, Solvent [D$_6$]-DMSO, spectrometer: 399.95 MHz: δ = 8.936 (4.6); 8.932 (4.5); 8.619 (8.2); 7.840 (5.4); 7.833 (6.1); 7.729 (2.6); 7.722 (2.4); 7.706 (2.9); 7.700 (2.7); 7.283 (4.6); 7.260 (4.2); 4.066 (3.7); 4.050 (7.9); |

| Example | NMR data |
|---|---|
| | 4.034 (3.8); 3.336 (9.3); 2.676 (0.5); 2.672 (0.7); 2.667 (0.5); 2.525 (1.6); 2.512 (36.5); 2.507 (74.3); 2.503 (98.0); 2.498 (71.6); 2.494 (35.3); 2.334 (0.5); 2.330 (0.6); 2.325 (0.5); 1.745 (0.5); 1.727 (2.0); 1.711 (4.0); 1.693 (4.2); 1.676 (2.1); 1.658 (0.5); 0.917 (7.6); 0.898 (16.0); 0.880 (7.1); 0.146 (0.4); 0.008 (3.3); 0.000 (96.1); −0.009 (3.7); −0.150 (0.4) |
| I-1-314 | $^1$H-NMR, Solvent [D$_6$]-DMSO, spectrometer: 399.95 MHz: <br> δ = 8.936 (3.7); 8.932 (3.7); 8.624 (9.0); 7.861 (3.1); 7.857 (3.3); 7.588 (1.5); 7.583 (1.5); 7.567 (1.8); 7.562 (1.7); 7.424 (2.0); 7.312 (2.8); 7.291 (2.4); 7.242 (4.3); 7.059 (2.1); 3.450 (0.4); 3.433 (0.5); 3.415 (0.5); 3.357 (0.7); 2.526 (0.7); 2.513 (13.4); 2.508 (26.7); 2.504 (34.9); 2.499 (25.6); 2.495 (12.7); 2.401 (16.0); 2.354 (0.6); 0.008 (1.6); 0.000 (39.5); −0.009 (1.6) |
| I-1-315 | $^1$H-NMR, Solvent [D$_6$]-DMSO, spectrometer: 399.95 MHz: <br> δ = 8.912 (0.4); 8.726 (11.6); 8.520 (6.1); 8.515 (6.8); 8.317 (0.4); 8.199 (3.4); 8.194 (3.6); 8.178 (4.0); 8.173 (4.2); 7.919 (7.2); 7.898 (6.3); 3.431 (0.3); 2.671 (1.0); 2.666 (0.9); 2.616 (14.8); 2.611 (16.0); 2.507 (122.5); 2.502 (167.7); 2.498 (133.7); 2.440 (1.9); 2.436 (1.8); 2.333 (1.3); 2.329 (1.6); 2.325 (1.3); 2.297 (0.5); 1.056 (0.6); 1.038 (0.3); 0.146 (0.7); 0.008 (4.2); 0.000 (180.0); −0.150 (1.0) |
| I-1-316 | $^1$H-NMR, Solvent [D$_6$]-DMSO, spectrometer: 399.95 MHz: <br> δ = 8.751 (4.5); 7.910 (3.7); 7.660 (0.4); 7.599 (0.7); 7.578 (6.6); 7.555 (0.7); 3.521 (0.5); 3.467 (0.8); 3.449 (1.3); 3.432 (1.3); 3.414 (0.9); 3.341 (0.6); 3.279 (0.5); 3.205 (0.4); 3.188 (0.4); 3.173 (0.3); 2.670 (1.2); 2.615 (9.3); 2.564 (16.0); 2.502 (91.6); 2.441 (0.9); 2.329 (0.6); 1.073 (0.6); 1.056 (1.2); 1.038 (0.6); 0.000 (55.5) |
| I-1-317 | $^1$H-NMR, Solvent [D$_6$]-DMSO, spectrometer: 399.95 MHz: <br> δ = 2.62 (s, 3H); 7.48-7.56 (2 m, 2H); 8.12 (d, 1H); 8.21 (s, 1H) ppm |
| I-1-318 | $^1$H-NMR, Solvent [D$_6$]-DMSO, spectrometer: 399.95 MHz: <br> δ = 2.32 (s, 3H); 2.62 (s, 3H); 7.07 (br. d, 1H); 7.13 (t, 1H, J = 76.4 Hz); 7.29 (br. d, 1H); 7.71 (br. s, 1H); 8.26 (br. s, 1H) ppm |
| I-1-319 | $^1$H-NMR, Solvent [D$_6$]-DMSO, spectrometer: 399.95 MHz: <br> δ = 1.34 (t, 3H); 2.62 (br. s, 1H); 4.04 (q, 2H); 6.97 (br. d, 1H); 7.30 (br. d, 1H); 7.53 (d, 1H); 8.23 (br. s, 1H) ppm |
| I-1-320 | $^1$H-NMR, Solvent [D$_6$]-DMSO, spectrometer: 399.95 MHz: <br> δ = 1.13 (t, 3H); 2.61 (s, 3H); 3.00 (q, 2H); 7.49 (d, 1H); 7.718br. d, 1H); 7.98 (d, 1H); 8.70 (s, 1H) ppm |
| I-1-321 | $^1$H-NMR, Solvent [D$_6$]-DMSO, spectrometer: 399.95 MHz: <br> δ = 1.06 (d, 6H); 1.21 (d, 6H); 2.89 (m, 1H); 4.16 (m, 1H); 7.27 (br. s, 1H); 7.75 (br. s, 1H); 7.99 (br. s, 1H) 8.74 (br. s, 1H) ppm |
| I-1-322 | $^1$H-NMR, Solvent [D$_6$]-DMSO, spectrometer: 399.95 MHz: <br> δ = 3.36 (s, 3H); 7.97/d, 1H); 8.23 (br. d, 1H); 8.56 (d, 1H); 8.58 (s, 1H); 8.90 (s, 1H) ppm |
| I-1-323 | $^1$H-NMR, Solvent [D$_6$]-DMSO, spectrometer: 399.95 MHz: <br> δ = 3.85 (s, 3H); 7.17 (t, 1H); 7.22 (d, 1H); 7.69 (t, 1H); 7.90 (d, 1H); 8.64 (s, 1H); 8.92 (s, 1H) ppm |
| I-1-324 | $^1$H-NMR, Solvent [D$_6$]-DMSO, spectrometer: 399.95 MHz: <br> δ = 7.1-7.2 (br.); 7.2-7.27 (br.); 7.30-7.65 (Br.); 7.7-7.9 (Br.); 8.05-8.15 (m); 8.75-8.9 (Br.) ppm |
| I-1-325 | $^1$H-NMR, Solvent [D$_6$]-DMSO, spectrometer: 399.95 MHz: <br> δ = 2.67 (s, 3H); 7.18 (m, 1H); 7.51 (m, 1H); 8.00 (s, 1H); 8.11 (br. s, 1H); 8.75 (s, 1H) ppm |
| I-1-326 | $^1$H-NMR, Solvent [D$_6$]-DMSO, spectrometer: 399.95 MHz: <br> δ = 1.20 (t, 3H); 2.56 (s, 3H); 2.68 (q, 2H); 7.30 (d, 1H); 7.43 (dd, 1H); 7.86 (d, 1H); 8.60 (s, 1H); 8.90 (s, 1H) ppm |
| I-1-327 | $^1$H-NMR, Solvent [D$_6$]-DMSO, spectrometer: 399.95 MHz: <br> δ = 7.46 (br. t, 1H); 7.52 (br. d, 1H); 7.68-7.74 (m, 1H); 8.63 (s, 1H); 8.92 (s, 1H) ppm |
| I-1-328 | $^1$H-NMR, Solvent [D$_6$]-DMSO, spectrometer: 399.95 MHz: <br> δ = 1.24 (d, 6H); 3.68 (m, 1H); 7.39 (d, 1H); 7.52 (t, 1H); 7.57 (d, 1H); 8.64 (s, 1H); 8.92 (s, 1H) ppm |
| I-1-329 | $^1$H-NMR, Solvent [D$_6$]-DMSO, spectrometer: 399.95 MHz: <br> δ = 2.75 (s, 3H); 7.42 (dd, 1H); 7.48-7.54 (m, 2H); 8.63 (s, 1H); 8.92 (s, 1H) ppm |
| I-1-330 | $^1$H-NMR, Solvent [D$_6$]-DMSO, spectrometer: 399.95 MHz: <br> δ = 2.47 (s, 3H); 7.37 (d, 1H); 7.42 (d, 1H); 7.54 (t, 1H); 8.63 (s, 1H); 8.92 (s, 1H) ppm |
| I-1-331 | $^1$H-NMR, Solvent [D$_6$]-DMSO, spectrometer: 399.95 MHz: <br> δ = 1.19 (d, 6H); 4.75 (m, 1H); 7.17 (d, 1H); 7.23 (d, 1H); 7.53 (t, 1H); 8.63 (s, 1H); 8.94 (s, 1H) ppm |
| I-1-332 | $^1$H-NMR, Solvent [D$_6$]-DMSO, spectrometer: 399.95 MHz: <br> δ = 1.26 (t, 3H); 2.97 (q, 2H); 7.37 (d, 1H); 7.45-7.54 (m, 2H); 8.63 (s, 1H); 8.92 (s. 1H) ppm |

TABLE 3

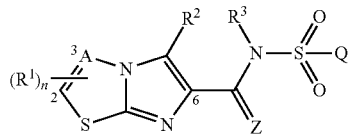

(I-2)

Z = O, R² and R³ are H and Q = substituted hetaryl

| Example | R¹ | n | A | Q | Remarks |
|---|---|---|---|---|---|
| I-2-1 | 2-CF₃ | 1 | CH | 3-Me, 1-Et pyrazol-4-yl | NMR |
| I-2-2 | 2-CF₃ | 1 | CH | 4-Me-thien-2-yl | NMR |
| I-2-3 | 2-CF₃ | 1 | CH | 2-Cl-pyridin-3-yl | NMR |
| I-2-4 | 2-CF₃ | 1 | CH | 3-Cl, 1-Et pyrazol-4-yl | |
| I-2-5 | 2-CF₃ | 1 | CH | 2,6-diCl-pyridin-3-yl | |
| I-2-6 | 2-CF₃ | 1 | CH | 2-Cl-4-CH₃-pyridin-3-yl | |
| I-2-7 | 2-CF₃ | 1 | CH | 2,5-diCl-pyridin-3-yl | |
| I-2-8 | 2-CF₃ | 1 | CH | 2-Cl-5-CH₃-pyridin-3-yl | |

TABLE 3-continued

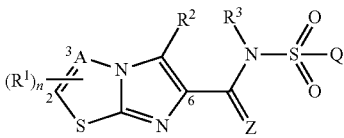

(I-2)

Z = O, R² and R³ are H and Q = substituted hetaryl

| Example | R¹ | n | A | Q | Remarks |
|---|---|---|---|---|---|
| I-2-9 | 2-CF₃ | 1 | CH | 2-Cl-5-OMe-pyridin-3-yl | |
| I-2-10 | 2-CF₃ | 1 | CH | 3,4-diCl-pyridazin-? | |
| I-2-11 | 2-CF₃ | 1 | CH | 2-Cl-5-CH₃-pyridin-3-yl | |
| I-2-12 | 2-CF₃ | 1 | CH | 2,5-diCl-thien-3-yl | |
| I-2-13 | 2-CF₃ | 1 | CH | 2-Cl-thien-3-yl | |
| I-2-14 | 2-C₄H₉-t | 1 | CH | 3-Me, 1-Et pyrazol-4-yl | |
| I-2-15 | 2-C₄H₉-t | 1 | CH | 4-Me-thien-2-yl | |
| I-2-16 | 2-C₄H₉-t | 1 | CH | 2-Cl-pyridin-3-yl | |
| I-2-17 | 2-C₄H₉-t | 1 | CH | 3-Cl, 1-Et pyrazol-4-yl | |

TABLE 3-continued

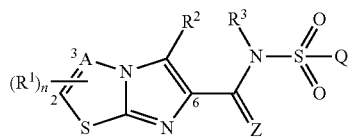

(I-2)

Z = O, R² and R³ are H and Q = substituted hetaryl

| Example | R¹ | n | A | Q | Remarks |
|---|---|---|---|---|---|
| I-2-18 | 2-C₄H₉-t | 1 | CH | 2,6-dichloropyridin-3-yl | |
| I-2-19 | 2-C₄H₉-t | 1 | CH | 2-chloro-4-methylpyridin-3-yl | |
| I-2-20 | 2-C₄H₉-t | 1 | CH | 2,5-dichloropyridin-3-yl | |
| I-2-21 | 2-C₄H₉-t | 1 | CH | 2-chloro-5-methylpyridin-3-yl | |
| I-2-22 | 2-C₄H₉-t | 1 | CH | 2-chloro-5-methoxypyridin-3-yl | |
| I-2-23 | 2-C₄H₉-t | 1 | CH | 2,4-dichloropyridin-3-yl | |
| I-2-24 | 2-C₄H₉-t | 1 | CH | 2-chloro-5-methylpyridin-3-yl | |
| I-2-25 | 2-C₄H₉-t | 1 | CH | 2-chloro-5-chlorothiophen-3-yl | |

TABLE 3-continued

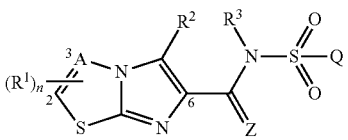

(I-2)

Z = O, R² and R³ are H and Q = substituted hetaryl

| Example | R¹ | n | A | Q | Remarks |
|---|---|---|---|---|---|
| I-2-26 | 2-C₄H₉-t | 1 | CH | 2-chlorothiophen-3-yl | |
| I-2-27 | 2-Cl | 1 | CH | 3-methyl-1-ethylpyrazol-4-yl | |
| I-2-28 | 2-Cl | 1 | CH | 4-methylthiophen-3-yl | |
| I-2-29 | 2-Cl | 1 | CH | 2-chloropyridin-3-yl | |
| I-2-30 | 2-Cl | 1 | CH | 3-chloro-1-ethylpyrazol-4-yl | |
| I-2-31 | 2-Cl | 1 | CH | 2,6-dichloropyridin-3-yl | |
| I-2-32 | 2-Cl | 1 | CH | 2-chloro-4-methylpyridin-3-yl | |
| I-2-33 | 2-Cl | 1 | CH | 2,5-dichloropyridin-3-yl | |
| I-2-34 | 2-Cl | 1 | CH | 2-chloro-5-methylpyridin-3-yl | |

TABLE 3-continued (I-2)

Z = O, R² and R³ are H and Q = substituted hetaryl

| Example | R¹ | n | A | Q | Remarks |
|---|---|---|---|---|---|
| I-2-35 | 2-Cl | 1 | CH | 2-Cl-5-OMe-pyridin-3-yl | |
| I-2-36 | 2-Cl | 1 | CH | 3,4-diCl-pyridazin-? | |
| I-2-37 | 2-Cl | 1 | CH | 2-Cl-5-CH₃-pyridin-3-yl | |
| I-2-38 | 2-Cl | 1 | CH | 2,5-diCl-thiophen-3-yl | |
| I-2-39 | 2-Cl | 1 | CH | 2-Cl-thiophen-3-yl | |
| I-2-40 | 2-Br | 1 | CH | 3-Me-1-Et-pyrazol-4-yl | |
| I-2-41 | 2-Br | 1 | CH | 4-Me-thiophen-2-yl | |
| I-2-42 | 2-Br | 1 | CH | 2-Cl-pyridin-3-yl | |
| I-2-43 | 2-Br | 1 | CH | 3-Cl-1-Et-pyrazol-4-yl | |
| I-2-44 | 2-Br | 1 | CH | 2,6-diCl-pyridin-3-yl | |
| I-2-45 | 2-Br | 1 | CH | 2-Cl-4-CH₃-pyridin-3-yl | |
| I-2-46 | 2-Br | 1 | CH | 2,5-diCl-pyridin-3-yl | |
| I-2-47 | 2-Br | 1 | CH | 2-Cl-5-CH₃-pyridin-3-yl | |
| I-2-48 | 2-Br | 1 | CH | 2-Cl-5-OMe-pyridin-3-yl | |
| I-2-49 | 2-Br | 1 | CH | 2,4-diCl-pyridin-3-yl | |
| I-2-50 | 2-Br | 1 | CH | 2-Cl-5-CH₃-pyridin-3-yl | |
| I-2-51 | 2-Br | 1 | CH | 2,5-diCl-thiophen-3-yl | |

TABLE 3-continued

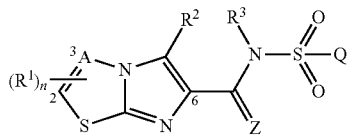
(I-2)

Z = O, R² and R³ are H and Q = substituted hetaryl

| Example | R¹ | n | A | Q | Remarks |
|---|---|---|---|---|---|
| I-2-52 | 2-Br | 1 | CH | 3-(2-Cl)thienyl | |
| I-2-53 | 3-CF$_3$ | 1 | CH | 3-Me-1-Et-pyrazol-4-yl | |
| I-2-54 | 3-CF$_3$ | 1 | CH | 4-Me-thien-2-yl | |
| I-2-55 | 3-CF$_3$ | 1 | CH | 2-Cl-pyridin-3-yl | |
| I-2-56 | 3-CF$_3$ | 1 | C—R¹ | 3-Cl-1-Et-pyrazol-4-yl | |
| I-2-57 | 3-CF$_3$ | 1 | C—R¹ | 2-Cl-5-OMe-pyridin-3-yl | |
| I-2-58 | 3-CF$_3$ | 1 | C—R¹ | 2,4-diCl-pyridin-3-yl | |
| I-2-59 | 3-CF$_3$ | 1 | C—R¹ | 2-Cl-5-CH$_3$-pyridin-3-yl | |
| I-2-60 | 3-CF$_3$ | 1 | C—R¹ | 5-Cl-thien-2-yl | |

TABLE 3-continued

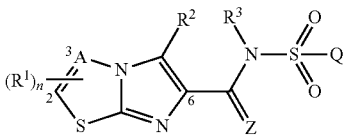
(I-2)

Z = O, R² and R³ are H and Q = substituted hetaryl

| Example | R¹ | n | A | Q | Remarks |
|---|---|---|---|---|---|
| I-2-61 | 2-CF$_3$ | 1 | N | 4-Me-thien-2-yl | |
| I-2-62 | 2-CF$_3$ | 1 | N | 3-Me-1-Et-pyrazol-4-yl | |
| I-2-63 | 2-C$_2$F$_3$ | 1 | CH | 2-Cl-pyridin-3-yl | NMR |
| I-2-64 | 2-C$_2$F$_5$ | 1 | CH | 3-Br-5-Cl-thien-2-yl | NMR |
| I-2-65 | 2-C$_2$F$_5$ | 1 | CH | 4-Me-thien-2-yl | NMR |
| I-2-66 | 2-C$_2$F$_5$ | 1 | CH | 3-Me-1-Et-pyrazol-4-yl | NMR |
| I-2-67 | 2-CF$_3$ | 1 | CH | 3-Br-5-Cl-thien-2-yl | NMR |

| Example | NMR data |
|---|---|
| I-2-1 | ¹H-NMR, Solvent [D$_6$]-DMSO, spectrometer: 399.95 MHz: δ = 8.905(2.6); 8.902(2.6); 8.559(6.6); 8.379(4.9); 5.757(0.7); 4.140(1.1); 4.121(3.6); 4.103(3.7); 4.085(1.2); 3.331(11.1); 3.187(0.4); 2.671(0.4); 2.525(1.0); 2.511(24.0); 2.507(49.3); 2.502(65.4); 2.498(47.9); 2.494(23.6); 2.334(16.0); 2.282(0.6); 1.366(4.3); 1.347(9.4); 1.329(4.3); 0.146(0.5); 0.008(4.1); 0.000(115.3); −0.009(4.4); −0.150(0.5) |
| I-2-2 | ¹H-NMR, Solvent [D$_6$]-DMSO, spectrometer: 399.95 MHz: δ = 8.753(3.8); 8.750(3.7); 8.317(0.3); 8.033(7.8); 7.326(3.8); 7.322(3.9); 7.159(3.3); 4.055(0.4); 4.038(1.2); 4.020(1.2); 4.002(0.4); 3.326(98.4); 2.675(0.7); 2.671(0.9); 2.666(0.7); 2.541(0.5); 2.524(2.3); 2.511(53.3); 2.506(106.2); 2.502 (137.7); 2.497(98.3); 2.493(46.8); 2.333(0.7); 2.329(1.0); 2.324(0.7); 2.173(16.0); 1.989(5.0); 1.235(0.8); 1.193(1.3); 1.175(2.6); 1.157(1.3); 0.146(1.1); 0.008(9.0); 0.000(225.1); −0.009(8.2); |

| Example | NMR data |
|---|---|
| I-2-3 | $^1$H-NMR, Solvent [D$_6$]-DMSO, spectrometer: 399.95 MHz: δ = 8.751(6.1); 8.428(3.8); 8.424(4.3); 8.417(4.0); 8.413(4.0); 8.365(4.0); 8.361(3.7); 8.346(4.2); 8.341(3.7); 8.318(0.6); 8.102(1.4); 8.098(1.2); 8.077(6.7); 7.527(3.1); 7.515(3.4); 7.507(3.3); 7.495(2.8); 6.586(1.2); 6.582(0.9); 6.574(0.9); 6.570(1.2); 4.365(1.2); 4.352(2.4); 4.339(1.2); 4.056(0.4); 4.038(1.2); 4.020(1.2); 4.002(0.4); 3.473(0.7); 3.460(0.8); 3.455(2.1); 3.443(2.1); 3.438(2.2); 3.425(2.1); 3.420(0.9); 3.408(0.8); 3.329(195.7); 2.943(16.0); 2.676(1.2); 2.671(1.6); 2.667(1.2); 2.542(1.1); 2.525(4.2); 2.511(92.3); 2.507(186.0); 2.502(242.8); 2.498(172.4); 2.493(81.0); 2.338(0.5); 2.334(1.1); 2.329(1.5); 2.325(1.1); 1.989(5.5); 1.812(2.2); 1.397(1.3); 1.336(0.7); 1.270(0.7); 1.249(1.5); 1.234(6.3); 1.193(1.6); 1.175(2.9); 1.157(1.5); 1.073(5.1); 1.055(10.0); 1.038(5.0); 0.870(0.4); 0.854(1.1); 0.836(0.7); 0.812(0.4); 0.146(1.0); 0.008(8.0); 0.000(226.6); −0.009(8.0); −0.150(1.0) |
| I-2-63 | $^1$H-NMR, Solvent [D$_6$]-DMSO, spectrometer: 399.95 MHz: δ = 8.788 (14.7); 8.457 (7.0); 8.449 (6.8); 8.389 (6.9); 8.370 (7.2); 8.316 (1.7); 8.145 (5.0); 7.573 (0.5); 7.554 (5.6); 7.542 (6.1); 7.535 (6.0); 7.523 (5.1); 4.056 (1.3); 4.038 (3.8); 4.020 (3.8); 4.002 (1.4); 3.677 (0.3); 3.659 (0.3); 3.650 (0.4); 3.571 (0.6); 3.565 (0.6); 3.333 (29.3); 3.149 (0.8); 3.078 (0.5); 3.059 (0.4); 3.044 (0.4); 3.016 (0.3); 2.676 (3.9); 2.671 (5.3); 2.667 (4.1); 2.621 (0.5); 2.524 (14.8); 2.511 (289.5); 2.507 (582.9); 2.502 (774.1); 2.498 (579.0); 2.494 (297.0); 2.438 (0.5); 2.333 (3.6); 2.329 (5.0); 2.324 (3.7); 2.197 (0.4); 1.989 (16.0); 1.909 (1.9); 1.398 (0.9); 1.351 (0.7); 1.336 (0.5); 1.298 (3.1); 1.259 (4.6); 1.235 (7.7); 1.193 (4.5); 1.175 (8.6); 1.157 (4.4); 0.868 (0.5); 0.854 (1.2); 0.836 (0.7); 0.812 (0.4); 0.146 (3.8); 0.008 (30.3); 0.000 (833.4); −0.008 (38.5); −0.150 (0.8) |
| I-2-64 | $^1$H-NMR, Solvent [D$_6$]-DMSO, spectrometer: 601.6 MHz: δ = 19.976 (0.4); 8.948 (9.4); 8.627 (14.3); 8.322 (0.4); 8.089 (2.7); 7.662 (0.8); 7.508 (16.0); 7.455 (3.1); 5.761 (0.6); 4.035 (0.5); 4.023 (0.4); 3.745 (0.4); 3.188 (0.8); 2.769 (0.4); 2.616 (0.9); 2.525 (1.1); 2.522 (1.4); 2.519 (1.4); 2.510 (51.7); 2.507 (115.2); 2.504 (161.4); 2.501 (117.3); 2.499 (54.3); 2.388 (0.9); 1.991 (1.1); 1.336 (1.2); 1.299 (0.4); 1.259 (0.5); 1.249 (0.6); 1.235 (0.7); 1.176 (0.6); 0.096 (0.8); 0.005 (4.6); 0.000 (173.5); −0.006 (6.0); −0.100 (0.8) |
| I-2-65 | $^1$H-NMR, Solvent [D$_6$]-DMSO, spectrometer: 399.95 MHz: δ = 8.923 (4.5); 8.560 (5.6); 7.671 (4.7); 7.636 (4.1); 3.360 (1.5); 3.354 (1.5); 2.671 (0.7); 2.502 (105.4); 2.329 (0.7); 2.242 (16.0); 2.176 (0.5); 0.000 (13.5) |
| I-2-66 | $^1$H-NMR, Solvent [D$_6$]-DMSO, spectrometer: 399.95 MHz: δ = 12.177 (0.5); 8.924 (3.5); 8.557 (5.7); 8.378 (4.9); 4.140 (1.2); 4.122 (3.8); 4.103 (3.9); 4.085 (1.3); 3.327 (6.7); 2.672 (0.4); 2.507 (46.3); 2.503 (59.2); 2.499 (46.2); 2.332 (16.0); 1.366 (4.3); 1.348 (9.2); 1.329 (4.3); 0.000 (18.3) |
| I-2-67 | $^1$H-NMR, Solvent [D$_6$]-DMSO, spectrometer: 399.95 MHz: δ = 7.15 (s, 1 H); 8.07 (s, 1 H); 8.75 (s, 1 H) ppm |

TABLE 4

(I-1)

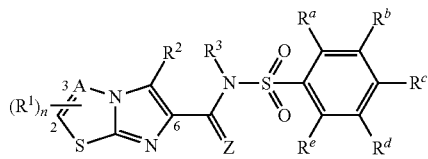

Z = O, R$^3$ = H and Q = substituted aryl

| Example | R$^1$ | n | A | R$^2$ | R$^a$ | R$^b$ | R$^c$ | R$^d$ | R$^e$ | Remarks |
|---|---|---|---|---|---|---|---|---|---|---|
| I-3-1 | 2-CF$_3$ | 1 | CH | Br | Cl | H | H | H | H | NMR |
| I-3-2 | 2-CF$_3$ | 1 | CH | Br | Cl | H | H | OMe | H | NMR |
| I-3-3 | 2-CF$_3$ | 1 | CH | Cl | Cl | H | H | H | H | NMR |
| I-3-4 | 2-CF$_3$ | 1 | CH | Cl | Cl | H | H | OMe | H | NMR |
| I-3-5 | 2-CF$_3$ | 1 | CH | I | Cl | H | H | H | H | NMR |
| I-3-6 | 2-CF$_3$ | 1 | CH | I | Cl | H | H | OMe | H | NMR |
| I-3-7 | 2-CF$_3$ | 1 | CH | CH$_3$ | Cl | H | H | H | H | NMR |
| I-3-8 | 2-CF$_3$ | 1 | CH | CH$_3$ | Cl | H | H | OMe | H | NMR |

| Example | NMR data |
|---|---|
| I-3-1 | 1H-NMR, Solvent [D$_6$]-DMSO, spectrometer: 399.95 MHz: δ = 8.799 (7.5); 8.797 (7.6); 8.318 (0.4); 8.047 (4.9); 8.042 (2.7); 8.032 (4.7); 8.027 (4.2); 7.529 (0.3); 7.428 (6.8); 7.419 (16.0); 7.400 (3.6); 7.394 (4.7); 7.384 (2.7); 7.371 (1.5); 7.334 (0.3); 7.271 (0.5); 7.265 (0.5); 7.249 (0.4); 7.244 (0.4); 7.182 (0.4); 3.573 (0.3); 3.482 (0.3); 3.428 (0.4); 3.416 (0.5); 3.328 (192.8); 3.250 (0.4); 3.243 (0.5); 2.891 (1.9); 2.731 (1.7); 2.695 (0.4); 2.671 (1.8); 2.667 (1.4); 2.565 (4.2); 2.506 (220.3); 2.502 (284.8); 2.498 (214.6); 2.329 (1.9); 2.324 (1.5); 2.285 (0.6); 1.988 (0.6); 1.352 (1.0); 1.336 (3.4); 1.298 (9.1); 1.258 (11.9); 1.249 (5.3); 1.234 (5.3); 1.187 (0.8); 1.174 (0.6); 1.119 (0.4); 0.853 (1.4); 0.835 (1.0); 0.146 (1.0); 0.000 (195.1); −0.008 (9.1); −0.150 (1.0) |
| I-3-2 | $^1$H-NMR, Solvent [D$_6$]-DMSO, spectrometer: 399.95 MHz: δ = 8.799 (2.1); 8.797 (2.1); 7.565 (2.8); 7.557 (2.8); 7.339 (1.9); 7.317 (2.1); 7.014 (1.1); 7.007 (1.1); 6.993 (1.0); 6.985 (1.0); 3.792 (16.0); 3.327 (41.1); 2.891 (0.5); 2.731 (0.4); 2.676 (0.4); 2.671 (0.5); 2.667 (0.4); 2.565 (0.9); 2.507 (64.1); 2.502 (83.6); 2.498 (62.7); 2.333 (0.4); 2.329 (0.5); 2.325 (0.4); 1.989 (0.3); 1.336 (0.7); 1.298 (1.6); 1.259 (2.1); 1.249 (1.1); 1.234 (1.0); 0.008 (2.2); 0.000 (63.3); −0.008 (2.7) |
| I-3-3 | $^1$H-NMR, Solvent [D$_6$]-DMSO, spectrometer: 399.95 MHz: δ = 9.071 (16.0); 8.170 (9.9); 8.152 (10.5); 7.734 (3.1); 7.716 (8.9); 7.698 (9.5); 7.677 (15.4); 7.659 (7.1); 7.643 (7.3); 7.623 (10.3); 7.605 (4.7); 3.739 (0.5); 3.506 (1.6); 3.365 (3.6); 3.188 (1.2); 3.056 (0.5); 3.047 (0.4); 2.672 (2.0); 2.641 (2.5); 2.503 (276.5); 2.369 (0.4); 2.329 (1.9); 0.000 (18.2) |
| I-3-4 | $^1$H-NMR, Solvent [D$_6$]-DMSO, spectrometer: 399.95 MHz: δ = 9.074 (2.7); 9.072 (2.7); 7.612 (2.9); 7.604 (3.1); 7.585 (2.6); 7.563 (3.0); 7.307 (1.6); 7.299 (1.6); 7.285 (1.4); 7.277 (1.4); 3.861 (16.0); 3.431 (0.3); 3.411 (0.3); 3.402 (0.3); 3.385 (0.4); 3.368 (0.4); 3.358 (0.4); 3.350 (0.3); 2.671 (0.4); 2.502 (54.6); 2.329 (0.3); 0.000 (4.9) |
| I-3-5 | $^1$H-NMR, Solvent [D$_6$]-DMSO, spectrometer: 399.95 MHz: δ = 12.454 (0.4); 8.997 (1.2); 8.895 (16.0); 8.174 (10.0); 8.155 (11.1); 7.740 (2.9); 7.721 (8.6); 7.703 (9.8); 7.683 (15.9); 7.664 (7.9); 7.653 (8.3); 7.632 (10.6); 7.616 (5.5); 7.451 (0.4); 3.345 (12.4); 3.187 (1.9); 2.672 (2.9); 2.503 (407.7); 2.330 (2.7); 1.073 (0.5); 1.056 (0.9); 1.039 (0.5); 0.000 (25.6) |
| I-3-6 | $^1$H-NMR, Solvent [D$_6$]-DMSO, spectrometer: 399.95 MHz: δ = 8.901 (2.8); 8.898 (2.9); 7.612 (3.2); 7.605 (3.4); 7.593 (2.7); 7.584 (0.6); 7.571 (3.0); 7.314 (1.6); 7.306 (1.7); 7.292 (1.5); 7.284 (1.4); 3.870 (16.0); 3.347 (1.2); 3.187 (0.3); 2.672 (0.5); 2.507 (57.8); 2.503 (72.0); 2.499 (58.3); 2.330 (0.5); 0.000 (5.9) |
| I-3-7 | $^1$H-NMR, Solvent [D$_6$]-DMSO, spectrometer: 399.95 MHz: δ = = 2.58 (s, 3 H); 7.60-7.73 (m, 3 H); 8.16 (d, 1 H); 9.01 (s, 1 H) ppm |
| I-3-8 | $^1$H-NMR, Solvent [D$_6$]-DMSO, spectrometer: 399.95 MHz: δ 2.66 (s, 3 H); 3.86 (s, 3 H); 7.29 (dd, 1 H); 7.57 (d, 1 H); 7.60 (d, 1 H); 9.02 (s, 1 H) ppm |

BIOLOGICAL EXAMPLES

Meloidogyne Incognita

Test (MELGIN)

Solvent: 125.0 parts by weight of acetone

To produce a suitable preparation of active compound, 1 part by weight of active compound is mixed with the stated amount of solvent, and the concentrate is diluted with water to the desired concentration.

Vessels are filled with sand, a solution of the active ingredient, a suspension containing eggs and larvae of the southern root-knot nematode (*Meloidogyne incognita*) and salad seeds. The salad seeds germinate and the seedlings grow. Galls develop in the roots.

After 14 days the nematicidal activity is determined on the basis of the percentage of gall formation. 100% means that no galls were found; 0% means that the number of galls found on the roots of the treated plants was equal to that in untreated control plants.

In this test, for example, the following compounds from the preparation examples showed good activity of 100% at an application rate of 20 ppm: I-1-1, I-1-3, I-1-4, I-1-5, I-1-6, I-1-8, I-1-9, I-1-10, I-1-11, I-1-12, I-1-13, I-1-14, I-1-15, I-1-16, I-1-17, I-1-19, I-1-20, I-1-21, I-1-22, I-1-23, I-1-27, I-1-31, I-1-43, I-1-45, I-1-50, I-1-51, I-1-60, I-1-142, I-1-147, I-1-145, I-1-146, I-1-155, I-1-159, I-1-204, I-1-205, I-1-206, I-1-207, I-1-208, I-1-209, I-1-212, I-1-216, I-1-219, I-1-220, I-1-222, I-1-223, I-1-224, I-1- 226, I-1-227, I-1-232, I-1-233, I-1-234, I-1-235, I-1-236, I-1-238, I-1-243, I-1-248, I-1-251, I-1-254, I-1- 255, I-1-263, I-1-270, I-1-282, I-1-286, I-1-289, I-1-290, I-1-291, I-1-292, I-1-293, I-1-296, I-1-298, I-1- 300, I-1-301, I-1-302, I-1-305, I-1-307, I-1-308, I-1-309, I-1-312, I-1-313, I-2-2, I-2-65, I-2-66, I-3-1, I-3-2, I-3-3, I-3-4, I-3-5, I-3-6.

In this test, for example, the following compounds from the preparation examples showed good activity of 90% at an application rate of 20 ppm: I-1-7, I-1-18, I-1-29, I-1-143, I-1-144, I-1-154, I-1-156, I-1-158, I-1-191, I-1-202, I-1-225, I-1-250, I-1-252, I-1-272, I-1-275, I-1-279, I-1-281, I-1-288, I- 1-295, I-1-297, I-1-299, I-1-310, I-1-314, I-2-1.

Meloidogyne incognita—Test

Solvent: 7 parts by weight of dimethylformamide

Emulsifier: 2.5 parts by weight of alkylarylpolyglycolether

To produce a suitable preparation of active compound, 1 part by weight of active compound is mixed with the stated amount of solvent and emulsifier and is diluted with water to the desired concentration. In the calculation of the concentration the soil volume has to be included. Care has to be taken that the emulsifier concentration in the soil does not exceed 20 ppm. Further test concentrations are prepared by dilution with water.

The compound solution is poured into pots filled with soil (loamy sand). A suspension containing eggs and larvae of the southern root-knot nematode (*Meloidogyne incognita*) is added, salad seeds are spread on the soil surface and covered with quartz sand. The salad seeds germinate and the seedlings grow. Galls develop on the roots.

After 21 days the nematicidal activity is determined on the basis of the percentage of gall formation. 100% means no galls were found; 0% means the number of galls found on the roots of the treated plants was equal to that in untreated control plants.

In this test, for example, the following compounds from the preparation examples showed good activity of 100% at an application rate of 8 ppm: I-1-9, I-1-227, I-1-255, I-2-66

In this test, for example, the following compounds from the preparation examples showed good activity of 98% at an application rate of 8 ppm: I-1-10, I-1-251

In this test, for example, the following compounds from the preparation examples showed good activity of 95% at an application rate of 8 ppm: I-1-12, I-1-216, I-1-243, I-1-252

In this test, for example, the following compounds from the preparation examples showed good activity of 90% at an application rate of 8 ppm: I-1-146, I-1-222

In this test, for example, the following compounds from the preparation examples showed good activity of 85% at an application rate of 8 ppm: I-1-147, I-1-254

In this test, for example, the following compounds from the preparation examples showed good activity of 80% at an application rate of 8 ppm: I-1-225, I-1-226, I-1-282

In this test, for example, the following compounds from the preparation examples showed good activity of 100% at an application rate of 4 ppm: I-1-206

In this test, for example, the following compounds from the preparation examples showed good activity of 99% at an application rate of 4 ppm: I-1-154

In this test, for example, the following compounds from the preparation examples showed good activity of 95% at an application rate of 4 ppm: I-1-8, I-1-205, I-1-207

In this test, for example, the following compounds from the preparation examples showed good activity of 90% at an application rate of 4 ppm: I-1-5, I-1-209

In this test, for example, the following compounds from the preparation examples showed good activity of 85% at an application rate of 4 ppm: I-1-289, I-1-291

In this test, for example, the following compounds from the preparation examples showed good activity of 80% at an application rate of 4 ppm: I-1-142, I-1-223

In this test, for example, the following compounds from the preparation examples showed good activity of 98% at an application rate of 2 ppm: I-1-158

In this test, for example, the following compounds from the preparation examples showed good activity of 97% at an application rate of 2 ppm: I-1-4

In this test, for example, the following compounds from the preparation examples showed good activity of 95% at an application rate of 2 ppm: I-1-1, I-1-3, I-1-159

In this test, for example, the following compounds from the preparation examples showed good activity of 80% at an application rate of 2 ppm: I-1-27

In this test, for example, the following compounds from the preparation examples showed good activity of 90% at an application rate of 1 ppm: I-1-208

In this test, for example, the following compounds from the preparation examples showed good activity of 85% at an application rate of 1 ppm: I-1-286

*Meloidogyne incognita*—Spray Test (MELGIN)

Solvent: 7 parts by weight of dimethylformamide

Emulsifier: alkylaryl polyglycol ether

To produce a suitable preparation of active compound, 1 part by weight of active compound is mixed with the stated amount of solvent and is diluted with water, containing an emulsifier concentration of 1000 ppm, to the desired concentration. Further test concentrations are prepared by dilution with emulsifier containing water. Ammonium sulfate and rape oil methyl ester (RME) in a dosage of 1000 ppm are added to the desired concentration.

Salad and tomato plants are treated by being sprayed on the leaves with the preparation of the active compound of the desired concentration, the soil surface is covered by a protection film. 3 days after spraying, a suspension containing eggs and larvae of the southern root-knot nematode (*Meloidogyne incognita*) is added on the soil surface. Galls develop on the roots.

24 days after spraying, the nematicidal activity is determined on the basis of the percentage of gall formation. 100% means no galls were found; 0% means the number of galls found on the roots of the treated plants was equal to that in untreated control plants.

In this test, for example, the following compounds from the preparation examples showed good levels of activity at application rates as indicated in the following tables.

Test plant: Tomato, *Lycopersicon esculentum*

| Concentration [ppm] | Example I-1-4 | Example I-1-158 | Example I-1-159 |
|---|---|---|---|
| 2500 | 98 | 50 | 95 |
| 1000 | 35 | 0 | 75 |
| 100 | 25 | 0 | 0 |

Test plant: Salad, *Lactuca sativa*

| Concentration [ppm] | Example I-1-4 | Example I-1-158 | Example I-1-159 |
|---|---|---|---|
| 2500 | 75 | 80 | 95 |
| 1000 | 20 | 75 | 60 |
| 100 | 0 | 15 | 25 |

The invention claimed is:
1. A compound of formula (I)

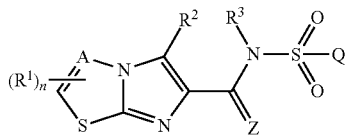

wherein
A is N or C—$R^1$;
Z is O or S;
each $R^1$ is independently H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R^{10})S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$;

$R^2$ is H, halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^7$, $C(O)OR^8$, $C(O)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R^{10})C(O)NR^{11}R^{12}$, $N(R^{10})S(O)_2R^9$ or $N(R10)S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyyl, $C_2$-$C_4$-haloalkenyl, $C(X)R^7$, $C(O)OR^8$, $C(O)NR^{11}R^{12}$, $S(O)_mR^9$ and $S(O)_2NR^{11}R^{12}$, $C_2$-$C_6$-alkoxyalkyl, $OC(O)R^{7a}$ and $N(R^{10})C(O)R^{7a}$;

$R^3$ is H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $OR^{4a}$, and $S(O)_mR^{9a}$;

or $C_1$-$C_6$-alkyl substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or $C_1$-$C_6$-alkyl substituted with 1 to 2 substituents independently selected from the group consisting of phenyl or a 5- or 6-membered heteroaromatic ring, each optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

or phenyl optionally substituted with 1 to 5 substituents independently selected from the group consisting of halogen, cyano, nitro, $OR^4$, $NR^5R^6$, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

Q is phenyl, naphthalenyl, a 5- or 6-membered heteroaromatic ring or an 8- to 10-membered heteroaromatic bicyclic ring system, each optionally substituted with 1 to 5 substituents independently selected from the group consisting of halogen, cyano, nitro, $SF_5$, OCN, SCN, $Si(R^{15})_3$, $OR^4$, $NR^5R^6$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(X)NR^{11}R^{12}$, $S(O)_mR^9$, $S(O)_2NR^{11}R^{12}$, $OC(O)R^7$, $OC(O)OR^8$, $OC(O)NR^{11}R^{12}$, $OS(O)_2R^9$, $OS(O)_2NR^{11}R^{12}$, $N(R^{10})C(O)R^7$, $N(R10)C(O)NR^{11}R^{12}$, $N(R^{10})S(O)_2R^9$, $N(R^{10})S(O)_2NR^{11}R^{12}$ and $R^{14}$;

each $R^4$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{4a}$ is independently H, $C_1$-$C_6$-alkyl or $C_1$-$C_6$-haloalkyl;

each $R^5$ is independently H, $NR^{5a}R^{6a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$, $C(O)NR^{11}R^{12}$, $S(O)_mR^9$ or $S(O)_2NR^{11}R^{12}$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{5a}$ is independently H or $C_1$-$C_6$-alkyl;

each $R^6$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

each $R^{6a}$ is independently H, $C(O)R^{13}$ or $C(O)OR^{13}$;

each $R^7$ is independently H, $C_1$-$C_6$-alkyl, $C_1$-$C_6$ haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{7a}$ is independently $C_1$-$C_6$-alkyl or $C_1$-$C_6$-haloalkyl;

each $R^8$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$ haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{8a}$ is independently $C_1$-$C_6$-alkyl or $C_1$-$C_6$-haloalkyl;

each $R^9$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^{4a}$, $NR^{5a}R^{6a}$, $C(X)R^{7a}$, $C(O)OR^{8a}$, $C(O)NR^{11}R^{12}$, $S(O)_mR^{9a}$ and $S(O)_2NR^{11}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11}R^{12}$, $OR^{4a}$, $C_2$-$C_6$-alkoxyalkyl, $S(O)_mR^{9a}$, $S(O)_2NR^{11}R^{12}$, $NR^{5a}R^{6a}$, $OC(O)R^{7a}$ and $N(R^{10})C(O)R^{7a}$;

each $R^{9a}$ is independently $C_1$-$C_6$-alkyl or $C_1$-$C_6$-haloalkyl;

each $R^{10}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C_3$-$C_7$-cycloalkyl, $C(X)R^{7a}$, $C(O)OR^{8a}$, $C(O)NR^{11}R^{12}$, $S(O)_mR^{9a}$ or $S(O)_2NR^{11}R^{12}$;

each $R^{11}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^{4a}$, $NR^{5a}R^{6a}$, $C(X)R^{7a}$, $C(O)OR^{8a}$, $C(O)NR^{11a}R^{12}$, $S(O)_mR^{9a}$ and $S(O)_2NR^{11a}R^{12}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $C(O)NR^{11a}R^{12}$, $C_2$-$C_6$-alkoxyalkyl, $S(O)_mR^{9a}$, $S(O)_2NR^{11a}R^{12}$, $NR^{5a}R^{6a}$, $OC(O)R^{7a}$ and $N(R^{10})C(O)R^{7a}$;

each $R^{11a}$ is independently H, $C_1$-$C_6$-alkyl, $C_2$-$C_6$-alkenyl or $C_2$-$C_6$-alkynyl;

each $R^{12}$ is independently H, $NR^{5a}R^{6a}$, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl, $C_2$-$C_6$-haloalkynyl, $C(X)R^7$, $C(O)OR^8$ or $S(O)_mR^9$;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 3 substituents independently selected from the group consisting of halogen, cyano, nitro, $C_1$-$C_4$-alkyl, $C_2$-$C_4$-alkenyl, $C_2$-$C_4$-alkynyl, $C_1$-$C_4$-haloalkyl, $C_2$-$C_4$-haloalkenyl, $C(X)R^{7a}$, $C(O)OR^{8a}$, $OR^{4a}$, $C_2$-$C_6$-alkoxyalkyl, $S(O)_mR^{9a}$, $NR^{5a}R^{6a}$, $OC(O)R^{7a}$ and $N(R^{10})C(O)R^{7a}$;

each $R^{13}$ is independently H, $C_1$-$C_6$-alkyl, $C_1$-$C_6$-haloalkyl, $C_2$-$C_6$-alkenyl, $C_2$-$C_6$-haloalkenyl, $C_2$-$C_6$-alkynyl or $C_2$-$C_6$-haloalkynyl;

or $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$ haloalkyl, $OR^{4a}$ and $S(O)_mR^{9a}$;

each $R^{14}$ is independently $C_3$-$C_7$-cycloalkyl, $C_4$-$C_8$-cycloalkylalkyl, $C_6$-$C_{14}$-cycloalkylcycloalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or $C_1$-$C_6$-alkyl, $C_2$-$C_6$-alkenyl or $C_2$-$C_6$-alkynyl, each substituted with 1 to 4 substituents independently selected from the group consisting of cyano, nitro, $OR^4$, $NR^5R^6$, $C(X)R^7$, $C(O)OR^8$, $C(O)NR^{11}R^{12}$, $S(O)_mR^9$ and $S(O)_2NR^{11}R^{12}$;

or phenyl, naphthalenyl or a 5- or 6-membered heteroaromatic ring, each optionally substituted with 1 to 5 substituents independently selected from the group consisting of halogen, cyano, nitro, $OR^4$, $NR^5R^6$, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

or $C_1$-$C_6$-alkyl substituted with a substituent selected from the group consisting of a 5- or 6-membered heteroaromatic ring, each optionally substituted with 1 to 5 substituents independently selected from the group consisting of halogen, cyano, nitro, $OR^4$, $NR^5R^6$, $C_1$-$C_4$ alkyl, $C_2$-$C_4$-alkenyl, $C_2$-$C_4$-alkynyl, $C_1$-$C_4$ haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

each $R^{15}$ is independently $C_1$-$C_6$-alkyl, $C_1$-$C_6$ haloalkyl, $C_2$-$C_6$-alkenyl, $C_2$-$C_6$-haloalkenyl, $C_2$-$C_6$-alkynyl or $C_2$-$C_6$-haloalkynyl; or $C_3$-$C_7$-cycloalkyl, $C_4$-$C_8$-cycloalkylalkyl or $C_5$-$C_7$-cycloalkenyl, each optionally substituted with 1 to 4 substituents independently selected from the group consisting of halogen, cyano, nitro, $C_1$-$C_4$-alkyl, $C_1$-$C_4$-haloalkyl, $OR^{4a}$ and $S(O)_mR^{9a}$;

or phenyl optionally substituted with 1 to 5 substituents independently selected from the group consisting of halogen, cyano, nitro, $OR^4$, $NR^5R^6$, $C_1$-$C_4$ alkyl, $C_2$-$C_4$-alkenyl, $C_2$-$C_4$-alkynyl, $C_1$-$C_4$-haloalkyl, $C_2$-$C_4$-haloalkenyl, $C_2$-$C_6$-alkoxyalkyl, $C(X)R^7$, $C(O)OR^8$, $C(O)NR^{11}R^{12}$, $S(O)_mR^9$, $S(O)_2NR^{11}R^{12}$, $OC(O)R^{7a}$ and $N(R^{10})C(O)R^{7a}$;

X is O or S;

each m is independently 0, 1 or 2;

and n is 0, 1 or 2.

2. A compound according to claim 1, wherein A, $R^1$, $R^2$, $R^3$, $R^4$, $R^{4a}$, $R^5$, $R^{5a}$, $R^6$, $R^{6a}$, $R^7$, $R^{7a}$, $R^8$, $R^{8a}$, $R^9$, $R^{9a}$, $R^{10}$, $R^{11a}$, $R^{12}$, $R^{13}$, $R^{14}$, $R^{15}$, Z, X, m and n have the meanings as defined in claim 1;

Q is selected from the group consisting of (U-1) to (U-61), (U-81) to (U-87), (U-89) to (U-103) and (U-105) to (U-123):

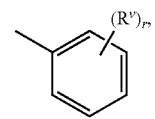
U-1

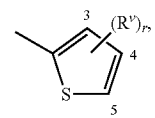
U-2

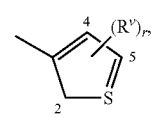
U-3

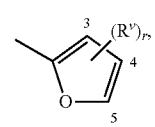
U-4

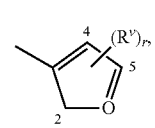
U-5

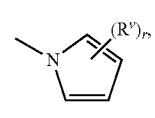
U-6

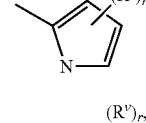
U-7

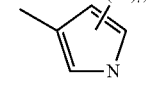
U-8

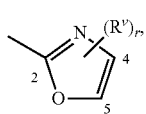 U-9
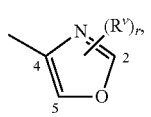 U-10
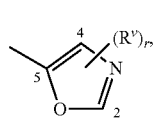 U-11
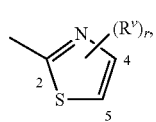 U-12
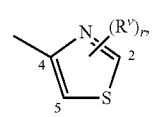 U-13
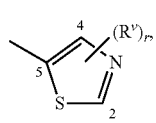 U-14
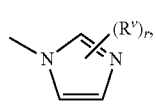 U-15
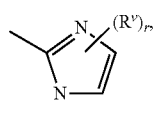 U-16
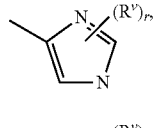 U-17
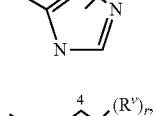 U-18
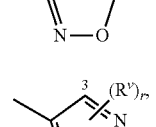 U-19
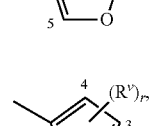 U-20
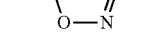 U-21
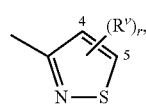 U-22
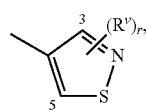 U-23
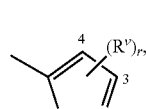 U-24
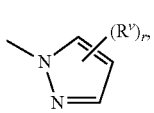 U-25
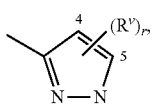 U-26
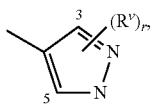 U-27
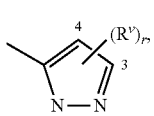 U-28
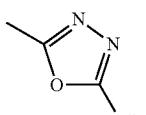 U-29
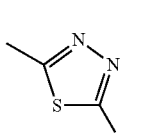 U-30
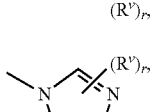 U-31
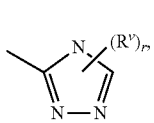 U-32
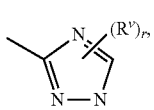 U-33
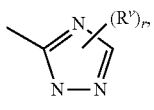 U-34

-continued
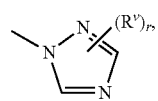 U-35
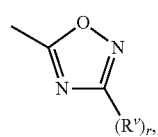 U-36
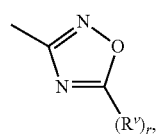 U-37
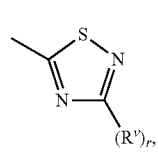 U-38
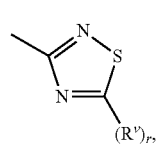 U-39
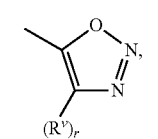 U-40
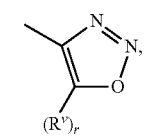 U-41
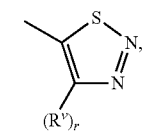 U-42
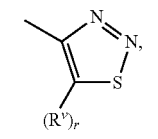 U-43
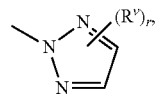 U-44
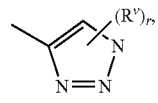 U-45
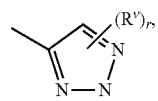 U-46
-continued
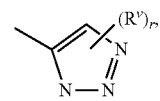 U-47
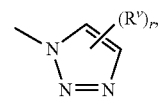 U-48
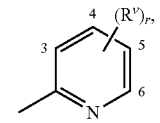 U-49
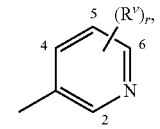 U-50
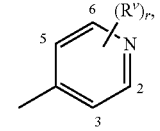 U-51
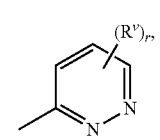 U-52
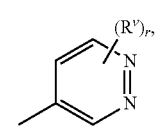 U-53
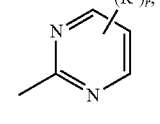 U-54
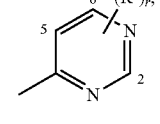 U-55
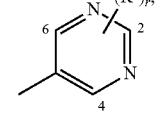 U-56
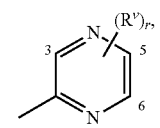 U-57
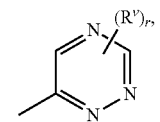 U-58
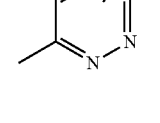

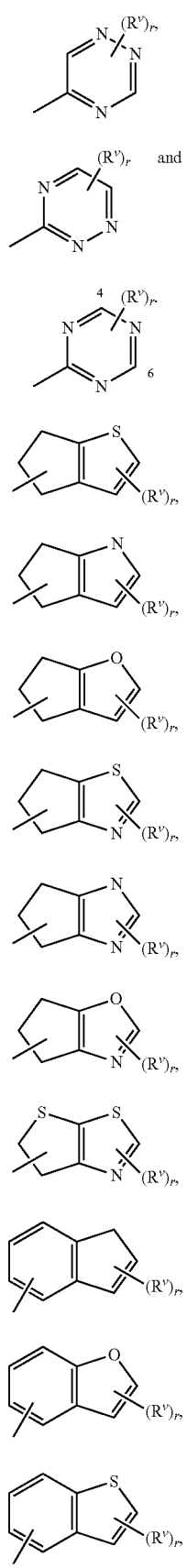
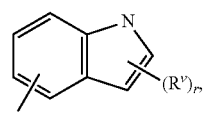
U-92
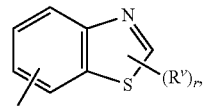
U-93
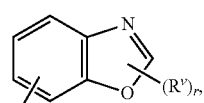
U-94
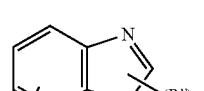
U-95
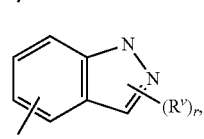
U-96
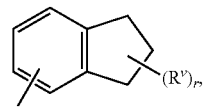
U-97
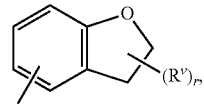
U-98
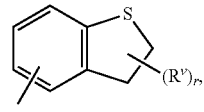
U-99
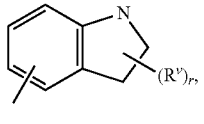
U-100
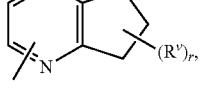
U-101
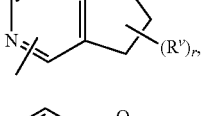
U-102
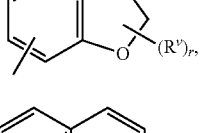
U-103
U-105 wherein R^v is any substituent as defined for $R^1$, $R^2$ or $R^3$ in claim 1 and r is 0, 1, 2, 3, 4 or 5, limited by the number of available positions on each U group.

3. A compound according to claim 1 which is represented by formula (Ia):

(Ia)

4. A compound according to claim 1 which is represented by formula (Ib):

(Ib)

5. A compound according to claim 1 which is represented by formula (Ic):

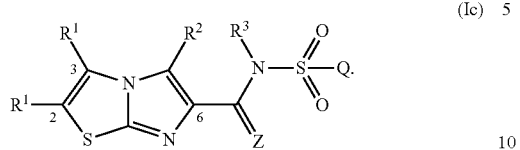

(Ic)

6. A compound according to claim 1 which is represented by formula (Id):

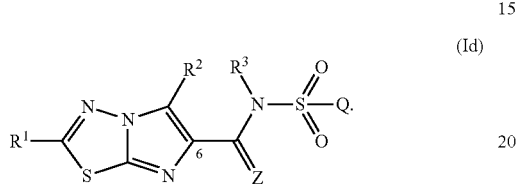

(Id)

7. A method for controlling a parasitic nematode in crop protection comprising contacting the parasitic nematode or an environment thereof with a biologically effective amount of a compound of formula (I) according to claim 1.

8. A method according to claim 7 wherein the compound is applied by spray application.

9. A method for protecting a seed from a parasitic nematode comprising contacting the seed with a biologically effective amount of a compound of formula (I) according to claim 1.

10. A seed obtained by a method according to claim 9.

11. A composition comprising at least one compound of formula (I) according to claim 1.

12. A composition according to claim 11 further comprising at least one additional active ingredient.

13. A composition according to claim 11 wherein the composition is in the form of a spray.

14. A method for controlling a parasitic nematode in crop protection comprising contacting the parasitic nematode or an environment thereof with a biologically effective amount of a composition according to claim 11.

15. A composition comprising an effective amount of at least one compound of formula (I) according to claim 1 and at least one surfactant, solid or liquid diluent.

16. A compound which is selected from the group consisting of:

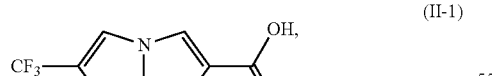

(II-1)

(II-13)

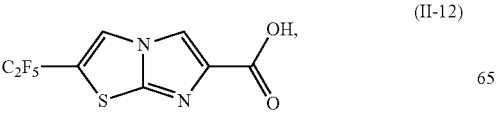

(II-12)

-continued

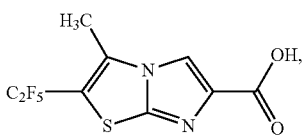

(II-17)

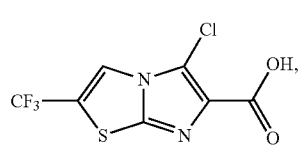

(II-22)

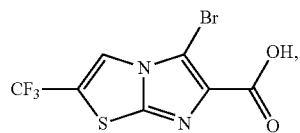

(II-21)

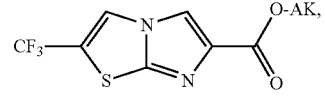

(VII-1)

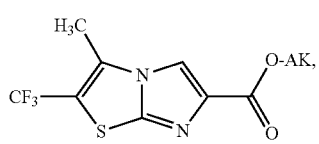

(VII-13)

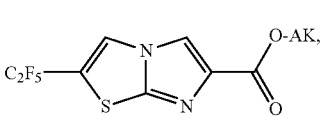

(VII-12)

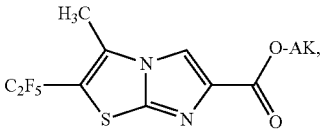

(VII-17)

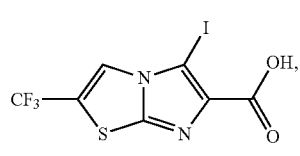

(II-23)

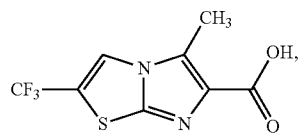

(II-21)

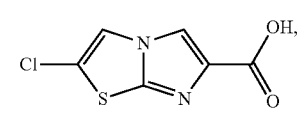

(II-5)

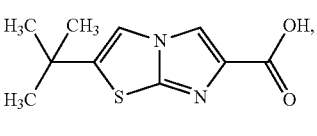

(II-3)

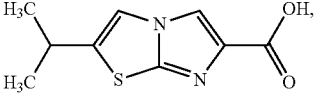

(II-10)

-continued
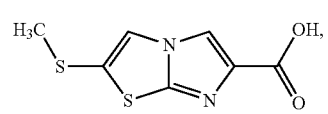
(II-19)
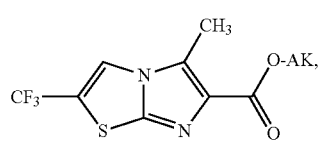
(VII-21)
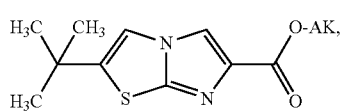
(VII-3)
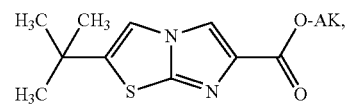
(VII-10)
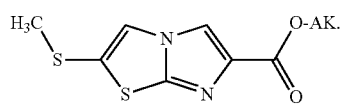
(VII-19)
wherein AK is alkyl, optionally $(C_1-C_4)$alkyl and optionally ethyl.
* * * * *